(12) United States Patent
Hong et al.

(10) Patent No.: US 7,776,847 B2
(45) Date of Patent: Aug. 17, 2010

(54) BENZISOTHIAZOLES USEFUL FOR TREATING OR PREVENTING HCV INFECTION

(75) Inventors: Hui Hong, Palo Alto, CA (US); Eileen Goldstein, Millbrae, CA (US); Emily Stauffer, San Francisco, CA (US); Dane Goff, Redwood City, CA (US); Rao Kolluri, Foster City, CA (US); Ihab Darwish, San Mateo, CA (US); Rajinder Singh, Belmont, CA (US); Henry Lu, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 865 days.

(21) Appl. No.: 11/362,553

(22) Filed: Feb. 24, 2006

(65) Prior Publication Data

US 2006/0229294 A1 Oct. 12, 2006

Related U.S. Application Data

(60) Provisional application No. 60/656,298, filed on Feb. 25, 2005, provisional application No. 60/756,289, filed on Jan. 5, 2006.

(51) Int. Cl.
*A61K 31/33* (2006.01)
(52) U.S. Cl. ...................................... 514/183
(58) Field of Classification Search .................. None
See application file for complete search history.

(56) References Cited

U.S. PATENT DOCUMENTS

| | | | |
|---|---|---|---|
| 3,707,364 A | 12/1972 | Becke et al. | |
| 3,997,548 A | 12/1976 | Singerman | |
| 4,104,388 A | 8/1978 | Wade et al. | |
| 4,590,192 A * | 5/1986 | Fake et al. ............... | 514/233.8 |
| 4,590,196 A | 5/1986 | Smith et al. | |
| 5,883,258 A | 3/1999 | Kraus et al. | |

FOREIGN PATENT DOCUMENTS

| | | |
|---|---|---|
| DE | 11 74 783 B | 7/1964 |
| DE | 19 60 026 A | 6/1971 |
| DE | 31 12 164 A1 | 10/1982 |
| DE | 32 02 298 A1 | 8/1983 |
| EP | 0 105 732 A 04 | 4/1984 |
| GB | 1 265 824 A | 3/1972 |
| WO | WO 03/064456 A | 8/2003 |
| WO | WO 2004/041818 A | 5/2004 |

OTHER PUBLICATIONS

Wyles et al Synergy of small molecular inhibitors of hepatitis C virus replication directed at mulitiple viral targets (J Virol 81(6):3005-3008, 2007).*
Njoroge et al Challenges in modern drug discovery. (Acc Chem Res 41(1):50-59, 2008).*
Zhi Chen and Min Zheng: Patents and development of HBV and HCV clinical treatment: Expert Opinion on Therapeutic Patents, vol. 15, No. 8, 2005, pp. 1027-1039, XP002384991.

* cited by examiner

*Primary Examiner*—Brandon J Fetterolf
*Assistant Examiner*—Craig Ricci
(74) *Attorney, Agent, or Firm*—McDonnell Boehnen Hulbert & Berghoff LLP

(57) ABSTRACT

The present invention relates to benzisothiazoles and pharmaceutical compositions thereof that inhibit replication and/or proliferation of HCV virus. The present invention also relates to the use of the benzisothiazoles and pharmaceutical compositions comprising the compounds to treat or prevent HCV infections.

5 Claims, No Drawings

BENZISOTHIAZOLES USEFUL FOR TREATING OR PREVENTING HCV INFECTION

This application claims priority to U.S. Provisional application 60/656,298 filed Feb. 25, 2005 and to U.S. Provisional application 60/756,289 filed Jan. 5, 2006.

FIELD OF THE INVENTION

The present invention relates to benzisothiazoles and compositions thereof useful for treating or preventing Hepatitis C virus (HCV) infections. In particular, the present invention relates to 3-substituted benzisothiazoles, compositions thereof and the use of such compounds and compositions to inhibit HCV replication and/or proliferation as a therapeutic approach towards the treatment and/or prevention of HCV infections in animals, particularly humans.

BACKGROUND OF THE INVENTION

Hepatitis C virus (HCV) infection is a global human health problem with approximately 150,000 new reported cases each year in the United States alone. HCV is a single stranded RNA virus, which is the etiological agent identified in most cases of non-A, non-B post-transfusion and post-transplant hepatitis and is a common cause of acute sporadic hepatitis (Choo et al., *Science* 244:359, 1989; Kuo et al., *Science* 244:362, 1989; and Alter et al., in *Current Perspective in Hepatology*, p. 83, 1989). It is estimated that more than 50% of patients infected with HCV become chronically infected and 20% of those develop cirrhosis of the liver within 20 years (Davis et al., *New Engl. J. Med.* 321:1501, 1989; Alter et al., in *Current Perspective in Hepatology*, p. 83, 1989; Alter et al., *New Engl. J. Med.* 327:1899, 1992; and Dienstag *Gastroenterology* 85:430, 1983). Moreover, the only therapy available for treatment of HCV infection is interferon-α (INTRON® A, PEG-INTRON® A, Schering-Plough; ROFERON-A®, Roche). Most patients are unresponsive, however, and among the responders, there is a high recurrence rate within 6-12 months after cessation of treatment (Liang et al., *J. Med. Virol.* 40:69, 1993). Ribavirin, a guanosine analog with broad spectrum activity against many RNA and DNA viruses, has been shown in clinical trials to be effective against chronic HCV infection when used in combination with interferon-□ or alpha-interferon (□-IFN) (see, e.g., Poynard et al., *Lancet* 352:1426-1432, 1998; Reichard et al., *Lancet* 351:83-87, 1998), and this combination therapy has been recently approved (REBETRON, Schering-Plough). However, the response rate is still well below 50%. Therefore, additional compounds for treatment and prevention of HCV infection are needed.

SUMMARY OF THE INVENTION

In one aspect, the present invention provides compositions comprising the compounds of the invention. The compositions generally comprise a benzisothiazole of the invention or a salt, hydrate, solvate S-oxide or N-oxide thereof and a suitable excipient, carrier or diluent. The composition may be formulated for veterinary uses or for use in humans.

The compounds of the invention are potent inhibitors of HCV replication and/or proliferation. Accordingly, in still another aspect, the present invention provides methods of inhibiting HCV replication and/or proliferation, comprising contacting a Hepatitis C virion with an amount of a compound or composition of the invention effective to inhibit HCV replication and/or proliferation. The methods may be practiced in vitro or in vivo, and may be used as a therapeutic approach towards the treatment and/or prevention of HCV infections.

In another aspect, the present invention provides methods of treating and/or preventing HCV infections. The methods generally involve administering to a subject that has an HCV infection or that is at risk of developing an HCV infection an amount of a compound or composition of the invention effective to treat or prevent the HCV infection. The method may be practiced in animals in veterinary contexts or in humans.

In another aspect, the invention provides methods of screening for modulators of HCV activity. The methods comprise combining a composition of the invention, an HCV, and at least one candidate agent and determining the effect of the candidate agent on the HCV activity.

In yet another aspect, the invention also provides pharmaceutical kits comprising one or more containers filled with one or more of the ingredients of pharmaceutical compounds and/or compositions of the present invention, including, one or more HCV modulators as described herein. Such kits can also include, for example, other compounds and/or compositions (for example, diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below with reference to the associated drawings.

DETAILED DESCRIPTION OF PREFERRED EMBODIMENTS

Definitions

As used in the present specification, the following words and phrases are generally intended to have the meanings as set forth below, except to the extent that the context in which they are used indicates otherwise or they are expressly defined to mean something different.

The symbol "—" means a single bond, "≡" means a double bond, "≡" means a triple bond. The symbol "⁓" refers to a group on a double-bond as occupying either position on the terminus of a double bond to which the symbol is attached; that is, the geometry, E- or Z-, of the double bond is ambiguous. When a group is depicted removed from its parent formula, the "~" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Thus, nine hydrogen atoms either implicit or shown in ortho-methylbenzyl bromide. Sometimes a particular atom in a structure is described in textual formula as having a hydrogen or hydrogens as substitution (expressly defined hydrogen), for example, —CH$_2$CH$_2$—. It is understood by one of ordinary skill in the art that the aforementioned descriptive techniques are common in the chemical arts to provide brevity and simplicity to description of otherwise complex structures.

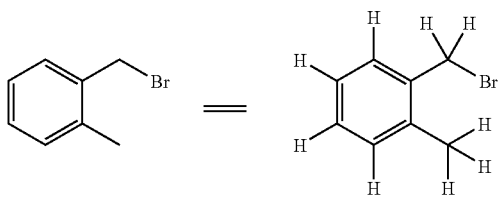

In this application, some ring structures are depicted generically and will be described textually. For example, in the schematic below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

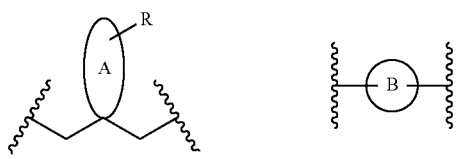

If a group "R" is depicted as "floating" on a ring system, as for example in the formula:

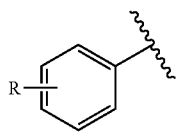

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

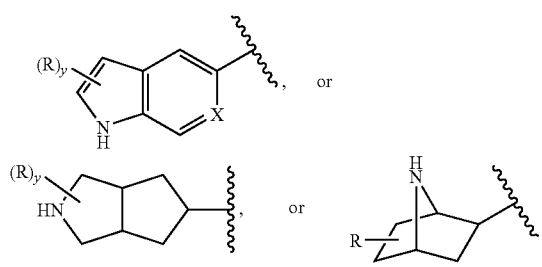

then, unless otherwise defined, a substituent "R" may reside on any atom of the fused ring system, assuming replacement of a depicted (for example the —NH— in the formula above), implied (for example as in the formula above, where the hydrogens are not shown but understood to be present), or expressly defined hydrogen (for example where in the formula above, "X" equals ═CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When there are more than one such depicted "floating" groups, as for example in the formulae:

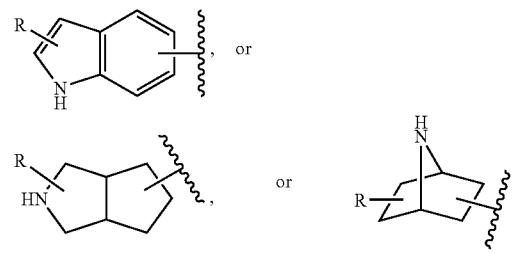

where there are two groups, namely, the "R" and the bond indicating attachment to a parent structure; then, unless otherwise defined, the "floating" groups may reside on any atoms of the ring system, again assuming each replaces a depicted, implied, or expressly defined hydrogen on the ring.

When a group "R" is depicted as existing on a ring system containing saturated carbons, as for example in the formula:

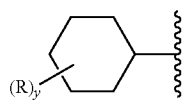

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon).

In another example, two R's on the same carbon, including that carbon, may form a ring, thus creating a spirocyclic ring (a "spirocyclyl" group) structure with the depicted ring as for example in the formula:

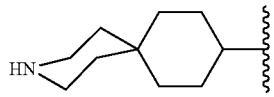

When a compound is described using a generic functional group descriptor, it is understood to mean that any compound of that class would fit into such a description, unless limited by previous language pertaining to such a class. For example if a compound is called "a phenol," then all phenols are included, unless previous descriptive language pertaining to other substitution on that class of compounds is expressed.

Generally, carbon-containing groups are described as containing a particular number of carbons, e.g., "a $C_6$ alkyl" and the like. Specific atom numbering may also be used in describing ring structures, both all-carbon and heteroatom-containing ring structures.

"Alicyclic" refers to a saturated carbocyclic ring system, for example cyclopropane and the like.

"Alkyl" by itself or as part of another substituent, refers to a saturated or unsaturated, branched, straight-chain or cyclic (and combinations thereof, inclusively) monovalent hydrocarbon radical derived by the removal of one hydrogen atom from a single carbon atom of a parent alkane, alkene or alkyne. For example, "$C_8$ alkyl" generically refers to an n-octyl, iso-octyl, cyclohexenylethyl, 2,2,4-trimethyl-1-pentyl, and the like. Unless otherwise specified, "alkyl" means a $C_1$-$C_{12}$ moiety. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like and may also be designated as "$C_{1-6}$ alkyl." Higher alkyl refers to alkyl groups containing more that six carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include cyclopropyl, cyclobutyl, cyclopentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, iso-butenyl and but-2-yne radicals; and for example, "propyl" or "$C_3$ alkyl" each include n-propyl, propenyl, and isopropyl. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; analogous pentyl isomers; hexyl isomers; heptyl isomers; octyl isomers; and the like.

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2$ $CH_2$—), and cyclohexylpropylene (—$CH_2CH_2CH$ ($C_6H_{13}$)—).

"Alkenylene" refers to a straight or branched chain unsaturated divalent radical consisting solely of carbon and hydrogen atoms, having from two to ten carbon atoms, for example, ethylidene, propylidene, n-butylidene, and the like. Alkenylene is a subset of alkyl, referring to the same residues as alkyl, but having two points of attachment and, specifically, double bond unsaturation. The unsaturation present includes at least one double bond.

"Alkynylene" refers to a straight or branched chain unsaturated divalent radical consisting solely of carbon and hydrogen atoms having from two to ten carbon atoms, for example, propylid-2-ynyl, n-butylid-1-ynyl, and the like. Alkynylene is a subset of alkyl, referring to the same residues as alkyl, but having two points of attachment and, specifically, triple bond unsaturation. The unsaturation present includes at least one triple bond.

Any of the above radicals, "alkylene," "alkenylene" and "alkynylene," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons and may also be designated as "$C_{1-6}$ alkoxy."

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —$OCH_2CH_2OCH_3$, and glycol ethers such as polyethyleneglycol and —$O(CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Alkoxycarbonyl" by itself or as part of another substituent, refers to a radical of the formula —C(=O)-alkoxy, where alkoxy is as defined herein.

"Alkylthio" by itself or as part of another substituent, refers to a radical of the formula —S-alkyl, where alkyl is as defined herein. Representative examples include, but are not limited to, methylthio, ethylthio, propylthio, isopropylthio, butylthio tert-butylthio, cyclopropylthio, cyclopentylthio, cyclohexylthio, and the like.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons, e.g. "$C_{1-6}$acyl" generically refers to —C(=O)H, —C(=O)$CH_3$, —C(=O)$CH_2CH_3$, —C(=O)$CH_2CH_2CH_3$, —C(=O)$CH_2CH_2CH_2CH_3$, —C(=O)$CH_2CH_2CH_2CH_2CH_3$ as well as unsaturated and geometric isomers thereof.

"Amino Acid" refers to naturally occurring or synthetic amino acids and optical isomers thereof. Typically the term "amino acid" refers to α- or β-amino acids, but is not limited to those. Typical naturally occurring or synthetic α-amino acids are glycine, alanine, serine, homoserine, threonine, valine, norvaline, leucine, isoleucine, norleucine, aspartic acid, glutamic acid, lysine, omithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —NH$_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, furanyl-oxy-sulfonamino.

"Annular" refers to a single ring system either aromatic or not.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Biaryl," for the purposes of this invention, refers to a group having two aryls, two heteroaryls, or a combination of an aryl and a heteroaryl bound directly to each to other, for example biphenyl, phenylnapthyl, phenylpyridine and the like.

"Arylene" generically refers to any aryl that has at least two groups attached thereto. For a more specific example, "phenylene" refers to a divalent phenyl ring radical. A phenylene, thus may have more than two groups attached, but is defined by a minimum of two non-hydrogen groups attached thereto.

"Arylalkyl" refers to a residue in which an aryl moiety is attached to a parent structure via one of an alkylene, alkenylene, or alkynylene radical. Examples include benzyl, phenethyl, phenylvinyl, phenylallyl and the like. Both the aryl, and the corresponding alkylene, alkenylene, or alkynylene radical portion of an arylalkyl group may be optionally substituted. "Lower arylalkyl" refers to an arylalkyl where the "alkyl" portion of the group has one to six carbons; this can also be referred to as $C_{1-6}$ arylalkyl. "$C_{0-6}$ arylalkyl" refers to a lower arylalkyl as well as an aryl (i.e., as used herein "$C_0$" refers to a chemical bond).

"Exo-alkenyl" refers to a double bond that emanates from an annular carbon, and is not within a ring system, for example the double bond depicted in the formula below.

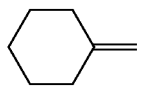

"Endo-alkenyl" refers to a double bond is within a ring system, for example the double bond depicted in the formula below.

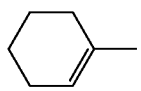

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by a minimum of two non-hydrogen groups attached thereto.

"Heteroatom" refers to a non-carbon atom, generally, but not necessarily, referring to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. A heterocyclyl group may be saturated, unsaturated, aromatic or non-aromatic. For purposes of this invention, the heterocyclyl radical may be, for example, a monocyclic, bicyclic, tricyclic or tetracyclic ring system, which may include fused or bridged ring systems as well as spirocyclic systems. Heteroatoms commonly included in heterocyclyls are nitrogen, phosphorus, carbon or sulfur atoms, and those may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkenylene, or alkynylene radical. Examples include (4-methylpiperazin-1-yl) methyl, (morpholin-4-yl) methyl, (pyridine-4-yl) methyl, 2-(oxazolin-2-yl) ethyl, 4-(4-methylpiperazin-1-yl)-2-butenyl, and the like. Both the heterocyclyl, and the corresponding alkylene, alkenylene, or alkynylene radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl $C_{1-6}$ alkyl" are equivalent terms.

"Hydroxyalkyl" means an alkyl group substituted with one or more hydroxy groups. For example, hydroxyalkyl includes such groups as —CH(OH)—CH$_3$, —CH$_2$(OH)—CH$_2$(OH), —C(OH)$_2$—CH$_3$, —C(OH)$_2$—CH$_2$(OH), —C(OH)$_2$—C(OH)$_3$, and the like.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, only sterically practical and/or synthetically feasible compounds are meant to be included. "Optionally substituted" refers to all subsequent modifiers in a term, for example in the term "optionally substituted aryl $C_{1-8}$ alkyl," optional substitution may occur on both the "$C_{1-8}$ alkyl" portion and the "aryl" portion of the molecule; and for example, an optionally substituted aryloxy $C_{0-3}$ alkylheterocyclyl includes substitution on the aryl, alkyl and heterocyclyl portions. Further, "optionally substituted alkyl" includes optionally substituted cycloalkyl groups, which in turn are defined as including optionally substituted alkyl groups. A list of exemplary optional substitution is provided below in the definition of "substituted."

As used herein, "R" (for example in "—CO$_2$R" and as opposed to R$^1$, R$^2$, etc.) refers to an —H, $C_{1-6}$ alkyl, —N(H)—$C_{1-6}$ alkyl, aryl $C_{0-6}$ alkyl and heterocyclyl $C_{0-6}$ alkyl, each optionally substituted. When "R" is on a nitrogen it can also be an acyl group (for example formyl, acetyl, benzoyl, trifluoroacetyl, Boc, CBZ and the like), optionally substituted alkyl, optionally substituted alkoxy, optionally substituted aryl, optionally substituted heterocyclyl, carboxy, alkoxycarbonyl, sulfanyl, sulfinyl and sulfonyl. For example, when "R" is on a nitrogen the group can be diethylamino, methylsulfonylamino, or furanyl-oxy-sulfonamino. When two of "R" are on a nitrogen, they can combine with the nitrogen to form a heterocyclyl such as morpholine, piperazine, piperadine, pyrrolidine, imidazole and the like). When more than one R's are attached to the same atom, each R may be the same or different.

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a fused ring system (collectively rings B and B') can share a carbon atom with a spirocyclyl (ring A) attached thereto. Thus for the purposes of this application, a spirocyclyl is generally described as a group emanating from an existing ring system. A spirocyclyl can be carbocyclic or heteroalicyclic.

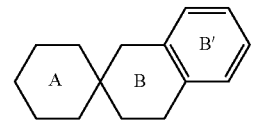

"Substituted" alkyl, aryl, alkoxyl, and heterocyclyl, for example, refer respectively to alkyl, aryl, alkoxyl, and heterocyclyl, wherein one or more (for example up to about five, in another example, up to about three) hydrogen atoms are replaced by a substituent independently selected from: alkyl, hydroxyalkyl, haloalkyl, aminoalkyl, aminodialkyl, aryl, arylalkyl, heterocyclylalkyl, heterocyclyl, heteroaryl, alkoxy, —O-haloalkyl, alkylenedioxy, amino, alkylamino, dialkylamino, —N(R)$C_{1-6}$ alkyl-N(R)(R), —N(R)—$C_{0-3}$ alkylheteroaryl, amidino, aryloxy, haloaryloxy, arylalkyloxy (for example, benzyloxy), carboxy (—CO$_2$H), carboalkoxy (that is, acyloxy or —OC(=O)R), carboxyalkyl (that is, esters or —CO$_2$R), —O—$C_{0-3}$ alkyl-CO$_2$R, carboxamido (or carboxyamino, —C(=O)N(R)R), tert-butoxycarbonylamino (Boc-amino), tert-butoxycarbonyl, benzyloxycarbonylamino (CBZ-amino), aminocarboxylate (or aminocarboxy, that is —NCO$_2$H or —NCO$_2$R), cyano, acyl (—C(=O)R), halogen, hydroxyl, nitro, sulfanyl, sulfinyl, sulfonyl (—SO$_2$R), halosulfonyl (—SO$_2$F, —SO$_2$Cl, —SO$_2$Br), sulfonamido (—SO$_2$N(R)R), aminosulfonyl (—N(R)SO$_2$R), thiol, halogen, hydroxyl, hydroxyalkyl (for example —CH$_2$OH), alkoxyalkyl (—CH$_2$OR), oxo, carbamyl, acylamino (—N(R)C(=O)R), (—C(=O)C(H)(R)N(R)R), heteroalicyclyl (for example morpholinyl, piperazinyl, N-arylpiperazinyl, N-benzylpiperazinyl, N-[benzodioxolanylmethyl]piperazinyl), heterocyclyl (for example pyridinyl, pyrrolyl, thiophenyl), heteroalicyclylalkyl (for example morpholinomethyl, N-phenylpiperazinylmethyl), acylaminoalkyl (for example —CH$_2$N(R)C(=O)R), aryloxyalkyl (for example, —CH$_2$OPh or —PhOCH$_3$) and aminosulfonyl (—N(R)SO$_2$R). Thus, a moiety that is "substituted" is a moiety having one or more of the foregoing chemical entities bonded to it, unless expressly stated otherwise.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —S(O$_2$)—H, —S(O$_2$)-(optionally substituted alkyl), —S(O$_2$)-optionally substituted aryl), —S(O$_2$)-(optionally substituted heterocyclyl), —S(O$_2$)-(optionally substituted alkoxy), —S(O$_2$)-optionally substituted aryloxy), and —S(O$_2$)-(optionally substituted heterocyclyloxy).

"Yield" for each of the reactions described herein is expressed as a percentage of the theoretical yield.

Some of the compounds of the invention may have imino, amino, oxo or hydroxyl substituents off aromatic heterocyclyl systems. For purposes of this disclosure, it is understood that such imino, amino, oxo or hydroxyl substituents may exist in their corresponding tautomeric form, i.e., amino, imino, hydroxyl or oxo, respectively.

Compounds of the invention are drawn using ChemDraw Ultra 8.0 chemical drawing program from CambridgeSoft Corporation of Cambridge Massachusetts and in some instances named according to application of CambridgeSoft proprietary naming software therein. Compounds of the invention may also be named herein according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quatemized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —$OCH_2$—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—$OCH_2$—" is meant to mean not only "—$OCH_2$—" as drawn, but also "—$CH_2O$—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

The term "enantiomerically enriched" is meant to define a chiral center of at least 50.5% of one enantiomer (1% enantiomeric excess), or a molecule having one or more chiral centers, where each chiral center is of at least 50.5% of one enantiomer (1% enantiomeric excess). "Enantiopure" is meant to define a chiral center of a single configuration, or a molecule having one (single enantiomer) or more (single diastereomer) chiral centers, where each chiral center is of a single configuration. For the purposes of this invention, any chiral center in >95% enantiomeric excess is considered "substantially enantiopure", or a molecule having one or more chiral centers, where each chiral center is of >95% enantiomeric excess.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood or the stomach contents. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes. An excellent review of prodrugs is provided in Ettmayer, et. al. *Journal of Medicial Chemistry*, 2004, 47(10) 2393-2404.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" $10^{th}$ Ed., Pergamon Press, Gilman et al. (eds), 2001 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular hepatitis C viral (HCV) gene products-ligand complexes, and their corresponding X-ray structure coordinates can be used to reveal new structural information useful for understanding the biological activity of HCV inhibitors as described herein. As well, the key structural features of the aforementioned proteins, particularly, the shape of the ligand binding site, are useful in methods for designing or identifying selective modulators of HCV and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of HCV gene products. Such methods may be characterized by the following aspects: a) introducing into a suitable computer program, information defining a ligand binding domain of an HCV gene product in a conformation (e.g. as defined by X-ray structure coordinates obtained from suitable X-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for modulation of HCV replication, and determining whether said candidate agent modulates HCV replication in the assay. Such methods may also include administering the candidate agent, determined to modulate HCV replication, to a mammal suffering from a condition treatable by HCV modulation, such as those described above.

Also, one skilled in the art would appreciate that compounds of the invention can be used in a method of evaluating the ability of a test agent to associate with a molecule or molecular complex comprising a ligand binding domain of an HCV gene product. Such a method may be characterized by the following aspects: a) creating a computer model of a ligand binding pocket using structure coordinates obtained from suitable x-ray quality crystals of the HCV gene product, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, inhaled nasally, parenterally (intravenous, intramuscular, intraperitoneal or subcutaneous), topically, transdermally, intravaginally, intravesically, intracistemally, or rectally, in the form of solid, semi-solid, lyophilized powder, or liquid dosage forms, such as for example, tablets, suppositories, pills, soft elastic or hard gelatin capsules, caplets, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with other antiviral or other agents that are generally administered to a patient being treated for HCV infection or HCV/HIV co-infection. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alginates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 0.1% to about 99% by weight of a compound(s) of the invention, or a pharmaceutically acceptable salt thereof, and 99.9% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, $10^{th}$ Ed., (Mack Publishing Company, Easton, Pa., 2001). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts or solvates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.01 to about 7,000 mg per day. For a normal human adult having a body weight of about 70 kilograms, a dosage in the range of about 0.0001 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

The Compounds

In one aspect, embodiment [0096], the invention comprises a compound of structural Formula I,

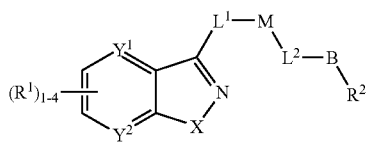

I or a pharmaceutically acceptable salt, N-oxide, S-oxide, hydrate, solvate or prodrug thereof, wherein, $Y^1$ and $Y^2$ are independently nitrogen or carbon;

each $R^1$ is independently selected from —H, halogen, mono- to trihalomethyl, —CN, —NO$_2$, —OR$^3$, —N(R$^3$)R$^3$, —S(O)$_{0-2}$R$^3$, —N(R$^3$)C(=O)N(R$^3$)R$^3$, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$)SO$_2$R$^3$, —N(R$^3$)C(O)R$^3$, —NC(=O)CH(R$^3$)N(R$^3$)R$^3$, —NCO$_2$R$^3$, —C(=O)R$^3$, optionally substituted alkoxy, optionally substituted C$_{1-6}$ alkyl, optionally substituted aryl C$_{0-6}$ alkyl and optionally substituted heterocyclyl C$_{0-6}$ alkyl;

X is —S(O)$_{0-2}$—;

B is selected from absent, optionally substituted C$_{1-6}$ alkyl, —C(=O)—, —C(=O)C(=O)—, —S(O)$_{0-2}$—, —C(=O)N(R$^4$)—, —C(=NR$^5$)N(R$^4$)—, —C(=S)N(R$^4$)—, —C(=S)O—, —C(=O)O— and

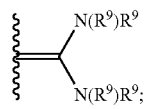

$R^2$ is selected from —H, an optionally substituted C$_{1-20}$ alkyl, an optionally substituted C$_{1-6}$ alkyl-N(R)—C(=O)aryl, an optionally substituted three- to seven-membered heteroalicyclic C$_{0-6}$ alkyl, an optionally substituted six- to fourteen-membered aryl C$_{0-3}$ alkyl, an optionally substituted aryl-heteroaryl, an optionally substituted heteroaryl-aryl, an optionally substituted heteroaryl-heteroaryl, an optionally substituted heterocyclyl-heteroaryl, an optionally substituted aryl-aryl, an optionally substituted aryl-heterocyclyl, an optionally substituted aryloxy C$_{0-3}$ alkylheterocyclyl, an optionally substituted aryloxy C$_{0-3}$ alkylheteroaryl, an optionally substituted aryloxy C$_{0-3}$ alkylaryl, an optionally substituted heteroaryl-N(R)—C$_{0-3}$ alkyl-heteroaryl, an optionally substituted five- to fifteen-membered heteroaryl C$_{0-3}$ alkyl, phenylethyl, benzyl, 2,3-dihydrobenzofuranyl, benzimidazoyl, benzo[d][1,3]dioxolyl, benzoxalyl, indolylmethyl, phenyl, optionally substituted biphenyl, pyridyl, indolyl, dihydroindolyl, furanyl, benzofuiranyl, 2,3-dihydrobenzo[b][1,4]dioxinyl, chromenyl, pyrrolidinyl, pyranyl, imidazoyl, dihydropyranyl, dihydropyran4-one-yl, phthalazinyl, imidazopyridinyl, piperazinyl, pyrazolinyl, napthyridinyl, piperadinyl, azepinyl, isoquinolinyl, quinolinyl, dihydroquinolinyl, tetrahydroquinolinyl, isoquinolinyl, dihydroisoquinolinyl, tetrahydroisoquinolinyl, pyrrolyl, thiophenyl, benzothiophenyl, benzthiazolyl, benzisothiazolyl, triazolyl, benzotriazolyl, isoindolyl, benzotetrazolyl, pyrazinyl, pyrimidinyl, isothiazolyl, thiazolyl, thiadiazolyl, purinyl, isoxazolyl, oxazolyl, oxadiazolyl, dihydropyranoyl, tetrahydropyranyl, tetrahydropyranoyl and indazolyl;

each $R^3$ is independently selected from —H, optionally substituted C$_{1-6}$ alkyl, optionally substituted —C(=O)C$_{1-6}$ alkyl, optionally substituted aryl C$_{0-6}$ alkyl, optionally substituted heteroaryl C$_{0-6}$alkyl and optionally substituted heterocyclyl C$_{0-6}$alkyl; optionally two of R$^3$, together with the nitrogen to which they are attached, combine to form an optionally substituted heterocyclyl containing one to three heteroatoms;

$L^1$ and $L^2$ are each independently selected from —N(R$^4$)—, —O— and —S(O)$_{0-2}$—; or the moeity formed by $L^1$-M-$L^2$ and B is

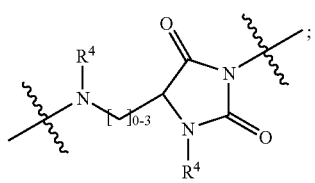

each $R^4$ is independently selected from —H and optionally substituted C$_{1-6}$ alkyl, —S(O)$_{0-2}$R$^3$, —C(=O)N(R$^3$)(R$^3$), optionally substituted —C(=O)C$_{1-6}$ alkyl, optionally substituted aryl C$_{1-6}$ alkyl, provided that B is not

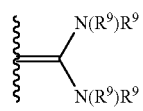

when $R^4$ of $L^2$ is part of the double bond structure of B, and $R^2$ is absent;

each $R^5$ is independently selected from —H, —CN, —NO$_2$, —OR$^3$, —S(O)$_{0-2}$R$^3$, —CO$_2$R$^2$, optionally substituted C$_{1-6}$ alkyl, optionally substituted C$_{2-6}$ alkenyl, and optionally substituted C$_{2-6}$ alkynyl;

M is an optionally substituted C$_{2-4}$ alkylene, C$_{2-4}$ alkenylene, or C$_{2-4}$ alkynylene; and each $R^9$ is independently selected from —H, optionally substituted C$_{1-6}$ alkyl, optionally substituted aryl C$_{0-6}$ alkyl and optionally substituted heterocyclyl $C_{0-6}$alkyl; and optionally two of $R^9$, together with the nitrogen to which they are attached, combine to form an optionally substituted heterocyclyl containing one to three heteroatoms;
provided the compound is not selected from Table 1.
TABLE 1
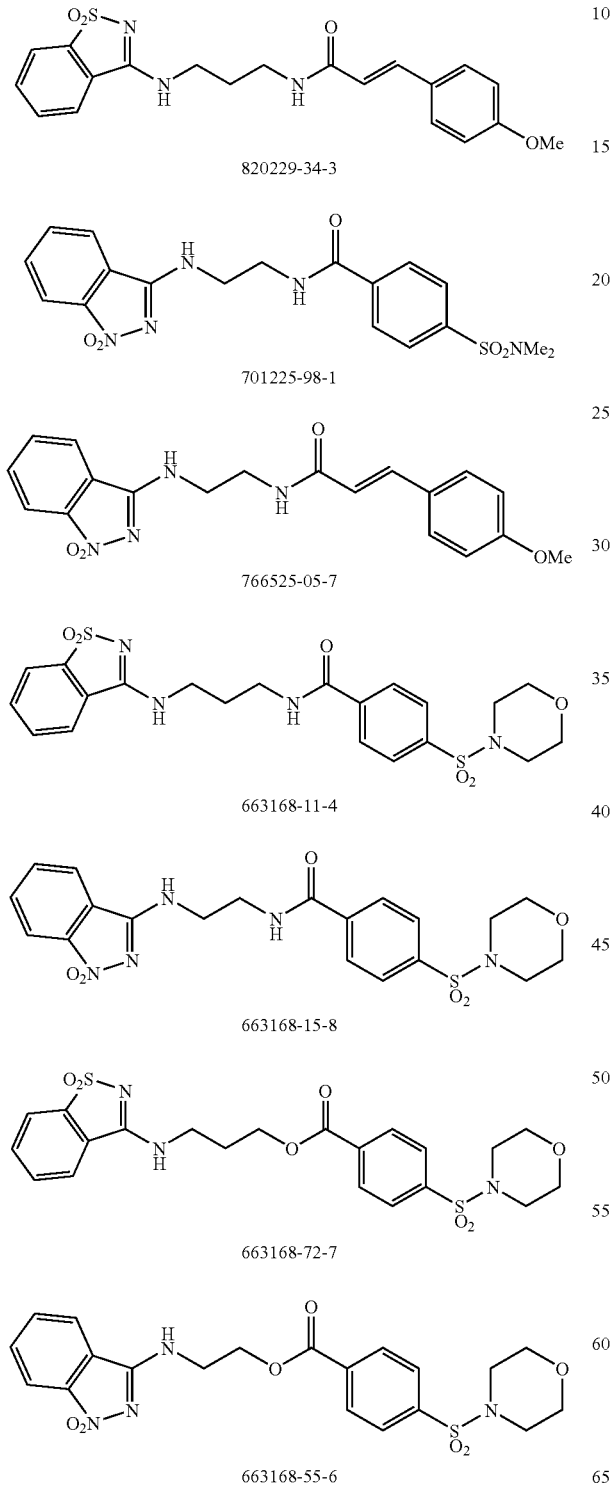
TABLE 1-continued
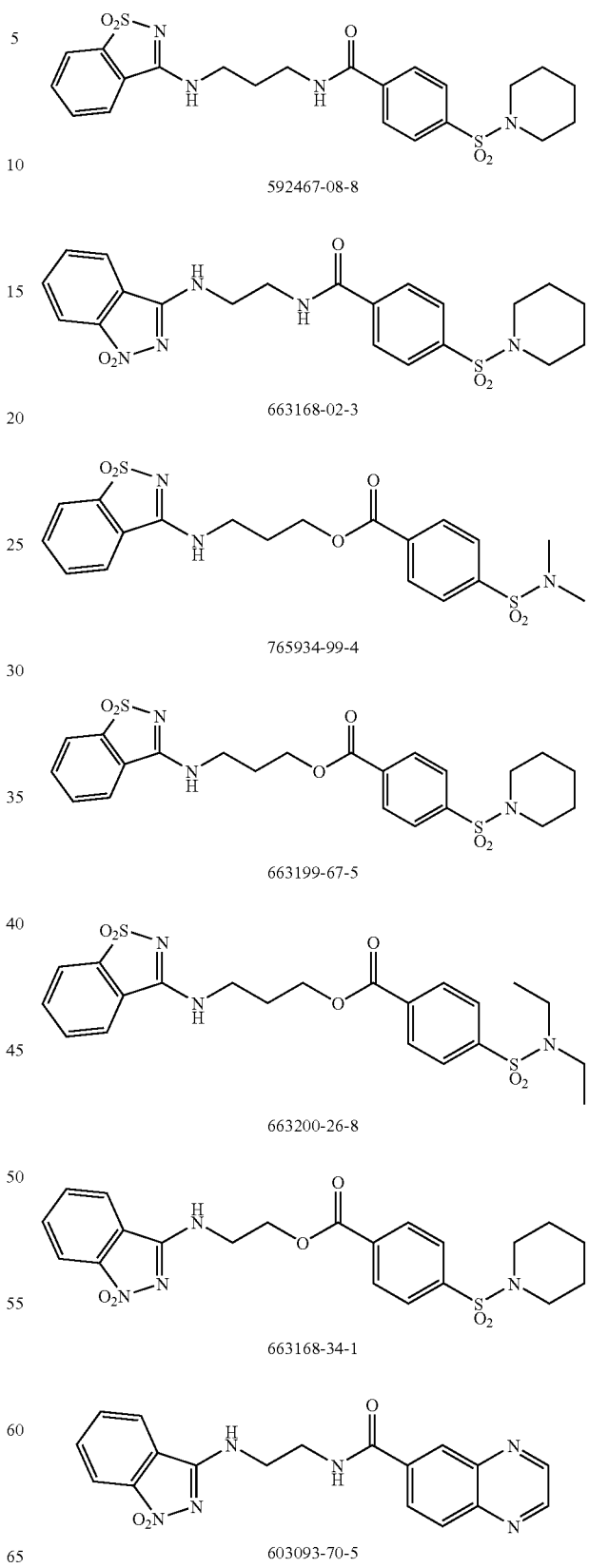

TABLE 1-continued
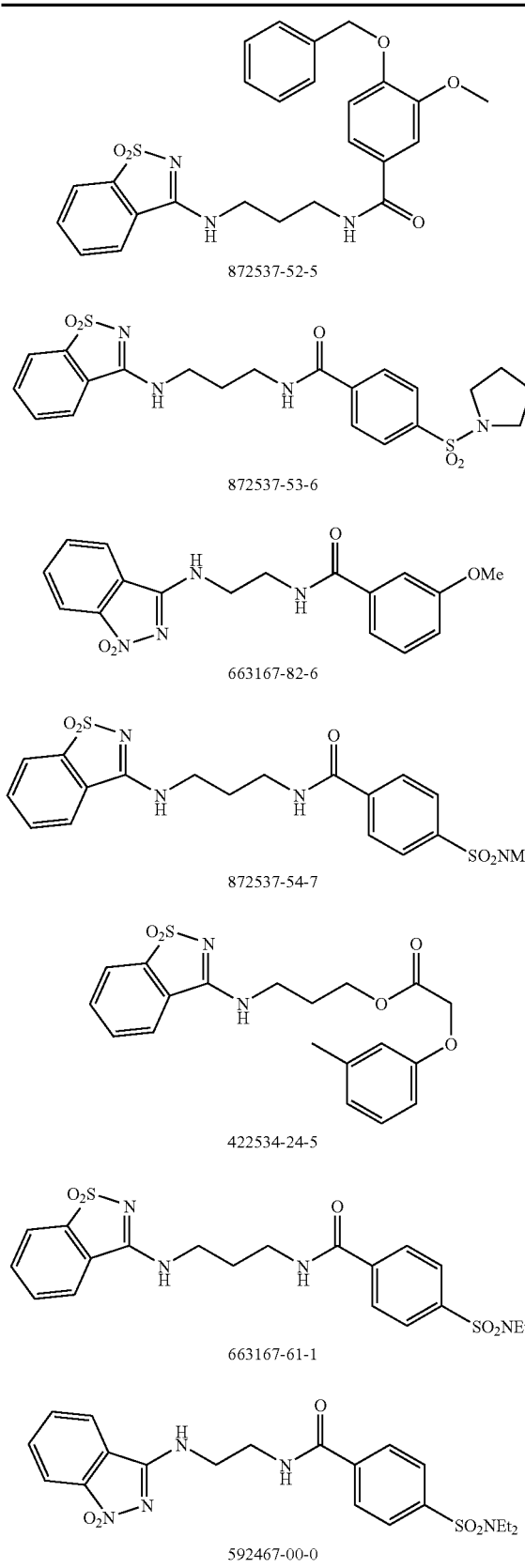
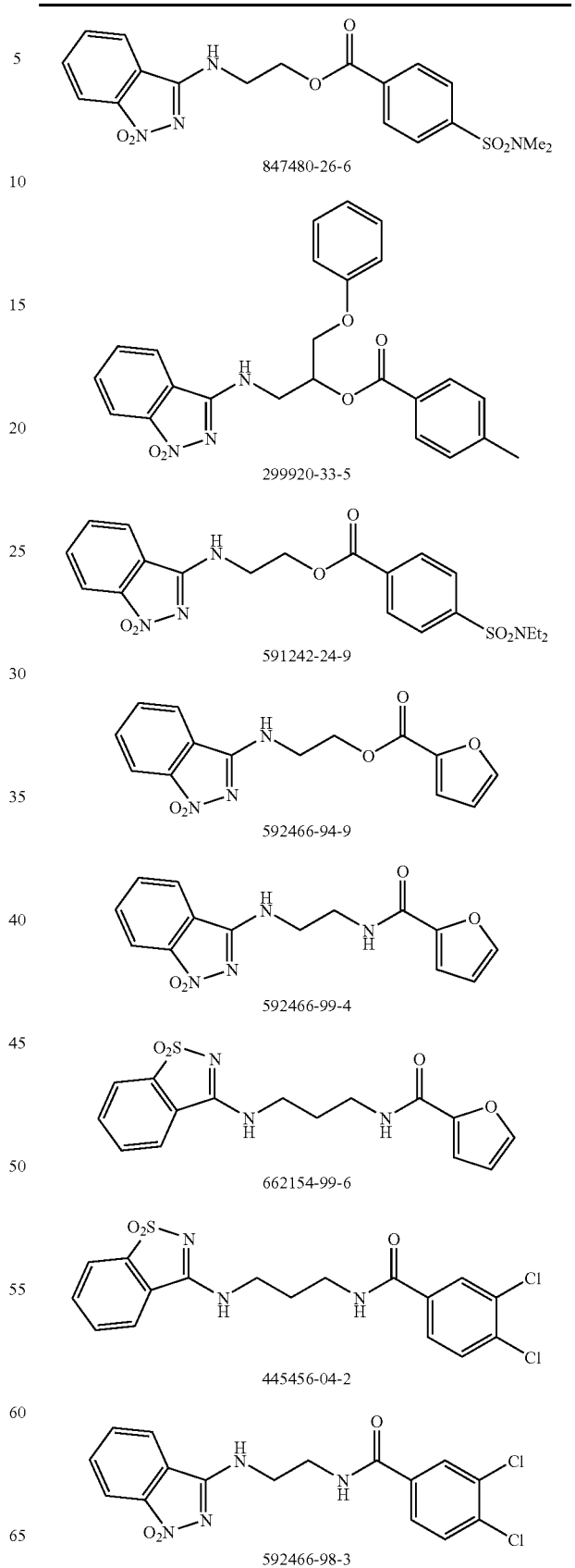

TABLE 1-continued 591242-73-8

591242-63-6

510760-33-5

591242-72-7

445456-07-5

510718-16-8

510760-25-5

TABLE 1-continued 510760-44-8

422534-38-1

443319-34-4

422534-28-9

663168-10-3

443319-22-0

510760-27-7

443319-30-0

TABLE 1-continued
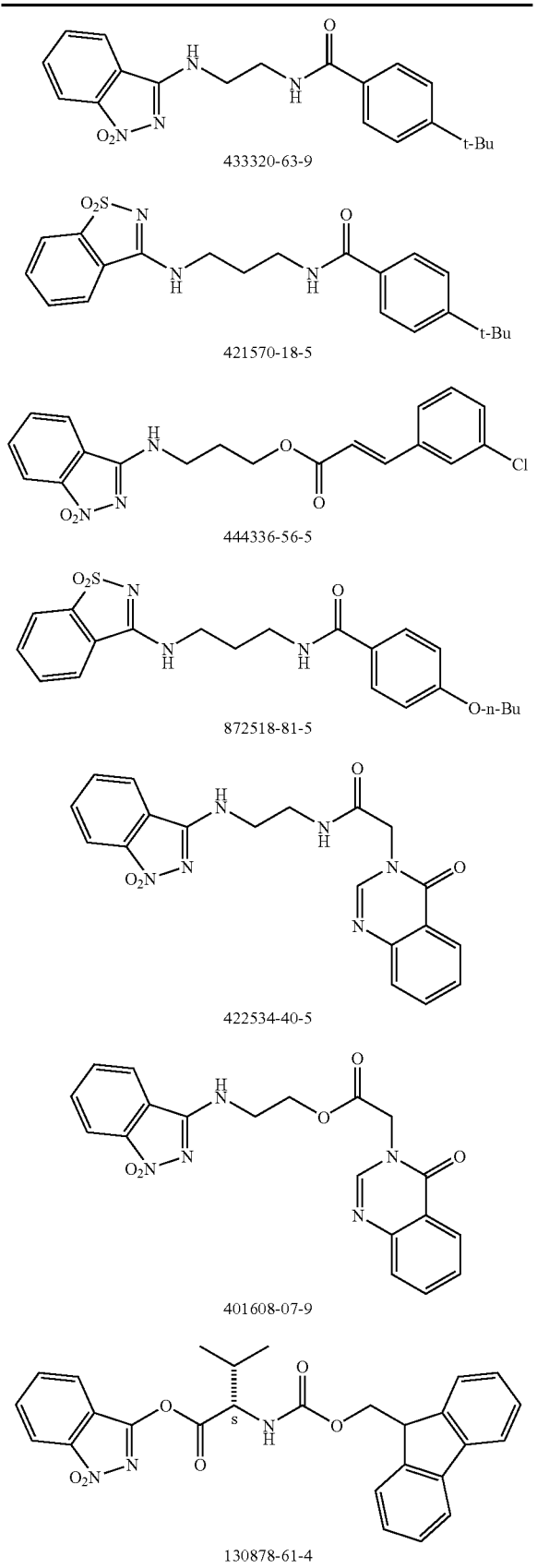
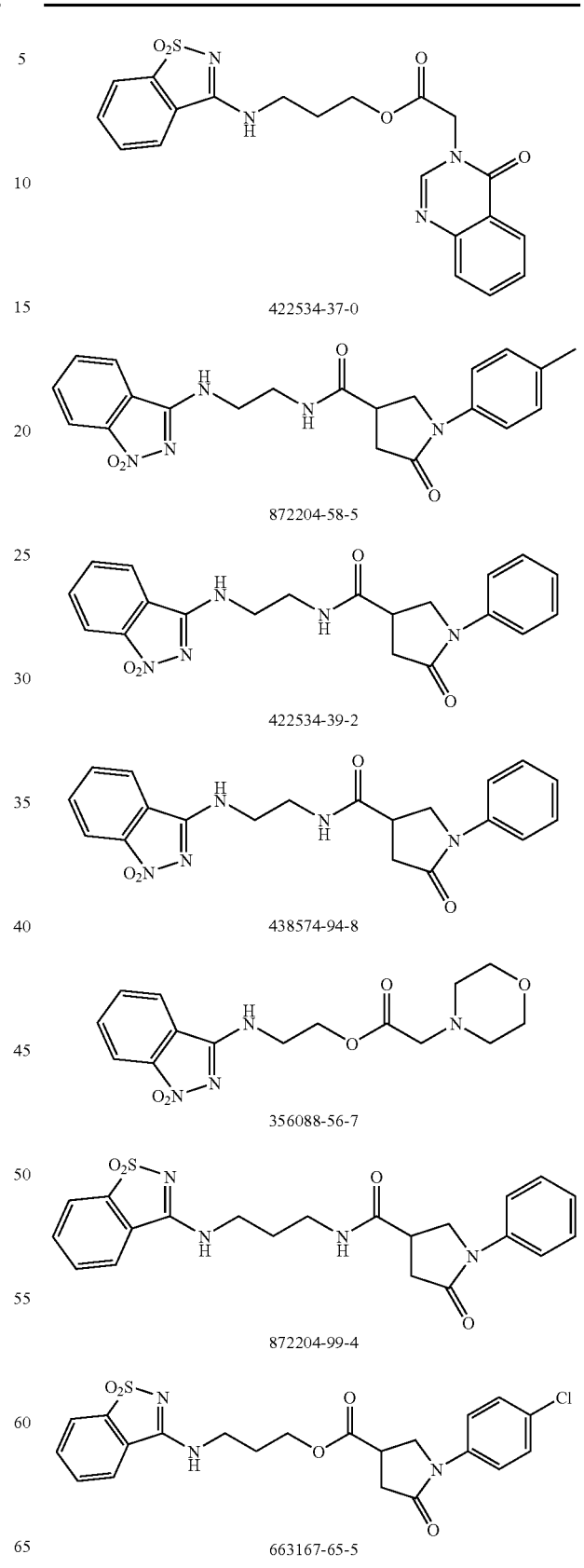

TABLE 1-continued
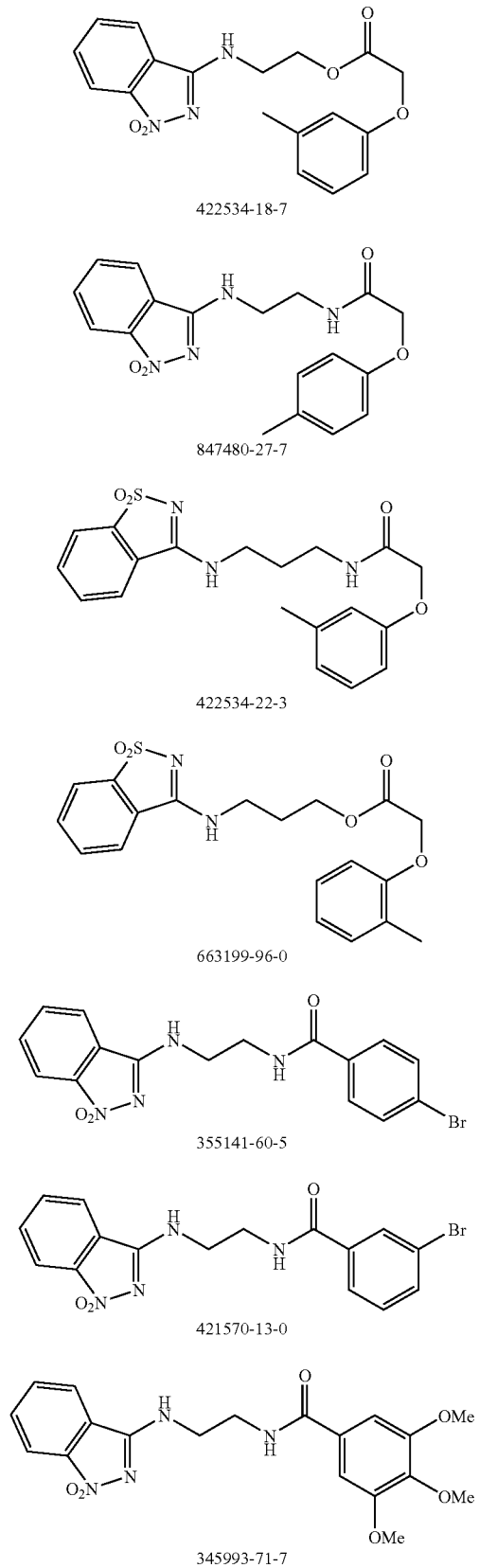
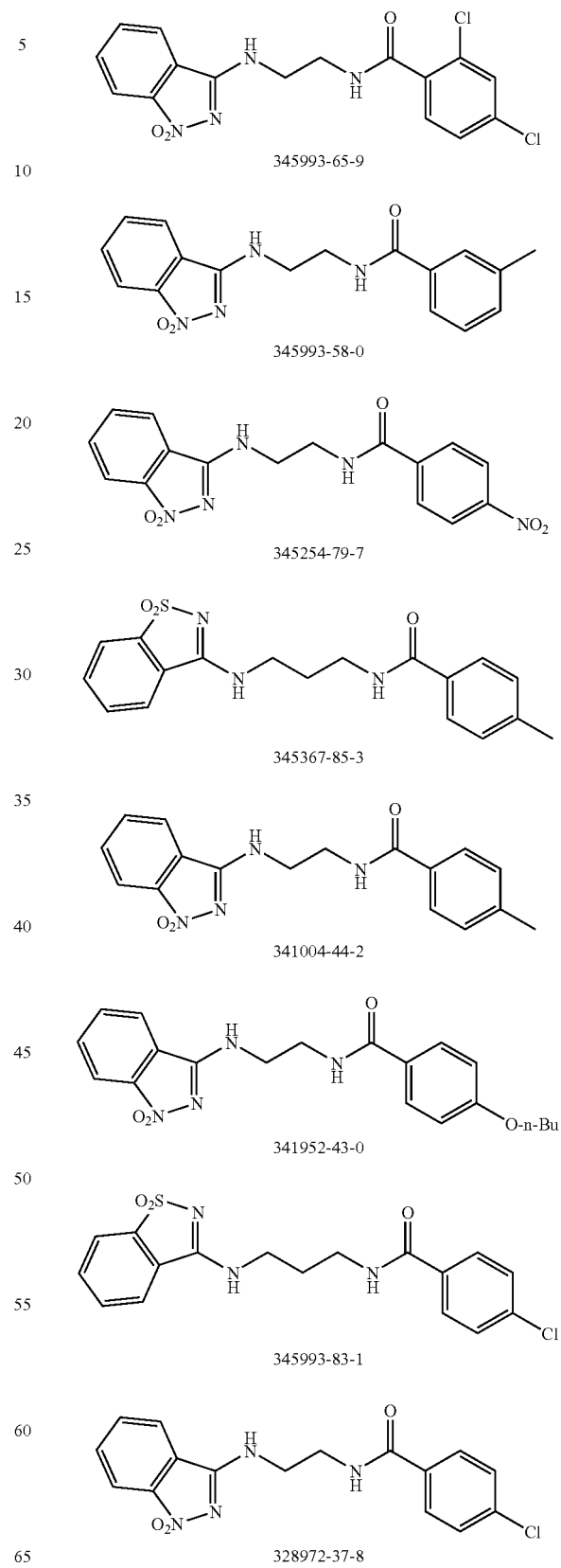

TABLE 1-continued

| CAS Number |
|---|
| 328090-32-0 |
| 314042-61-0 |
| 314042-59-6 |
| 336179-85-2 |
| 314042-56-3 |
| 329929-62-6 |
| 313481-13-9 |
| 345367-83-1 |
| 328282-74-2 |
| 313481-08-2 |
| 300689-53-6 |
| 355141-68-3 |
| 355141-72-9 |
| 312536-62-2 |
| 345367-54-6 |
| 309970-98-7 |

TABLE 1-continued
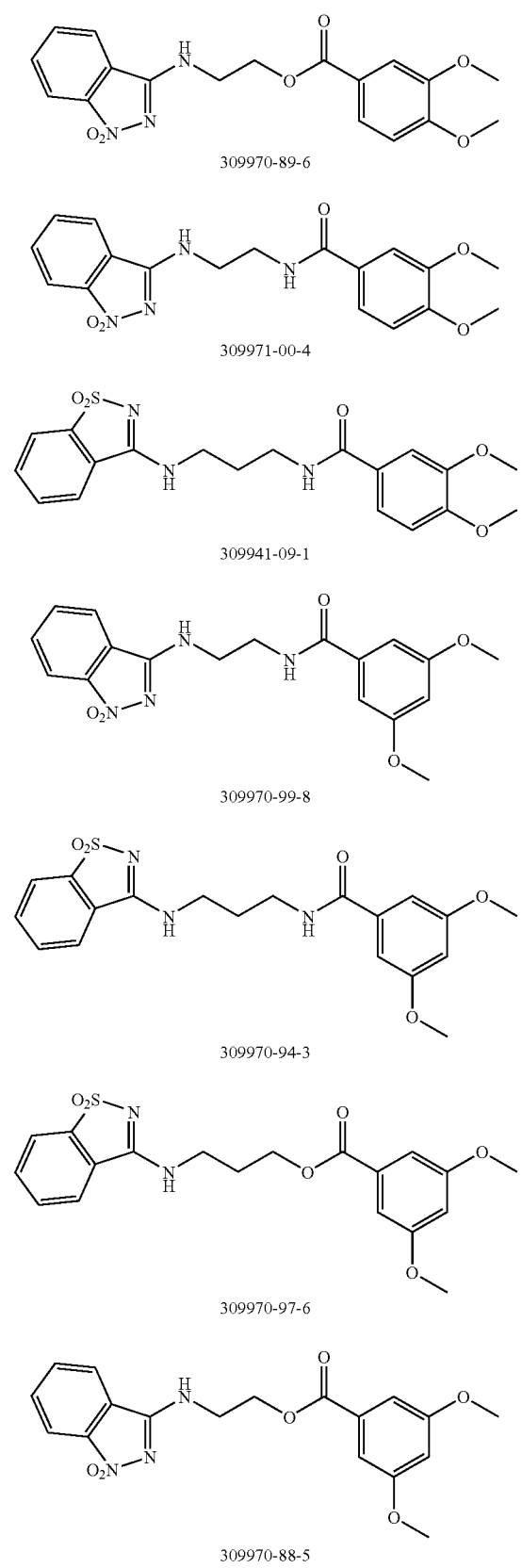
309970-89-6
309971-00-4
309941-09-1
309970-99-8
309970-94-3
309970-97-6
309970-88-5
TABLE 1-continued
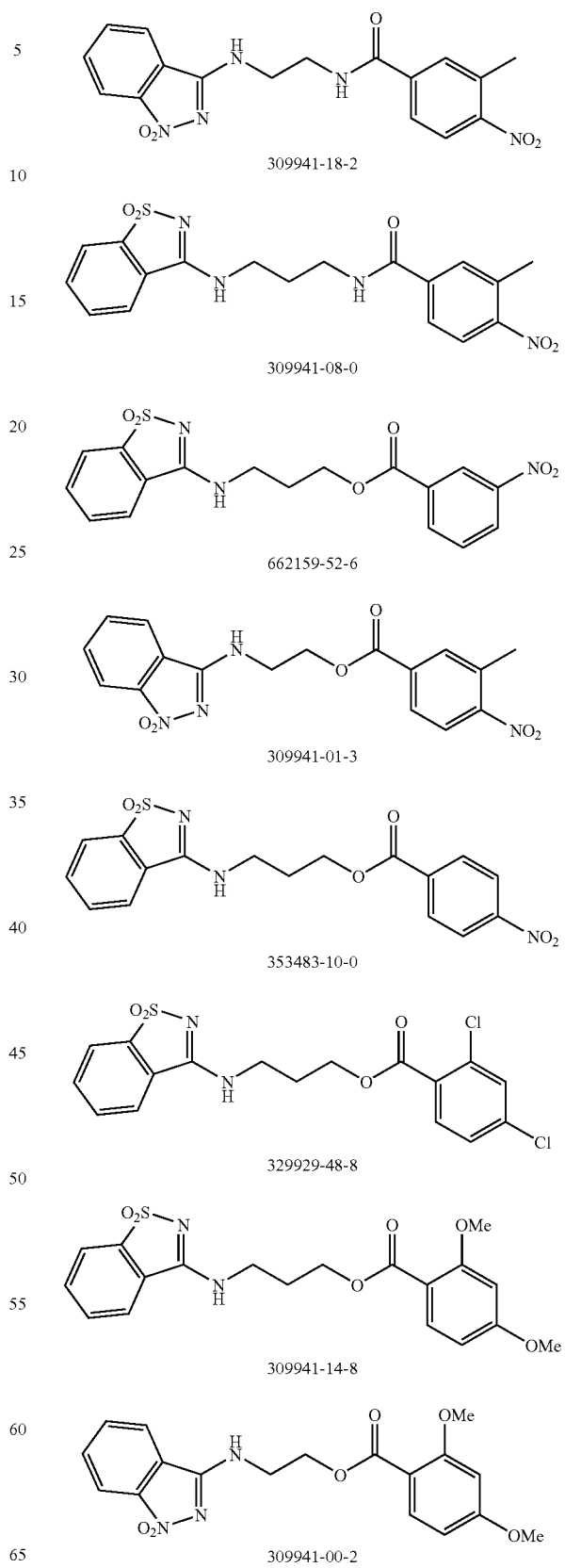
309941-18-2
309941-08-0
662159-52-6
309941-01-3
353483-10-0
329929-48-8
309941-14-8
309941-00-2

TABLE 1-continued
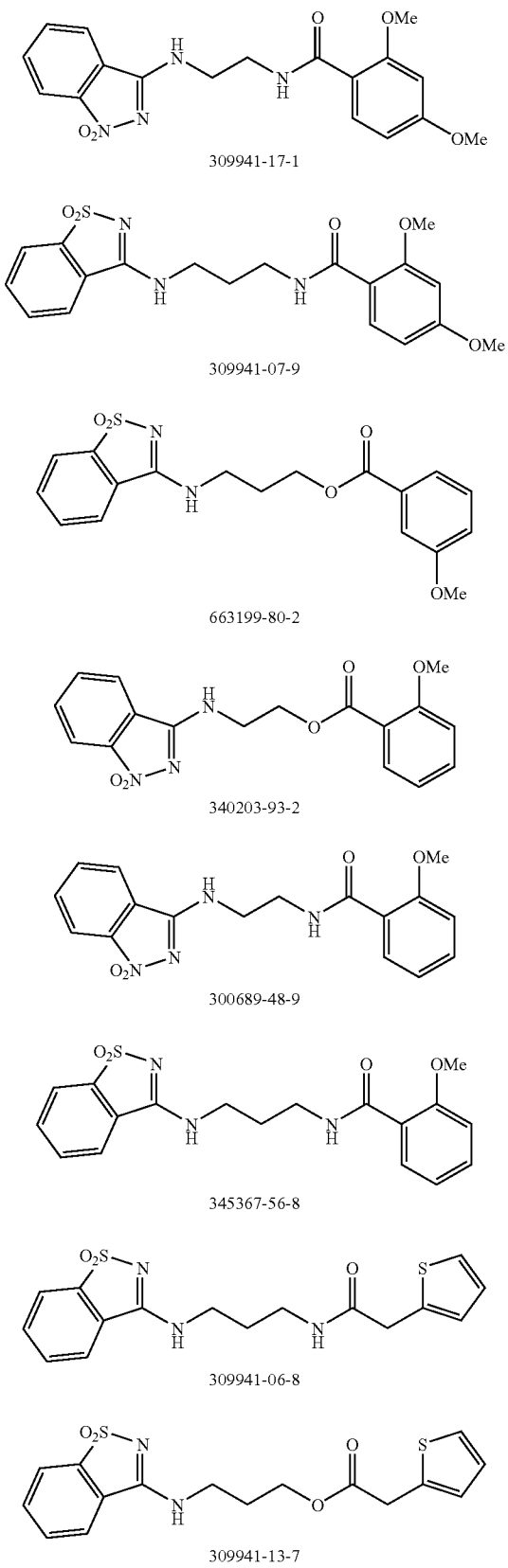
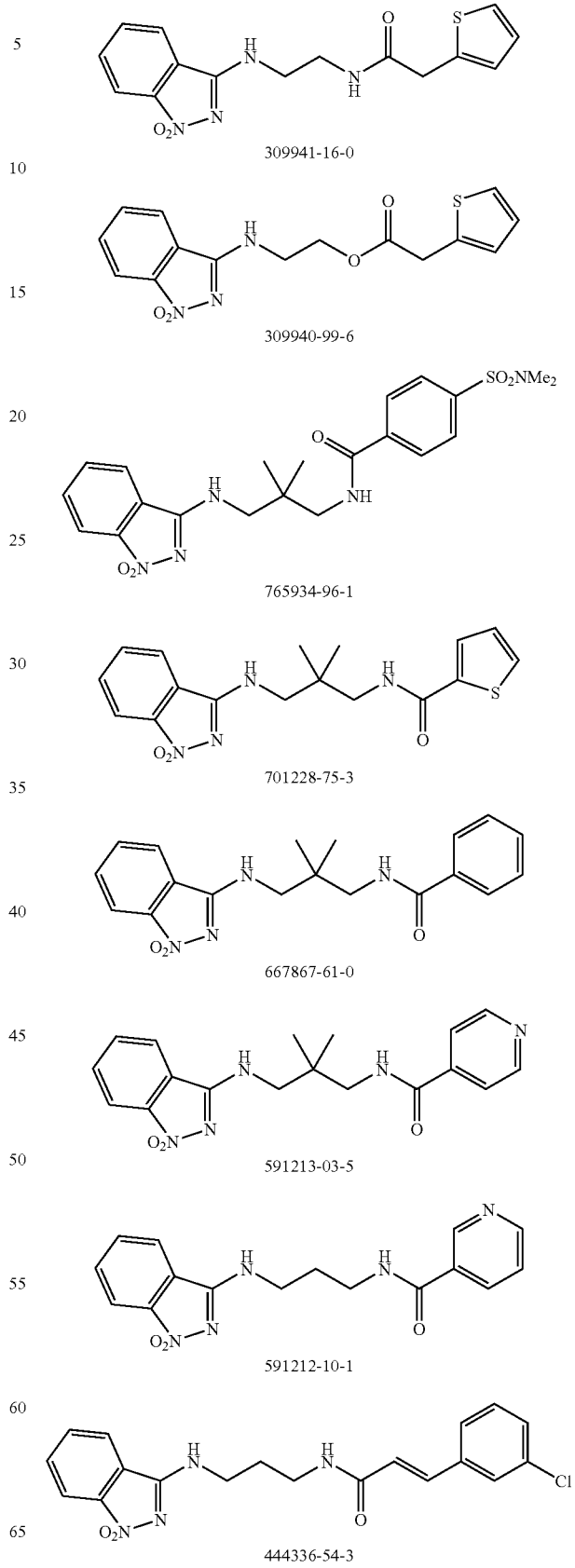

TABLE 1-continued 346644-45-9

345367-67-1

336179-86-3

335210-81-6

312517-97-8

312516-92-0

872204-88-1

872204-72-3

765934-97-2

765934-98-3

312516-90-8

510760-32-4

872519-06-7

421570-17-4

591212-97-4

353483-09-7

TABLE 1-continued
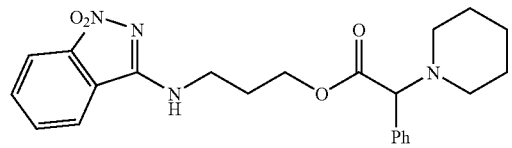
421566-61-2
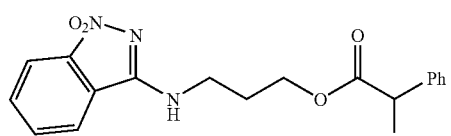
356088-58-9
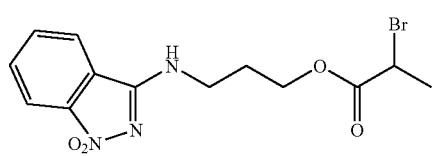
591213-01-3
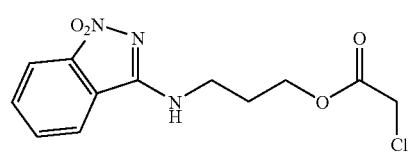
591212-99-6
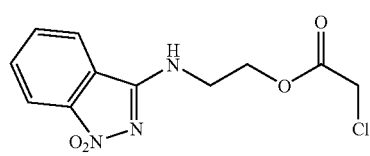
591212-93-0
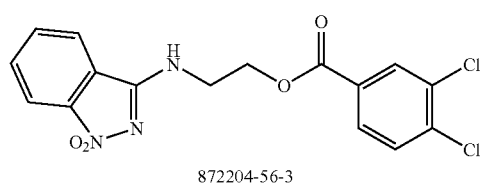
872204-56-3
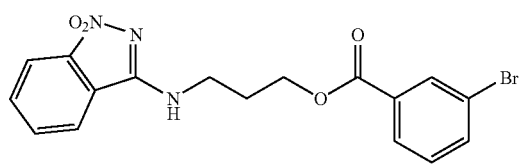
591212-31-6
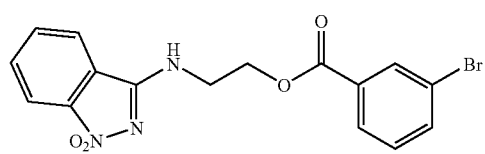
361199-37-3
TABLE 1-continued
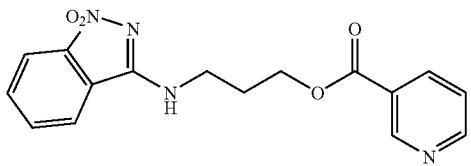
591212-11-2
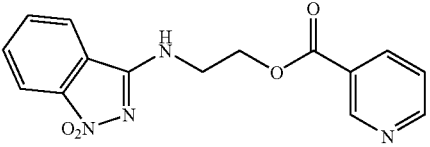
510760-31-3
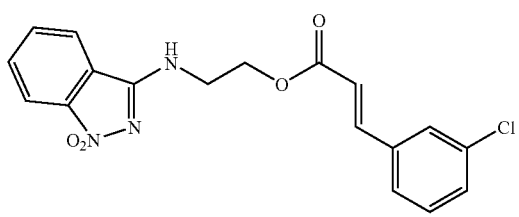
444336-50-9
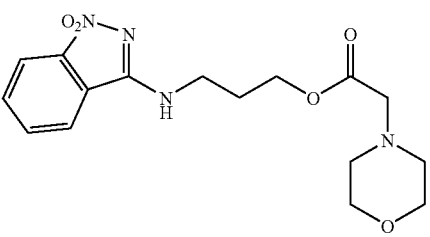
438622-87-8
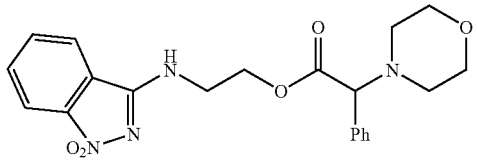
872519-70-5
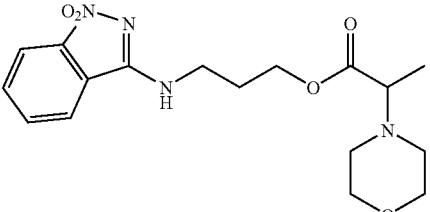
872547-77-8
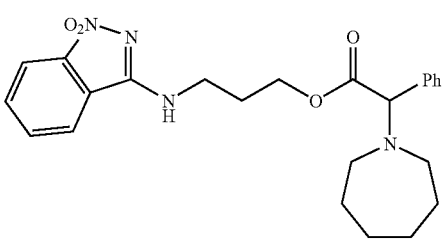
430444-04-5

TABLE 1-continued
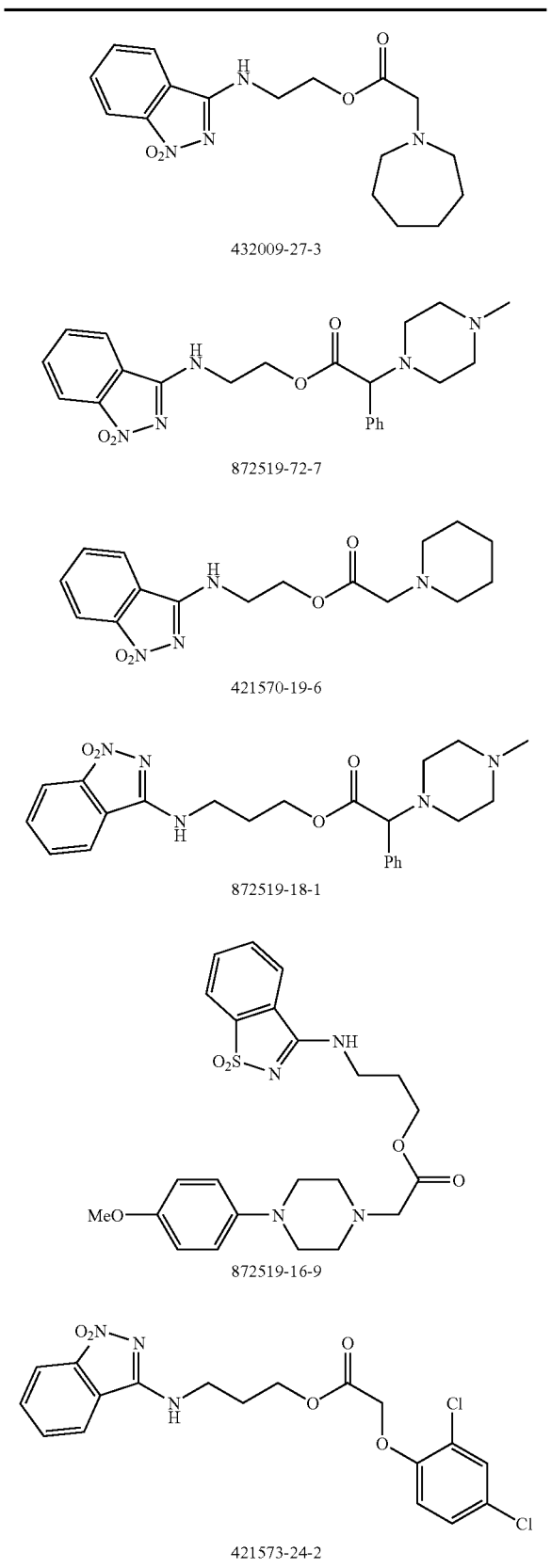
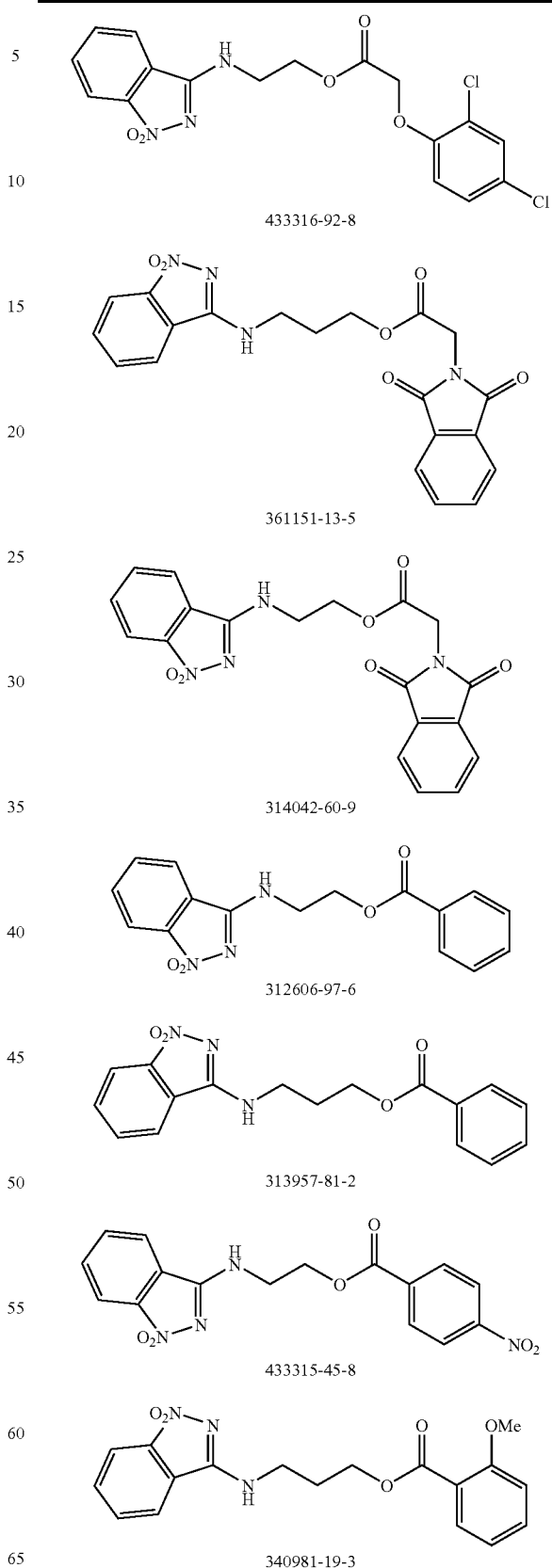

TABLE 1-continued
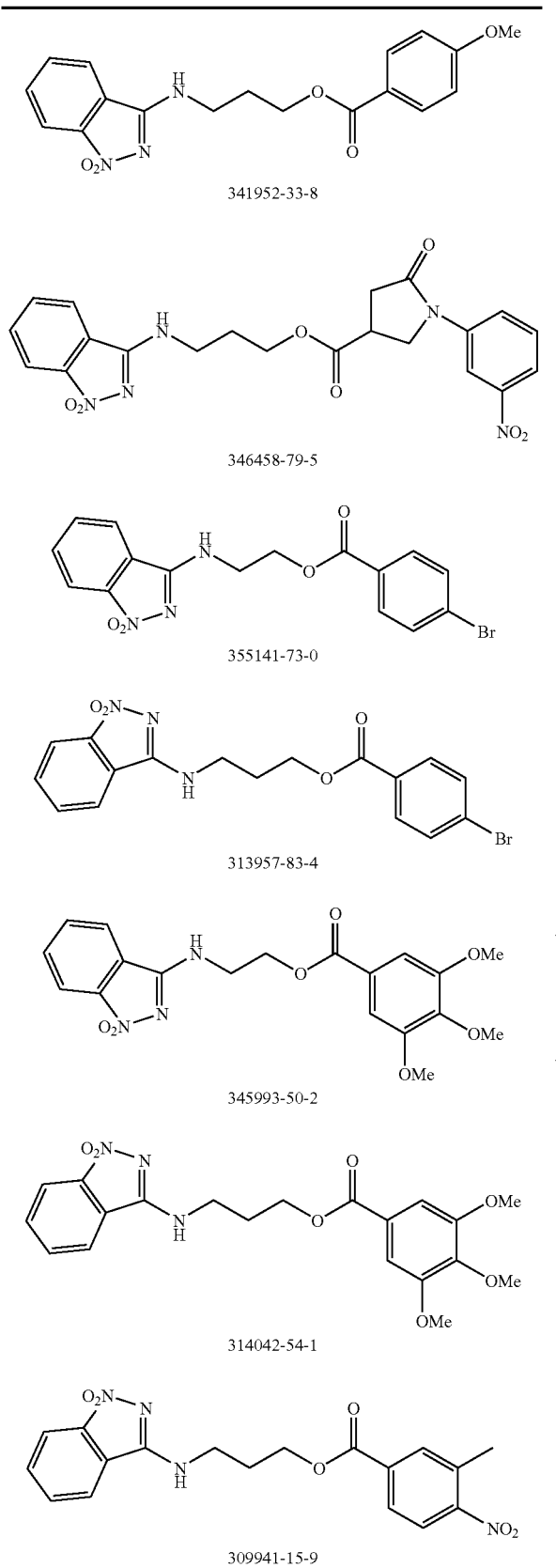
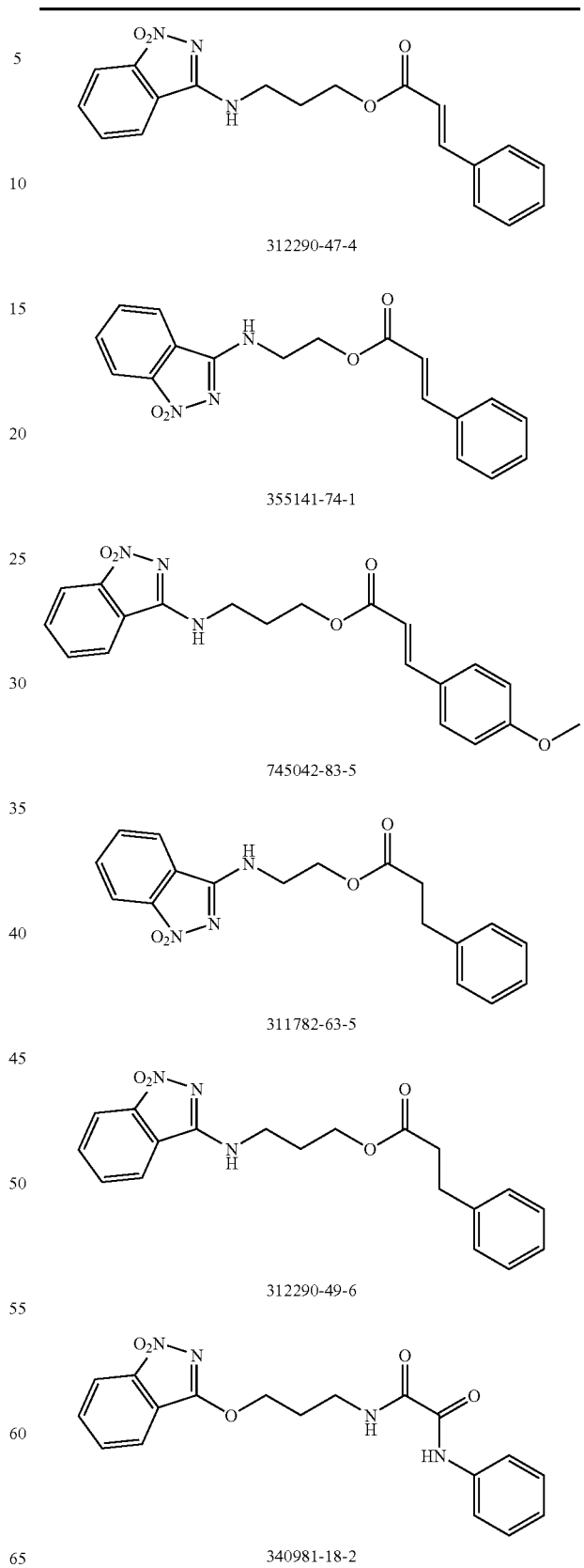

TABLE 1-continued
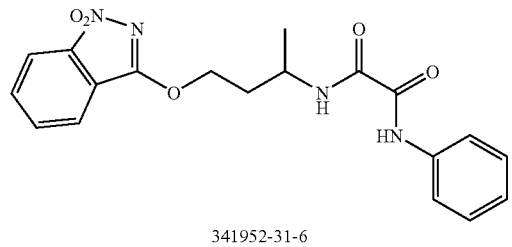
341952-31-6
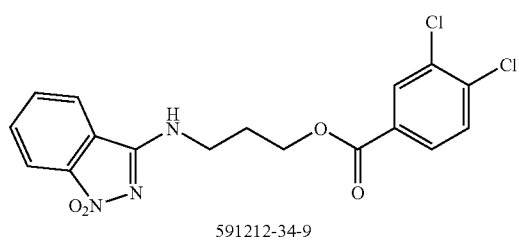
591212-34-9
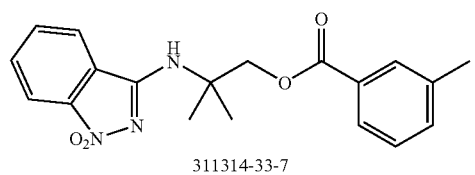
311314-33-7
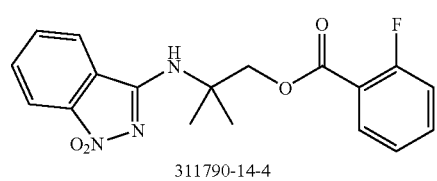
311790-14-4
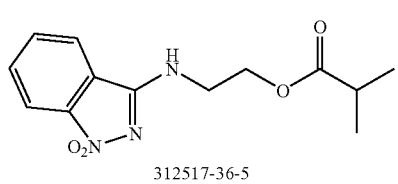
312517-36-5
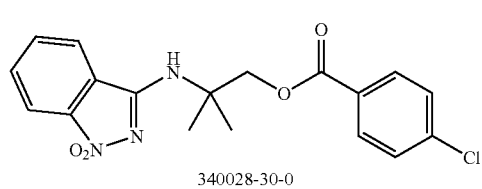
340028-30-0
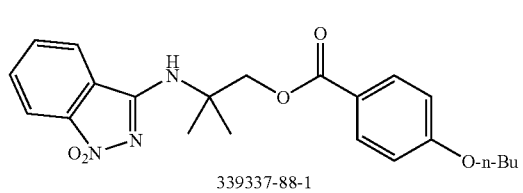
339337-88-1
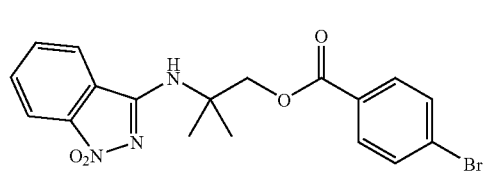
350246-97-8
TABLE 1-continued
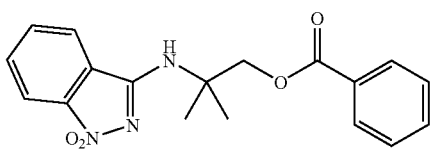
332026-10-5
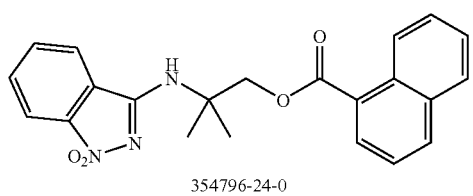
354796-24-0
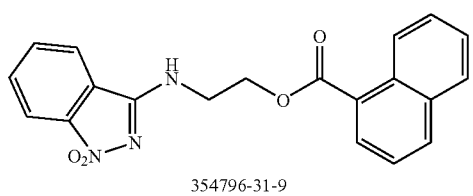
354796-31-9
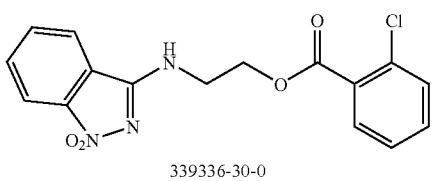
339336-30-0
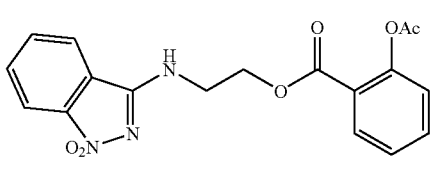
329929-73-9
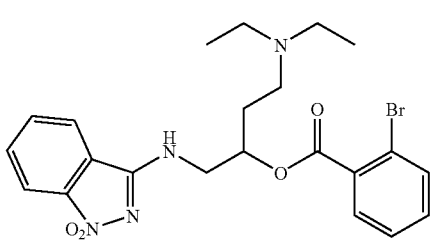
521971-48-2
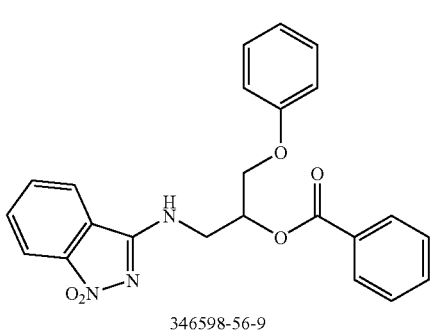
346598-56-9

TABLE 1-continued
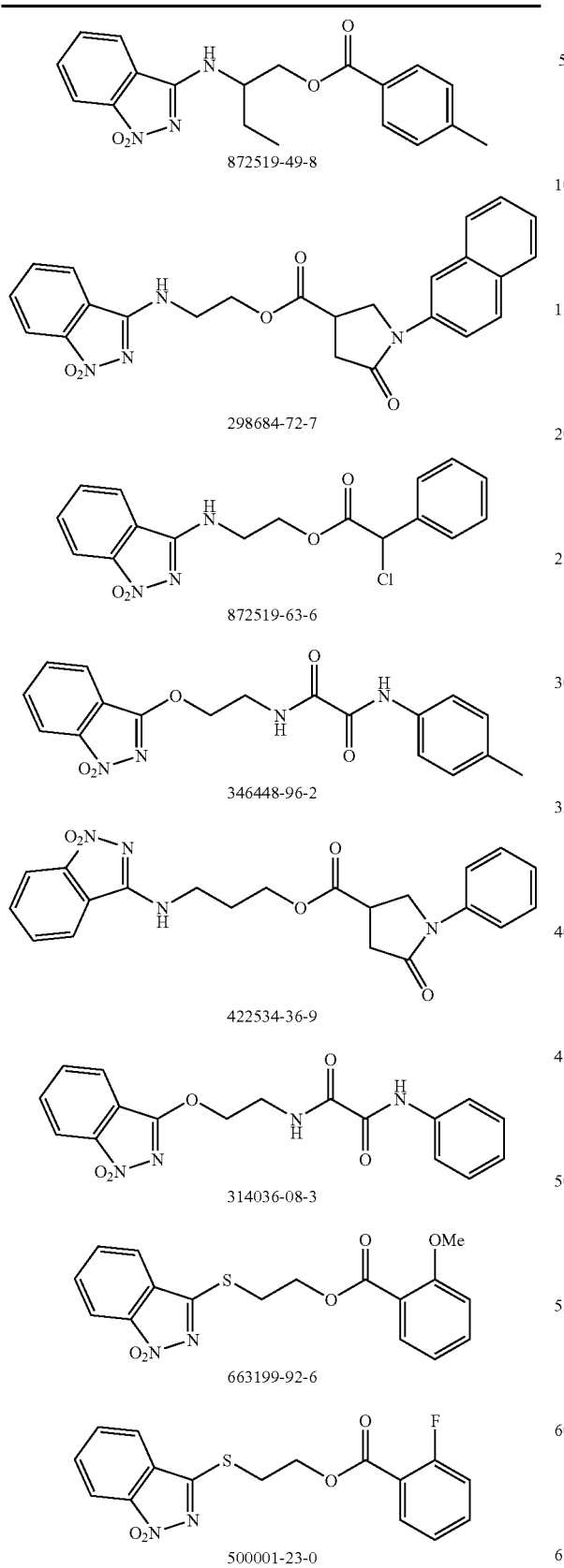
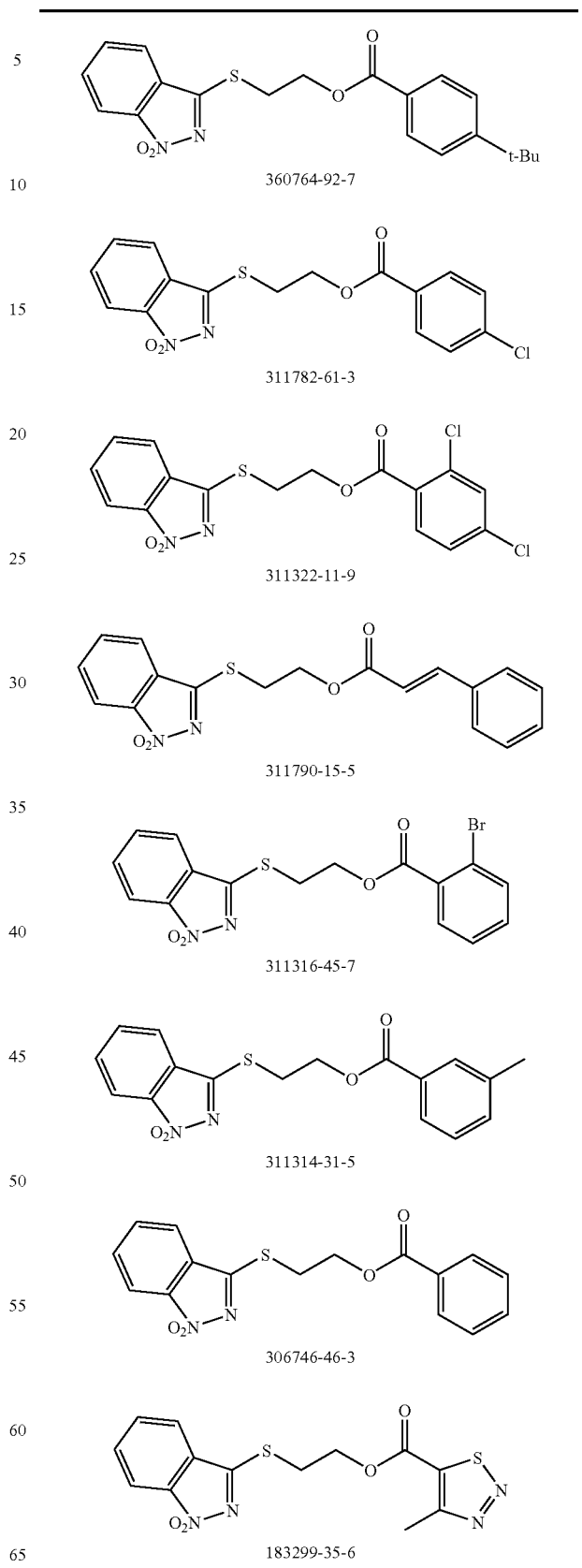

TABLE 1-continued
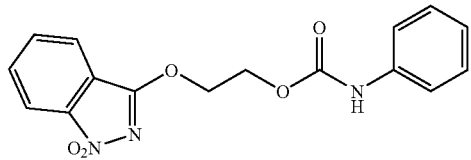
21309-69-3
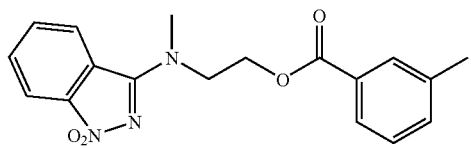
591212-85-0
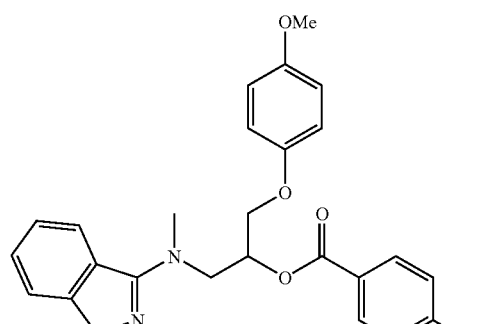
680208-03-1
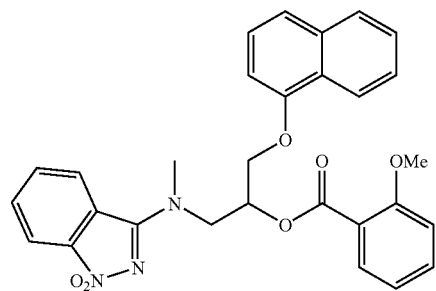
491614-74-5
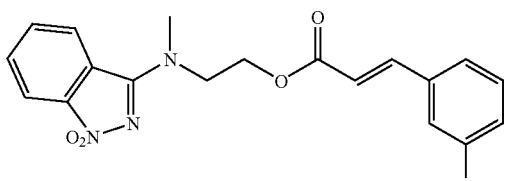
444336-57-6
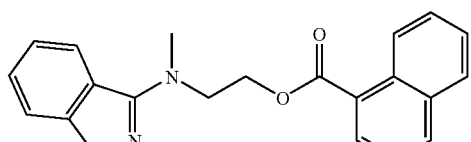
428836-05-9
TABLE 1-continued
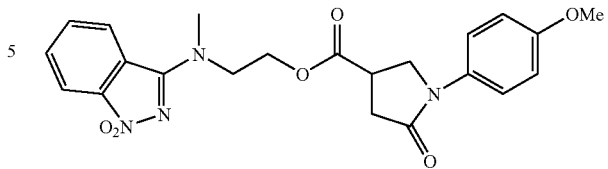
422534-41-6
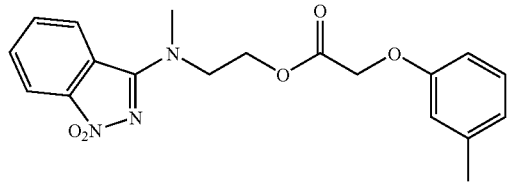
422534-27-8
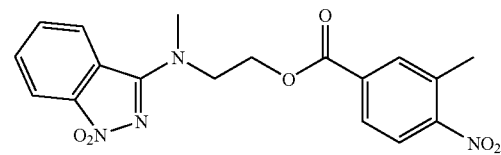
422534-26-7
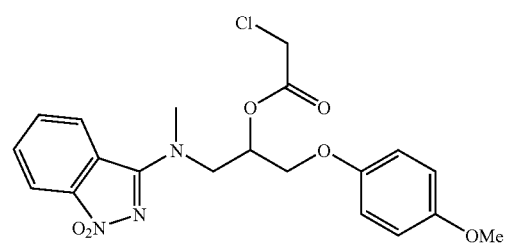
360770-16-7
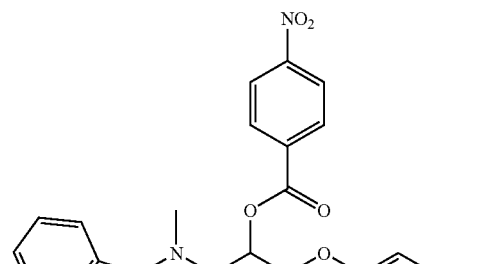
346449-02-3
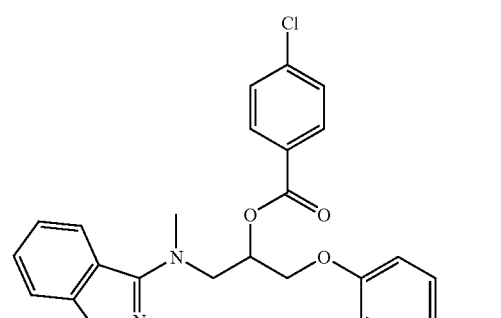
345993-99-9

TABLE 1-continued
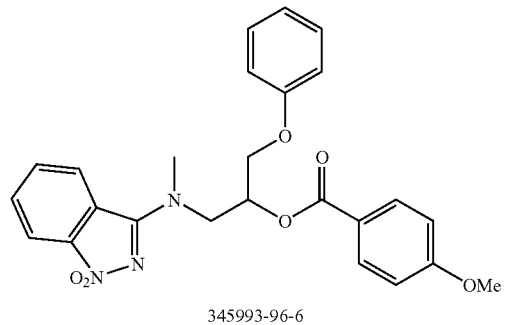
345993-96-6
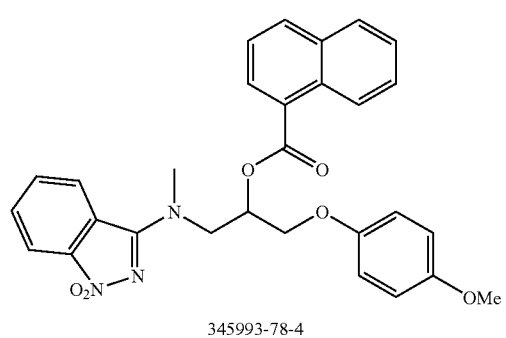
345993-78-4
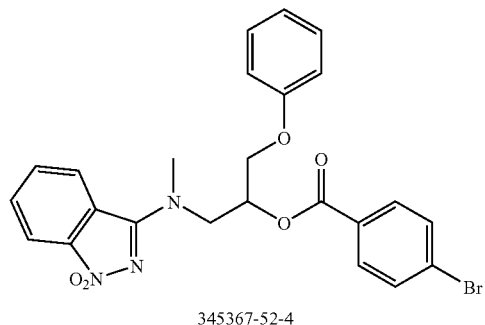
345367-52-4
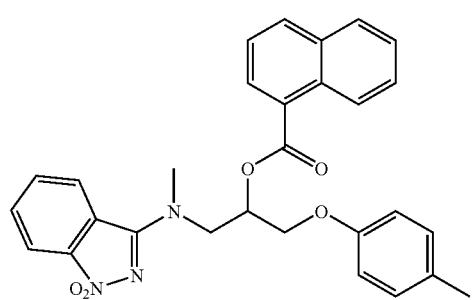
872135-91-6
TABLE 1-continued
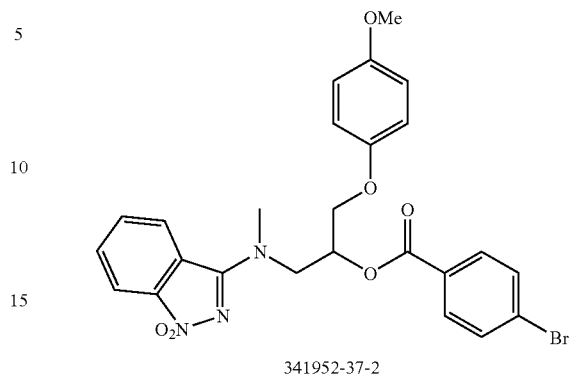
341952-37-2
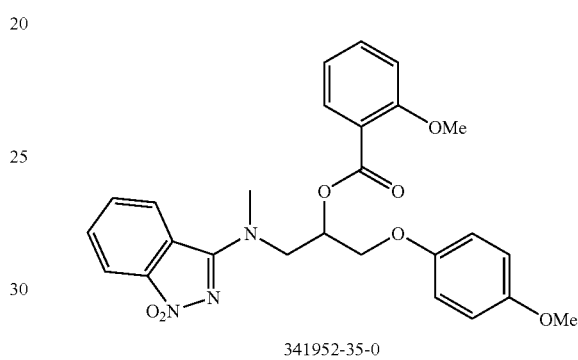
341952-35-0
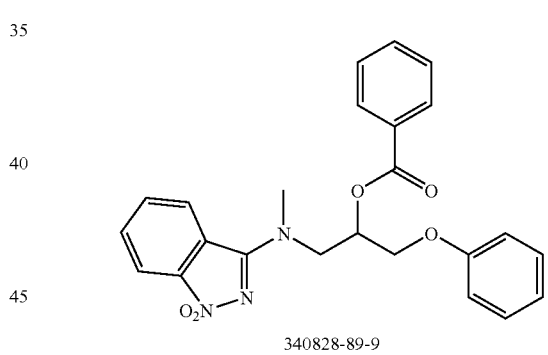
340828-89-9
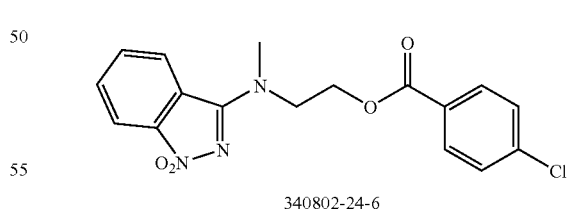
340802-24-6
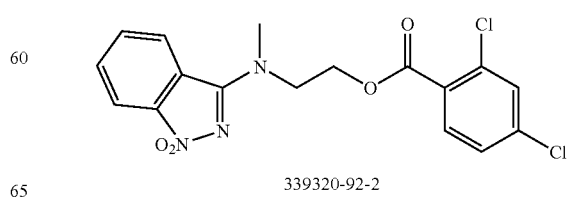
339320-92-2

TABLE 1-continued
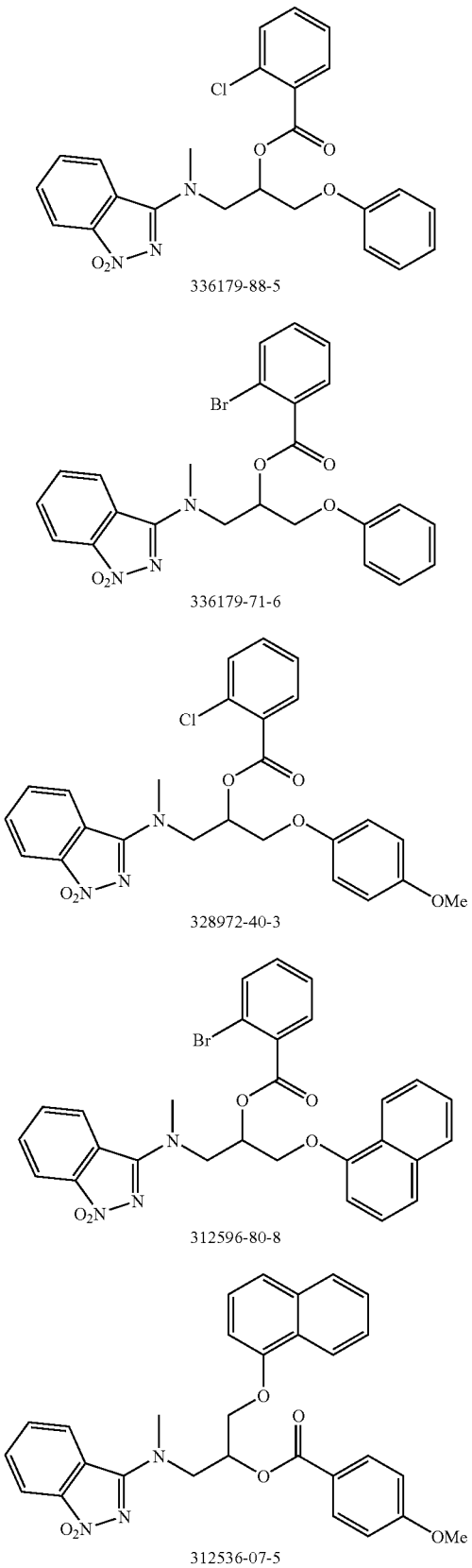
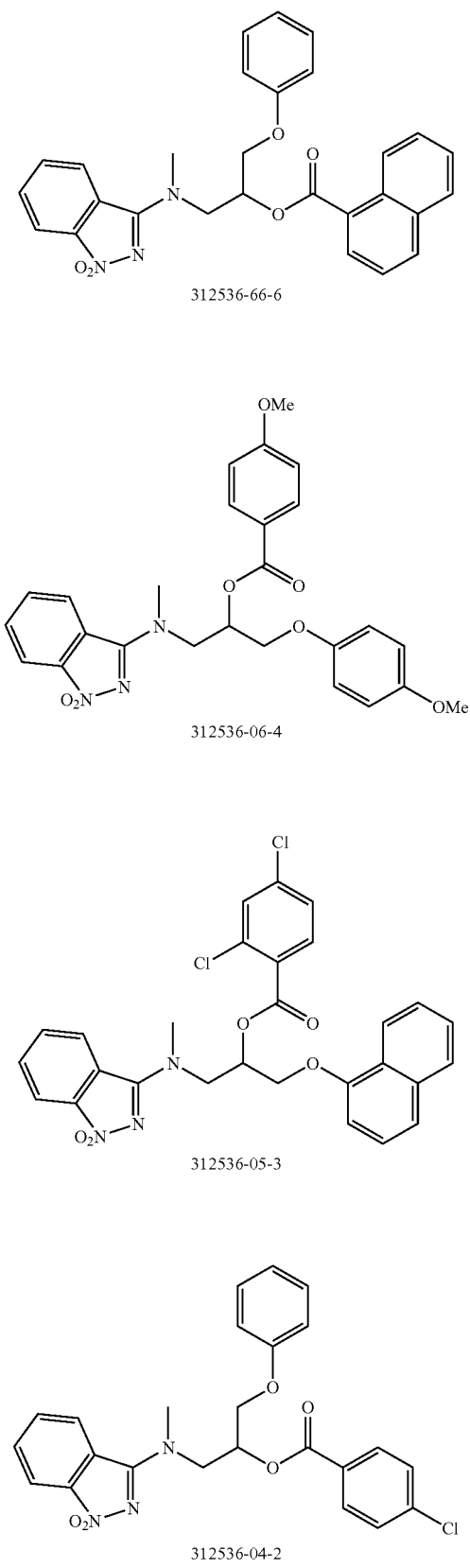

TABLE 1-continued
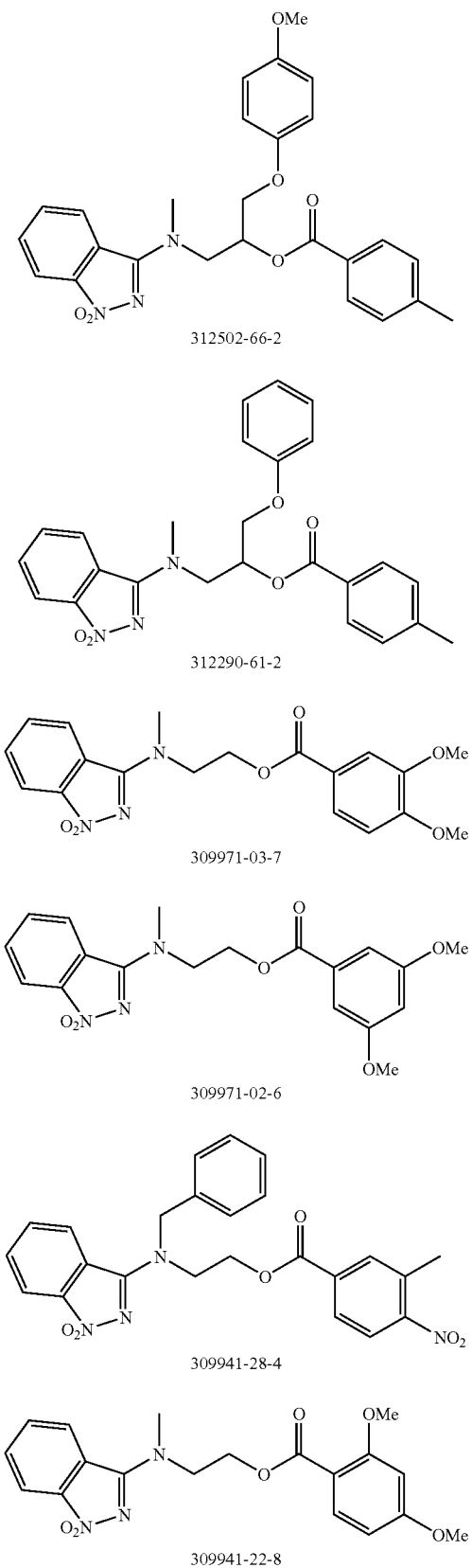
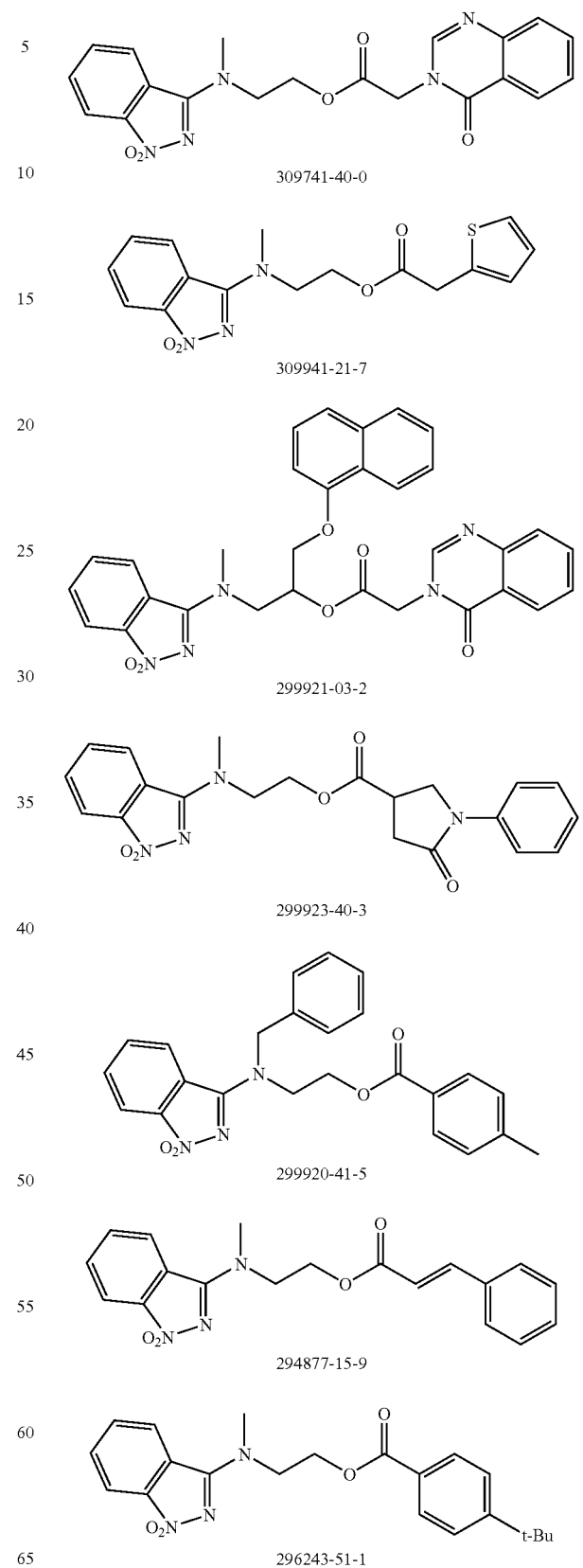

TABLE 1-continued 299920-40-4

294873-45-3

433259-66-6

341952-39-4

872537-51-4

872537-50-3

872519-33-0

TABLE 1-continued 422534-25-6

872547-78-9

872519-73-8

The numbers associated with each structure in Table 1 are their corresponding unique CAS (Chemical Abstracts Service) registry numbers.

In one example, embodiment [0097], the compound is according to embodiment [0096], wherein X is —S—.

In another example, embodiment [0098], the compound is according to embodiment [0097], wherein $L^1$ and $L^2$ are both —N($R^4$)—.

In another example, embodiment [0099], the compound is according to embodiment [0098], wherein M is an optionally substituted $C_{2-3}$ alkylene.

In another example, embodiment [0100], the compound is according to embodiment [0099], of formula II,

II wherein $R^2$ is selected from an optionally substituted $C_{1-6}$ alkyl, an optionally substituted three- to seven-membered heteroalicyclic $C_{0-3}$ alkyl, an optionally substituted six- to ten-membered aryl $C_{0-3}$ alkyl and an optionally substituted five- to fifteen-membered heteroaryl $C_{0-3}$ alkyl, phenylethyl, biphenyl, benzyl, 2,3-dihydrobenzofuranyl, benzimidazoyl, benzo[d][1,3]dioxolyl, benzoxalyl, indolylmethyl, phenyl, pyridyl, indolyl, dihydroindolyl, furanyl, benzofuranyl, 2,3-dihydrobenzo[b][1,4]dioxinyl, chromenyl, pyrrolidinyl, pyranyl, imidazoyl, dihydropyranyl, dihydropyran-4-one-yl, imidazopyridinyl, piperazinyl, pyrazolinyl, napthyridinyl, piperadinyl, azepinyl, isoquinolinyl, quinolinyl, dihydroquinolinyl, tetrahydroquinolinyl, isoquinolinyl, dihydroisoquinolinyl, tetrahydroisoquinolinyl, pyrrolyl, thiophenyl, benzothiophenyl, benzthiazolyl, benzisothiazolyl, triazolyl, benzotriazolyl, isoindolyl, benzotetrazolyl, pyrazinyl, pyrimidinyl, isothiazolyl, thiazolyl, thiadiazolyl, purinyl, isoxazolyl, oxazolyl, oxadiazolyl, dihydropyranoyl, tetrahydropyranyl, tetrahydropyranoyl and indazolyl; B is selected from —C(=O)—, —SO$_2$—, —C(=O)N(R$^4$)—, —C(=NR$^5$)N(R$^4$)—, and —C(=O)O—.

In another example, embodiment [0101], the compound is according to embodiment [0100] of formula III,

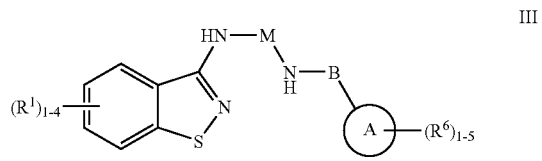

wherein A is selected from a five- to ten-membered heteroaryl, a six- to ten-membered aryl, and a three- to seven-membered heteroalicyclyl; each R$^6$ is independently selected from —H, halogen, trihalomethyl, —CN, —NO$_2$, —OR$^3$, —N(R$^3$)R$^3$, —S(O)$_{0-2}$R$^3$, —N(R$^3$)C(=O)N(R$^3$)R$^3$, —C(=O)CH(R$^3$)N(R$^3$)R$^3$, —SO$_2$-halogen, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$)SO$_2$R$^3$, —N(R$^3$)C(O)R$^3$, —NCO$_2$R$^3$, —C(=O)R$^3$, —C(=O)biaryl, optionally substituted alkoxy, optionally substituted C$_{1-6}$ alkyl, optionally substituted C$_{1-6}$ cycloalkyl, optionally substituted aryl C$_{0-6}$ alkyl and optionally substituted heterocyclyl C$_{0-6}$ alkyl; two of R$^6$, together with the atoms to which they are attached, can combine to form a bridge fused with A, said bridge can contain between three and six carbons and optionally one to three heteroatoms.

In another example, embodiment [0102], the compound is according to embodinment [0101], wherein A is selected from 2,3-dihydrobenzofuranyl, benzimidazoyl, benzo[d][1,3]dioxolyl, benzoxalyl, indolylmethyl, phenyl, pyridyl, indolyl, dihydroindolyl, furanyl, benzofuranyl, 2,3-dihydrobenzo[b][1,4]dioxinyl, chromenyl, pyrrolidinyl, pyranyl, imidazoyl, dihydropyranyl, dihydropyran-4-one-yl, imidazopyridinyl, piperazinyl, pyrazolinyl, napthyridinyl, piperadinyl, azepinyl, isoquinolinyl, quinolinyl, dihydroquinolinyl, tetrahydroquinolinyl, isoquinolinyl, dihydroisoquinolinyl, tetrahydroisoquinolinyl, pyrrolyl, thiophenyl, benzothiophenyl, benzthiazolyl, benzisothiazolyl, triazolyl, benzotriazolyl, isoindolyl, benzotetrazolyl, pyrazinyl, pyrimidinyl, isothiazolyl, thiazolyl, thiadiazolyl, purinyl, isoxazolyl, oxazolyl, oxadiazolyl, dihydropyranoyl, tetrahydropyranyl, tetrahydropyranoyl and indazolyl.

In another example, embodiment [0193], the compound is according to embodiment [0102], wherein A is selected from phenyl, 2-pyridyl, 3-pyridyl, 2-indolyl, 3-indolyl, 2-pyrrolidinyl, 3-pyrrolidinyl, 2-piperadinyl, 3-piperadinyl, 4-piperadinyl, 2-piperazinyl, 2-benzofuranyl, 2-[2,3-dihydrobenzo[b][1,4]dioxinyl], 2-quinolinyl, 3-quinolinyl, 2-pyrrolyl, 3-pyrrolyl, 2-furanyl, 3-furanyl, 2-thiophenyl, 3-thiophenyl, 2-benzothiophenyl, 3-benzothiophenyl, 2-dihydroindolyl, and 3-dihydroindolyl.

In another example, embodiment [0104], the compound is according to embodiment [0103], wherein at least one of R$^6$ is selected from fluorine, chlorine, bromine, trifluoromethyl, C$_{1-6}$ alkyl, C$_{1-6}$ alkoxyl, benzyloxy, —C(=O)aryl, —C(=O)heteroaryl, —C(=O)biaryl, —C(=O)C$_{1-6}$alkyl, —CN, —NO$_2$, —NH$_2$, —OH, —CO$_2$C$_{1-6}$alkyl, —C(=O)CH(R$^3$)N(R$^3$)R$^3$, —C(=O)N(R$^3$)R$^3$, —N(R$^3$)R$^3$, —N(R$^3$)C(=O)N(R$^3$)R$^3$, —N(R$^3$)SO$_2$R$^3$, —N(R$^3$)C(O)R$^3$, —NCO$_2$R$^3$, —C(=O)R$^3$, 1-[piperazin-4-yl]-aryl, 1-[piperazin-4-yl]-C$_{1-6}$ alkyl, optionally substituted C$_{1-6}$ alkyl, optionally substituted aryl, optionally substituted aryl C$_{1-6}$ alkyl, optionally substituted heterocyclyl, and optionally substituted heterocyclyl.

In another example, embodiment [0105], the compound is according to embodiment [0104], wherein A is selected from phenyl, 2-pyridyl, 3-pyridyl, 4-pyridyl, 2-indolyl, 2-pyrrolidinyl, 3-pyrrolidinyl, 2-piperadinyl, 3-piperadinyl, 4-piperadinyl, 2-benzofuranyl, 2-[2,3-dihydrobenzo[b][1,4]dioxinyl], 2-quinolinyl and 3-quinolinyl.

In another example, embodiment [0106], the compound is according to embodiment [0105], wherein M is a C$_{2-3}$alkylene.

In another example, embodiment [0107], the compound is according to embodiment [0106], wherein B is —C(=O)—.

In another example, embodiment [0108], the compound is according to embodiment [0106], wherein B is —C(=O)N(H)—.

In another example, embodiment [0109], the compound is according to embodiment [0106], wherein B is —C(=NH)N(H)—.

In another example, embodiment [0110], the compound is according to embodiment [0106], wherein B is —C(=O)O—.

In another example, embodiment [0111], the compound is according to embodiment [0100], of formula IV,

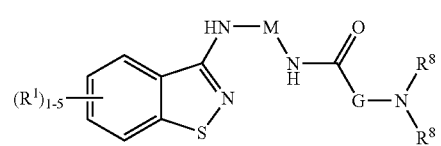

wherein G is —(C(R$^7$)R$^7$)$_{1-3}$—; each R$^7$ is independently selected from —H, halogen, mono- to tri-halomethyl, —CN, —CO$_2$R$^3$, —C(=O)N(R$^3$)R$^3$, —C(=NR$^5$)N(R$^3$)R$^3$, —C(=NR$^5$)R$^3$, —C(=O)CH(R$^3$)N(R$^3$)R$^3$, —C(=O)R$^3$, optionally substituted C$_{1-6}$ alkyl, optionally substituted aryl C$_{0-6}$ alkyl and optionally substituted heterocyclyl C$_{0-6}$ alkyl; optionally two of R$^7$, together with the carbon to which they are attached, combine to form a three- to seven-membered alicyclyl or heteroalicyclyl; each R$^8$ is independently selected from —H, —CO$_2$R$^3$, —C(=O)N(R$^3$)R$^3$, —S(O)$_{0-2}$R$^3$, —C(=O)R$^3$, optionally substituted C$_{1-4}$alkyl, optionally substituted aryl C$_{0-4}$alkyl and optionally substituted heterocyclyl C$_{0-6}$alkyl; optionally two of R$^8$, together with the nitrogen to which they are attached, combine to form an optionally substituted heterocyclyl containing one to three heteroatoms; and optionally one of R$^7$ and one of R$^8$, together with the atoms to which they are attached, combine to form an optionally substituted three- to seven-membered heteroalicyclyl.

1 In another example, embodiment [0112], the compound is according to embodiment [0111], wherein G is —C(R$^7$)R$^7$—.

In another example, embodiment [0113], the compound is according to embodiment [0112], wherein one of R$^7$ is —H and the other R$^7$ is a side chain of an α-amino acid, optionally substituted C$_{1-6}$ alkyl, optionally substituted aryl C$_{0-6}$ alkyl or optionally substituted heterocyclyl C$_{0-6}$ alkyl.

In another example, embodiment [0114], the compound is according to embodiment [0113], wherein R$^7$ is optionally substituted C$_{1-6}$ alkyl or optionally substituted phenyl C$_{1-6}$ alkyl.

In another example, embodiment [0115], the compound is according to embodiment [0114], wherein R⁸ is selected from —H, —CO₂R³, —C(=O)R³ and optionally substituted C₁₋₆alkyl.

In another example, embodiment [0116], the compound is according to embodiment [0115], wherein M is a C₂₋₃ alkylene.

In another example, embodiment [0117], the compound is according to embodiment [0116], wherein the carbon bearing R⁷ is enantiomerically enriched.

In another example, embodiment [0118], the compound is according to embodiment [0117], wherein the carbon bearing R⁷ is substantially enantiopure.

In another example, embodiment [0119], the compound is according to embodiment [0118], wherein the carbon bearing R⁷ of the major enantiomer is of the S-configuration.

In another example, embodiment [0120], the compound is according to embodiment [0119], wherein the carbon bearing R⁷ of the major enantiomer is of the R-configuration.

In another example, embodiment [0121], the compound is according to embodiment [0111], wherein one of R⁷ and one of R⁸ combine to form an optionally substituted five- to seven-membered heteroalicyclic.

In another example, embodiment [0122], the compound is according to embodiment [0121], wherein one of R⁷ and one of R⁸ combine to form an optionally substituted pyrrolidine or an optionally substituted piperidine.

In another example, embodiment [0123], the compound is according to embodiment [0122], wherein the other R⁸ is selected from —H, —CO₂R³, —C(=O)R³ and optionally substituted C₁₋₆ alkyl.

In another example, embodiment [0124], the compound is according to embodiment [0123], M is a C₂₋₃ alkylene optionally substituted with —CO₂R⁹.

In another aspect, embodiment [0125], the invention comprises a compound of structural Formula V,

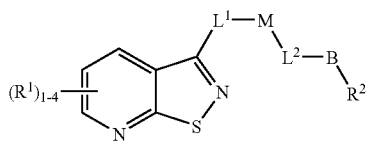

V or a pharmaceutically acceptable salt, N-oxide, S-oxide, hydrate, solvate or prodrug thereof, wherein, each R¹ is independently selected from —H, halogen, mono- to trihalomethyl, —CN, —NO₂, —OR³, —N(R³)R³, —S(O)₀₋₂R³, —N(R³)C(=O)N(R³)R³, —SO₂N(R³)R³, —CO₂R³, —C(=O)N(R³)R³, —C(=NR⁵)N(R³)R³, —C(=NR⁵)R³, —N(R³)SO₂R³, —N(R³)C(O)R³, —NC(=O)CH(R³)N(R³)R³, —NCO₂R³, —C(=O)R³, optionally substituted alkoxy, optionally substituted C₁₋₆ alkyl, optionally substituted aryl C₀₋₆ alkyl and optionally substituted heterocyclyl C₀₋₆ alkyl;

B is selected from absent, optionally substituted C₁₋₆ alkyl, —C(=O)—, —C(=O)C(=O)—, —S(O)₀₋₂—, —C(=O)N(R⁴)—, —C(=NR⁵)N(R⁴)—, —C(=S)N(R⁴)—, —C(=S)O—, —C(=O)O— and

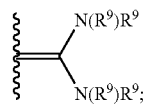

R² is selected from —H, an optionally substituted C₁₋₂₀ alkyl, an optionally substituted C₁₋₆ alkyl-N(R)—C(=O)aryl, an optionally substituted three- to seven-membered heteroalicyclic C₀₋₆ alkyl, an optionally substituted six- to fourteen-membered aryl C₀₋₃ alkyl, an optionally substituted aryl-heteroaryl, an optionally substituted heteroaryl-aryl, an optionally substituted heteroaryl-heteroaryl, an optionally substituted heterocyclyl-heteroaryl, an optionally substituted aryl-aryl, an optionally substituted aryl-heterocyclyl, an optionally substituted aryloxy C₀₋₃ alkylheterocyclyl, an optionally substituted aryloxy C₀₋₃ alkylheteroaryl, an optionally substituted aryloxy C₀₋₃ alkylaryl, an optionally substituted heteroaryl-N(R)—C₀₋₃ alkyl-heteroaryl, an optionally substituted five- to fifteen-membered heteroaryl C₀₋₃ alkyl, phenylethyl, benzyl, 2,3-dihydrobenzofuiranyl, benzimidazoyl, benzo[d][1,3]dioxolyl, benzoxalyl, indolylmethyl, phenyl, optionally substituted biphenyl, pyridyl, indolyl, dihydroindolyl, furanyl, benzofuiranyl, 2,3-dihydrobenzo[b][1,4]dioxinyl, chromenyl, pyrrolidinyl, pyranyl, imidazoyl, dihydropyranyl, dihydropyran-4-one-yl, phthalazinyl, imidazopyridinyl, piperazinyl, pyrazolinyl, napthyridinyl, piperadinyl, azepinyl, isoquinolinyl, quinolinyl, dihydroquinolinyl, tetrahydroquinolinyl, isoquinolinyl, dihydroisoquinolinyl, tetrahydroisoquinolinyl, pyrrolyl, thiophenyl, benzothiophenyl, benzthiazolyl, benzisothiazolyl, triazolyl, benzotriazolyl, isoindolyl, benzotetrazolyl, pyrazinyl, pyrimidinyl, isothiazolyl, thiazolyl, thiadiazolyl, purinyl, isoxazolyl, oxazolyl, oxadiazolyl, dihydropyranoyl, tetrahydropyranyl, tetrahydropyranoyl and indazolyl;

each R³ is independently selected from —H, optionally substituted C₁₋₆ alkyl, optionally substituted —C(=O)C₁₋₆ alkyl, optionally substituted aryl C₀₋₆ alkyl, optionally substituted heteroaryl C₀₋₆alkyl and optionally substituted heterocyclyl C₀₋₆alkyl; optionally two of R³, together with the nitrogen to which they are attached, combine to form an optionally substituted heterocyclyl containing one to three heteroatoms;

L¹ and L² are each independently selected from —N(R⁴)—, —O— and —S(O)₀₋₂—; or the moeity formed by L¹-M-L² and B is

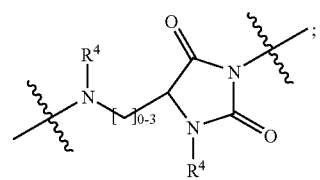

each R⁴ is independently selected from —H and optionally substituted C₁₋₆ alkyl, —S(O)₀₋₂R³, —C(=O)N(R³)(R³), optionally substituted —C(=O)C₁₋₆alkyl, optionally substituted aryl C₁₋₆ alkyl, provided that B is not

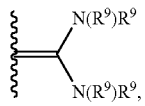

in the event that $R^4$ of $L^2$ is part of the double bond structure of B, and $R^2$ is absent;

each $R^5$ is independently selected from —H, —CN, —NO$_2$, —OR$^3$, —S(O)$_{0-2}$R$^3$, —CO$_2$R$^3$, optionally substituted C$_{1-6}$ alkyl, optionally substituted C$_{2-6}$ alkenyl, and optionally substituted C$_{2-6}$ alkynyl;

M is an optionally substituted C$_{2-4}$ alkylene, C$_{2-4}$ alkenylene, or C$_{2-4}$ alkynylene; and each $R^9$ is independently selected from —H, optionally substituted C$_{1-6}$ alkyl, optionally substituted aryl C$_{0-6}$ alkyl and optionally substituted heterocyclyl C$_{0-6}$alkyl; and optionally two of $R^9$, together with the nitrogen to which they are attached, combine to form an optionally substituted heterocyclyl containing one to three heteroatoms.

In another aspect, embodiment [0126], the invention comprises a compound of structural Formula VI,

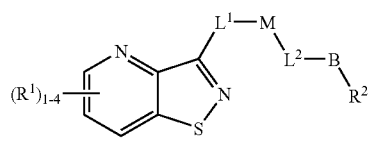

VI or a pharmaceutically acceptable salt, N-oxide, S-oxide, hydrate, solvate or prodrug thereof, wherein, each $R^1$ is independently selected from —H, halogen, mono- to trihalomethyl, —CN, —NO$_2$, —OR$^3$, —N(R$^3$)R$^3$, —S(O)$_{0-2}$R$^3$, —N(R$^3$)C(=O)N(R$^3$)R$^3$, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$)SO$_2$R$^3$, —N(R$^3$)C(O)R$^3$, —NC(=O)CH(R$^3$)N(R$^3$)R$^3$, —NCO$_2$R$^3$, —C(=O)R$^3$, optionally substituted alkoxy, optionally substituted C$_{1-6}$ alkyl, optionally substituted aryl C$_{0-6}$ alkyl and optionally substituted heterocyclyl C$_{0-6}$ alkyl;

B is selected from absent, optionally substituted C$_{1-6}$ alkyl, —C(=O)—, —C(=O)C(=O)—, —S(O)$_{0-2}$—, —C(=O)N(R$^4$)—, —C(=NR$^5$)N(R$^4$)—, —C(=S)N(R$^4$)—, —C(=S)O—, —C(=O)O— and

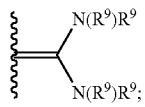

$R^2$ is selected from —H, an optionally substituted C$_{1-20}$ alkyl, an optionally substituted C$_{1-6}$ alkyl-N(R)—C(=O)aryl, an optionally substituted three- to seven-membered heteroalicyclic C$_{0-6}$ alkyl, an optionally substituted six- to fourteen-membered aryl C$_{0-3}$ alkyl, an optionally substituted aryl-heteroaryl, an optionally substituted heteroaryl-aryl, an optionally substituted heteroaryl-heteroaryl, an optionally substituted heterocyclyl-heteroaryl, an optionally substituted aryl-aryl, an optionally substituted aryl-heterocyclyl, an optionally substituted aryloxy C$_{0-3}$ alkylheterocyclyl, an optionally substituted aryloxy C$_{0-3}$ alkylheteroaryl, an optionally substituted aryloxy C$_{0-3}$ alkylaryl, an optionally substituted heteroaryl-N(R)—C$_{0-3}$ alkyl-heteroaryl, an optionally substituted five- to fifteen-membered heteroaryl C$_{0-3}$ alkyl, phenylethyl, benzyl, 2,3-dihydrobenzofuranyl, benzimidazoyl, benzo[d][1,3]dioxolyl, benzoxalyl, indolylmethyl, phenyl, optionally substituted biphenyl, pyridyl, indolyl, dihydroindolyl, furanyl, benzofuiranyl, 2,3-dihydrobenzo[b][1,4]dioxinyl, chromenyl, pyrrolidinyl, pyranyl, imidazoyl, dihydropyranyl, dihydropyran-4-one-yl, phthalazinyl, imidazopyridinyl, piperazinyl, pyrazolinyl, napthyridinyl, piperadinyl, azepinyl, isoquinolinyl, quinolinyl, dihydroquinolinyl, tetrahydroquinolinyl, isoquinolinyl, dihydroisoquinolinyl, tetrahydroisoquinolinyl, pyrrolyl, thiophenyl, benzothiophenyl, benzthiazolyl, benzisothiazolyl, triazolyl, benzotriazolyl, isoindolyl, benzotetrazolyl, pyrazinyl, pyrimidinyl, isothiazolyl, thiazolyl, thiadiazolyl, purinyl, isoxazolyl, oxazolyl, oxadiazolyl, dihydropyranoyl, tetrahydropyranyl, tetrahydropyranoyl and indazolyl;

each $R^3$ is independently selected from —H, optionally substituted C$_{1-6}$ alkyl, optionally substituted —C(=O)C$_{1-6}$ alkyl, optionally substituted aryl C$_{0-6}$ alkyl, optionally substituted heteroaryl C$_{0-6}$alkyl and optionally substituted heterocyclyl C$_{0-6}$alkyl; optionally two of $R^3$, together with the nitrogen to which they are attached, combine to form an optionally substituted heterocyclyl containing one to three heteroatoms;

$L^1$ and $L^2$ are each independently selected from —N(R$^4$)—, —O— and —S(O)$_{0-2}$—; or the moeity formed by $L^1$-M-$L^2$ and B is

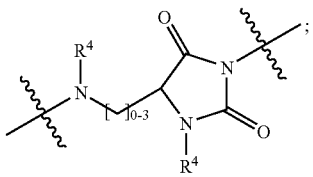

each $R^4$ is independently selected from —H and optionally substituted C$_{1-6}$ alkyl, —S(O)$_{0-2}$R$^3$, —C(=O)N(R$^3$)(R$^3$), optionally substituted —C(=O)C$_{1-6}$ alkyl, optionally substituted aryl C$_{1-6}$ alkyl, provided that B is not

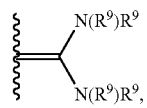

in the event that $R^4$ of $L^2$ is part of the double bond structure of B, and $R^2$ is absent;

each $R^5$ is independently selected from —H, —CN, —NO$_2$, —OR$^3$, —S(O)$_{0-2}$R$^3$, —CO$_2$R$^3$, optionally substituted C$_{1-6}$ alkyl, optionally substituted C$_{2-6}$ alkenyl, and optionally substituted C$_{2-6}$ alkynyl;

M is an optionally substituted C$_{2-4}$ alkylene, C$_{2-4}$ alkenylene, or C$_{2-4}$ alkynylene; and each $R^9$ is independently selected from —H, optionally substituted C$_{1-6}$ alkyl, optionally substituted aryl C$_{0-6}$ alkyl and optionally substituted heterocyclyl C$_{0-6}$alkyl; and optionally two of $R^9$, together with the nitrogen to which they are attached, combine to form an optionally substituted heterocyclyl containing one to three heteroatoms.

In another aspect, embodiment [0127], the invention comprises a compound of structural Formula VII,

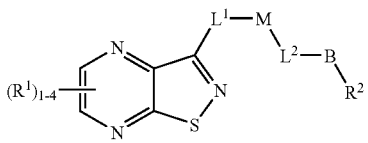

or a pharmaceutically acceptable salt, N-oxide, S-oxide, hydrate, solvate or prodrug thereof, wherein, each $R^1$ is independently selected from —H, halogen, mono- to trihalomethyl, —CN, —NO$_2$, —OR$^3$, —N(R$^3$)R$^3$, —S(O)$_{0-2}$R$^3$, —N(R$^3$)C(=O)N(R$^3$)R$^3$, —SO$_2$N(R$^3$)R$^3$, —CO$_2$R$^3$, —C(=O)N(R$^3$)R$^3$, —C(=NR$^5$)N(R$^3$)R$^3$, —C(=NR$^5$)R$^3$, —N(R$^3$)SO$_2$R$^3$, —N(R$^3$)C(O)R$^3$, —NC(=O)CH(R$^3$)N(R$^3$)R$^3$, —NCO$_2$R$^3$, —C(=O)R$^3$, optionally substituted alkoxy, optionally substituted C$_{1-6}$ alkyl, optionally substituted aryl C$_{0-6}$ alkyl and optionally substituted heterocyclyl C$_{0-6}$ alkyl;

B is selected from absent, optionally substituted C$_{1-6}$ alkyl, —C(=O)—, —C(=O)C(=O)—, —S(O)$_{0-2}$—, —C(=O)N(R$^4$)—, —C(=NR$^5$)N(R$^4$)—, —C(=S)N(R$^4$)—, —C(=S)O—, —C(=O)O— and

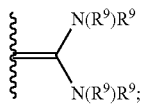

$R^2$ is selected from —H, an optionally substituted C$_{1-20}$ alkyl, an optionally substituted C$_{1-6}$ alkyl-N(R)—C(=O)aryl, an optionally substituted three- to seven-membered heteroalicyclic C$_{0-6}$ alkyl, an optionally substituted six- to fourteen-membered aryl C$_{0-3}$ alkyl, an optionally substituted aryl-heteroaryl, an optionally substituted heteroaryl-aryl, an optionally substituted heteroaryl-heteroaryl, an optionally substituted heterocyclyl-heteroaryl, an optionally substituted aryl-aryl, an optionally substituted aryl-heterocyclyl, an optionally substituted aryloxy C$_{0-3}$ alkylheterocyclyl, an optionally substituted aryloxy C$_{0-3}$ alkylheteroaryl, an optionally substituted aryloxy C$_{0-3}$ alkylaryl, an optionally substituted heteroaryl-N(R)—C$_{0-3}$ alkyl-heteroaryl, an optionally substituted five- to fifteen-membered heteroaryl C$_{0-3}$ alkyl, phenylethyl, benzyl, 2,3-dihydrobenzofuranyl, benzimidazoyl, benzo[d][1,3]dioxolyl, benzoxalyl, indolylmethyl, phenyl, optionally substituted biphenyl, pyridyl, indolyl, dihydroindolyl, furanyl, benzofuranyl, 2,3-dihydrobenzo[b][1,4]dioxinyl, chromenyl, pyrrolidinyl, pyranyl, imidazoyl, dihydropyranyl, dihydropyran-4-one-yl, phthalazinyl, imidazopyridinyl, piperazinyl, pyrazolinyl, napthyridinyl, piperadinyl, azepinyl, isoquinolinyl, quinolinyl, dihydroquinolinyl, tetrahydroquinolinyl, isoquinolinyl, dihydroisoquinolinyl, tetrahydroisoquinolinyl, pyrrolyl, thiophenyl, benzothiophenyl, benzthiazolyl, benzisothiazolyl, triazolyl, benzotriazolyl, isoindolyl, benzotetrazolyl, pyrazinyl, pyrimidinyl, isothiazolyl, thiazolyl, thiadiazolyl, purinyl, isoxazolyl, oxazolyl, oxadiazolyl, dihydropyranoyl, tetrahydropyranyl, tetrahydropyranoyl and indazolyl;

each $R^3$ is independently selected from —H, optionally substituted C$_{1-6}$ alkyl, optionally substituted —C(=O)C$_{1-6}$ alkyl, optionally substituted aryl C$_{0-6}$ alkyl, optionally substituted heteroaryl C$_{0-6}$alkyl and optionally substituted heterocyclyl C$_{0-6}$alkyl; optionally two of R$^3$, together with the nitrogen to which they are attached, combine to form an optionally substituted heterocyclyl containing one to three heteroatoms;

$L^1$ and $L^2$ are each independently selected from —N(R$^4$)—, —O— and —S(O)$_{0-2}$—; or the moeity formed by $L^1$-M-$L^2$ and B is

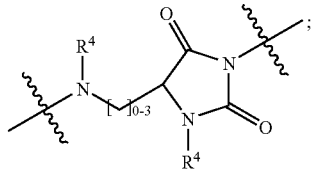

each $R^4$ is independently selected from —H and optionally substituted C$_{1-6}$ alkyl, —S(O)$_{0-2}$R$^3$, —C(=O)N(R$^3$)(R$^3$), optionally substituted —C(=O)C$_{1-6}$ alkyl, optionally substituted aryl C$_{1-6}$ alkyl, provided that B is not

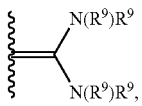

in the event that $R^4$ of $L^2$ is part of the double bond structure of B, and $R^2$ is absent;

each $R^5$ is independently selected from —H, —CN, —NO$_2$, —OR$^3$, —S(O)$_{0-2}$R$^3$, —CO$_2$R$^3$, optionally substituted C$_{1-6}$ alkyl, optionally substituted C$_{2-6}$ alkenyl, and optionally substituted C$_{2-6}$ alkynyl;

M is an optionally substituted C$_{2-3}$ alkylene, C$_{2-4}$ alkenylene, or C$_{2-4}$ alkynylene; and each $R^9$ is independently selected from —H, optionally substituted C$_{1-6}$ alkyl, optionally substituted aryl C$_{0-6}$ alkyl and optionally substituted heterocyclyl C$_{0-6}$alkyl; and optionally two of R$^9$, together with the nitrogen to which they are attached, combine to form an optionally substituted heterocyclyl containing one to three heteroatoms.

In another aspect, the invention comprises compounds having Formula II,

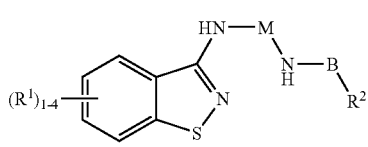

or a pharmaceutically acceptable salt, N-oxide, S-oxide, hydrate, solvate or prodrug thereof, wherein, each $R^1$ is independently selected from —H, halogen, mono- to trihalomethyl, —NO$_2$, —N(R$^3$)R$^3$, —S(O)$_{0-2}$R$^3$, —SO$_2$N(R$^3$)R$^3$, optionally substituted alkoxy, optionally substituted C$_{1-6}$ alkyl and optionally substituted aryl C$_{0-6}$ alkyl. In one example, $R^1$ is chloro, bromo, trifluoromethyl, methoxy, C$_{1-3}$ alkyl, —N(H)—C$_{1-3}$ alkyl, —SO$_2$-C$_{1-5}$ alkyl, —SO$_2$NH$_2$, —SO$_2$N(H)C$_{1-5}$ alkyl, or phenyl optionally substituted with one or more methoxy, isopropoxy or fluoro. In another example, $R^1$ is methyl, —N(H)—C$_3$H$_7$, —SO$_2$N(H)-tert-butyl or —SO$_2$-tert-butyl.

In another aspect, embodiment [0129], the invention comprises compounds according to embodiment [0096] having Formula II,

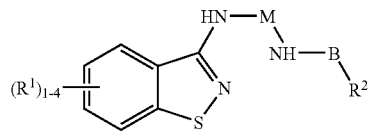

II or a pharmaceutically acceptable salt, N-oxide, S-oxide, hydrate, solvate or prodrug thereof, wherein B is selected from optionally substituted $C_{1-6}$ alkyl, —C(=O)—, —S(O)$_{0-2}$—, —C(=O)N(R$^4$)— or is absent. In one example, B is $C_{1-3}$ alkyl, —S(O)$_2$— or —C(=O)N(H)—. In another example B is methylene.

In another example, the compound is according to embodiments [0096] to [0128], selected from Table 2.

TABLE 2

| Entry | Name | Structure |
|---|---|---|
| 1 | N-(2-(Benzo[d]isothiazol-3-ylamino)ethyl)-4-methylnicotinamide | 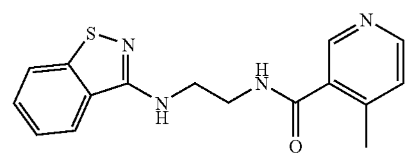 |
| 2 | N-(2-(Benzo[d]isothiazol-3-ylamino)ethyl)-5-nitropicolinamide | 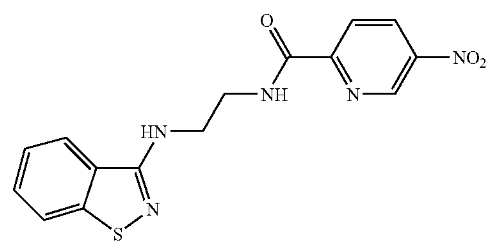 |
| 3 | N-(2-(Benzo[d]isothiazol-3-ylamino)ethyl)-5-methoxy-1H-indole-2-carboxamide | 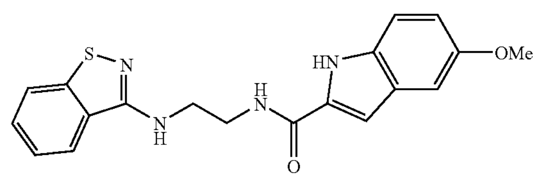 |
| 4 | N-(2-(Benzo[d]isothiazol-3-ylamino)ethyl)-5-fluoro-1H-indole-2-carboxamide | 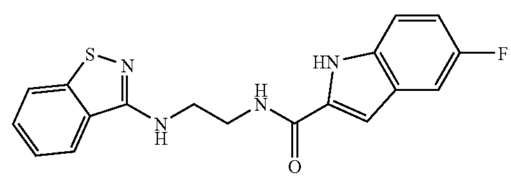 |
| 5 | N-(2-(Benzo[d]isothiazol-3-ylamino)ethyl)-5-chloro-1H-indole-2-carboxamide | 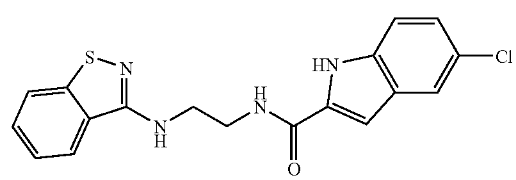 |
| 6 | (S)-tert-Butyl 2-(3-(Benzo[d]isothiazol-3-ylamino)propylamino)-2-oxo-1-phenylethylcarbamate | 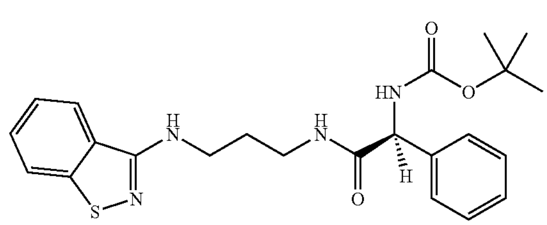 |

TABLE 2-continued

| Entry | Name | Structure |
|-------|------|-----------|
| 7 | 6-Acetamido-N-(2-(benzo[d]isothiazol-3-ylamino)ethyl)picolinamide | 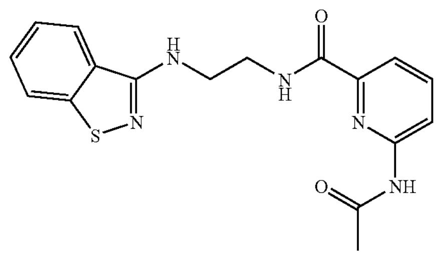 |
| 8 | N-(2-(Benzo[d]isothiazol-3-ylamino)ethyl)-5-(benzyloxy)-1H-indole-2-carboxamide | 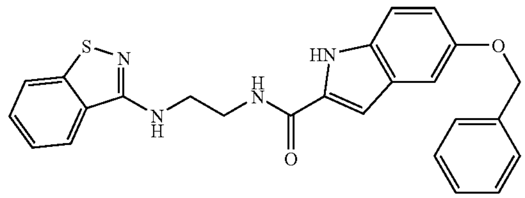 |
| 9 | N-(2-(Benzo[d]isothiazol-3-ylamino)ethyl)-1H-indole-2-carboxamide | 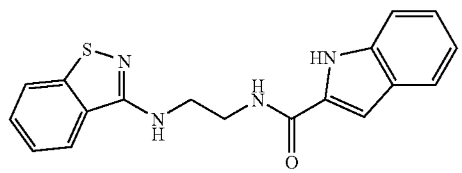 |
| 10 | N-(2-(Benzo[d]isothiazol-3-ylamino)ethyl)-1-(3,5-dichlorobenzoyl)pyrrolidine-2-carboxamide | 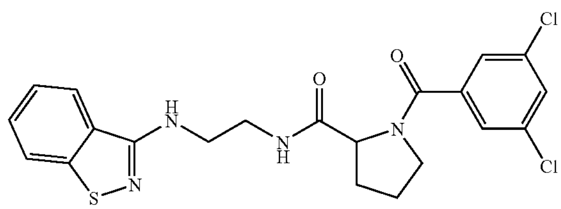 |
| 11 | (S)-tert-Butyl 2-(2-(Benzo[d]isothiazol-3-ylamino)ethylamino)-2-oxo-1-phenylethylcarbamate | 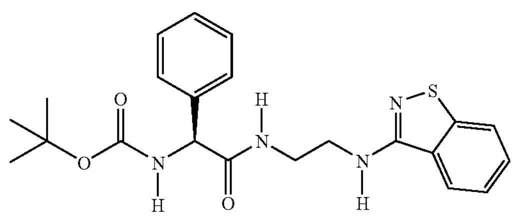 |
| 12 | N-(2-(Benzo[d]isothiazol-3-ylamino)ethyl)-3-benzoylpicolinamide | 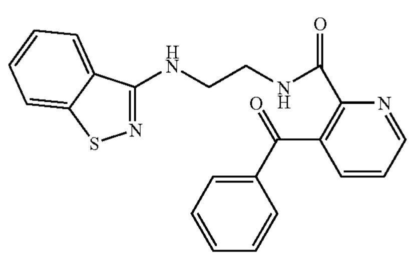 |
| 13 | N-(2-(Benzo[d]isothiazol-3-ylamino)ethyl)-6-methylpicolinamide | 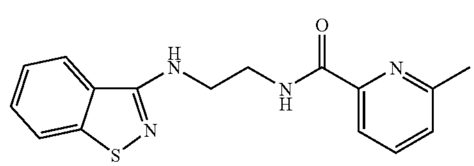 |

TABLE 2-continued

| Entry | Name | Structure |
|---|---|---|
| 14 | N-(2-(Benzo[d]isothiazol-3-ylamino)ethyl)-4-methoxybenzamide | 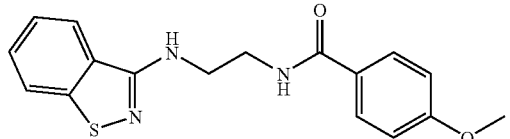 |
| 15 | N-(2-(Benzo[d]isothiazol-3-ylamino)ethyl)benzofuran-2-carboxamide | 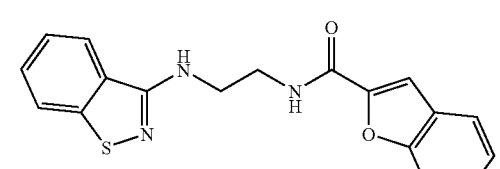 |
| 16 | N-(2-(Benzo[d]isothiazol-3-ylamino)ethyl)-2,3-dihydrobenzo[b][1,4]dioxine-2-carboxamide | 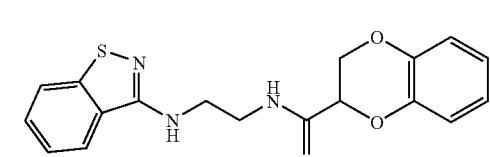 |
| 17 | N-(2-(Benzo[d]isothiazol-3-ylamino)ethyl)-1-(biphenylcarbonyl)piperidine-3-carboxamide | 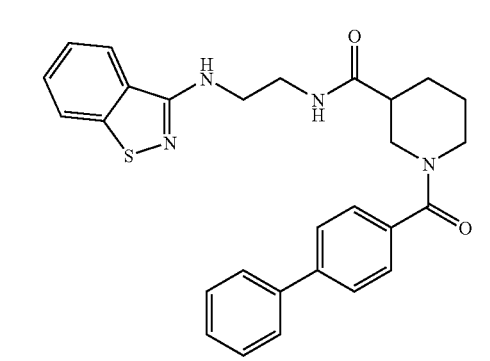 |
| 18 | (S)-tert-Butyl 1-(2-(Benzo[d]isothiazol-3-ylamino)ethylamino)-3-methyl-1-oxobutan-2-ylcarbamate | 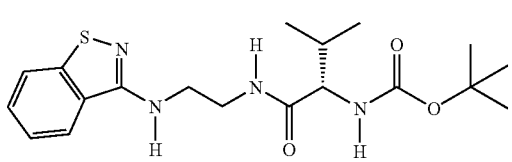 |
| 19 | (R)-tert-Butyl 2-(2-(Benzo[d]isothiazol-3-ylamino)ethylamino)-2-oxo-1-phenylethylcarbamate | 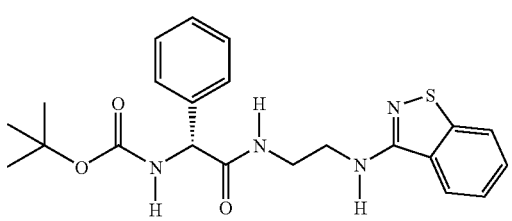 |
| 20 | N-(2-(Benzo[d]isothiazol-3-ylamino)ethyl)-5-methyl-1H-indole-2-carboxamide | 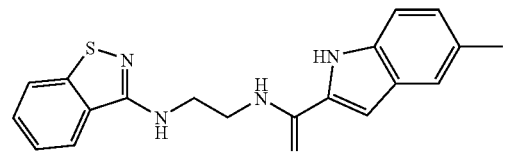 |

TABLE 2-continued

| Entry | Name | Structure |
|---|---|---|
| 21 | N-(2-(Benzo[d]isothiazol-3-ylamino)ethyl)-7-nitro-1H-indole-2-carboxamide | 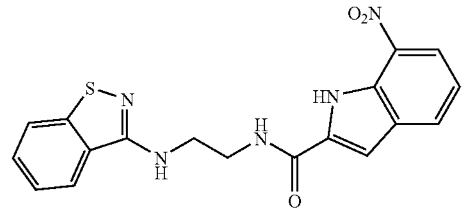 |
| 22 | N-(2-(Benzo[d]isothiazol-3-ylamino)ethyl)-5-hydroxy-1H-indole-2-carboxamide | 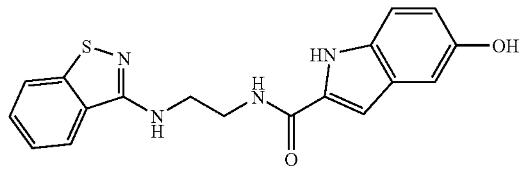 |
| 23 | N-(2-(Benzo[d]isothiazol-3-ylamino)ethyl)-2,4-dichlorobenzamide | 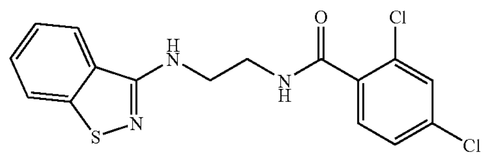 |
| 24 | N-(2-(Benzo[d]isothiazol-3-ylamino)ethyl)-1-(3,5-dichlorobenzoyl)piperidine-2-carboxamide | 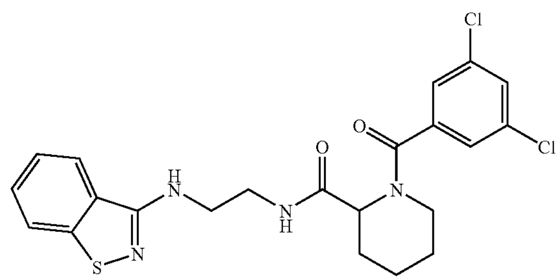 |
| 25 | N-(2-(Benzo[d]isothiazol-3-ylamino)ethyl)picolinamide | 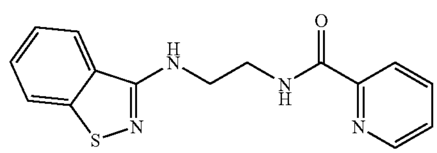 |
| 26 | tert-Butyl 3-(2-(Benzo[d]isothiazol-3-ylamino)ethylcarbamoyl)piperidine-1-carboxylate | 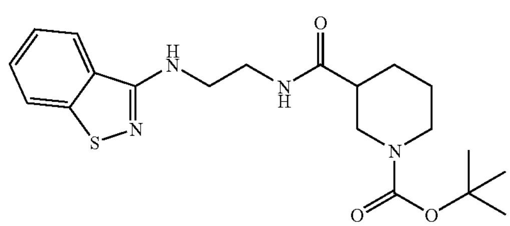 |
| 27 | N-(2-(Benzo[d]isothiazol-3-ylamino)ethyl)-6-bromopicolinamide | 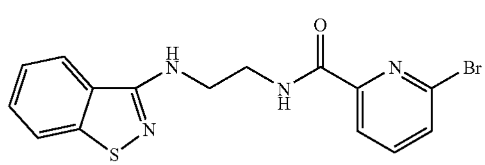 |

TABLE 2-continued

| Entry | Name | Structure |
|---|---|---|
| 28 | (S)-N-(2-(2-(Benzo[d]isothiazol-3-ylamino)ethylamino)-2-oxo-1-phenylethyl)-4-methoxybenzamide | 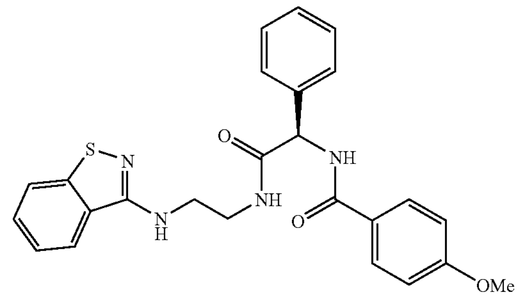 |
| 29 | N-(2-(Benzo[d]isothiazol-3-ylamino)ethyl)-2-oxo-2-(thiophen-2-yl)acetamide | 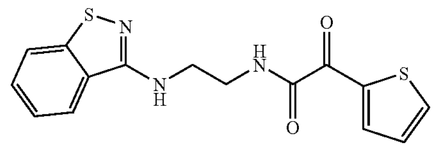 |
| 30 | N-(2-(Benzo[d]isothiazol-3-ylamino)ethyl)quinoline-3-carboxamide | 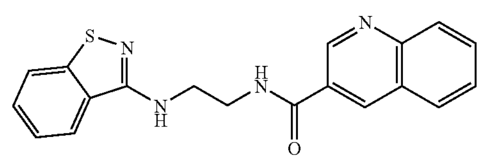 |
| 31 | N-(2-(Benzo[d]isothiazol-3-ylamino)ethyl)-4-chloropicolinamide | 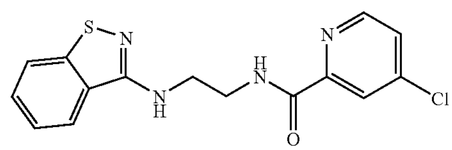 |
| 32 | tert-Butyl 1-(3-(2-(Benzo[d]isothiazol-3-ylamino)ethylcarbamoyl)piperidin-1-yl)-1-oxo-3-phenylpropan-2-ylcarbamate | 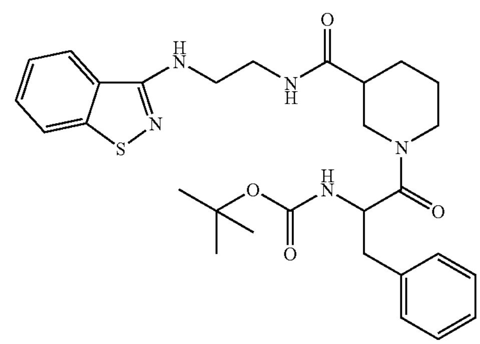 |
| 33 | N-(2-(Benzo[d]isothiazol-3-ylamino)ethyl)-3-chlorobenzamide | 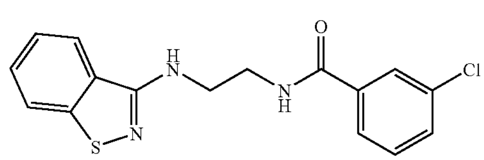 |
| 34 | $N^2$-(2-(Benzo[d]isothiazol-3-ylamino)ethyl)-N5-methylpyridine-2,5-dicarboxamide | 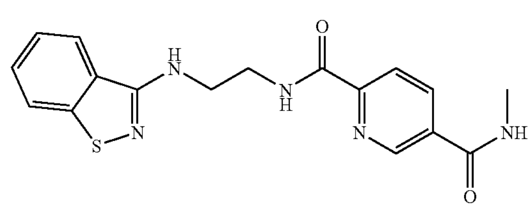 |

TABLE 2-continued

| Entry | Name | Structure |
|---|---|---|
| 35 | tert-Butyl 4-(2-(Benzo[d]isothiazol-3-ylamino)ethylcarbamoyl)piperidine-1-carboxylate | 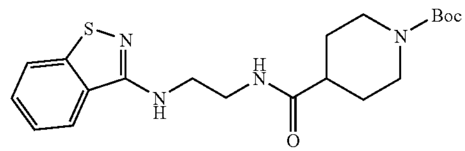 |
| 36 | tert-Butyl 6-(2-(Benzo[d]isothiazol-3-ylamino)ethylcarbamoyl)pyridin-2-ylcarbamate | 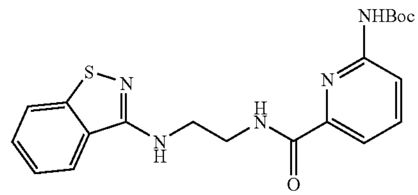 |
| 37 | 6-Amino-N-(2-(benzo[d]isothiazol-3-ylamino)ethyl)picolinamide | 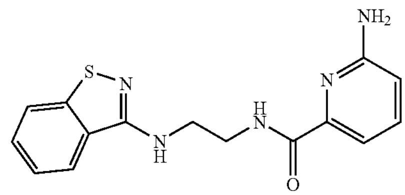 |
| 38 | N-(2-(Benzo[d]isothiazol-3-ylamino)ethyl)-4-(4-phenylpiperazin-1-yl)picolinamide | 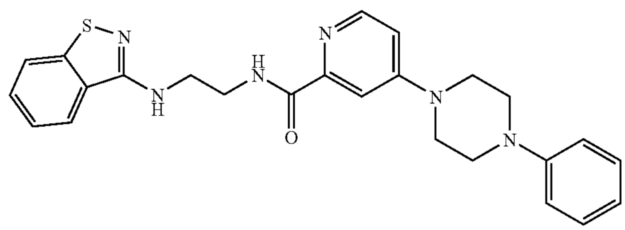 |
| 39 | N-(2-(Benzo[d]isothiazol-3-ylamino)ethyl)-4-methylbenzamide | 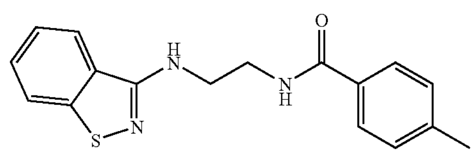 |
| 40 | N-(2-(Benzo[d]isothiazol-3-ylamino)ethyl)-4,6-dichloro-1H-indole-2-carboxamide | 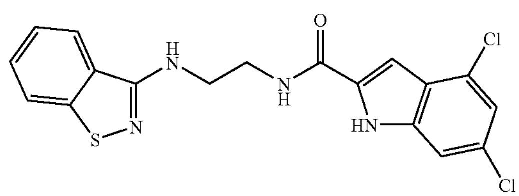 |
| 41 | N-(2-(Benzo[d]isothiazol-3-ylamino)ethyl)-2,6-dichlorobenzamide | 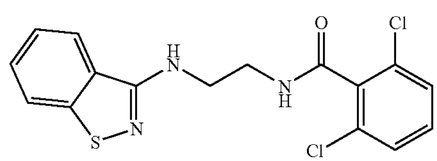 |
| 42 | (S)-N-(2-(2-(Benzo[d]isothiazol-3-ylamino)ethylamino)-2-oxo-1-phenylethyl)-2,2,2-trifluoroacetamide | 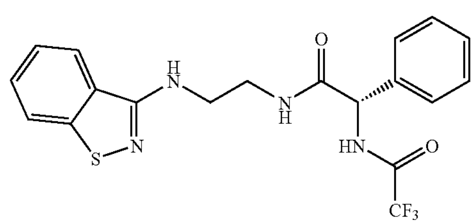 |

TABLE 2-continued

| Entry | Name | Structure |
|---|---|---|
| 43 | (S)-N-(2-(2-(Benzo[d]isothiazol-3-ylamino)ethylamino)-2-oxo-1-phenylethyl)cyclopentanecarboxamide | 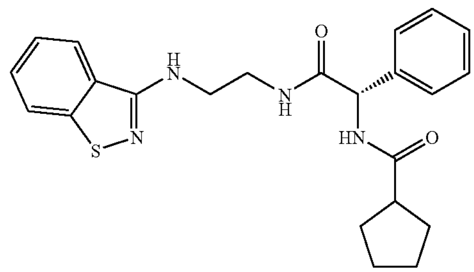 |
| 44 | (S)-tert-Butyl 1-(2-(Benzo[d]isothiazol-3-ylamino)ethylamino)-3-(4-hydroxyphenyl)-1-oxopropan-2-ylcarbamate | 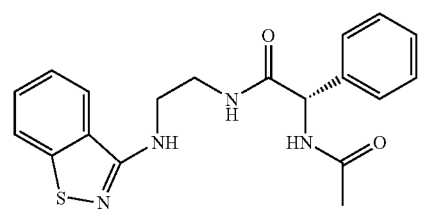 |
| 45 | N-(2-(Benzo[d]isothiazol-3-ylamino)ethyl)-1-methyl-1H-pyrrole-2-carboxamide | 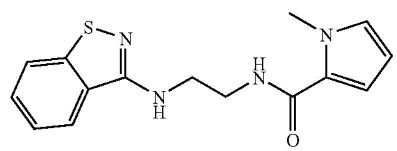 |
| 46 | N-(3-(Benzo[d]isothiazol-3-ylamino)propyl)picolinamide | 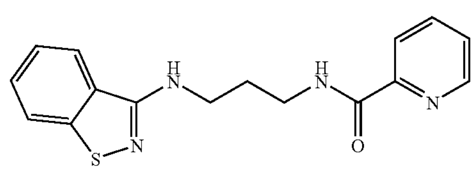 |
| 47 | 1-Acetyl-N-(2-(benzo[d]isothiazol-3-ylamino)ethyl)piperidine-3-carboxamide | 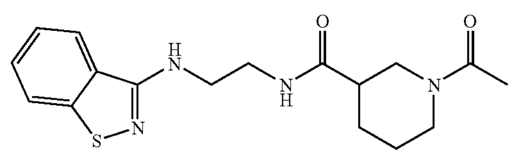 |
| 48 | N-(2-(Benzo[d]isothiazol-3-ylamino)ethyl)-1-picolinoylpiperidine-3-carboxamide | 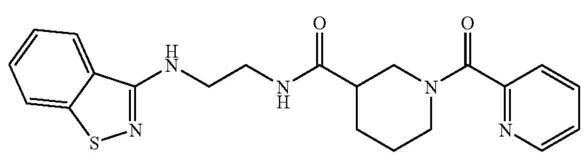 |
| 49 | tert-Butyl 2-(3-(2-(Benzo[d]isothiazol-3-ylamino)ethylcarbamoyl)piperidin-1-yl)-2-oxo-1-phenylethylcarbamate | 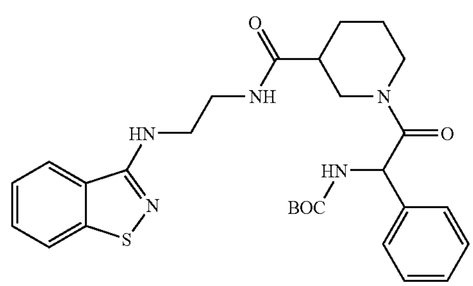 |

TABLE 2-continued

| Entry | Name | Structure |
|---|---|---|
| 50 | (S)-2-Acetamido-N-(2-(benzo[d]isothiazol-3-ylamino)ethyl)-2-phenylacetamide | 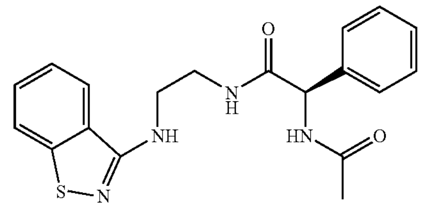 |
| 51 | N-(2-(2-(Benzo[d]isothiazol-3-ylamino)ethylamino)-2-oxoethyl)benzamide | 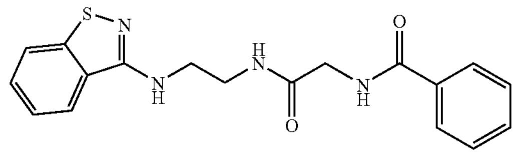 |
| 52 | N-(2-(Benzo[d]isothiazol-3-ylamino)ethyl)-4-(trifluoromethyl)benzamide | 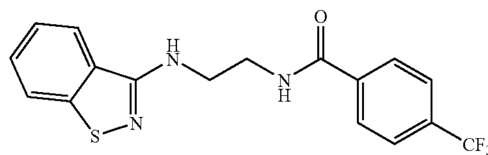 |
| 53 | N-(2-(Benzo[d]isothiazol-3-ylamino)ethyl)benzamid | 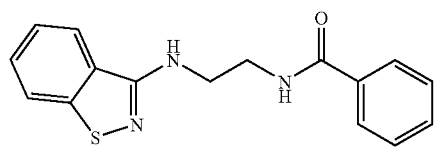 |
| 54 | N-(2-(Benzo[d]isothiazol-3-ylamino)ethyl)-1-picolinoylpiperidine-2-carboxamide | 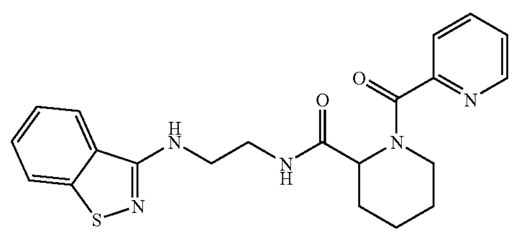 |
| 55 | 5-Amino-N-(2-(benzo[d]isothiazol-3-ylamino)ethyl)picolinamide | 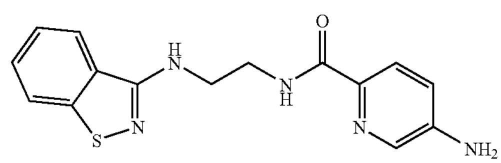 |
| 56 | (S)-N-(2-(2-(Benzo[d]isothiazol-3-ylamino)ethylamino)-2-oxo-1-phenylethyl)pivalamide | 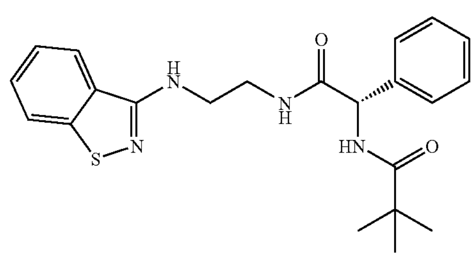 |
| 57 | N-(2-(Benzo[d]isothiazol-3-ylamino)ethyl)-4-(4-methylpiperazin-1-yl)picolinamide | 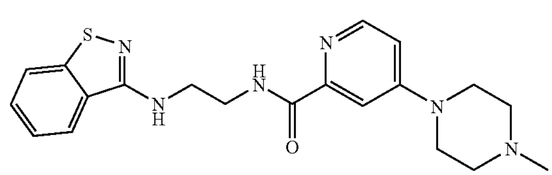 |

TABLE 2-continued

| Entry | Name | Structure |
|---|---|---|
| 58 | 1-Acetyl-N-(2-(benzo[d]isothiazol-3-ylamino)ethyl)pyrrolidine-2-carboxamide | 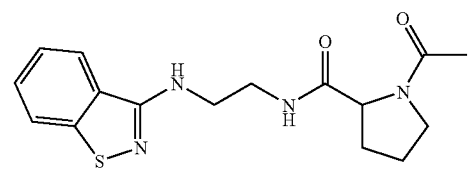 |
| 59 | N-(2-(Benzo[d]isothiazol-3-ylamino)ethyl)-1-picolinoylpyrrolidine-2-carboxamide | 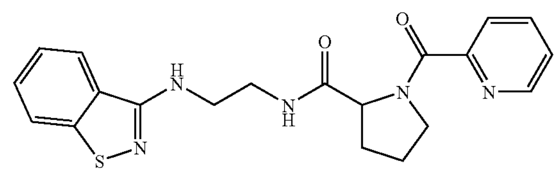 |
| 60 | N-(2-(Benzo[d]isothiazol-3-ylamino)ethyl)nicotinamide | 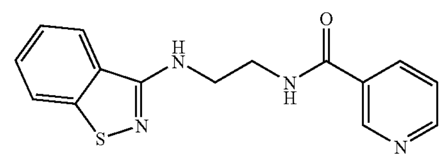 |
| 61 | tert-Butyl 2-(2-(Benzo[d]isothiazol-3-ylamino)ethylcarbamoyl)piperidin-1-carboxylate | 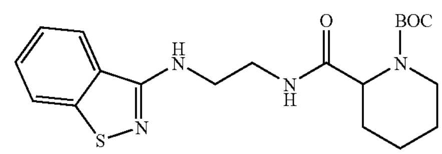 |
| 62 | N-(2-(Benzo[d]isothiazol-3-ylamino)ethyl)-5-morpholinopicolinamide | 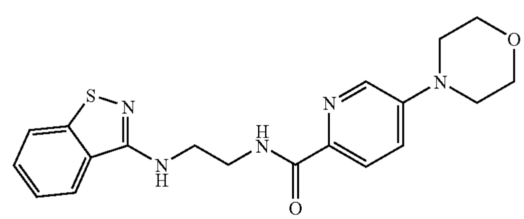 |
| 63 | N-(2-(Benzo[d]isothiazol-3-ylamino)ethyl)-3,4-dimethoxybenzamide | 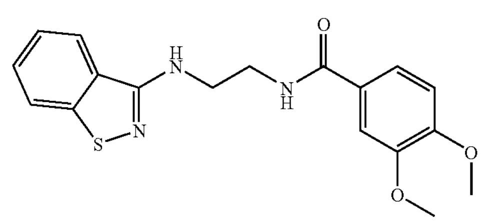 |
| 64 | 1-Acetyl-N-(2-(benzo[d]isothiazol-3-ylamino)ethyl)piperidine-2-carboxamide | 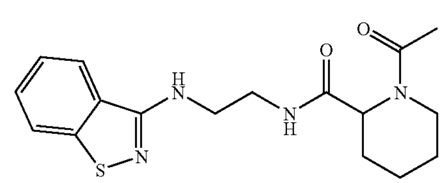 |
| 65 | N-(2-(Benzo[d]isothiazol-3-ylamino)ethyl)-3-chloro-2-methylbenzamide | 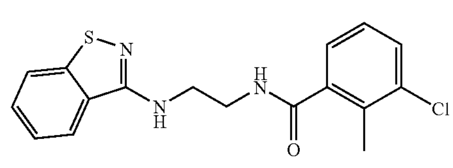 |

TABLE 2-continued

| Entry | Name | Structure |
|---|---|---|
| 66 | N-(2-(Benzo[d]isothiazol-3-ylamino)ethyl)-2-(1-methyl-1H-indol-3-yl)acetamide | 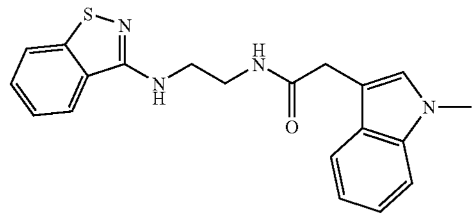 |
| 67 | N-(2-(Benzo[d]isothiazol-3-ylamino)ethyl)-2-phenoxypropanamide | 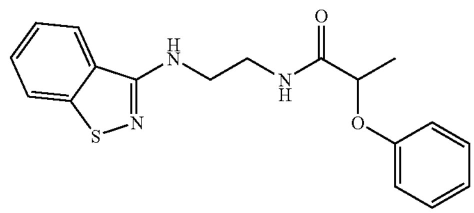 |
| 68 | N-(2-(Benzo[d]isothiazol-3-ylamino)ethyl)-2-(4-methoxyphenyl)acetamide | 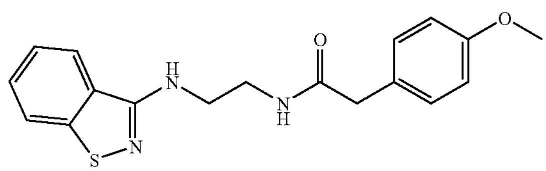 |
| 69 | N-(2-(Benzo[d]isothiazol-3-ylamino)ethyl)-2-(4-chlorophenyl)acetamide | 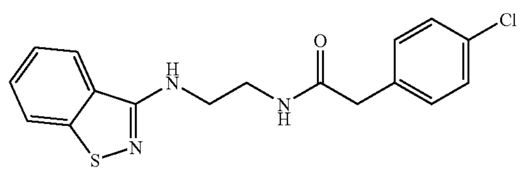 |
| 70 | N-(2-(Benzo[d]isothiazole-3-ylamino)ethyl-4-chlorobenzamide | 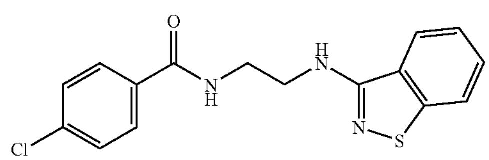 |
| 71 | N-(2-(Benzo[d]isothiazol-3-ylamino)ethyl)-2-cyclopropylacetamide | 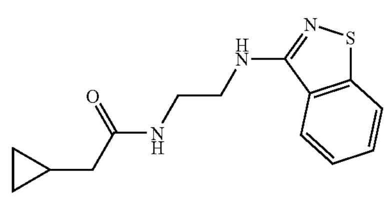 |
| 72 | N-(2-(Benzo[d]isothiazol-3-ylamino)ethyl)isobutyramide | 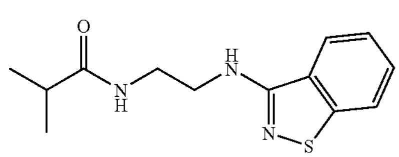 |
| 73 | N-(2-(Benzo[d]isothiazol-3-ylamino)ethyl)piperidine-3-carboxamide | 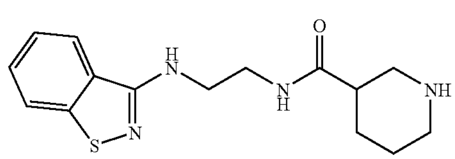 |

TABLE 2-continued

| Entry | Name | Structure |
|---|---|---|
| 74 | (S)-2-Amino-N-(2-(benzo[d]isothiazol-3-ylamino)ethyl)-2-phenylacetamide | 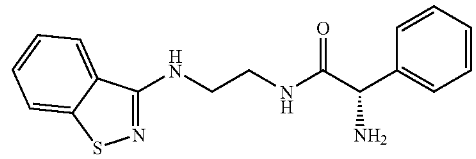 |
| 75 | (S)-2-Amino-N-(2-(benzo[d]isothiazol-3-ylamino)ethyl)-3-methylbutanamide | 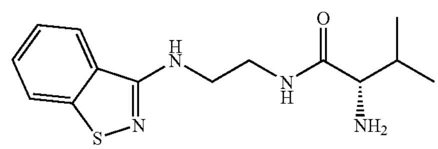 |
| 76 | N-(2-(Benzo[d]isothiazol-3-ylamino)ethyl)-3-methylpicolinamide | 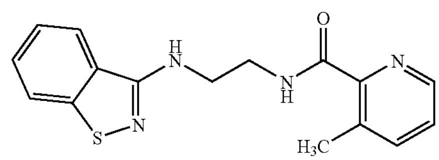 |
| 77 | Methyl 6-(2-(Benzo[d]isothiazol-3-ylamino)ethylcarbamoyl)nicotinate | 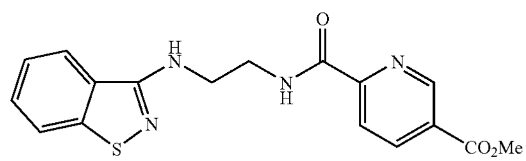 |
| 78 | 6-(2-(Benzo[d]isothiazol-3-ylamino)ethylcarbamoyl)nicotinic Acid | 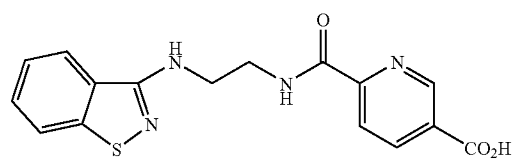 |
| 79 | N-(2-(Benzo[d]isothiazol-3-ylamino)ethyl)quinoline-2-carboxamide | 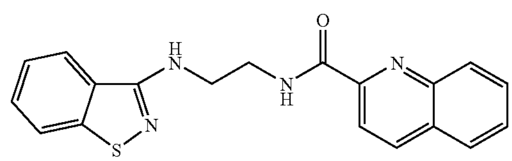 |
| 80 | Methyl 6-(2-(Benzo[d]isothiazol-3-ylamino)ethylcarbamoyl)picolinate | 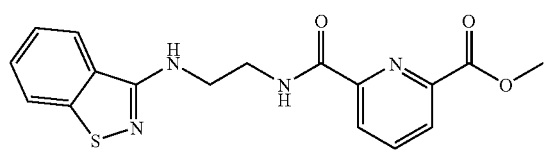 |
| 81 | 6-(2-(Benzo[d]isothiazol-3-ylamino)ethylcarbamoyl)picolinic Acid | 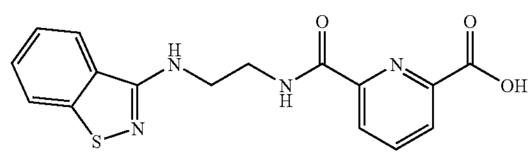 |
| 82 | N-(2-(Benzo[d]isothiazol-3-ylamino)ethyl)-2-(1H-indol-3-yl)acetamide | 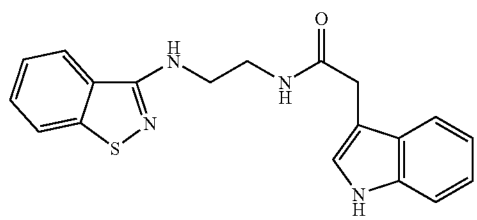 |

TABLE 2-continued

| Entry | Name | Structure |
|---|---|---|
| 83 | N-(2-(Benzo[d]isothiazol-3-ylamino)ethyl)furan-2-carboxamide | 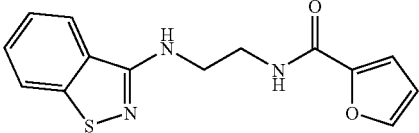 |
| 84 | (S)-N-(2-(Benzo[d]isothiazol-3-ylamino)ethyl)-2-phenyl-2-(phenylsulfonamido)acetamide | 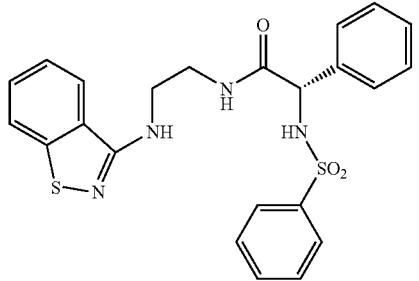 |
| 85 | (S)-N-(2-(2-(Benzo[d]isothiazol-3-ylamino)ethylamino)-2-oxo-1-phenylethyl)picolinamide | 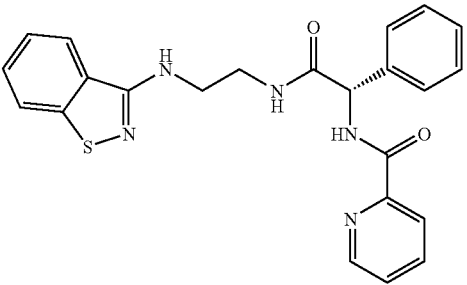 |
| 86 | (S)-N-(2-(2-(Benzo[d]isothiazol-3-ylamino)ethylamino)-2-oxo-1-phenylethyl)butyramide | 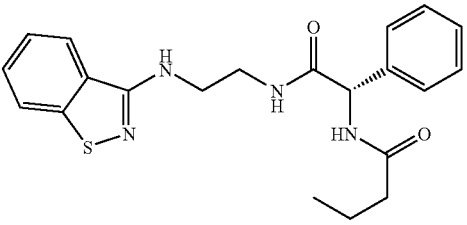 |
| 87 | (S)-N-(2-(2-(Benzo[d]isothiazol-3-ylamino)ethylamino)-2-oxo-1-phenylethyl)furan-3-carboxamide | 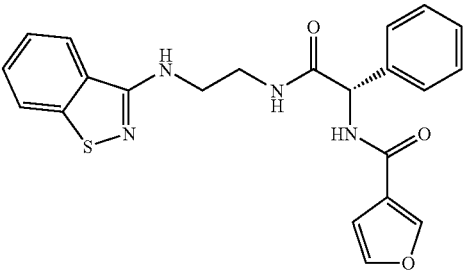 |
| 88 | N-(2-(Benzo[d]isothiazol-3-ylamino)ethyl)benzo[b]thiophene-2-carboxamide | 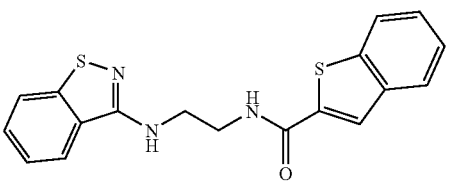 |

TABLE 2-continued

| Entry | Name | Structure |
|---|---|---|
| 89 | N-(2-(Benzo[d]isothiazol-3-ylamino)ethyl)-4-(1H-pyrrol-1-yl)benzamide | 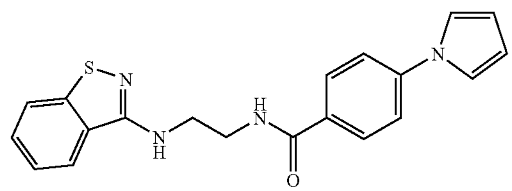 |
| 90 | N-(2-(Benzo[d]isothiazol-3-ylamino)ethyl)-3H-benzo[d][1,2,3]triazole-5-carboxamide | 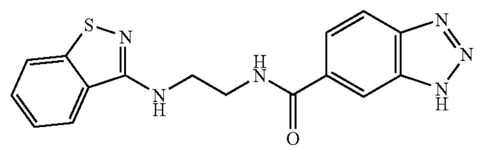 |
| 91 | N-(2-(Benzo[d]isothiazol-3-ylamino)ethyl)-2-methoxynicotinamide | 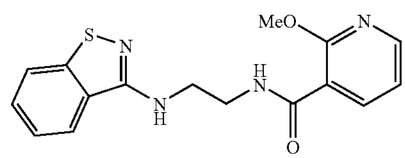 |
| 92 | N-(2-(Benzo[d]isothiazol-3-ylamino)ethyl)thiophene-2-carboxamide | 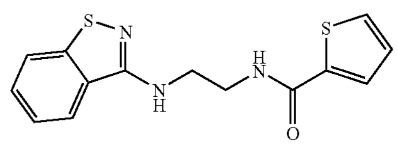 |
| 93 | tert-Butyl 2-(2-(Benzo[d]isothiazol-3-ylamino)ethylcarbamoyl)indoline-1-carboxylate | 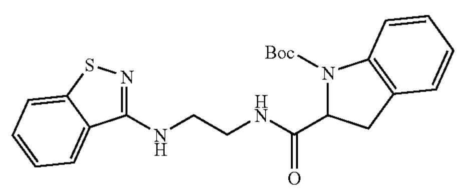 |
| 94 | N-(2-(Benzo[d]isothiazol-3-ylamino)ethyl)pyrazine-2-carboxamide | 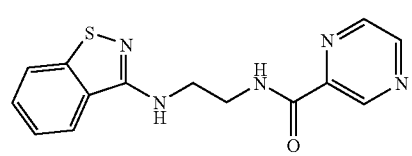 |
| 95 | (S)-tert-Butyl 1-(2-(Benzo[d]isothiazol-3-ylamino)ethylamino)-1-oxo-3-phenylpropan-2-ylcarbamate | 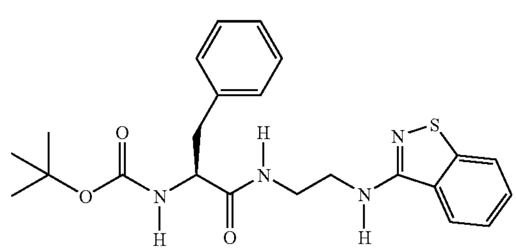 |
| 96 | N-(2-(Benzo[d]isothiazol-3-ylamino)ethyl)quinoline-8-carboxamide | 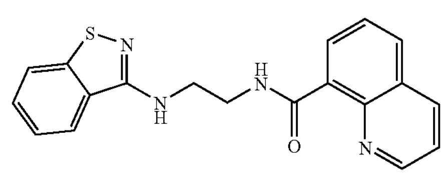 |

TABLE 2-continued

| Entry | Name | Structure |
|---|---|---|
| 97 | (R)-2-Amino-N-(2-(benzo[d]isothiazol-3-ylamino)ethyl)-2-phenylacetamide | 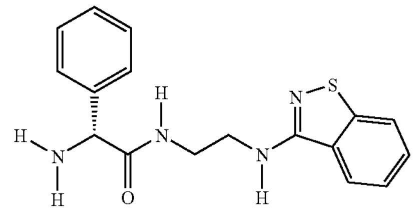 |
| 98 | N-(2-(Benzo[d]isothiazol-3-ylamino)ethyl)piperidine-4-carboxamide | 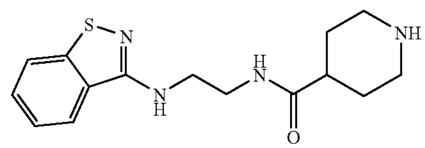 |
| 99 | N-(2-(Benzo[d]isothiazol-3-ylamino)ethyl)isoquinoline-1-carboxamide | 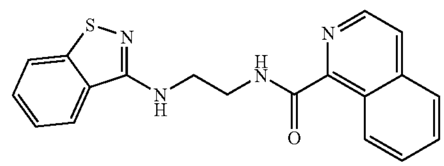 |
| 100 | N-(2-(Benzo[d]isothiazol-3-ylamino)ethyl)-4,5-dichloroisothiazole-3-carboxamide | 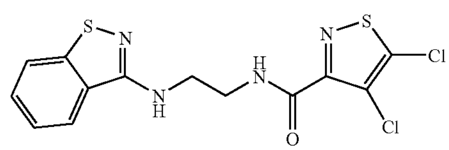 |
| 101 | (R)-Benzyl 1-(2-(Benzo[d]isothiazol-3-ylamino)ethylamino-1-oxo-3-phenylpropan-2-ylcarbamate | 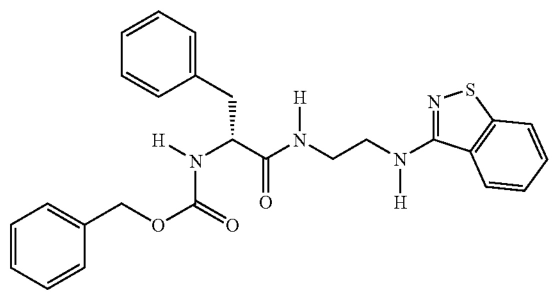 |
| 102 | (S)-N-(1-(2-(Benzo[d]isothiazol-3-ylamino)ethylamino)-1-oxo-3-phenylpropan-2-yl)benzamide | 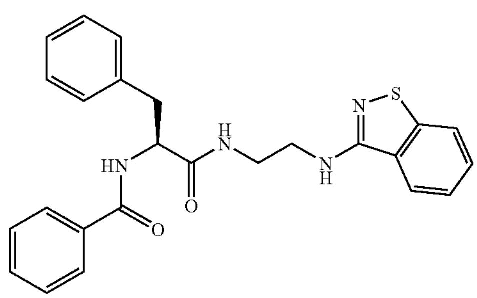 |
| 103 | (S)-2-Acetamido-N-(2-(benzo[d]isothiazol-3-ylamino)ethyl)-3-phenylpropanamide | 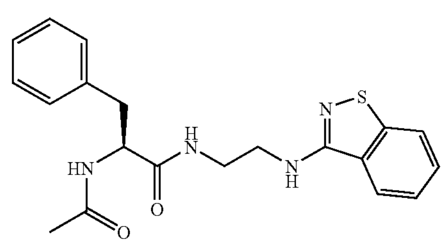 |

TABLE 2-continued

| Entry | Name | Structure |
|---|---|---|
| 104 | (S)-Benzyl 1-(2-(Benzo[d]isothiazol-3-ylamino)ethylamino)-1-oxo-3-phenylpropan-2-ylcarbamate | 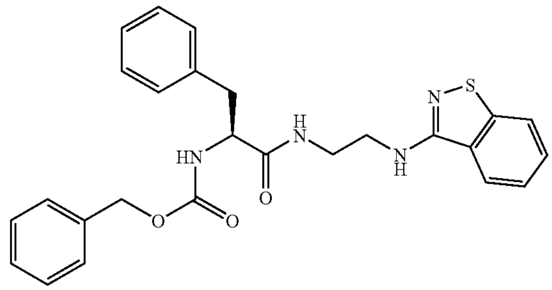 |
| 105 | (S)-Benzyl 2-(2-(Benzo[d]isothiazol-3-ylamino)ethylamino)-2-oxo-1-phenylethylcarbamate | 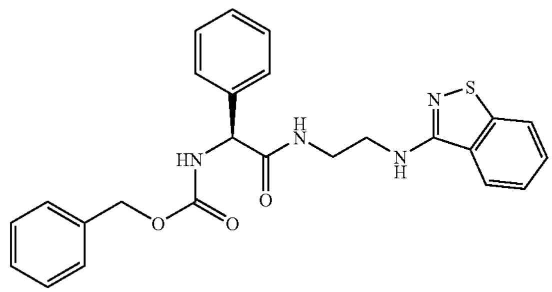 |
| 106 | N-(2-(6-Nitrobenzo[d]isothiazol-3-ylamino)ethyl)picolinamide | 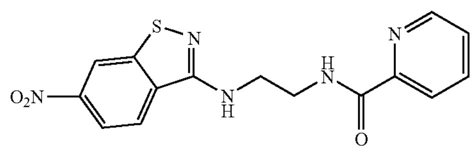 |
| 107 | N-(2-(6-Aminobenzo[d]isothiazol-3-ylamino)ethyl)picolinamide | 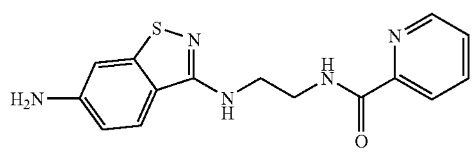 |
| 108 | N-(2-(6-Acetamidobenzo[d]isothiazol-3-ylamino)ethyl)picolinamide | 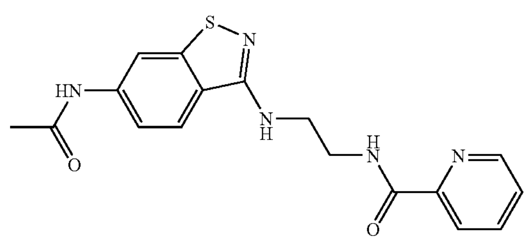 |
| 109 | N-(2-(Benzo[d]isothiazol-3-ylamino)ethyl)-5,6-dimethoxy-1H-indole-2-carboxamide | 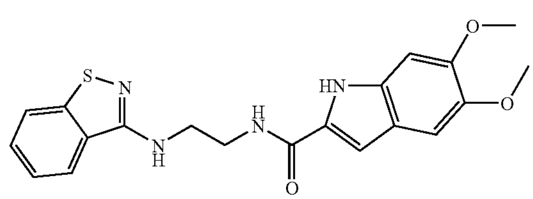 |
| 110 | N-(2-(Benzo[d]isothiazol-3-ylamino)ethyl)-1H-indole-3-carboxamide | 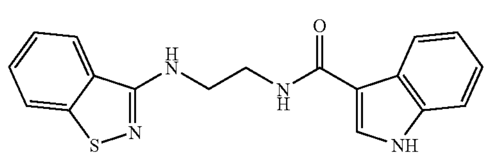 |

TABLE 2-continued

| Entry | Name | Structure |
|---|---|---|
| 111 | N-(2-(Benzo[d]isothiazol-3-ylamino)ethyl)-4-methyl-5-phenylisoxazole-3-carboxamide | 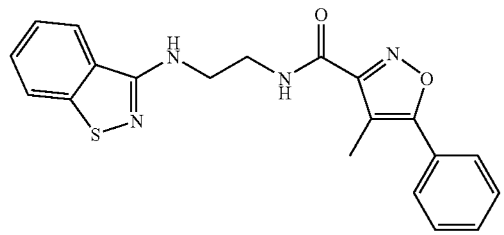 |
| 112 | N-(2-(Benzo[d]isothiazol-3-ylamino)ethyl)-6,6-dimethyl-4-oxo-5,6-dihydro-4H-pyran-2-carboxamide | 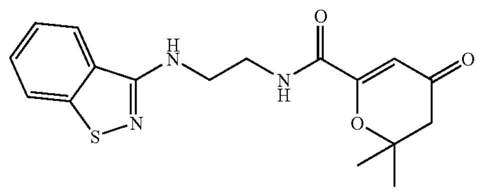 |
| 113 | N-(2-(Benzo[d]isothiazol-3-ylamino)ethyl)-3,5-dichlorobenzamide | 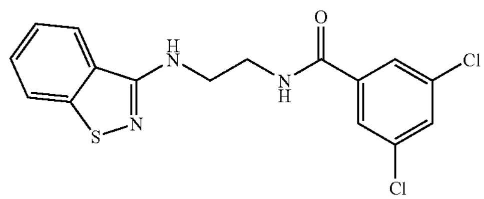 |
| 114 | N-(3-(Benzo[d]isothiazol-3-ylamino)propyl)-4-chlorobenzamide | 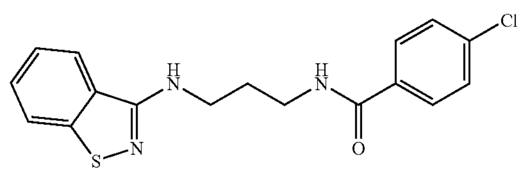 |
| 115 | N-(2-(Benzo[d]isothiazol-3-ylamino)ethyl)-1H-indazole-3-carboxamide | 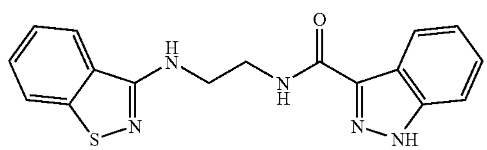 |
| 116 | N-(2-(Benzo[d]isothiazol-3-ylamino)ethyl)imidazo[1,2-a]pyridine-2-carboxamide | 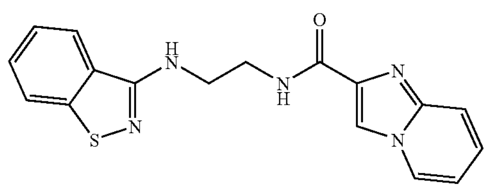 |
| 117 | (S)-2-Amino-N-(3-(benzo[d]isothiazol-3-ylamino)propyl)-2-phenylacetamide | 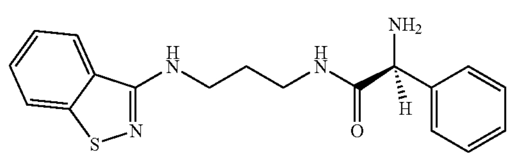 |
| 118 | tert-Butyl 2-(2-(Benzo[d]isothiazol-3-ylamino)ethylcarbamoyl)pyrrolidine-1-carboxylate | 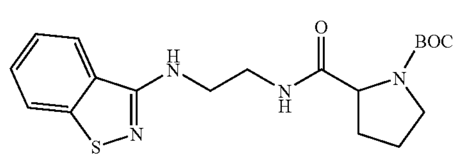 |

TABLE 2-continued

| Entry | Name | Structure |
|---|---|---|
| 119 | N-(2-(Benzo[d]isothiazol-3-ylamino)ethyl)-1-(3,5-dichlorobenzoyl)piperidine-3-carboxamide | 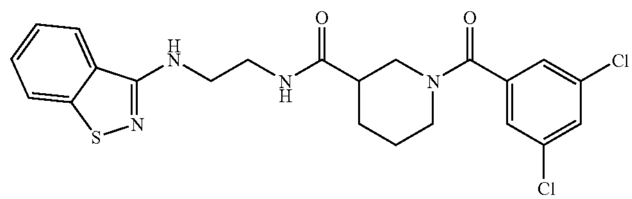 |
| 120 | N-(2-(Benzo[d]isothiazol-3-ylamino)ethyl)-1-(2-(2,2,2-trifluoroacetyl)-1,2,3,4-tetrahydroisoquinolin-7-ylsulfonyl)piperidine-3-carboxamide | 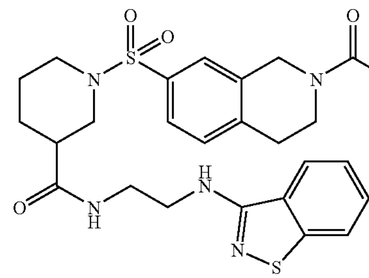 |
| 121 | 4-[N-(2-(Benzo[d]isothiazol-3-ylamino)ethyl)-aminosulfonyl]anisole | 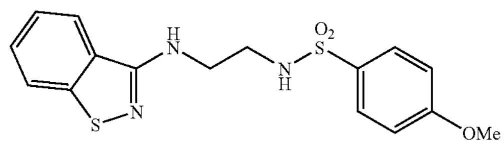 |
| 122 | N-(2-(benzo[d]isothiazol-3-ylamino)ethyl)-3,5-difluorobenzamide | 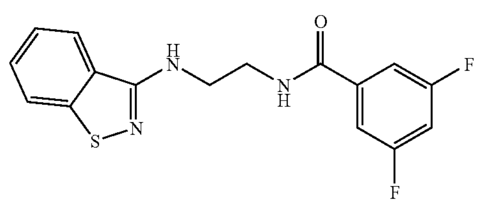 |
| 123 | N-(2-(benzo[d]isothiazol-3-ylamino)ethyl)benzo[d][1,3]dioxole-5-carboxamide | 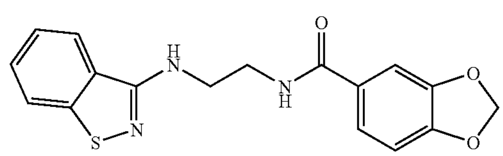 |
| 124 | N-(2-(benzo[d]isothiazol-3-ylamino)ethyl)-3-(trifluoromethyl)benzamide | 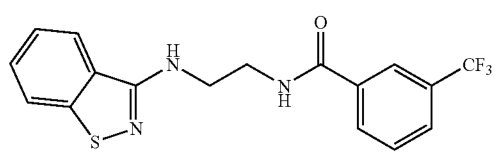 |
| 125 | 4-acetamido-N-(2-(benzo[d]isothiazol-3-ylamino)ethyl)benzamide | 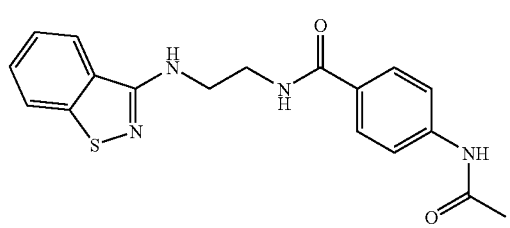 |
| 126 | 4-(2-(benzo[d]isothiazol-3-ylamino)ethylcarbamoyl)benzene-1-sulfonyl fluoride | 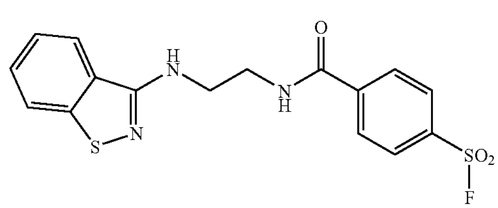 |

TABLE 2-continued

| Entry | Name | Structure |
|---|---|---|
| 127 | N-(2-(benzo[d]isothiazol-3-ylamino)ethyl)-3,5-bis(trifluoromethyl)benzamide | 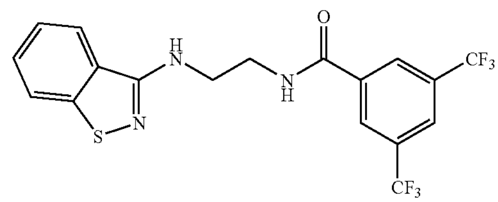 |
| 128 | N-(2-(benzo[d]isothiazol-3-ylamino)ethyl)-3,4-dichlorobenzamide | 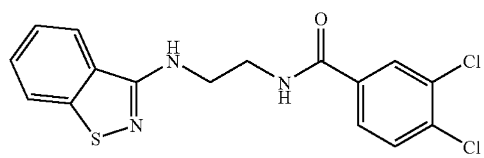 |
| 129 | N-(2-(benzo[d]isothiazol-3-ylamino)ethyl)-2-chloro-5-fluorobenzamide | 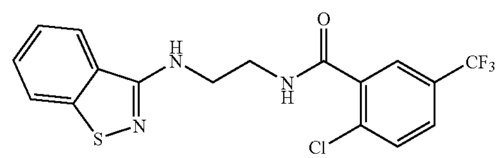 |
| 130 | N-(2-(benzo[d]isothiazol-3-ylamino)ethyl)-2-chloro-5-(trifluoromethyl)benzamide | 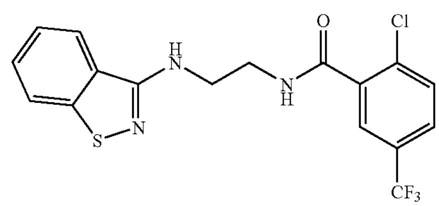 |
| 131 | N-(2-(benzo[d]isothiazol-3-ylamino)ethyl)-4-butylbenzamide | 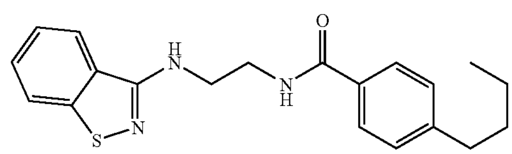 |
| 132 | N-(2-(benzo[d]isothiazol-3-ylamino)ethyl)-4-butoxybenzamide | 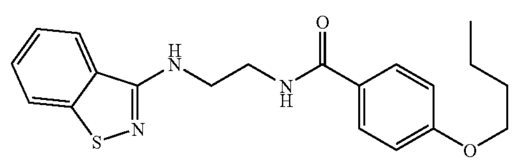 |
| 133 | N-(2-(benzo[d]isothiazol-3-ylamino)ethyl)-2,4,6-trimethylbenzamide | 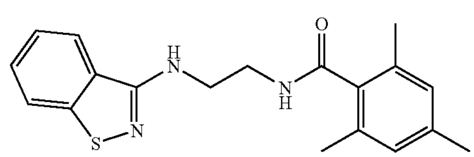 |
| 134 | N-(2-(benzo[d]isothiazol-3-ylamino)ethyl)-3-(morpholinomethyl)benzamide | 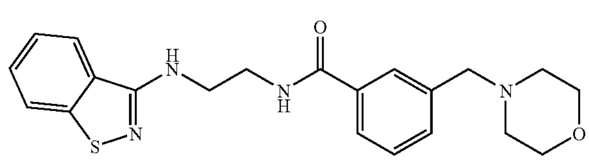 |

TABLE 2-continued

| Entry | Name | Structure |
|---|---|---|
| 135 | (benzo[d]isothiazol-3-ylamino)ethyl)-aminocarbonyl-(4-morpholine sulfono)benzene | 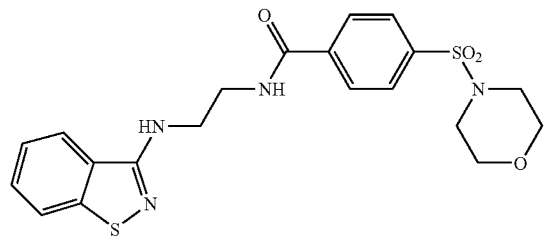 |
| 136 | N-(2-(benzo[d]isothiazol-3-ylamino)ethyl)-3-((3-(dimethylamino)cyclopentyl)methyl)benzamide | 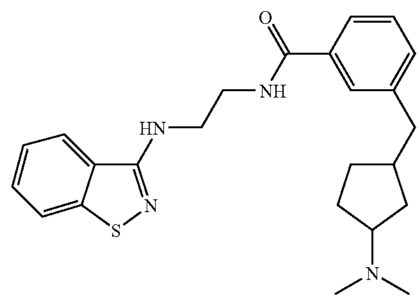 |
| 137 | N-(2-(benzo[d]isothiazol-3-ylamino)ethyl)-4-chloro-3-nitrobenzamide | 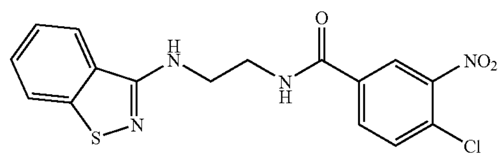 |
| 138 | N-(2-(benzo[d]isothiazol-3-ylamino)ethyl)-3-iodobenzamide | 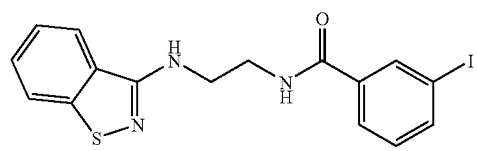 |
| 139 | N-(2-(benzo[d]isothiazol-3-ylamino)ethyl)aminocarbonyl-(3-phenyl)benzene | 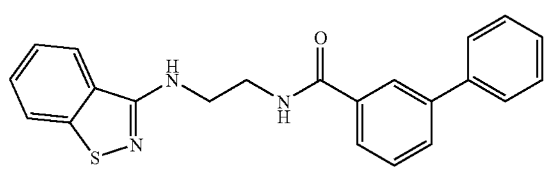 |
| 140 | N-(2-(benzo[d]isothiazol-3-ylamino)ethyl)-3-((4-benzylpiperazin-1-yl)methyl)benzamide | 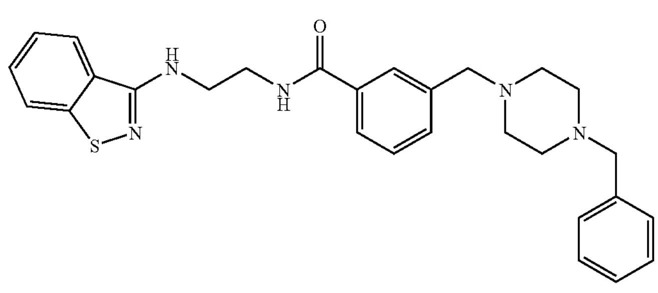 |
| 141 | N-(2-(benzo[d]isothiazol-3-ylamino)ethyl)aminocarbonyl-[3-(2-methoxyphenyl)]benzene | 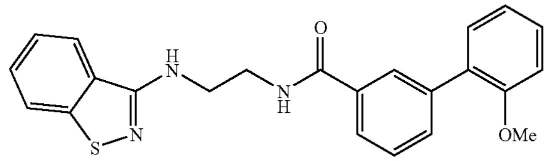 |

TABLE 2-continued

| Entry | Name | Structure |
|---|---|---|
| 142 | N-(2-(benzo[d]isothiazol-3-ylamino)ethyl)-3-((4-phenylpiperazin-1-yl)methyl)benzamide | 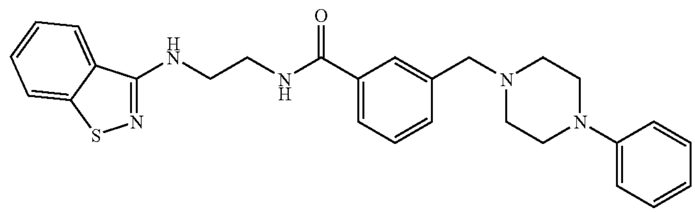 |
| 143 | N-(2-(benzo[d]isothiazol-3-ylamino)ethyl)-3-((dimethylamino)methyl)benzamide | 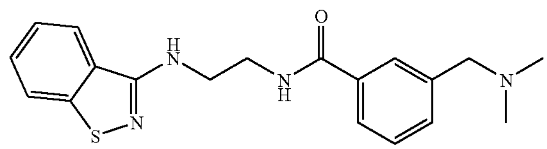 |
| 144 | N-(2-(benzo[d]isothiazol-3-ylamino)ethyl)-3-((benzylamino)methyl)benzamide | 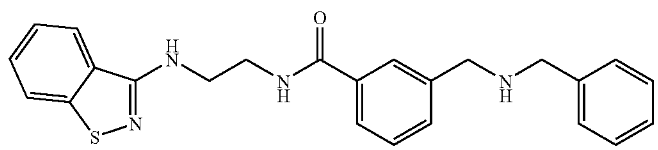 |
| 145 | 3-((4-((benzo[d][1,3]dioxol-5-yl)methyl)piperazin-1-yl)methyl)-N-(2-(benzo[d]isothiazol-3-ylamino)ethyl)benzamide | 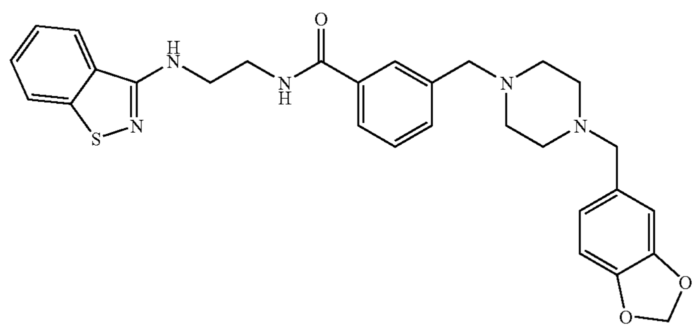 |
| 146 | 3-((3-acetamidopyrrolidin-1-yl)methyl)-N-(2-(benzo[d]isothiazol-3-ylamino)ethyl)benzamide | 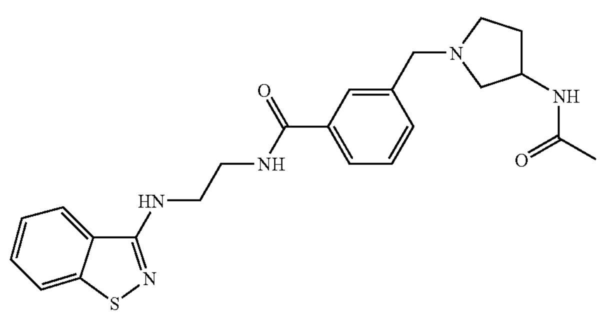 |
| 147 | 4-tert-butyl-N-(2-(benzo[d]isothiazol-3-ylamino)ethyl)benzamide | 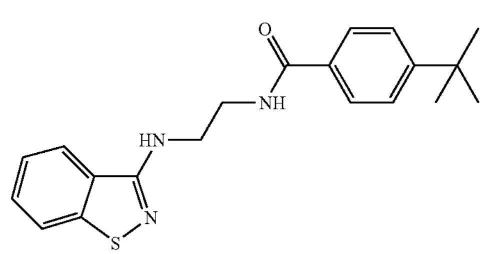 |

TABLE 2-continued

| Entry | Name | Structure |
|---|---|---|
| 148 | N-(2-(benzo[d]isothiazol-3-ylamino)ethyl)-3-(1H-indol-5-yl)benzamide | 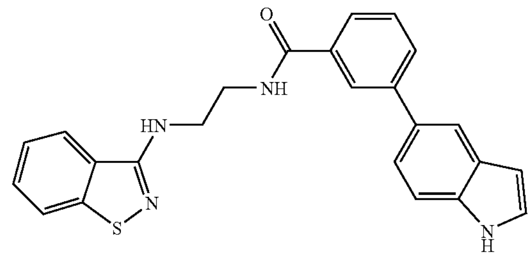 |
| 149 | N-(2-(benzo[d]isothiazol-3-ylamino)ethyl)aminocarbonyl-[3-(2,4-methoxyphenyl)]benzene | 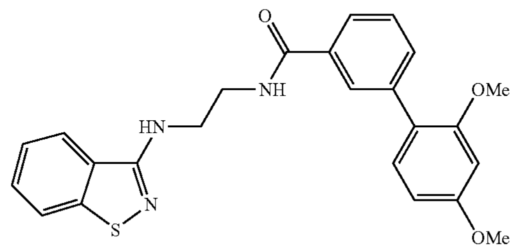 |
| 150 | 3-(benzo[b]thiophen-2-yl)-N-(2-(benzo[d]isothiazol-3-ylamino)ethyl)benzamide | 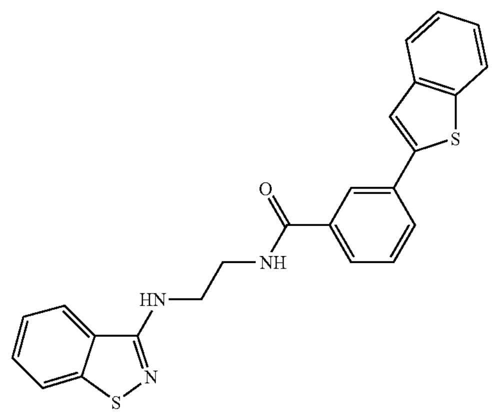 |
| 151 | N-(2-(benzo[d]isothiazol-3-ylamino)ethyl)aminocarbonyl-[4-(benzylsulfonamido)]benzene | 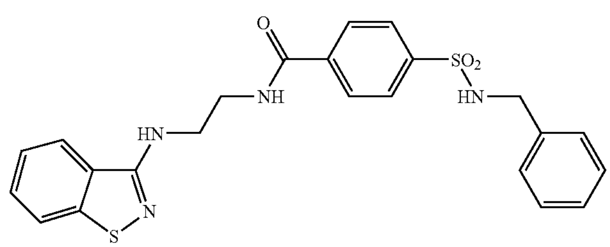 |
| 152 | N-(2-(benzo[d]isothiazol-3-ylamino)ethyl)-3-((methylamino)methyl)benzamide | 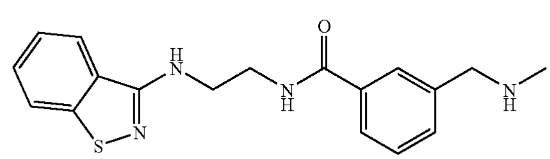 |
| 153 | N-(2-(benzo[d]isothiazol-3-ylamino)ethyl)-4-ethylbenzamide | 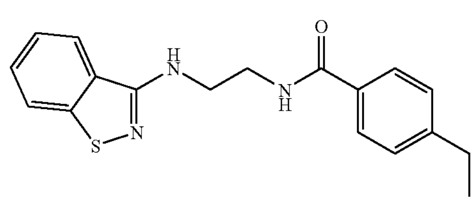 |

TABLE 2-continued

| Entry | Name | Structure |
|---|---|---|
| 154 | N-(2-(benzo[d]isothiazol-3-ylamino)ethyl)-4-(pentyloxy)benzamide | 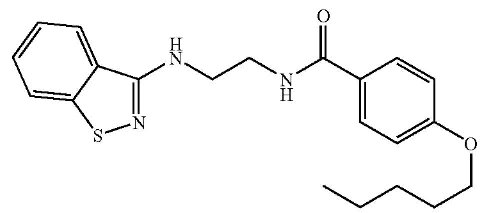 |
| 155 | N-(2-(benzo[d]isothiazol-3-ylamino)ethyl)-4-pentylbenzamide | 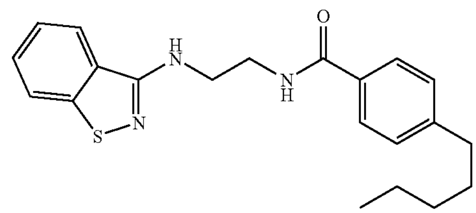 |
| 156 | N-(2-(benzo[d]isothiazol-3-ylamino)ethyl)-4-isopropylbenzamide | 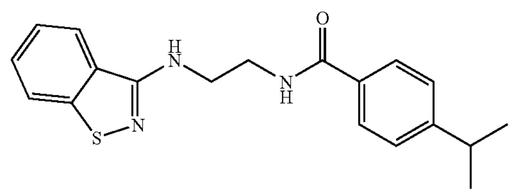 |
| 157 | N-(2-(benzo[d]isothiazol-3-ylamino)ethyl)-4-cyclohexylbenzamide | 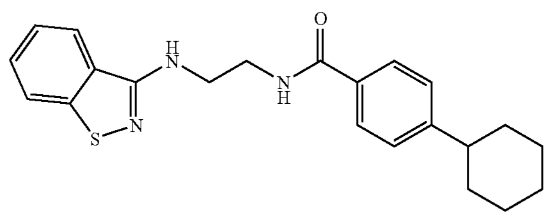 |
| 158 | N-(2-(benzo[d]isothiazol-3-ylamino)ethyl)-4-propoxybenzamide | 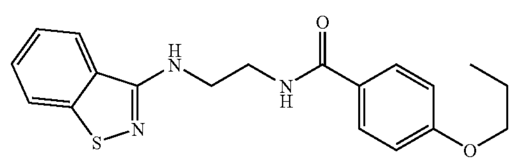 |
| 159 | N-(2-(benzo[d]isothiazol-3-ylamino)ethyl)aminocarbonyl-[-4-(2-methoxyphenyl)]benzene | 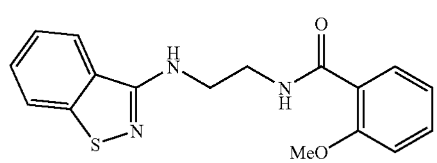 |
| 160 | N-(2-(benzo[d]isothiazol-3-ylamino)ethyl)aminocarbonyl-[-4-(n-butylsulfonamido)]benzene | 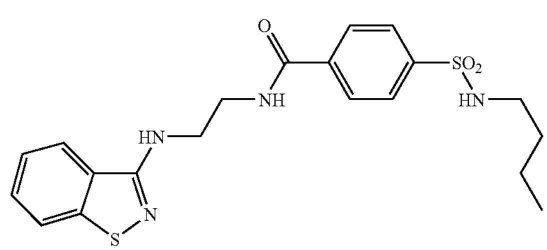 |

TABLE 2-continued

| Entry | Name | Structure |
|---|---|---|
| 161 | N-(2-(benzo[d]isothiazol-3-ylamino)ethyl)aminocarbonyl-[-4-(isopropylsulfonamido)]benzene | 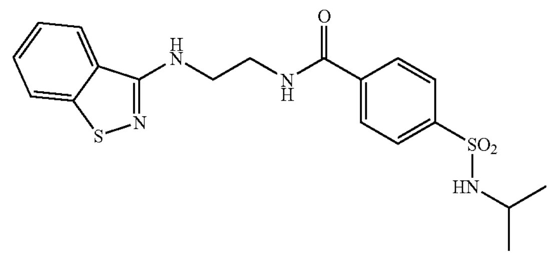 |
| 162 | 1-(2-(benzo[d]isothiazol-3-ylamino)ethyl)-3-(2,4-dichlorophenyl)urea | 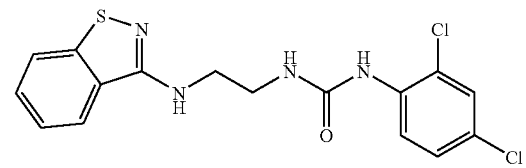 |
| 163 | N-(2-(benzo[d]isothiazol-3-ylamino)ethyl)-4-(hydroxymethyl)benzamide | 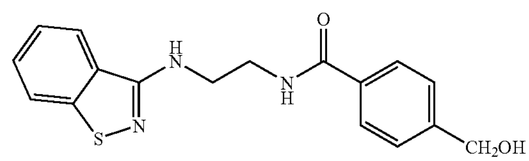 |
| 164 | N-(2-(benzo[d]isothiazol-3-ylamino)ethyl)aminocarbonyl-[-4-(sulfonamido)]benzene | 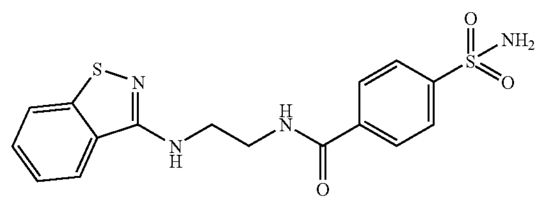 |
| 165 | N-(2-(benzo[d]isothiazol-3-ylamino)ethyl)-4-(methylsulfonyl)-2-chlorobenzamide | 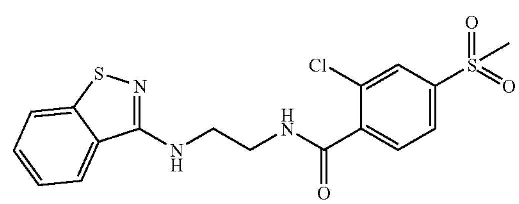 |
| 166 | N-(2-(benzo[d]isothiazol-3-ylamino)ethyl)aminocarbonyl-[-4-(methylsulfonyl)benzene | 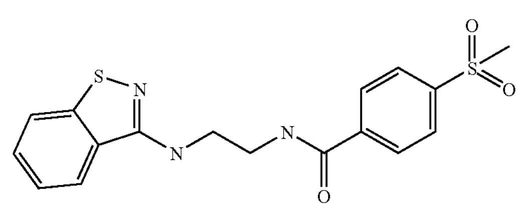 |
| 167 | 4-(2-(benzo[d]isothiazol-3-ylamino)ethylcarbamoyl)phenyl acetate | 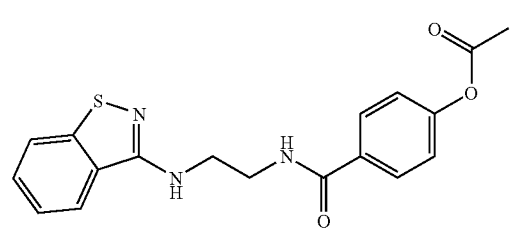 |

TABLE 2-continued

| Entry | Name | Structure |
|---|---|---|
| 168 | 4-(2-(benzo[d]isothiazol-3-ylamino)ethyl)aminocarbonyl-[-2-(4-methylbenzoyl)benzene | 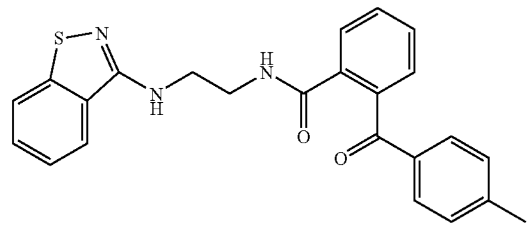 |
| 169 | 4-(2-(benzo[d]isothiazol-3-ylamino)ethyl)aminocarbonyl-(-2-benzoyl)benzene | 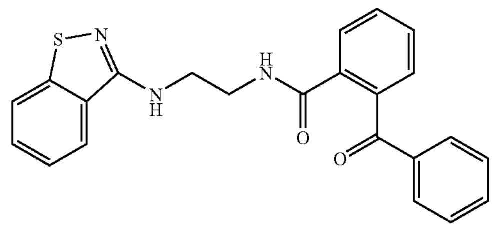 |
| 170 | N-(2-(benzo[d]isothiazol-3-ylamino)ethyl)-2,5-dimethylbenzamide | 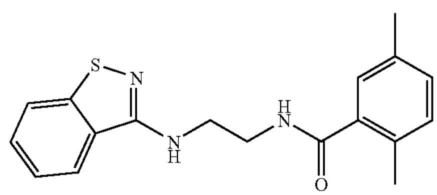 |
| 171 | N-(2-(benzo[d]isothiazol-3-ylamino)ethyl)-4-(3-methyl-5-oxopyrazolidin-1-yl)benzamide | 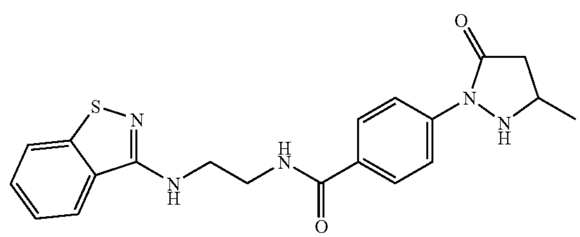 |
| 172 | N-(2-(benzo[d]isothiazol-3-ylamino)ethyl)-2,4,5-trifluorobenzamide | 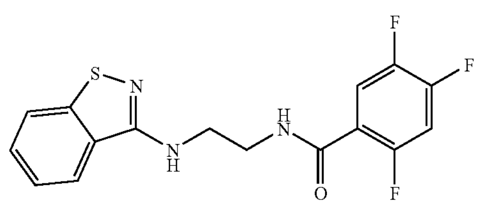 |
| 173 | N-(2-(benzo[d]isothiazol-3-ylamino)ethyl)-1H-benzo[d]imidazole-5-carboxamide | 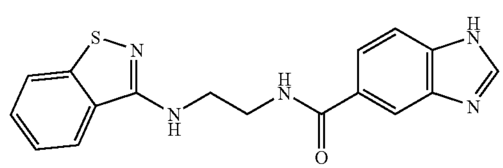 |
| 174 | N-(2-(benzo[d]isothiazol-3-ylamino)ethyl)-4-bromo-2-methylbenzamide | 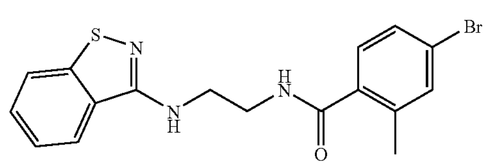 |

TABLE 2-continued

| Entry | Name | Structure |
|---|---|---|
| 175 | N-(2-(benzo[d]isothiazol-3-ylamino)ethyl)-2-chloro-4-fluorobenzamide | 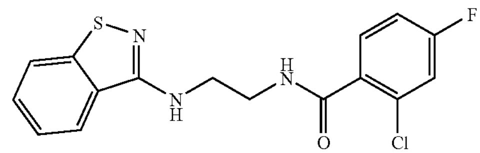 |
| 176 | N-(2-(benzo[d]isothiazol-3-ylamino)ethyl)-1H-indole-6-carboxamide | 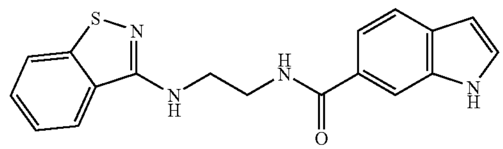 |
| 177 | N-(2-(benzo[d]isothiazol-3-ylamino)ethyl)-2,3-dihydrobenzofuran-7-carboxamide | 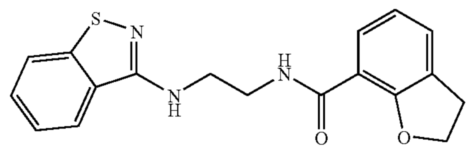 |
| 178 | 4-(2-(benzo[d]isothiazol-3-ylamino)ethyl)aminocarbonyl-(-4-benzoyl)benzene | 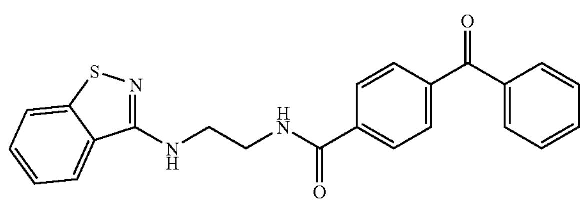 |
| 179 | N-(2-(benzo[d]isothiazol-3-ylamino)ethyl)-3-(methylsulfonyl)benzamide | 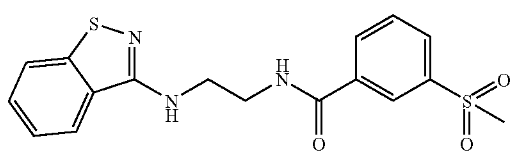 |
| 180 | 4-(2-(benzo[d]isothiazol-3-ylamino)ethyl)aminocarbonyl-[-2-(4-trifluoromethyl)phenyl]benzene | 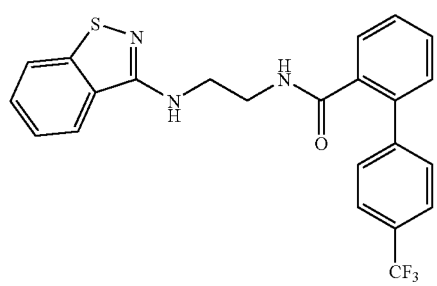 |
| 181 | N-(2-(benzo[d]isothiazol-3-ylamino)ethyl)-5-bromo-2-chlorobenzamide | 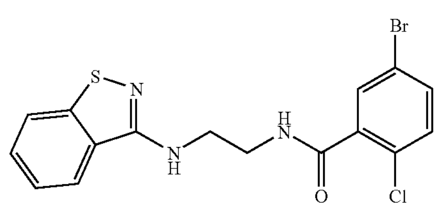 |
| 182 | N-(2-(benzo[d]isothiazol-3-ylamino)ethyl)-3-bromo-4-fluorobenzamide | 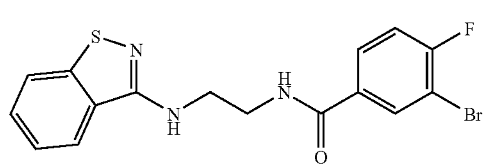 |

TABLE 2-continued

| Entry | Name | Structure |
|---|---|---|
| 183 | methyl 4-(2-(benzo[d]isothiazol-3-ylamino)ethylcarbamoyl)benzoate | 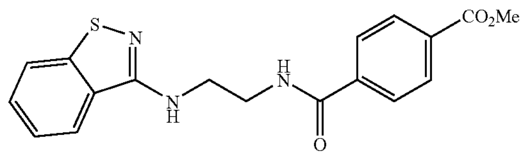 |
| 184 | N-(2-(benzo[d]isothiazol-3-ylamino)ethyl)-4-chloro-3-(trifluoromethyl)benzamide | 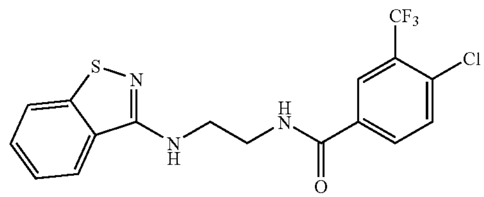 |
| 185 | N-(2-(benzo[d]isothiazol-3-ylamino)ethyl)-2,3-dihydrobenzofuran-6-carboxamide | 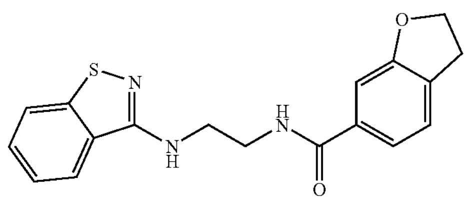 |
| 186 | N-(2-(benzo[d]isothiazol-3-ylamino)ethyl)benzo[d]thiazole-5-carboxamide | 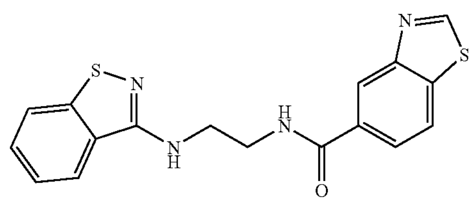 |
| 187 | 4-(2-(benzo[d]isothiazol-3-ylamino)ethylcarbamoyl)benzoic acid | 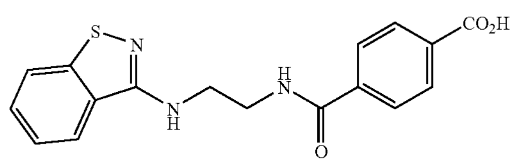 |
| 188 | 3-(2-(benzo[d]isothiazol-3-ylamino)ethylcarbamoyl)benzoic acid | 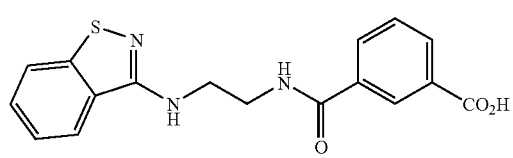 |
| 189 | N-(2-(benzo[d]isothiazol-3-ylamino)ethyl)benzo[d]oxazol-2-amine | 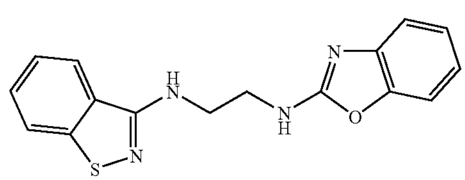 |
| 190 | N-(3-(benzo[d]isothiazol-3-ylamino)propyl)benzo[d]oxazol-2-amine | 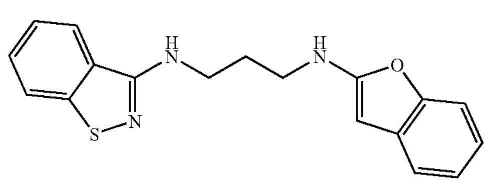 |

TABLE 2-continued

| Entry | Name | Structure |
|---|---|---|
| 191 | N-(2-(5-(trifluoromethyl)pyrimidin-2-ylamino)ethyl)benzo[d]isothiazol-3-amine | 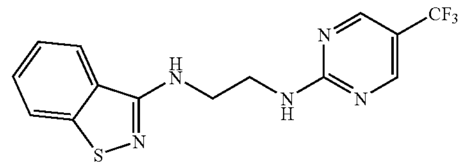 |
| 192 | N-(2-(benzo[d]isothiazol-3-ylamino)ethyl)aminosulfonyl-3,5-dichlorobenzene | 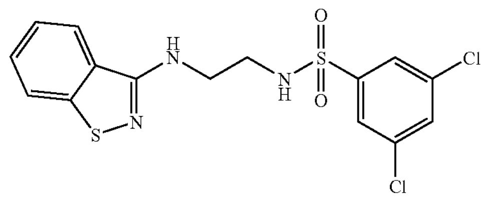 |
| 193 | N-(2-(benzo[d]isothiazol-3-ylamino)ethyl) aminosulfonyl-2,4-dichloro-5-methylbenzen | 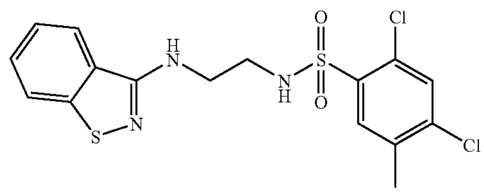 |
| 194 | N-(2-(benzo[d]isothiazol-3-ylamino)ethyl)aminosulfonyl-2,4-dichloro-5-methylbenzene | 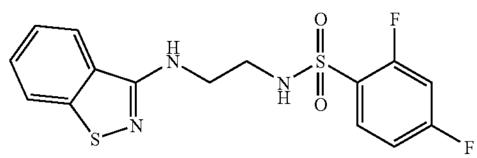 |
| 195 | 1-(3-(benzo[d]isothiazol-3-ylamino)propyl)-3-(2,4-dichlorophenyl)urea | 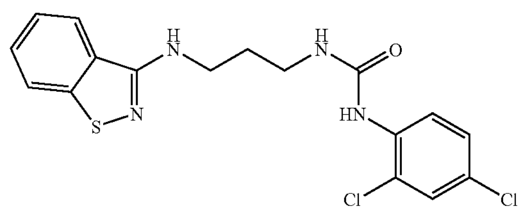 |
| 196 | N-(3-(benzo[d]isothiazol-3-ylamino)propyl)-5-methoxy-1H-indole-2-carboxamide | 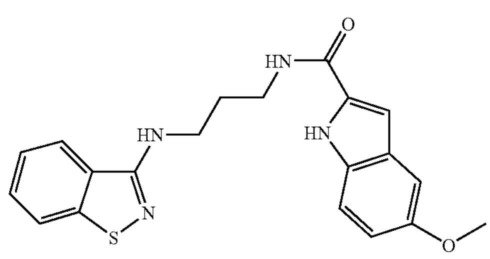 |
| 197 | (R)-1-(2-amino-2-phenylacetyl)-N-(2-(benzo[d]isothiazol-3-ylamino)ethyl)piperidine-3-carboxamide | 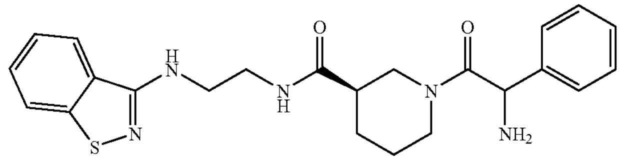 |

TABLE 2-continued

| Entry | Name | Structure |
|---|---|---|
| 198 | 6-acetamido-N-(3-(benzo[d]isothiazol-3-ylamino)propyl)pyridine-2-carboxamide | 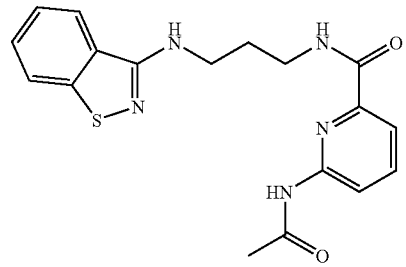 |
| 199 | (S)-1-(2-amino-2-phenylacetyl)-N-(2-(benzo[d]isothiazol-3-ylamino)ethyl)piperidine-3-carboxamide | 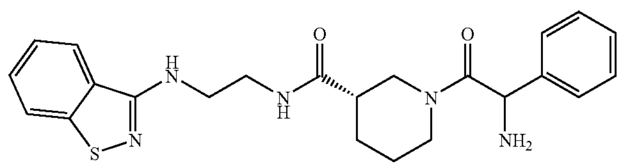 |
| 200 | (R)-1-(2-amino-2-benzylacetyl)-N-(2-(benzo[d]isothiazol-3-ylamino)ethyl)piperidine-3-carboxamide | 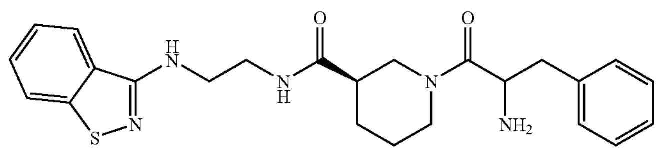 |
| 201 | (S)-1-(2-amino-2-benzylacetyl)-N-(2-(benzo[d]isothiazol-3-ylamino)ethyl)piperidine-3-carboxamide | 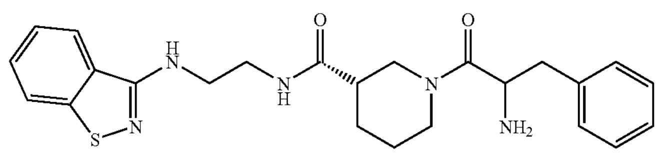 |
| 202 | 1-(3-(benzo[d]isothiazol-3-ylamino)propyl)-3-(2,4-dichlorophenyl)thiourea | 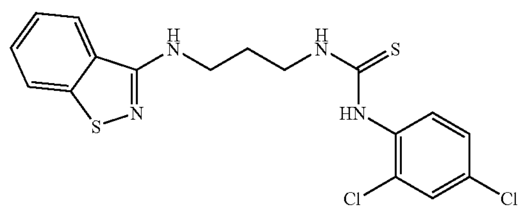 |
| 203 | methyl 6-(2-(benzo[d]isothiazol-3-ylamino)ethylamino)pyridine-3-carboxylate | 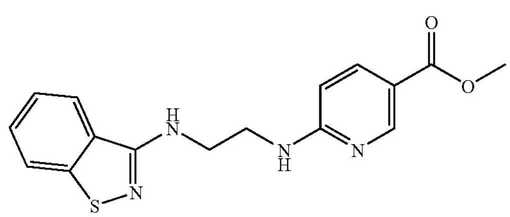 |
| 204 | tert-butyl 1-(methoxycarbonyl)-2-(benzo[d]isothiazol-3-ylamino)ethylcarbamate | 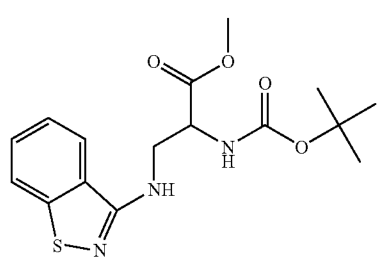 |

TABLE 2-continued

| Entry | Name | Structure |
|---|---|---|
| 205 | methyl 2-amino-3-(benzo[d]isothiazol-3-ylamino)propanoate | 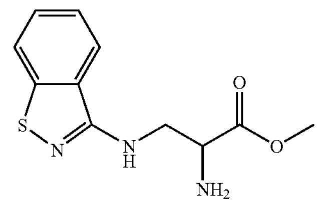 |
| 206 | N-(3-(benzo[d]isothiazol-3-ylamino)propyl)-4-butylbenzamide | 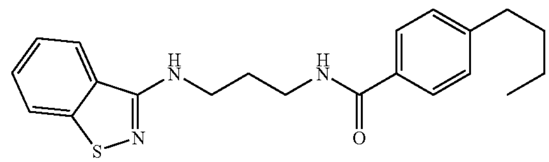 |
| 207 | N-(3-(benzo[d]isothiazol-3-ylamino)propyl)-2,4-dichlorobenzamide | 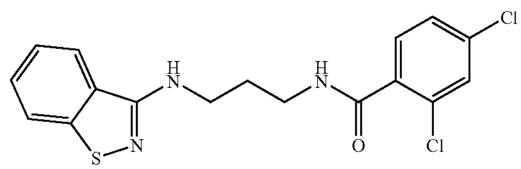 |
| 208 | N-(3-(benzo[d]isothiazol-3-ylamino)propyl)-3,4-dimethoxybenzamide | 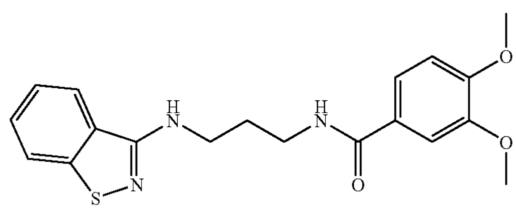 |
| 209 | N-(2-(benzo[d]isothiazol-3-ylamino)-(1-methoxycarbonyl)-ethyl)aminocarbonyl-(-4-butyl)benene | 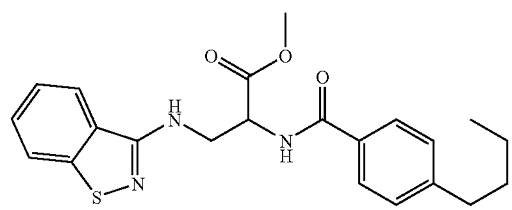 |
| 210 | N-(2-(benzo[d]isothiazol-3-ylamino)ethyl) aminosulfonyl-4-isopropylbenzene | 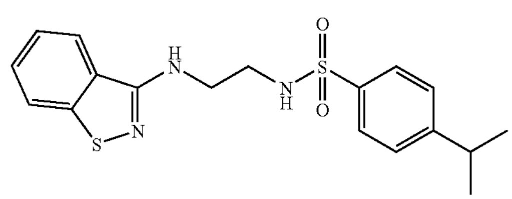 |
| 211 | N-(2-(benzo[d]isothiazol-3-ylamino)ethyl) aminosulfonyl-4-n-butylbenzene | 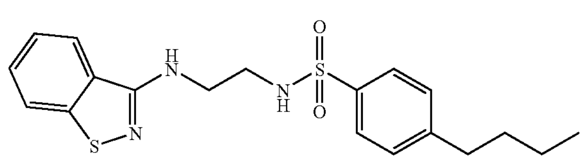 |
| 212 | N-(2-(benzo[d]isothiazol-3-ylamino)ethyl) aminosulfonyl-4-n-pentylbenzene | 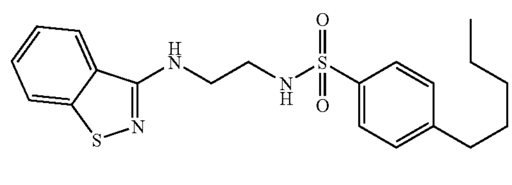 |

TABLE 2-continued

| Entry | Name | Structure |
|---|---|---|
| 213 | N-(2-(benzo[d]isothiazol-3-ylamino)ethyl) aminosulfonyl-4-n-propylbenzene | 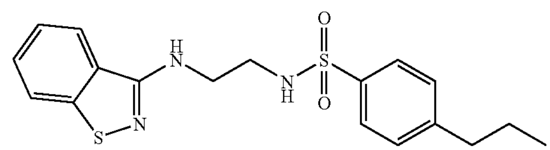 |
| 214 | N-(3-(benzo[d]isothiazol-3-ylamino)propyl) aminosulfonyl-2,4-difluoro benzene | 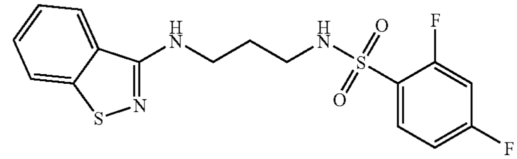 |
| 215 | N-(3-(benzo[d]isothiazol-3-ylamino)propyl) aminosulfonyl-4-n-butylbenzene | 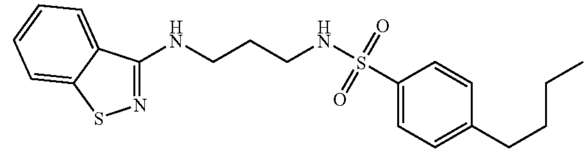 |
| 216 | N-(3-(benzo[d]isothiazol-3-ylamino)propyl) aminosulfonyl-4-n-butylbenzene | 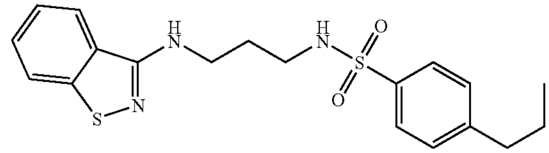 |
| 217 | N-(3-(benzo[d]isothiazol-3-ylamino)propyl) amino sulfonyl-2-trifluoromethylbenzene | 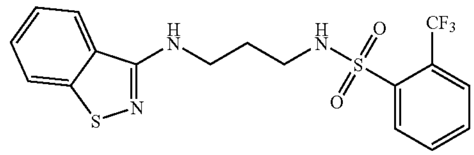 |
| 218 | (2-(Benzo[d]isothiazol-3-ylamino)ethyl)-[2-benzoyl-3-(pyrimidin-2-yl)]guanidine | 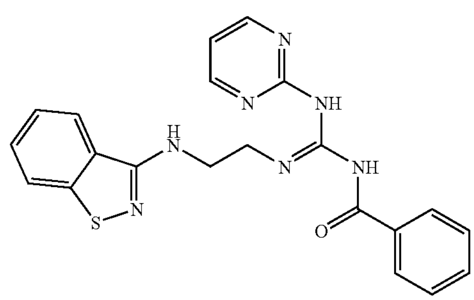 |
| 219 | (2-(benzo[d]isothiazol-3-ylamino)ethyl)-3-(pyrimidin-2-yl)guanidine | 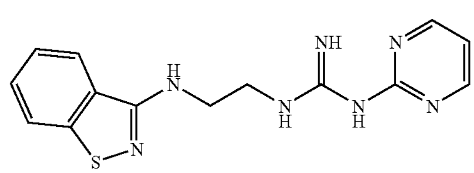 |
| 220 | N-(3-(benzo[d]isothiazol-3-ylamino)propyl)-3-methoxybenzenesulfonamide | 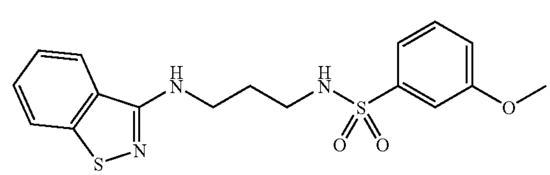 |

TABLE 2-continued

| Entry | Name | Structure |
|---|---|---|
| 221 | N-(3-(benzo[d]isothiazol-3-ylamino)propyl)-4-bromo-2,5-difluorobenzenesulfonamide | 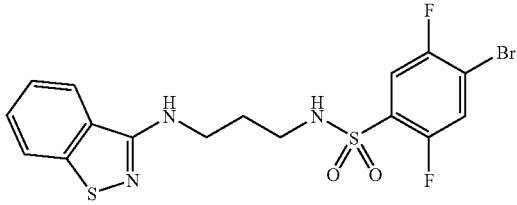 |
| 222 | N-(3-(benzo[d]isothiazol-3-ylamino)propyl)-5-bromothiophene-2-sulfonamide | 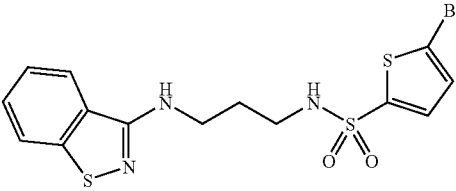 |
| 223 | N-(3-(benzo[d]isothiazol-3-ylamino)propyl)-4-(4-chlorophenoxy)benzenesulfonamide | 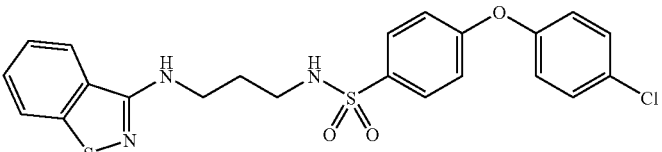 |
| 224 | 6-(3-(benzo[d]isothiazol-3-ylamino)propylamino)pyridine-3-carbonitrile | 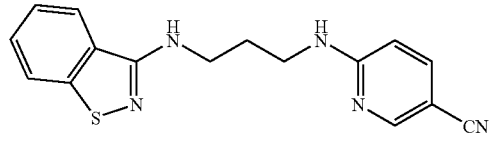 |
| 225 | methyl 2-(3-(benzo[d]isothiazol-3-ylamino)propylamino)-4-(trifluoromethyl)pyrimidine-5-carboxylate | 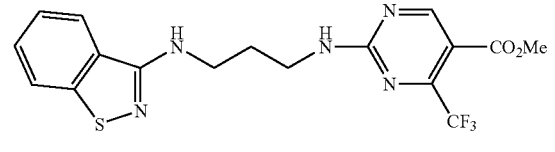 |
| 226 | N-(3-(5-chloropyridin-2-ylamino)propyl)benzo[d]isothiazol-3-amine | 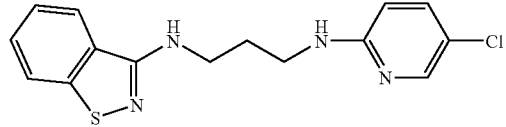 |
| 227 | N-(3-(4-methylpyridin-2-ylamino)propyl)benzo[d]isothiazol-3-amine | 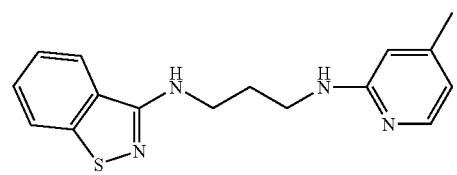 |
| 228 | N-(3-(5-(trifluoromethyl)pyridin-2-ylamino)propyl)benzo[d]isothiazol-3-amine | 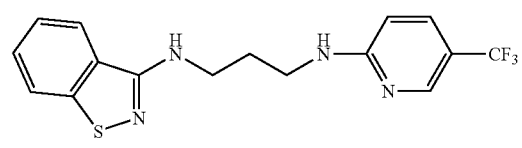 |
| 229 | 2-(3-(benzo[d]isothiazol-3-ylamino)propylamino)pyridine-4-carbonitrile | 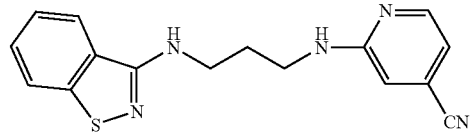 |

TABLE 2-continued

| Entry | Name | Structure |
|---|---|---|
| 230 | N¹-(benzo[d]isothiazol-3-yl)-N³-(6-chloropyridin-2-yl)propane-1,3-diamine | 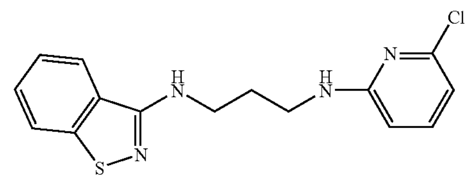 |
| 231 | N¹-(benzo[d]isothiazol-3-yl)-N³-(4-(trifluoromethyl)pyridin-2-yl)propane-1,3-diamine | 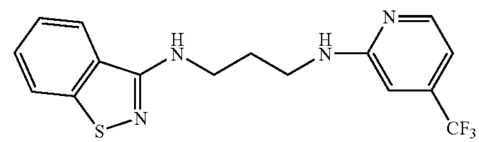 |
| 232 | N-(3-(benzo[d]isothiazol-3-ylamino)propyl)-3-(2-hydroxy-3-morpholinopropoxy)benzamide | 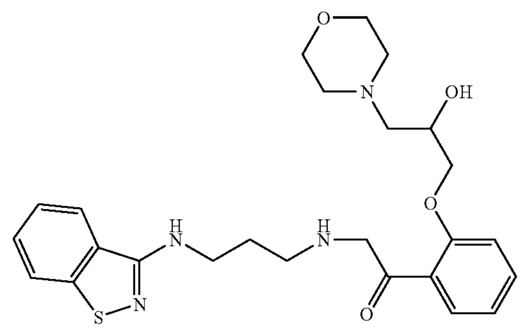 |
| 233 | N-(3-(benzo[d]isothiazol-3-ylamino)propyl)-3-(2-hydroxy-3-(4-(3-methoxyphenyl)piperazin-1-yl)propoxy)benzamide | 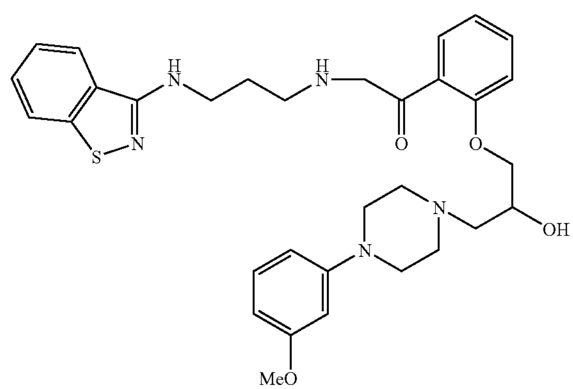 |
| 234 | N-(3-(benzo[d]isothiazol-3-ylamino)propyl)-4-fluorobenzamide | 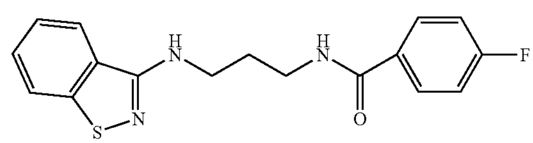 |
| 235 | N-(3-(benzo[d]isothiazol-3-ylamino)propyl)-4-(pyridin-4-ylmethoxy)benzamide | 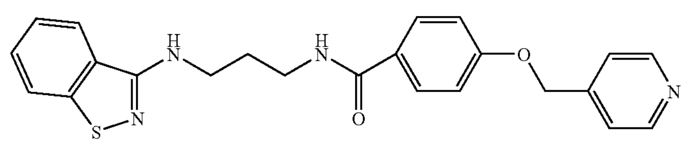 |
| 236 | N-(3-(benzo[d]isothiazol-3-ylamino)propyl)-4-(3-methoxybenzyloxy)benzamide | 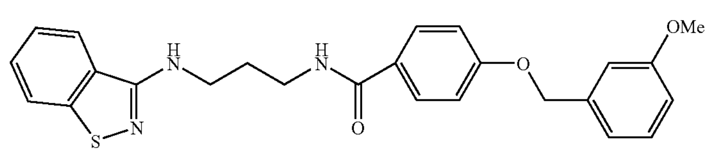 |

TABLE 2-continued

| Entry | Name | Structure |
|---|---|---|
| 237 | N-(3-(benzo[d]isothiazol-3-ylamino)propyl)-4-(3,4-dimethoxybenzyloxy)benzamide | 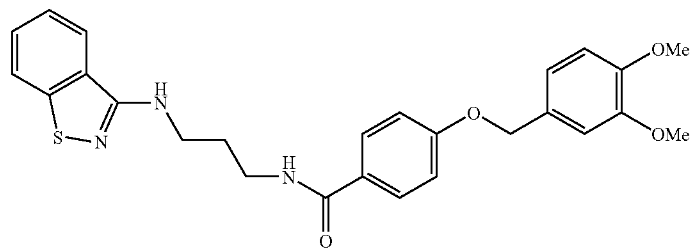 |
| 238 | 2-(4-(3-(benzo[d]isothiazol-3-ylamino)propylcarbamoyl)phenoxy)acetic acid | 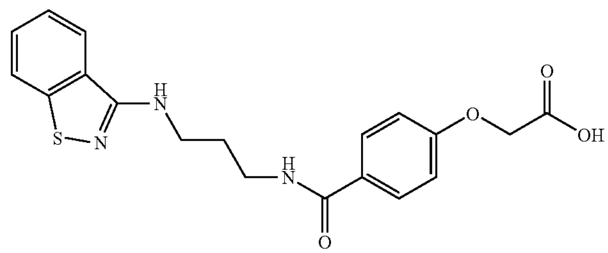 |
| 239 | tert-butyl 2-(4-(3-(benzo[d]isothiazol-3-ylamino)propylcarbamoyl)phenoxy)acetate | 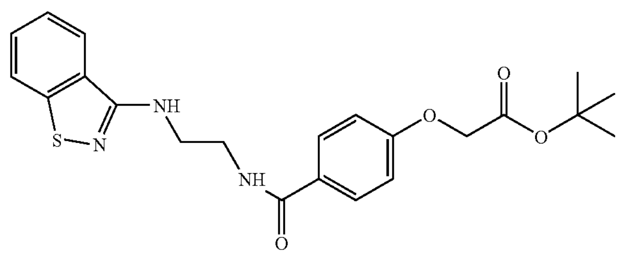 |
| 240 | N-(3-(benzo[d]isothiazol-3-ylamino)propyl)-N-methyl-2-(trifluoromethyl)benzenesulfonamide | 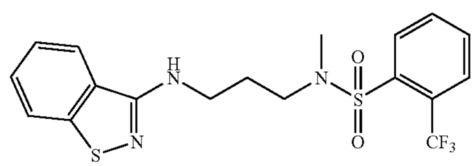 |
| 241 | $N^1$-(isothiazolo[5,4-b]pyrazin-3-yl)-$N^3$-((4'-methoxybiphenyl-4-yl)methyl)propane-1,3-diamine | 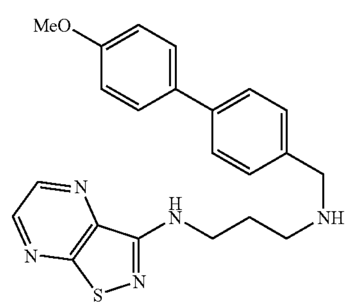 |
| 242 | N-(3-(benzo[d]isothiazol-3-ylamino)propyl)-3-nitrobenzenesulfonamide | 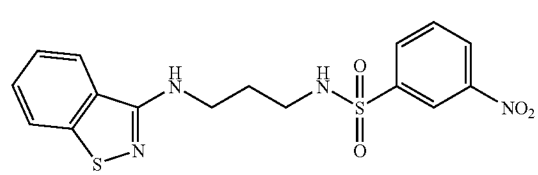 |
| 243 | methyl 2-(N-(3-(benzo[d]isothiazol-3-ylamino)propyl)sulfamoyl)benzoate | 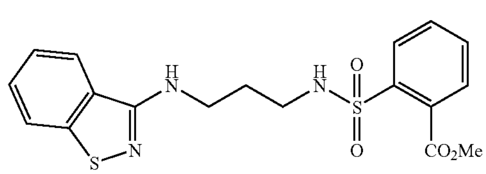 |

TABLE 2-continued

| Entry | Name | Structure |
|---|---|---|
| 244 | methyl 5-(N-(3-(benzo[d]isothiazol-3-ylamino)propyl)sulfamoyl)furan-2-carboxylate | 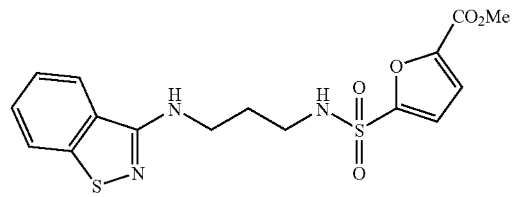 |
| 245 | N-(3-(benzo[d]isothiazol-3-ylamino)propyl)-4-(trifluoromethyl)benznesulfonamide | 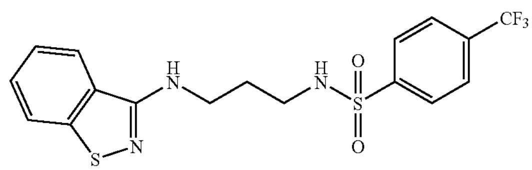 |
| 246 | N-(3-(benzo[d]isothiazol-3-ylamino)propyl)-3,5-bis(trifluoromethyl)benzenesulfonamide | 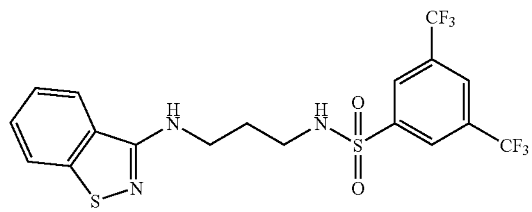 |
| 247 | N-(5-(N-(3-(benzo[d]isothiazol-3-ylamino)propyl)sulfamoyl)-4-methylthiazol-2-yl)acetamide | 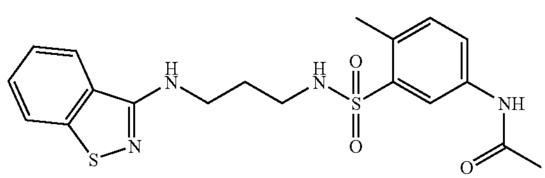 |
| 248 | N-(3-(benzo[d]isothiazol-3-ylamino)propyl)-1,2-dimethyl-1H-imidazole-4-sulfonamide | 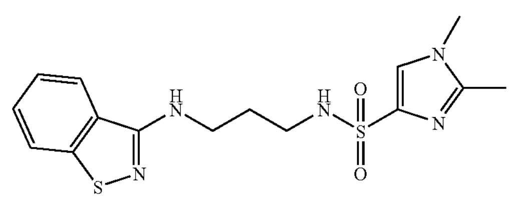 |
| 249 | N-(3-(benzo[d]isothiazol-3-ylamino)propyl)quinoline-8-sulfonamide | 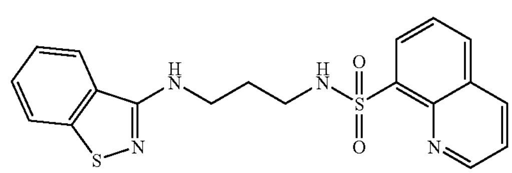 |
| 250 | N-(3-(benzo[d]isothiazol-3-ylamino)propyl)-2,3,4-trifluorobenzenesulfonamide | 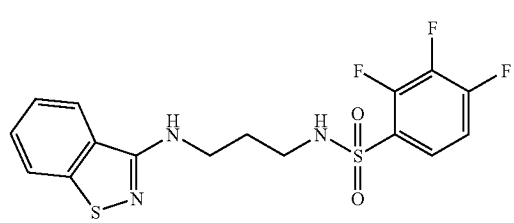 |
| 251 | N-(3-(benzo[d]isothiazol-3-ylamino)propyl)-4-methoxybenzenesulfonamide | 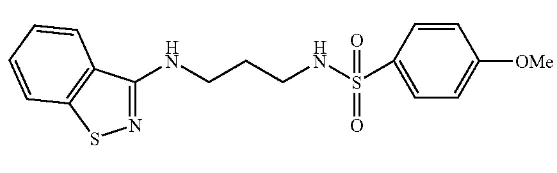 |

TABLE 2-continued

| Entry | Name | Structure |
|---|---|---|
| 252 | N-(3-(benzo[d]isothiazol-3-ylamino)propyl)-2-(2,2,2-trifluoroacetyl)-1,2,3,4-tetrahydroisoquinoline-7-sulfonamide | 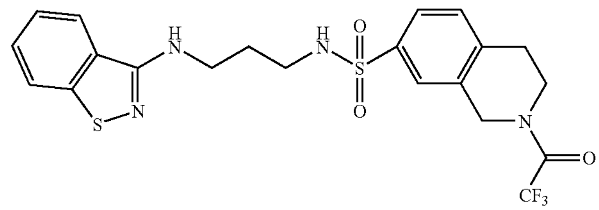 |
| 253 | N-(3-(benzo[d]isothiazol-3-ylamino)propyl)-2-bromo-4,6-difluorobenzenesulfonamide | 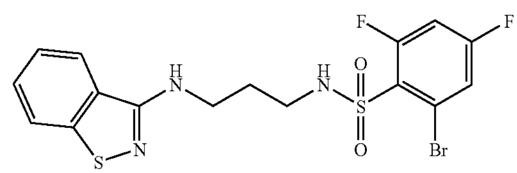 |
| 254 | N-(3-(benzo[d]isothiazol-3-ylamino)propyl)-N-benzyl-2-(trifluoromethyl)benzenesulfonamide | 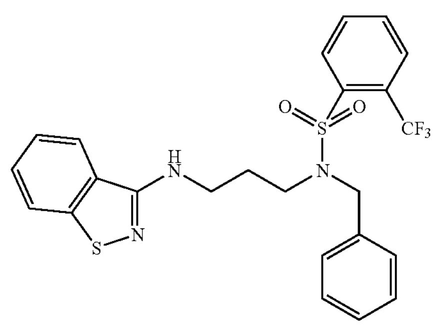 |
| 255 | N-(3-(benzo[d]isothiazol-3-ylamino)propyl)-N-((4'-methoxybiphenyl-4-yl)methyl)-2-morpholinoacetamide | 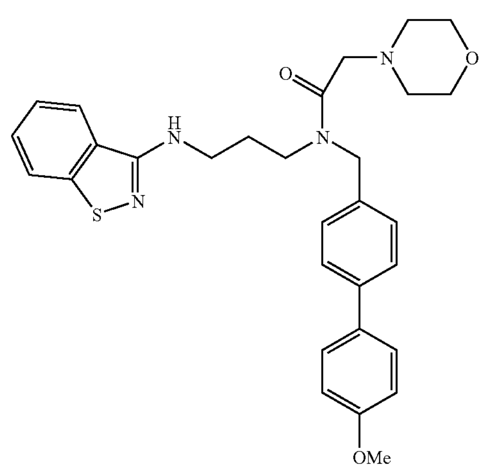 |

TABLE 2-continued

| Entry | Name | Structure |
|---|---|---|
| 256 | N-(3-(benzo[d]isothiazol-3-ylamino)propyl)-N-((4'-methoxybiphenyl-4-yl)methyl)-2-(4-phenylpiperazin-1-yl)acetamide | 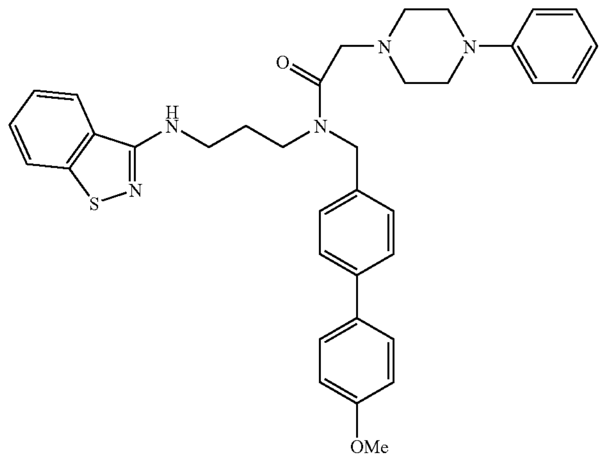 |
| 257 | N-(3-(benzo[d]isothiazol-3-ylamino)propyl)-2-(isopropylamino)-N-((4'-methoxybiphenyl-4-yl)methyl)acetamide | 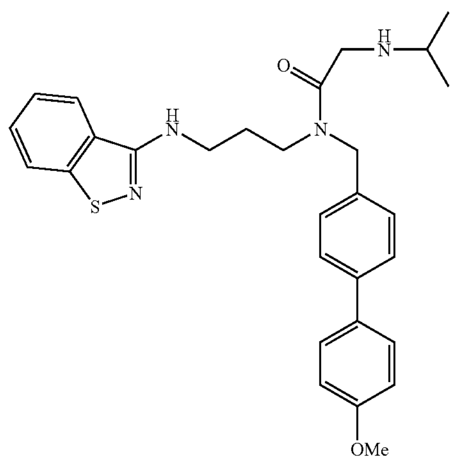 |
| 258 | 4-((3-(benzo[d]isothiazol-3-ylamino)propylamino)methyl)-N-(4-methoxyphenyl)benzenesulfonamide | 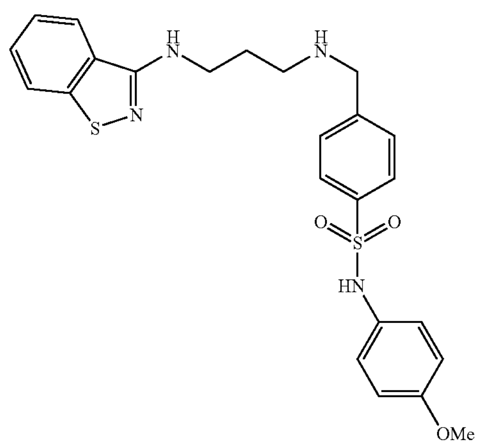 |

TABLE 2-continued

| Entry | Name | Structure |
|---|---|---|
| 259 | N¹-(benzo[d]isothiazol-3-yl)-N³-(4-(morpholinosulfonyl)benzyl)propane-1,3-diamine | 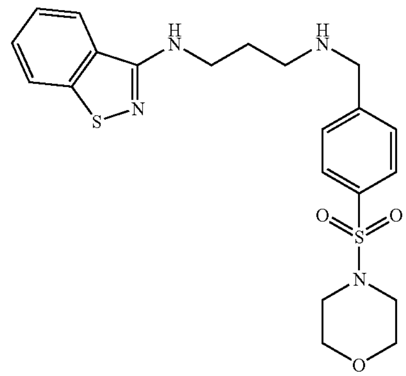 |
| 260 | N¹-(benzo[d]isothiazol-3-yl)-N³-(4-(pyrrolidin-1-ylsulfonyl)benzyl)propane-1,3-diamine | 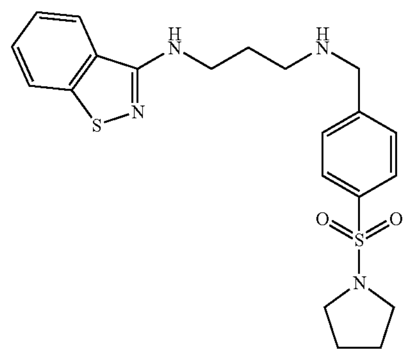 |
| 261 | N-(3-(benzo[d]isothiazol-3-ylamino)propyl)-2,5-dimethoxybenzenesulfonamide | 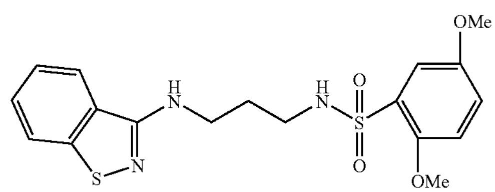 |
| 262 | N-(3-(benzo[d]isothiazol-3-ylamino)propyl)-4-bromo-2-chlorobenzenesulfonamide | 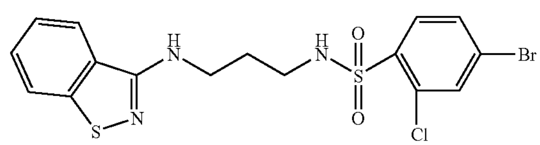 |
| 263 | N-(3-(benzo[d]isothiazol-3-ylamino)propyl)-4-bromo-2-(trifluoromethyl)benzenesulfonamide | 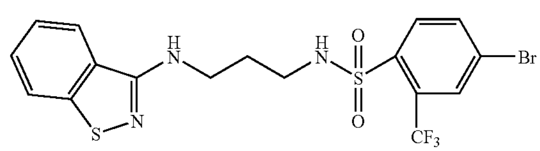 |
| 264 | N-(3-(benzo[d]isothiazol-3-ylamino)propyl)-3,4-dimethoxybenzenesulfonamide | 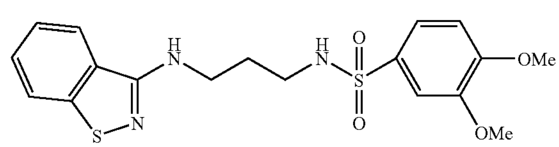 |
| 265 | N-(3-(benzo[d]isothiazol-3-ylamino)propyl)-4-bromo-3-methylbenzenesulfonamide | 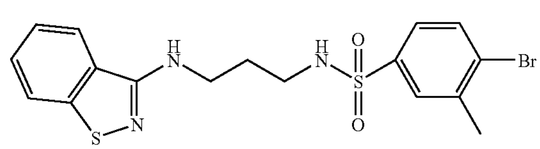 |

TABLE 2-continued

| Entry | Name |
|---|---|
| 266 | N-(3-(benzo[d]isothiazol-3-ylamino)propyl)-3-(trifluoromethoxy)benzenesulfonamide |
| 267 | N-(3-(benzo[d]isothiazol-3-ylamino)propyl)-4-bromo-2,6-dichlorobenzenesulfonamide |
| 268 | N-(3-(benzo[d]isothiazol-3-ylamino)propyl)-3-bromobenzenesulfonamide |
| 269 | N-(3-(benzo[d]isothiazol-3-ylamino)propyl)-4-bromo-3-(trifluoromethyl)benzenesulfonamide |
| 270 | N-(3-(benzo[d]isothiazol-3-ylamino)propyl)-N-((4'-methoxybiphenyl-4-yl)methyl)-2-(trifluoromethyl)benzenesulfonamide |
| 271 | N-(2-(benzo[d]isothiazol-3-ylamino)ethyl)-4-chlorobenzenesulfonamide |
| 272 | $N^1$-(benzo[d]isothiazol-3-yl)-$N^2$-(pyridin-2-ylmethyl)ethane-1,2-diamine |
| 273 | N-(3-(benzo[d]isothiazol-3-ylamino)propyl)-4-propylbenzamide |

TABLE 2-continued

| Entry | Name | Structure |
|---|---|---|
| 274 | N-(3-(benzo[d]isothiazol-3-ylamino)propyl)-4-hexylbenzamide | 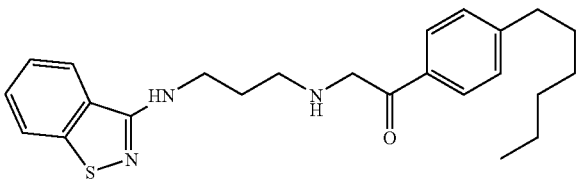 |
| 275 | $N^1$-(benzo[d]isothiazol-3-yl)-$N^3$-(3-methoxypyridin-2-yl)propane-1,3-diamine | 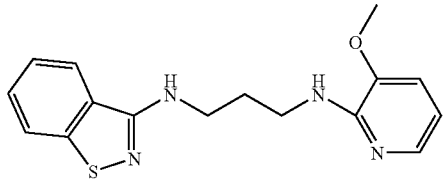 |
| 276 | $N^1$-(benzo[d]isothiazol-3-yl)-$N^3$-(3-(trifluoromethyl)pyridin-2-yl)propane-1,3-diamine | 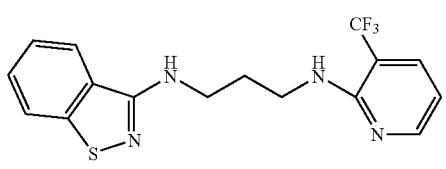 |
| 277 | 2-(3-(benzo[d]isothiazol-3-ylamino)propylamino)nicotinonitrile | 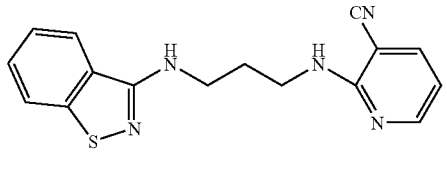 |
| 278 | $N^1$-(benzo[d]isothiazol-3-yl)-$N^3$-(3-methylpyridin-2-yl)propane-1,3-diamine | 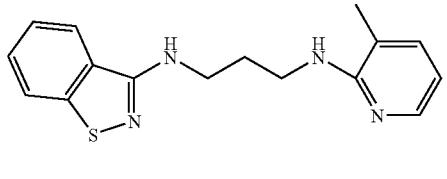 |
| 279 | N-(2-(benzo[d]isothiazol-3-ylamino)ethyl)-5-butylpicolinamide | 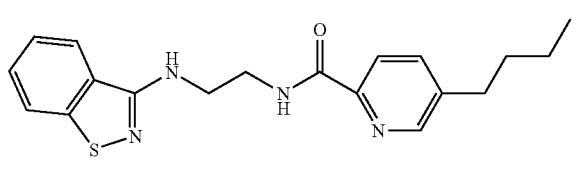 |
| 280 | 3-(benzo[d]isothiazol-3-ylamino)-2-(4-butylbenzamido)propanoic acid | 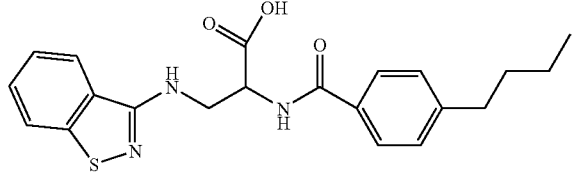 |
| 281 | $N^1$-(benzo[d]isothiazol-3-yl)-$N^3$-(6-methylpyridin-2-yl)propane-1,3-diamine | 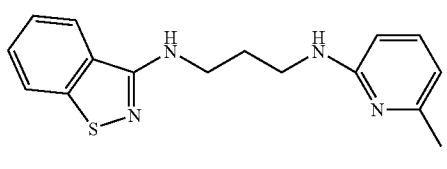 |
| 282 | $N^1$-(benzo[d]isothiazol-3-yl)-$N^3$-(5-methoxypyridin-2-yl)propane-1,3-diamine | 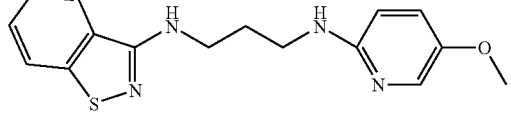 |

TABLE 2-continued

| Entry | Name | Structure |
| --- | --- | --- |
| 283 | $N^1$-(benzo[d]isothiazol-3-yl)-$N^3$-(6-methoxypyridin-2-yl)propane-1,3-diamine | 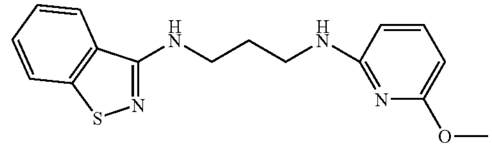 |
| 284 | methyl 6-(3-(benzo[d]isothiazol-3-ylamino)propylamino)-4-(trifluoromethyl)nicotinate | 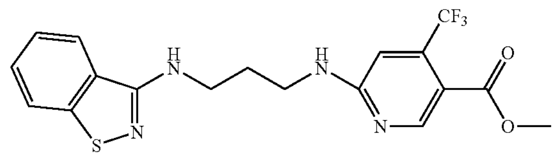 |
| 285 | N-(3-benzo[d]isothiazol-3-ylamino)propyl)-3-butoxy-4-methoxybenzamide | 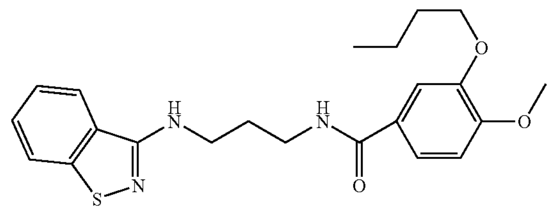 |
| 286 | N-(3-(benzo[d]isothiazol-3-ylamino)propyl)-3-(cyclopentyloxy)-4-methoxybenzamide | 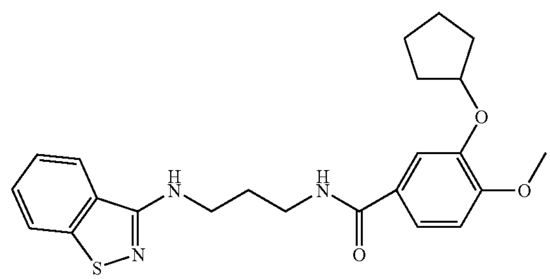 |
| 287 | $N^1$-(benzo[d]isothiazol-3-yl)-$N^3$-(4-bromobenzyl)propane-1,3-diamine | 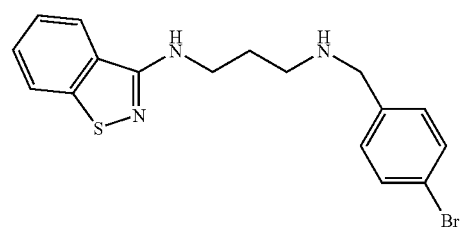 |
| 288 | $N^1$-(benzo[d]isothiazol-3-yl)-$N^3$-(4-butylbenzyl)propane-1,3-diamine | 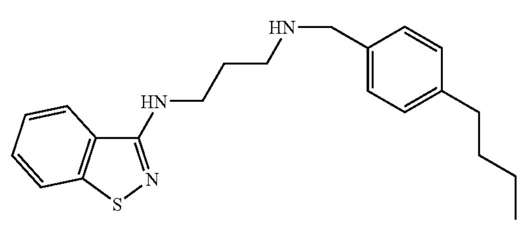 |
| 289 | N-(3-(benzo[d]isothiazol-3-ylamino)propyl)-4-bromobenzamide | 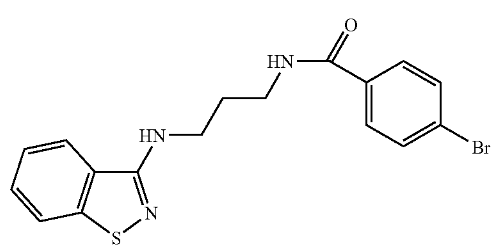 |

TABLE 2-continued

| Entry | Name | Structure |
|---|---|---|
| 290 | N-(3-(benzo[d]isothiazol-3-ylamino)propyl)-4-(propylamino)benzamide | 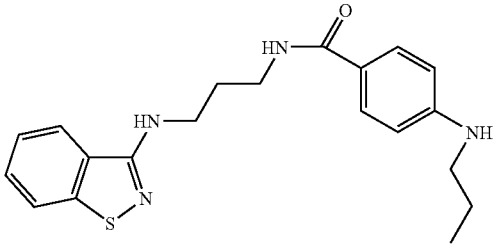 |
| 291 | $N^1$-(benzo[d]isothiazol-3-yl)-$N^3$-((4'-methoxybiphenyl-4-yl)methyl)propane-1,3-diamine | 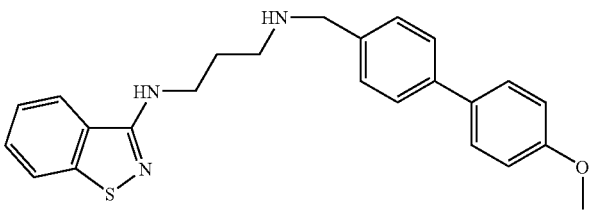 |
| 292 | $N^1$-(benzo[d]isothiazol-3-yl)-$N^3$-((3',4'-dimethoxybiphenyl-4-yl)methyl)propane-1,3-diamine | 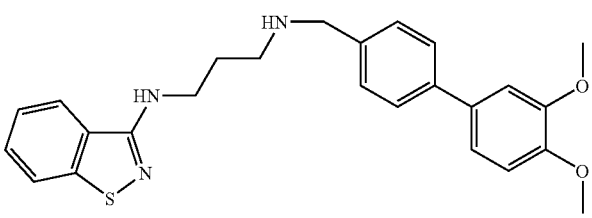 |
| 293 | N-(3-(benzo[d]isothiazol-3-ylamino)propyl)-N-(4-butylbenzyl)picolinamide | 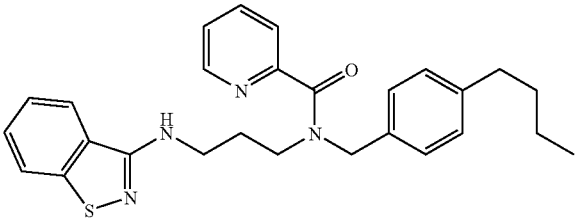 |
| 294 | $N^1$-(benzo[d]isothiazol-3-yl)-$N^3$-(5'-chloro-2'-methoxybiphenyl-4-yl)methyl)propane-1,3-diamine | 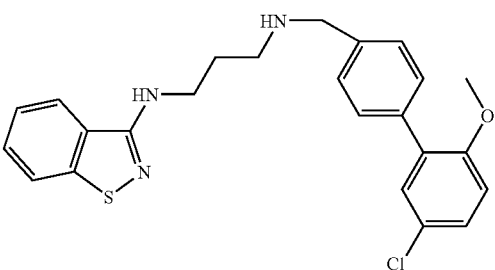 |
| 295 | $N^1$-(benzo[d]isothiazol-3-yl)-$N^3$-(4-butylphenyl)propane-1,3-diamine | 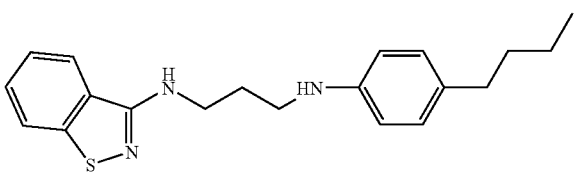 |

TABLE 2-continued

| Entry | Name | Structure |
|---|---|---|
| 296 | N-(3-(benzo[d]isothiazol-3-ylamino)propyl)-4-(4-ethylpiperazin-1-yl)benzamide | 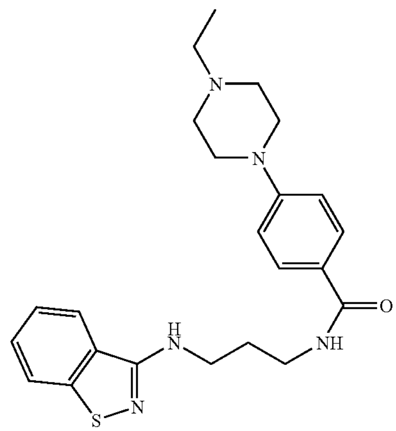 |
| 297 | 4-((pyridin-2-yl)methylamino)-N-(3-(benzo[d]isothiazol-3-ylamino)propyl)benzamide | 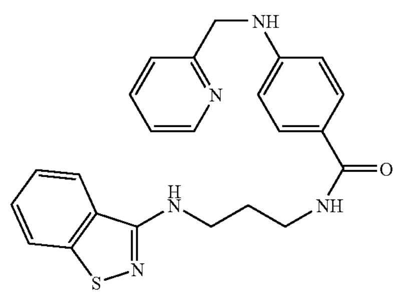 |
| 298 | N-(3-(benzo[d]isothiazol-3-ylamino)propyl)-4-(isopropylamino)benzamide | 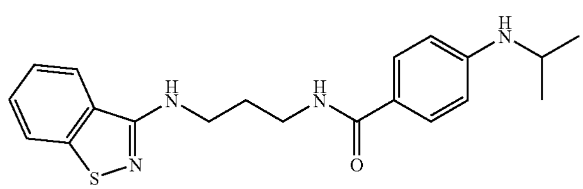 |
| 299 | $N^1$-(benzo[d]isothiazol-3-yl)-$N^3$-(3-bromobenzyl)propane-1,3-diamine | 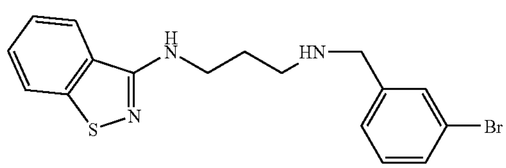 |
| 300 | $N^1$-(benzo[d]isothiazol-3-yl)-$N^3$-((4'-methoxybiphenyl-3-yl)methyl)propane-1,3-diamine | 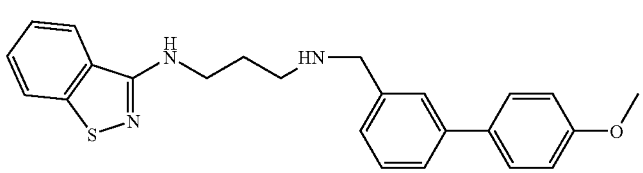 |
| 301 | $N^1$-(benzo[d]isothiazol-3-yl)-$N^3$-((4',5'-dimethoxybiphenyl-3-yl)methyl)propane-1,3-diamine | 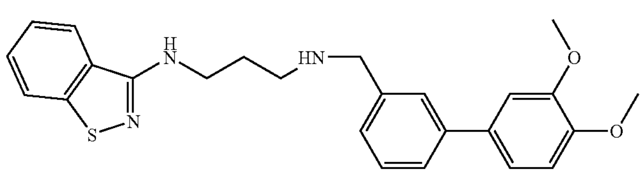 |

TABLE 2-continued

| Entry | Name | Structure |
|---|---|---|
| 302 | N$^1$-(benzo[d]isothiazol-3-yl)-N$^3$-((3'-chloro-6'-methoxybiphenyl-3-yl)methyl)propane-1,3-diamine | 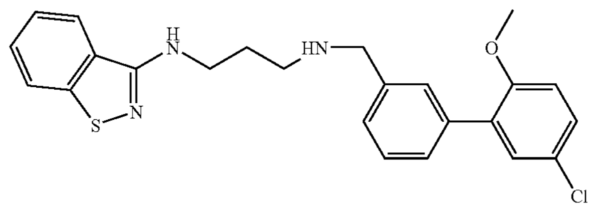 |
| 303 | 2-((3-(benzo[d]isothiazol-3-ylamino)propylamino)methyl)-4-bromophenol | 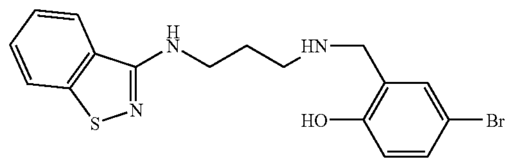 |
| 304 | 5-((3-(benzo[d]isothiazol-3-ylamino)propylamino)methyl)-2-methoxyphenol | 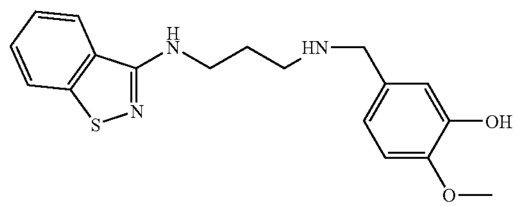 |
| 305 | N-(2-(5-chlorobenzo[d]isothiazol-3-ylamino)ethyl)-3-butoxy-4-methoxybenzamide | 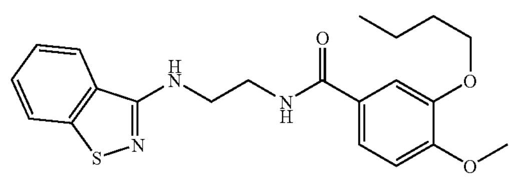 |
| 306 | N$^1$-(benzo[d]isothiazol-3-yl)-N$^3$-(1-benzylpiperidin-3-yl)propane-1,3-diamine | 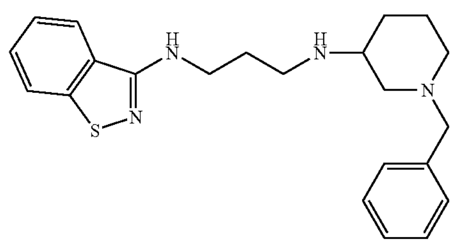 |
| 307 | tert-butyl 4-(3-(benzo[d]isothiazol-3-ylamino)propylamino)piperidine-1-carboxylate | 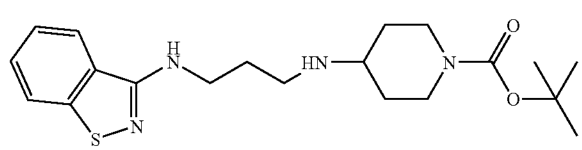 |
| 308 | N$^1$-(benzo[d]isothiazol-3-yl)-N$^3$-(pyridin-3-ylmethyl)propane-1,3-diamine | 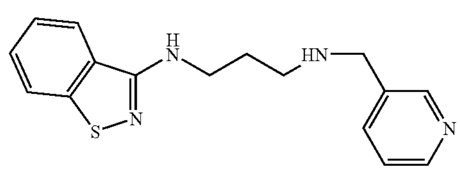 |
| 309 | N$^1$-(benzo[d]isothiazol-3-yl)-N$^3$-(pyridin-2-ylmethyl)propane-1,3-diamine | 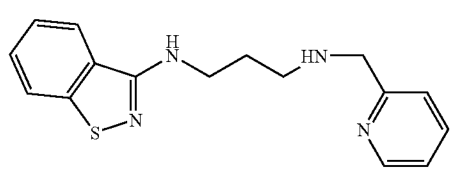 |

TABLE 2-continued

| Entry | Name | Structure |
|---|---|---|
| 310 | N-(2-(5-(propylamino)benzo[d]isothiazol-3-ylamino)ethyl)-3-butoxy-4-methoxybenzamide | 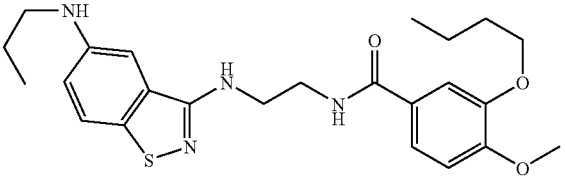 |
| 311 | 5-((benzo[d]isothiazol-3-ylamino)methyl)-3-(4-iodophenyl)imidazolidine-2,4-dione | 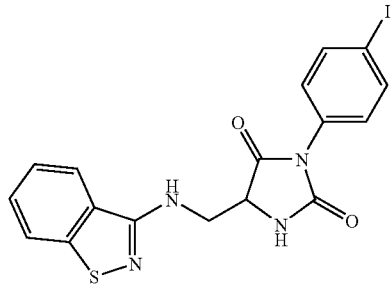 |
| 312 | N$^1$-(benzo[d]isothiazol-3-yl)-N$^3$-((4'-methoxybiphenyl-2-yl)methyl)propane-1,3-diamine | 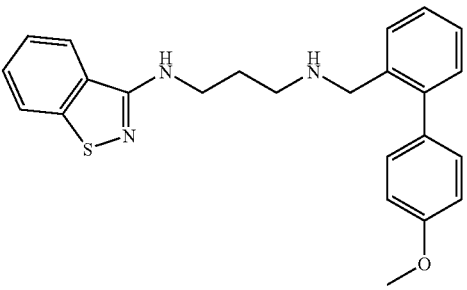 |
| 313 | N$^1$-(benzo[d]isothiazol-3-yl)-N$^3$-((3',4'-dimethoxybiphenyl-2-yl)methyl)propane-1,3-diamine | 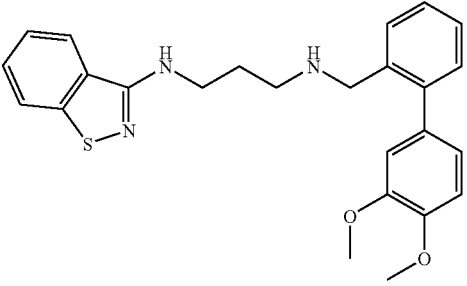 |
| 314 | N-(3-(benzo[d]isothiazol-3-ylamino)propyl)-N-((4'-methoxybiphenyl-4-yl)methyl)morpholine-4-carboxamide | 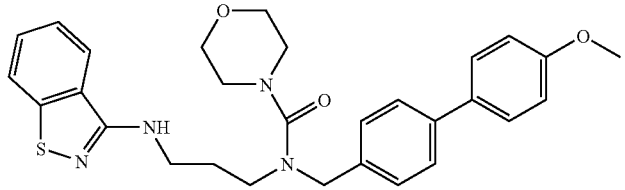 |
| 315 | 1-(3-(benzo[d]isothiazol-3-ylamino)propyl)-1-((4'-methoxybiphenyl-4-yl)methyl)-3,3-dimethylurea | 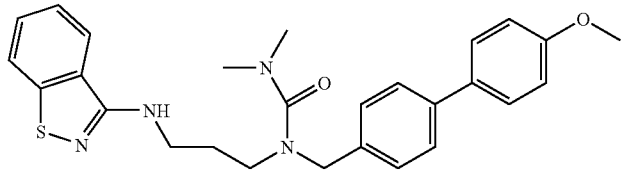 |

TABLE 2-continued

| Entry | Name | Structure |
|---|---|---|
| 316 | N-(3-(benzo[d]isothiazol-3-ylamino)propyl)-N-((4'-methoxybiphenyl-4-yl)methyl)-1,2-dimethyl-1H-imidazole-4-sulfonamide | 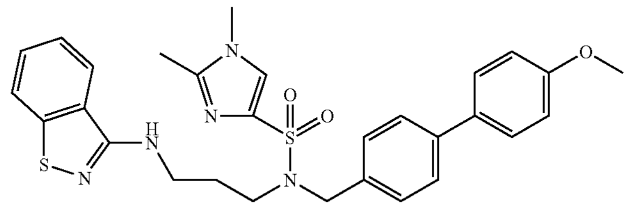 |
| 317 | methyl 5-(N-(3-(benzo[d]isothiazol-3-ylamino)propyl)-N-((4'-methoxybiphenyl-4-yl)methyl)sulfamoyl)-1-methyl-1H-pyrrole-2-carboxylate | 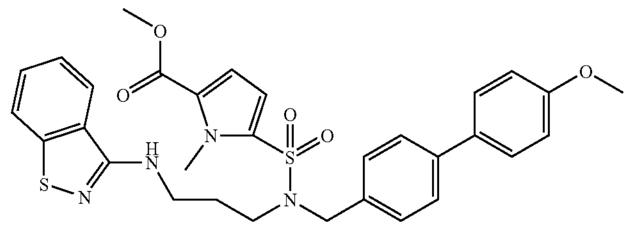 |
| 318 | tert-butyl 2-(2-((3-(benzo[d]isothiazol-3-ylamino)propyl)((4'-methoxybiphenyl-4-yl)methyl)amino)-2-oxoethyl)pyrrolidine-1-carboxylate | 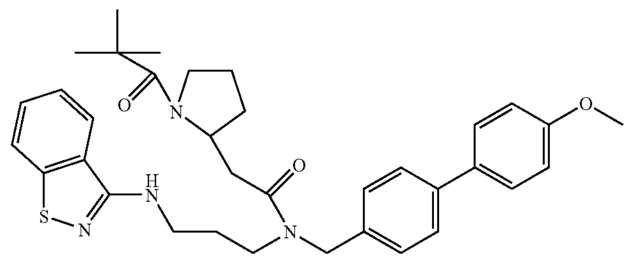 |
| 319 | N-(3-(benzo[d]isothiazol-3-ylamino)propyl)-2-cyano-N-((4'-methoxybiphenyl-4-yl)methyl)acetamide | 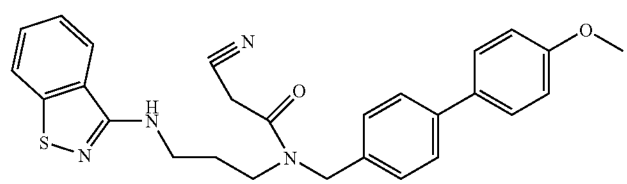 |
| 320 | N-(3-(benzo[d]isothiazol-3-ylamino)propyl)-N-((4'-methoxybiphenyl-4-yl)methyl)-2-(pyrrolidin-2-yl)acetamide | 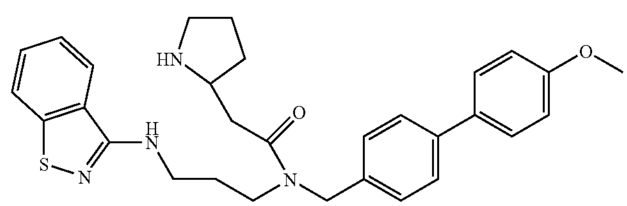 |
| 321 | 4-butyl-N-(3-[(1-oxido-1,2-benzisothiazol-3-yl)amino]propyl}benzamide | 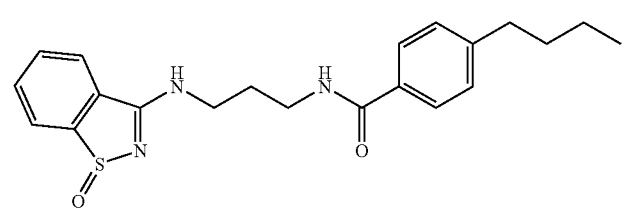 |
| 322 | 4-butyl-N-{3-[(1,1-dioxido-1,2-benzisothiazol-3-yl)amino]propyl}benzamide | 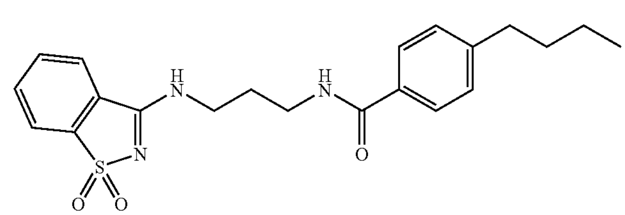 |

| Entry | Name | Structure |
|---|---|---|
| 323 | N-[(4'-methoxybiphenyl-4-yl)methyl]-N'-(1-oxido-1,2-benzisothiazol-3-yl)propane-1,3-diamine | 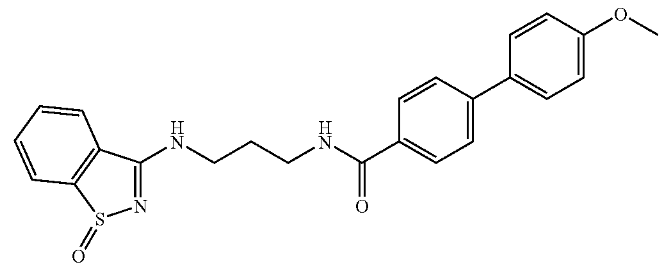 |
| 324 | N-(1,1-dioxido-1,2-benzisothiazol-3-yl)-N'-[(4'-methoxybiphenyl-4-yl)methyl]propane-1,3-diamine | 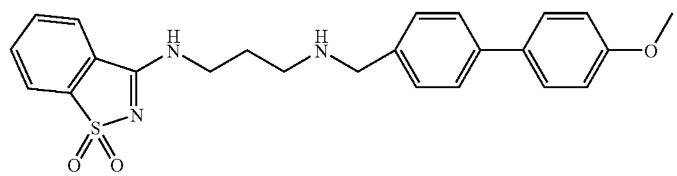 |
| 325 | N-(3-(benzo[d]isothiazol-3-ylamino)propyl)-4-iodobenzenesulfonamide | 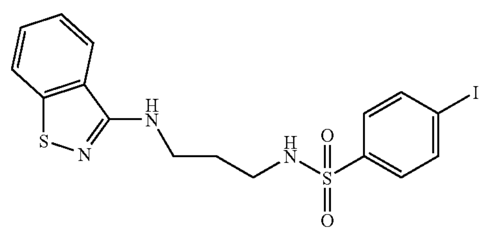 |
| 326 | $N^1$-(benzo[d]isothiazol-3-yl)-$N^3$-(2-(trifluoromethyl)benzyl)propane-1,3-diamine | 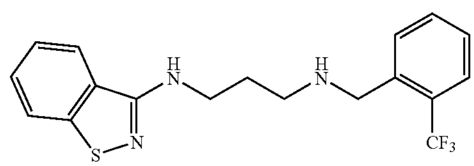 |
| 327 | $N^1$-(benzo[d]isothiazol-3-yl)-$N^3$-(2-(benzyloxy)-4,5-dimethoxybenzyl)propane-1,3-diamine | 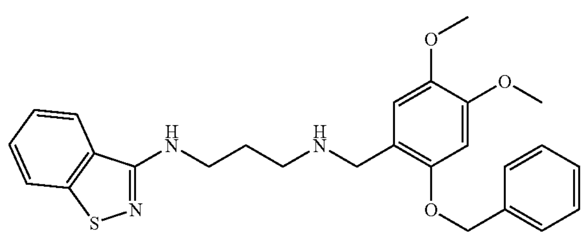 |
| 328 | $N^1$-(benzo[d]isothiazol-3-yl)-$N^3$-(3-(benzyloxy)benzyl)propane-1,3-diamine | 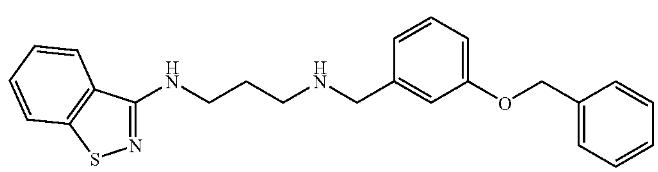 |
| 329 | $N^1$-(benzo[d]isothiazol-3-yl)-$N^3$-((2-phenyl-1H-imidazol-4-yl)methyl)propane-1,3-diamine | 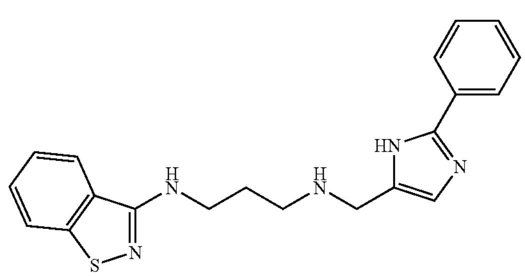 |

TABLE 2-continued

| Entry | Name | Structure |
|---|---|---|
| 330 | N¹-(benzo[d]isothiazol-3-yl)-N³-((2-phenyl-1H-indol-3-yl)methyl)propane-1,3-diamine | 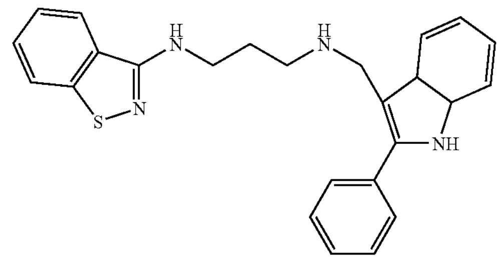 |
| 331 | N-(3-(benzo[d]isothiazol-3-ylamino)propyl)-4'-methoxybiphenyl-4-sulfonamide | 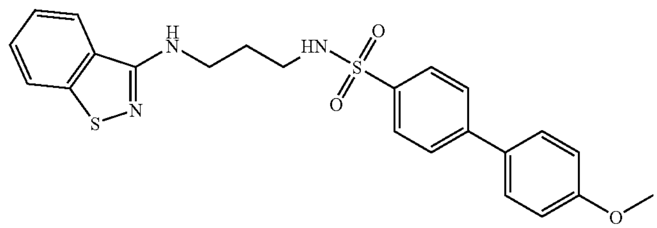 |
| 332 | N-(3-(benzo[d]isothiazol-3-ylamino)propyl)-3',4'-dimethoxybiphenyl-4-sulfonamide | 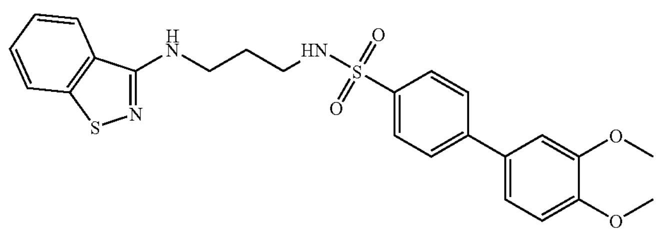 |
| 333 | N-(3-(benzo[d]isothiazol-3-ylamino)propyl)-4'-(trifluoromethoxy)biphenyl-4-sulfonamide | 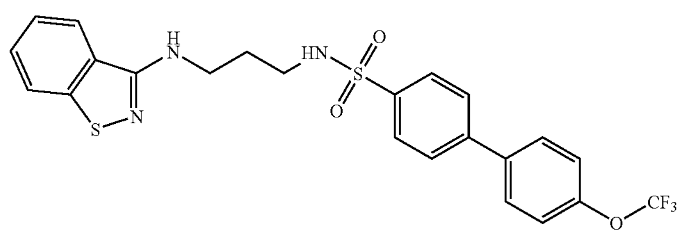 |
| 334 | methyl 4t-(N-(3-(benzo[d]isothiazol-3-ylamino)propyl)sulfamoyl)biphenyl-4-carboxylate | 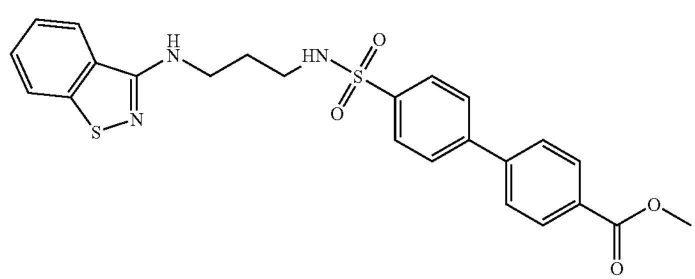 |
| 335 | N-(3-(benzo[d]isothiazol-3-ylamino)propyl)-2'-(trifluoromethyl)biphenyl-4-sulfonamide | 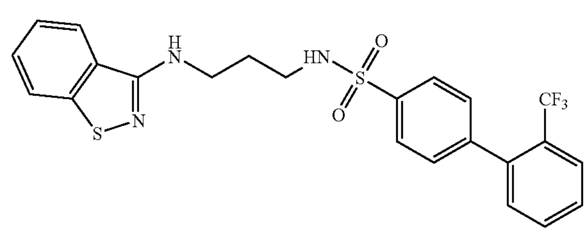 |

TABLE 2-continued

| Entry | Name | Structure |
|---|---|---|
| 336 | N¹-(benzo[d]isothiazol-3-yl)-N³-((4'-(trifluoromethoxy)biphenyl-4-yl)methyl)propane-1,3-diamine | 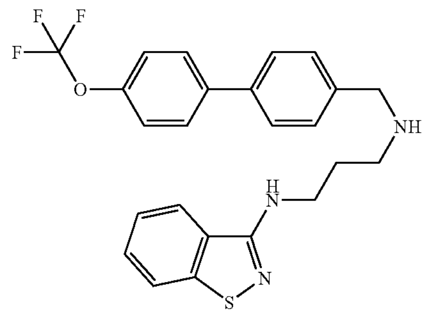 |
| 337 | N¹-(benzo[d]isothiazol-3-yl)-N³-(benzofuran-2-ylmethyl)propane-1,3-diamine | 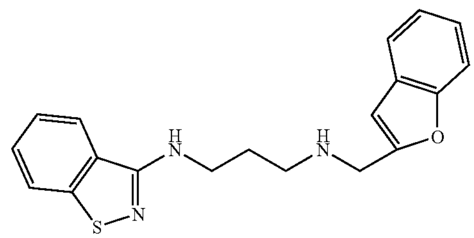 |
| 338 | N¹-(benzo[d]isothiazol-3-yl)-N³-(4-(pyrrolidin-1-yl)benzyl)propane-1,3-diamine | 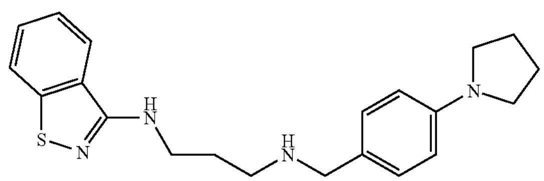 |
| 339 | N-(3-(benzo[d]isothiazol-3-ylamino)propyl)-N-((4'-methoxybiphenyl-4-yl)methyl)-2-(methylsulfonyl)acetamide | 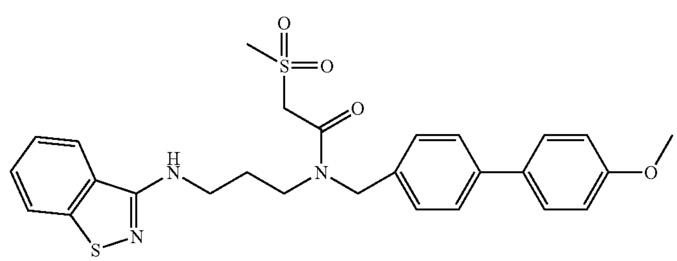 |
| 340 | N-{3-[(1,1-dioxido-1,2-benzisothiazol-3-yl)amino]propyl}-N-[(4'-methoxybiphenyl-4-yl)methyl]-1,2-dimethyl-1H-imidazole-4-sulfonamide | 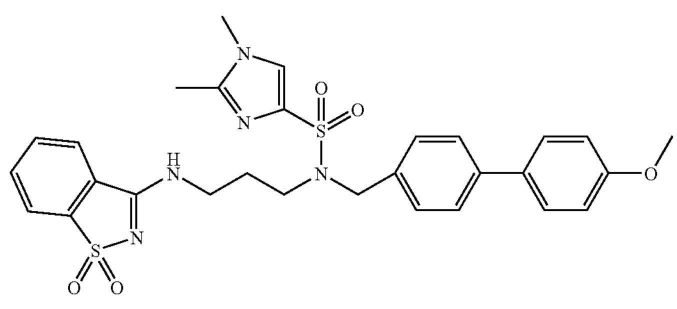 |
| 341 | N-(3-(benzo[d]isothiazol-3-ylamino)propyl)-2-(1H-imidazol-1-yl)-N-((4'-methoxybiphenyl-4-yl)methyl)acetamide | 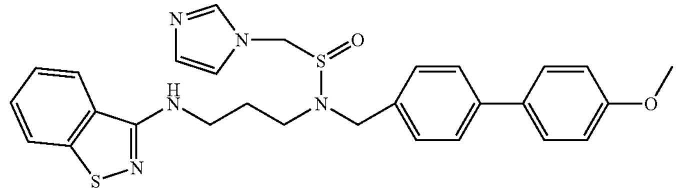 |

TABLE 2-continued

| Entry | Name | Structure |
|---|---|---|
| 342 | N-(3-(benzo[d]isothiazol-3-ylamino)propyl)-N-((4'-methoxybiphenyl-4-yl)methyl)picolinamide | 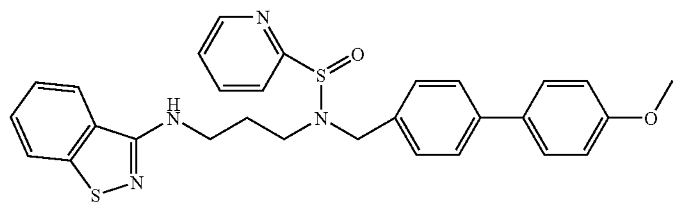 |
| 343 | N$^1$-(benzo[d]isothiazol-3-yl)-N$^3$-(3-methoxybenzyl)propane-1,3-diamine | 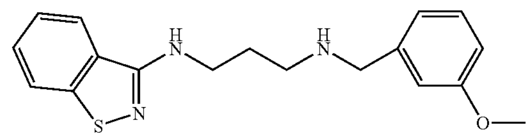 |
| 344 | N-(3-(benzo[d]isothiazol-3-yl(methyl)amino)propyl)-3-methoxy-N-methylbenzenesulfonamide | 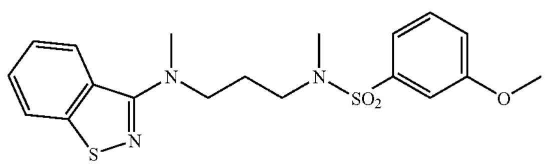 |
| 345 | N-(3-(benzo[d]isothiazol-3-yl(methyl)amino)propyl)-N-methyl-2-(trifluoromethyl)benzenesulfonamide | 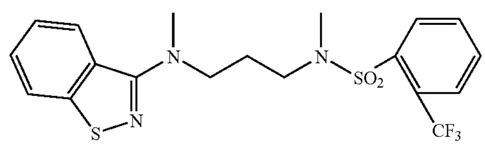 |
| 346 | 1-(4-((3-(benzo[d]isothiazol-3-ylamino)propylamino)methyl)phenyl)pyrrolidin-2-one | 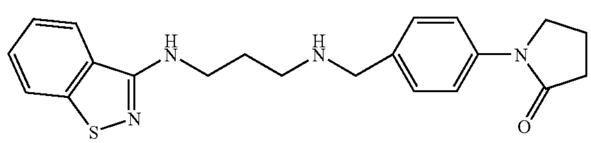 |
| 347 | N$^1$-(benzo[d]isothiazol-3-yl)-N$^3$-((4'-methoxybiphenyl-4-yl)methyl)-N,N -dimethylpropane-1,3-diamine | 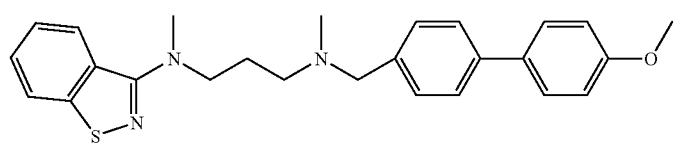 |
| 348 | (R)-N-(2-(2-(benzo[d]isothiazol-3-ylamino)ethylamino)-2-oxo-1-phenylethyl)-4-chlorobenzamide | 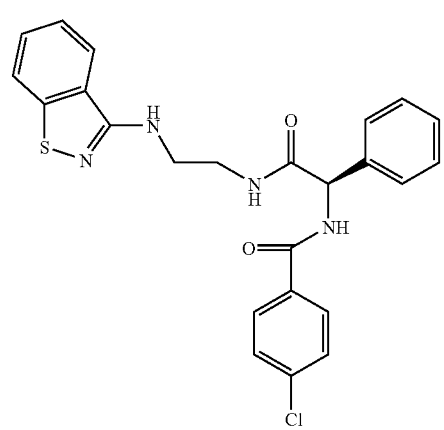 |
| 349 | N-(2-(benzo[d]isothiazol-3-ylamino)ethyl)-2,4-difluorobenzamide | 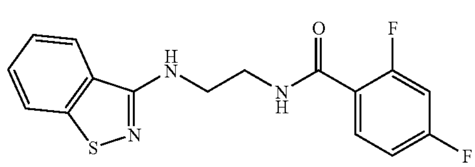 |

TABLE 2-continued

| Entry | Name | Structure |
|---|---|---|
| 350 | N-(2-(benzo[d]isothiazol-3-ylamino)ethyl)-2,5-difluorobenzamide | 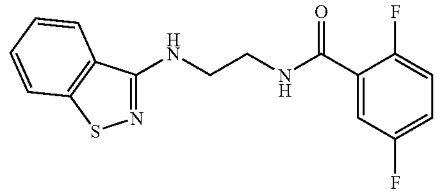 |
| 351 | N-(2-(benzo[d]isothiazol-3-ylamino)ethyl)-2-(trifluoromethyl)benzamide | 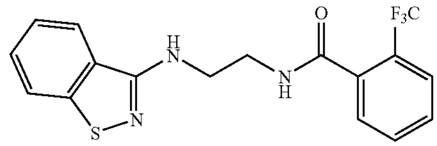 |
| 352 | N-(2-(benzo[d]isothiazol-3-ylamino)ethyl)-5-fluoro-2-(trifluoromethyl)benzamide | 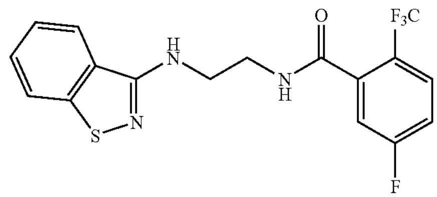 |
| 353 | N-(2-(benzo[d]isothiazol-3-ylamino)ethyl)-3-fluoro-5-(trifluoromethyl)benzamide | 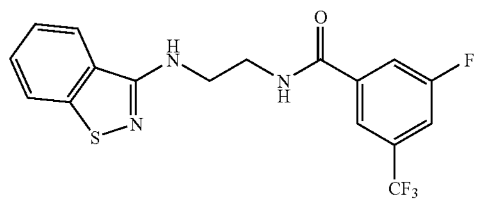 |
| 354 | N-(2-(benzo[d]isothiazol-3-ylamino)ethyl)-2-fluoro-4-(trifluoromethyl)benzamide | 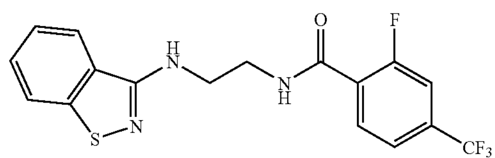 |
| 355 | N-(2-(benzo[d]isothiazol-3-ylamino)ethyl)-3-fluoro-4-(trifluoromethyl)benzamide | 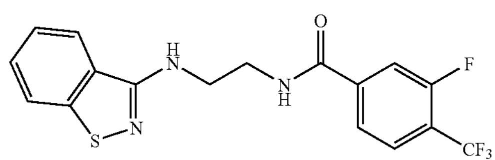 |
| 356 | N-(2-(benzo[d]isothiazol-3-ylamino)ethyl)-2,4-bis(trifluoromethyl)benzamide | 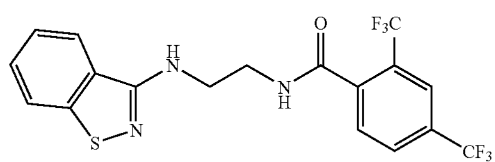 |
| 357 | N-(2-(benzo[d]isothiazol-3-ylamino)ethyl)-2,5-bis(trifluoromethyl)benzamide | 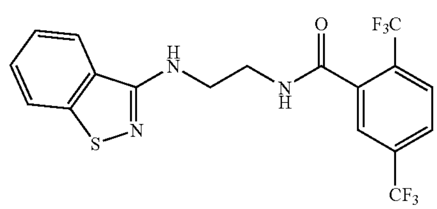 |

TABLE 2-continued

| Entry | Name | Structure |
|---|---|---|
| 358 | N-(2-(benzo[d]isothiazol-3-ylamino)ethyl)-2-fluoro-6-(trifluoromethyl)benzamide | 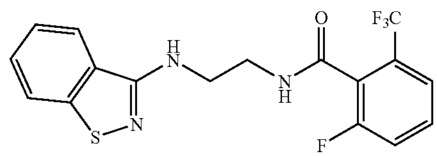 |
| 359 | N-(2-(benzo[d]isothiazol-3-ylamino)ethyl)-3,4-difluorobenzamide | 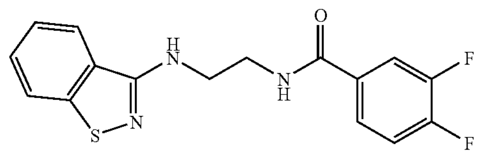 |
| 360 | N-(2-(benzo[d]isothiazol-3-ylamino)ethyl)-4'-methoxybiphenyl-4-carboxamide | 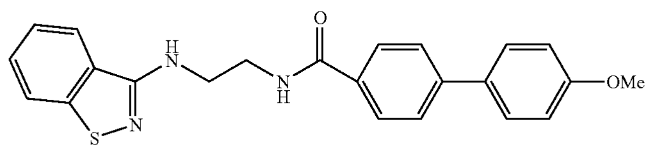 |
| 361 | N-(2-(benzo[d]isothiazol-3-ylamino)ethyl)-3',4'-dimethoxybiphenyl-4-carboxamide | 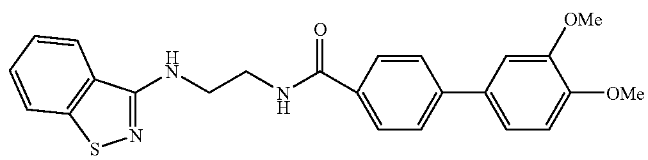 |
| 362 | N-(2-(benzo[d]isothiazol-3-ylamino)ethyl)-5'-chloro-2'-methoxybiphenyl-4-carboxamide | 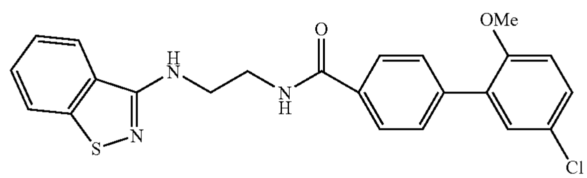 |
| 363 | N-(2-(benzo[d]isothiazol-3-ylamino)ethyl)-2'-isopropoxy-5'-methylbiphenyl-4-carboxamide | 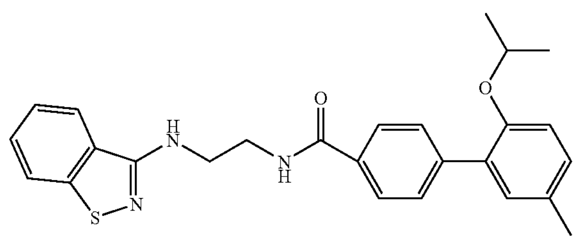 |
| 364 | N-(2-(benzo[d]isothiazol-3-ylamino)ethyl)-2',3'-dimethoxybiphenyl-4-carboxamide | 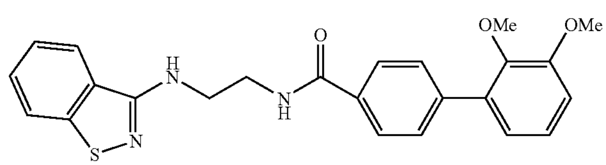 |
| 365 | N-(2-(benzo[d]isothiazol-3-ylamino)ethyl)-2'-methoxy-5'-methylbiphenyl-4-carboxamide | 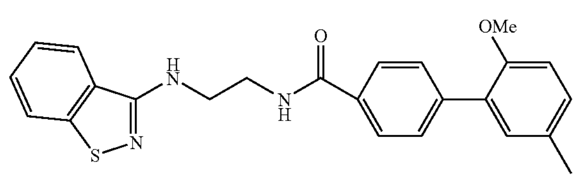 |
| 366 | N-(2-(benzo[d]isothiazol-3-ylamino)ethyl)-4'-methoxy-2'-methylbiphenyl-4-carboxamide | 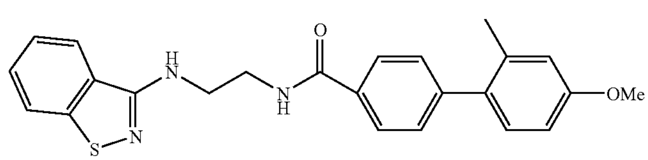 |

TABLE 2-continued

| Entry | Name | Structure |
|---|---|---|
| 367 | N-(2-(benzo[d]isothiazol-3-ylamino)ethyl)-5'-fluoro-2'-propoxybiphenyl-4-carboxamide | 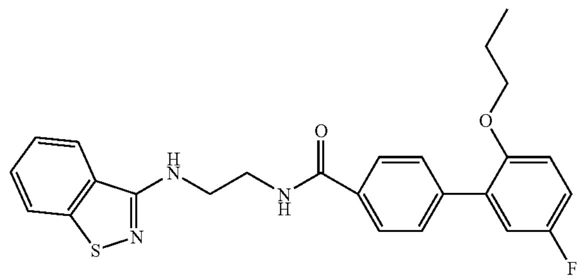 |
| 368 | N-(3-(benzo[d]isothiazol-3-ylamino)propyl)-4'-fluoro-6'-methoxybiphenyl-3-carboxamide | 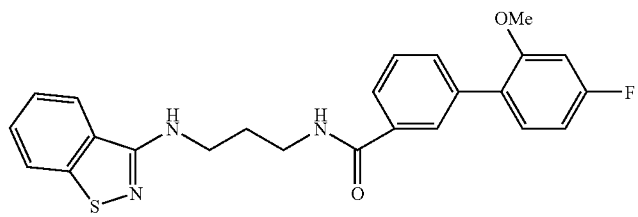 |
| 369 | N-(3-(benzo[d]isothiazol-3-ylamino)propyl)-5',6'-dimethoxybiphenyl-3-carboxamide | 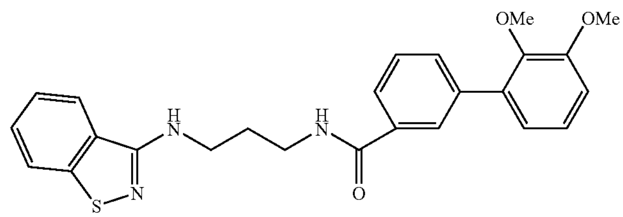 |
| 370 | N-(2-(benzo[d]isothiazol-3-ylamino)ethyl)-3',4'-dimethoxybiphenyl-3-carboxamide | 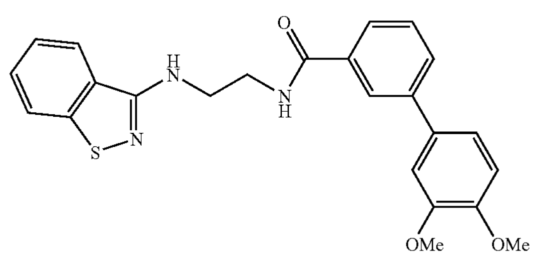 |
| 371 | N-(2-(benzo[d]isothiazol-3-ylamino)ethyl)-4'-methoxybiphenyl-3-carboxamide | 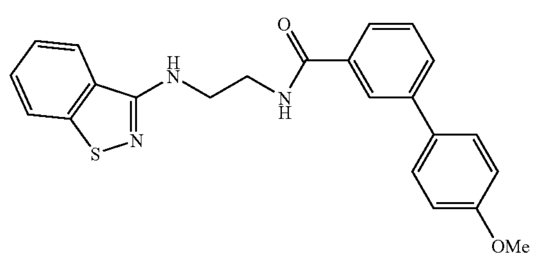 |
| 372 | N-(2-(benzo[d]isothiazol-3-ylamino)ethyl)-3',4'-dimethylbiphenyl-3-carboxamide | 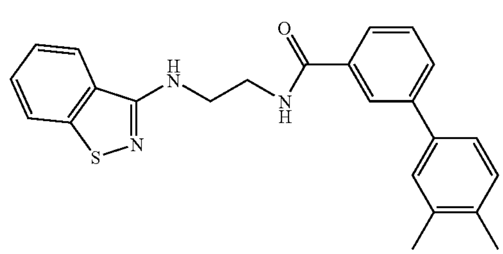 |

TABLE 2-continued

| Entry | Name | Structure |
|---|---|---|
| 373 | N-(2-(benzo[d]isothiazol-3-ylamino)ethyl)-3-(naphthalen-2-yl)benzamide | 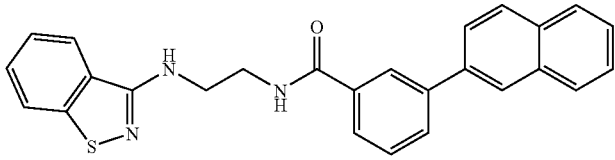 |
| 374 | N-(2-(benzo[d]isothiazol-3-ylamino)ethyl)-3-(quinolin-8-yl)benzamide | 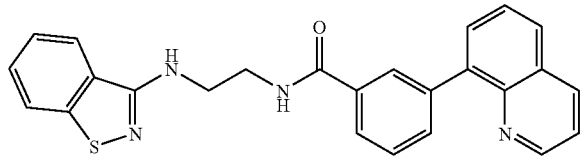 |
| 375 | N-(2-(benzo[d]isothiazol-3-ylamino)ethyl)-3-(quinolin-3-yl)benzamide | 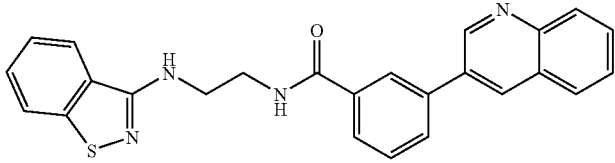 |
| 376 | N-(3-(benzo[d]isothiazol-3-ylamino)propyl)-6'-isopropoxybiphenyl-3-carboxamide | 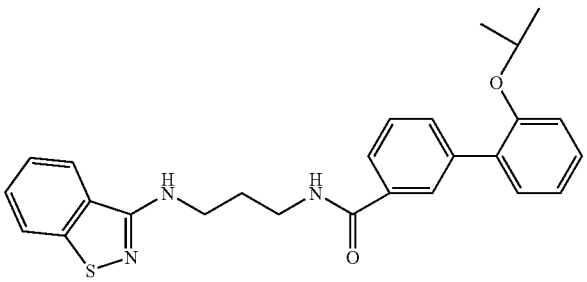 |
| 377 | N-(2-(benzo[d]isothiazol-3-ylamino)ethyl)-2'-isopropoxybiphenyl-4-carboxamide | 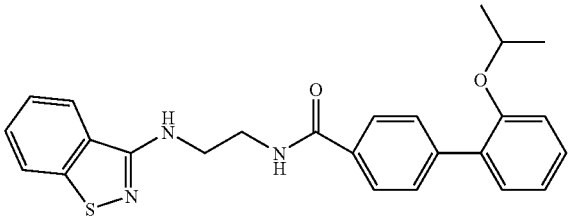 |
| 378 | N-(3-(benzo[d]isothiazol-3-ylamino)propyl)-4'-methoxybiphenyl-3-carboxamide | 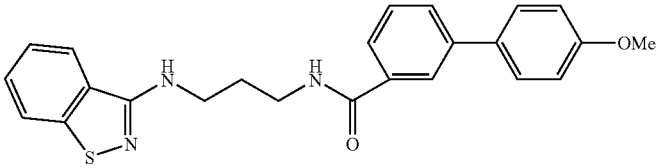 |
| 379 | 1-(3-(benzo[d]isothiazol-3-ylamino)propyl)-3-(4-butylphenyl)urea | 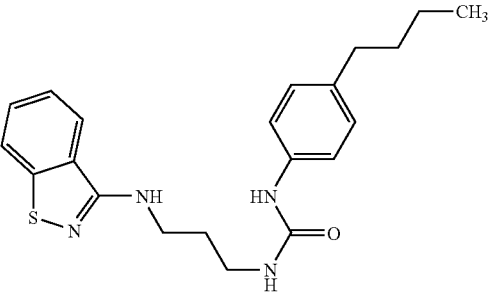 |

TABLE 2-continued

| Entry | Name | Structure |
|---|---|---|
| 380 | N-(3-(benzo[d]isothiazol-3-ylamino)propyl)-3-(6-chloropyridin-3-yl)benzamide | 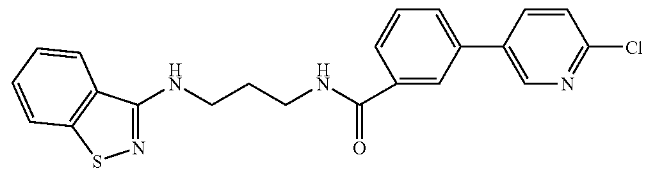 |
| 381 | N-(3-(benzo[d]isothiazol-3-ylamino)propyl)-3'-ethoxy-6'-methylbiphenyl-3-carboxamide | 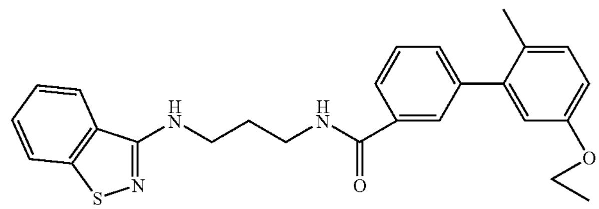 |
| 382 | N-(3-(benzo[d]isothiazol-3-ylamino)propyl)-3',6'-dimethoxybiphenyl-3-carboxamide | 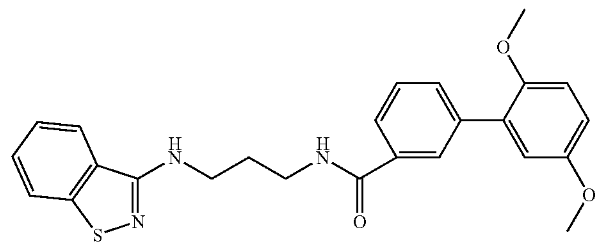 |
| 383 | N-(3-(benzo[d]isothiazol-3-ylamino)propyl)-4'-fluoro-6'-propoxybiphenyl-3-carboxamide | 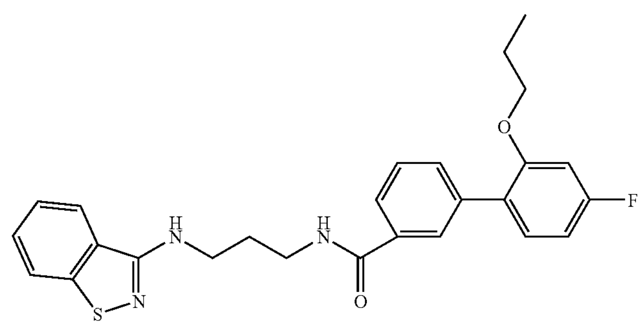 |
| 384 | N-(3-(benzo[d]isothiazol-3-ylamino)propyl)-6'-methoxybiphenyl-3-carboxamide | 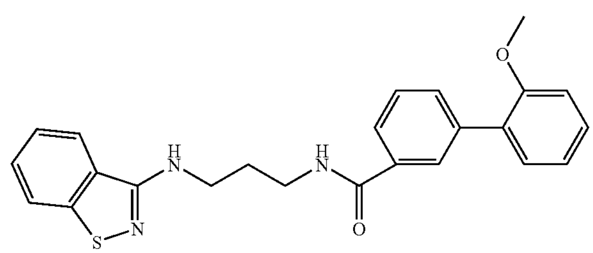 |
| 385 | N-(2-(benzo[d]isothiazol-3-ylamino)ethyl)-2'-hydroxybiphenyl-4-carboxamide | 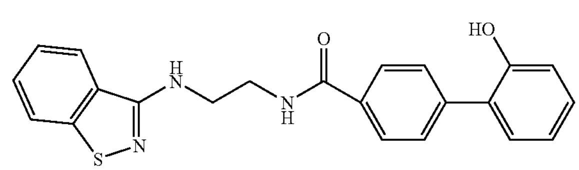 |
| 386 | N-(3-(benzo[d]isothiazol-3-ylamino)propyl)-3-iodobenzamide | 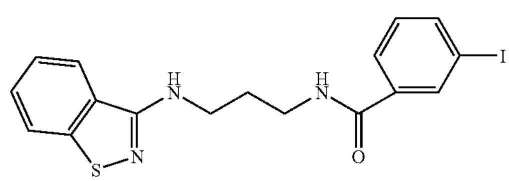 |

TABLE 2-continued

| Entry | Name | Structure |
|---|---|---|
| 387 | 1-(3-(benzo[d]isothiazol-3-ylamino)propyl)-3-(4-iodophenyl)urea | 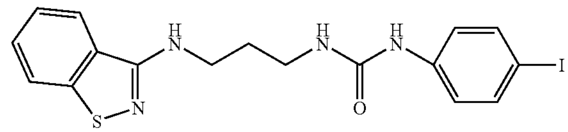 |
| 388 | N-(3-(benzo[d]isothiazol-3-ylamino)propyl)-3-(6-methoxypyridin-3-yl)benzamide | 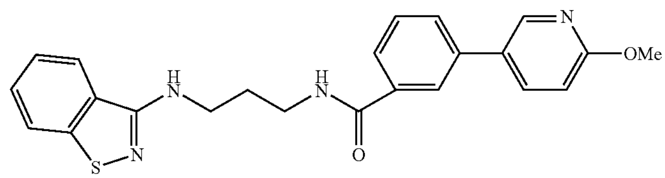 |
| 389 | 1-(3-(benzo[d]isothiazol-3-ylamino)propyl)-3-(2'-isopropoxybiphenyl-4-yl)urea | 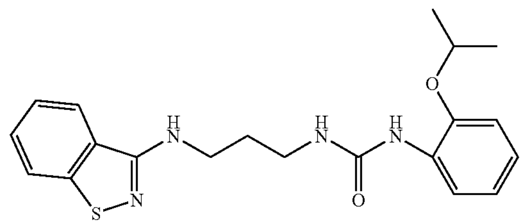 |
| 390 | tert-butyl 4-(3-(3-(benzo[d]isothiazol-3-ylamino)propylcarbamoyl)phenyl)-5,6-dihydropyridine-1(2H)-carboxylate | 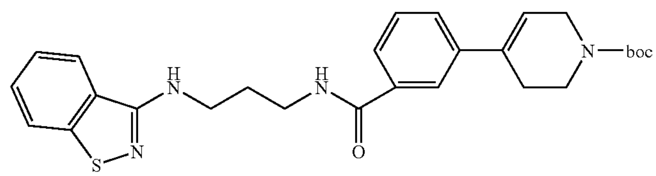 |
| 391 | N-(3-(benzo[d]isothiazol-3-ylamino)propyl)-3,5-diethoxybenzamide | 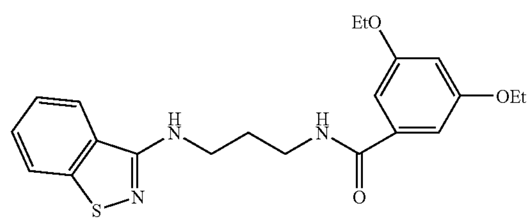 |
| 392 | 1-(3-(benzo[d]isothiazol-3-ylamino)propyl)-3-(2'-isopropoxy-5'-methylbiphenyl-4-yl)urea | 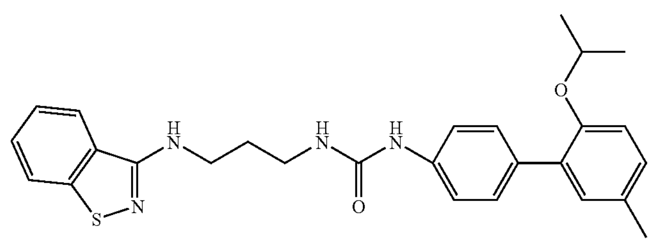 |
| 393 | 1-(3-(benzo[d]isothiazol-3-ylamino)propyl)-3-(4'-fluoro-2'-methoxybiphenyl-4-yl)urea | 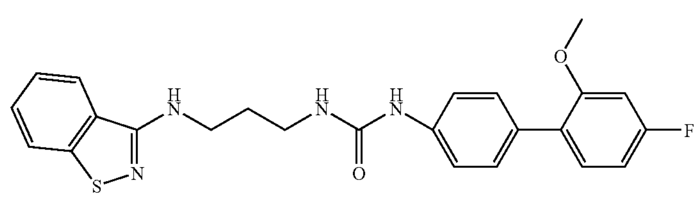 |
| 394 | N-(3-(benzo[d]isothiazol-3-ylamino)propyl)-3-(1,2,3,6-tetrahydropyridin-4-yl)benzamide | 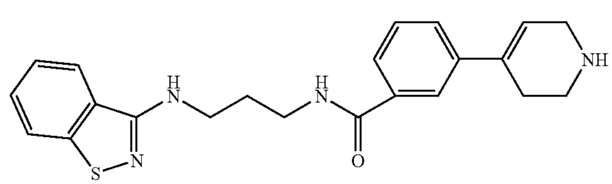 |

TABLE 2-continued

| Entry | Name | Structure |
|---|---|---|
| 395 | 1-(3-(benzo[d]isothiazol-3-ylamino)propyl)-3-(2'-methoxybiphenyl-4-yl)urea | 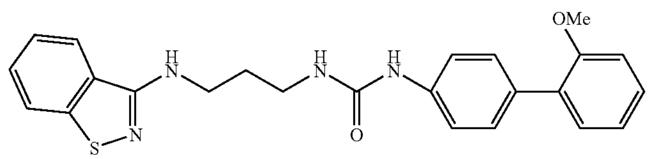 |
| 396 | N-(3-(benzo[d]isothiazol-3-ylamino)propyl)-3-bromo-4-hydroxybenzamide | 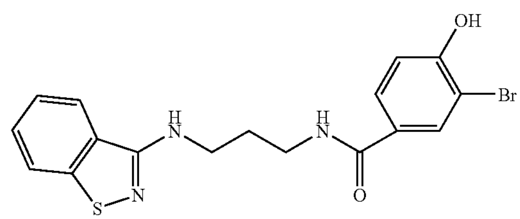 |
| 397 | N-(3-(benzo[d]isothiazol-3-ylamino)propyl)-3-bromo-4-(2-morpholinoethoxy)benzamide | 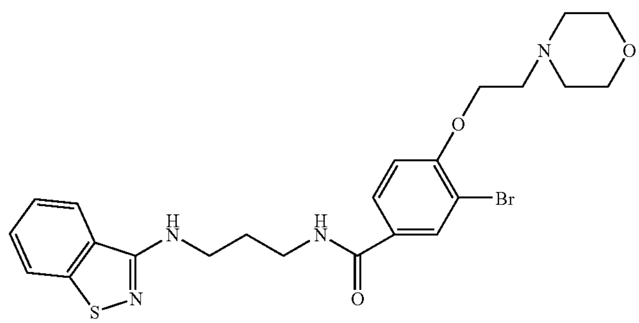 |
| 398 | N-(3-(4-(N-tert-butylsulfamoyl)benzo[d]isothiazol-3-ylamino)propyl)-4'-methoxybiphenyl-4-carboxamide | 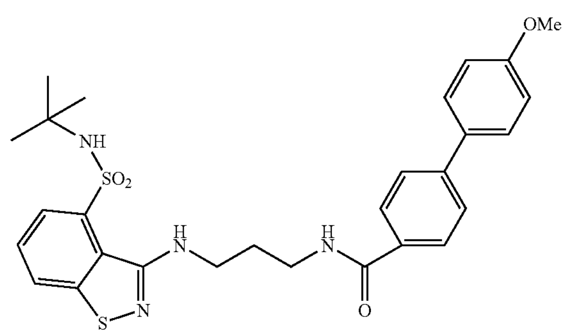 |
| 399 | N-(3-(6-(N-tert-butylsulfamoyl)benzo[d]isothiazol-3-ylamino)propyl)-4'-methoxybiphenyl-4-carboxamide | 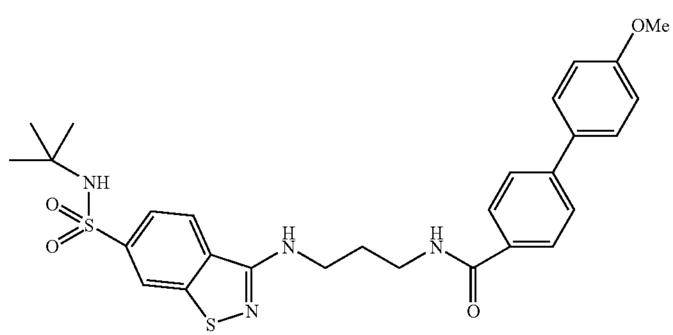 |

TABLE 2-continued

| Entry | Name | Structure |
|---|---|---|
| 400 | N-(3-(7-(tert-butylsulfonyl)benzo[d]isothiazol-3-ylamino)propyl)-4'-methoxybiphenyl-4-carboxamide | 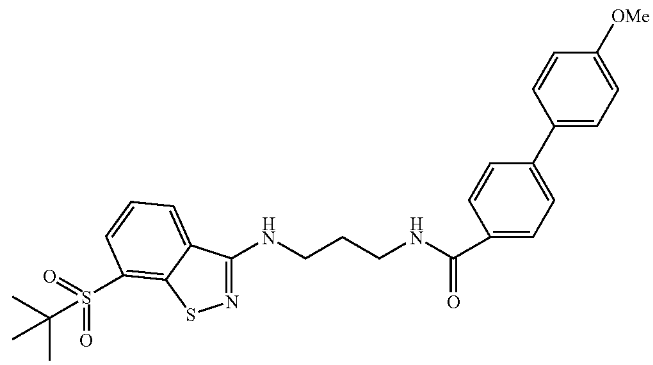 |
| 401 | 4'-methoxy-N-(3-(4-sulfamoylbenzo[d]isothiazol-3-ylamino)propyl)biphenyl-4-carboxamide | 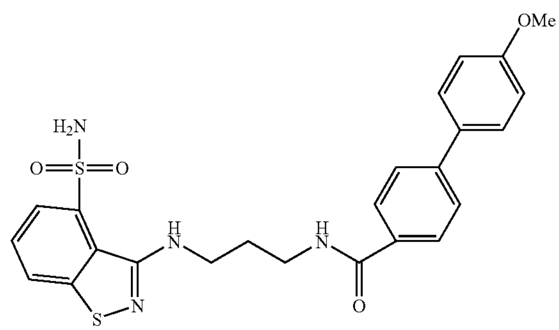 |
| 402 | 4'-methoxy-N-(3-(6-sulfamoylbenzo[d]isothiazol-3-ylamino)propyl)biphenyl-4-carboxamide | 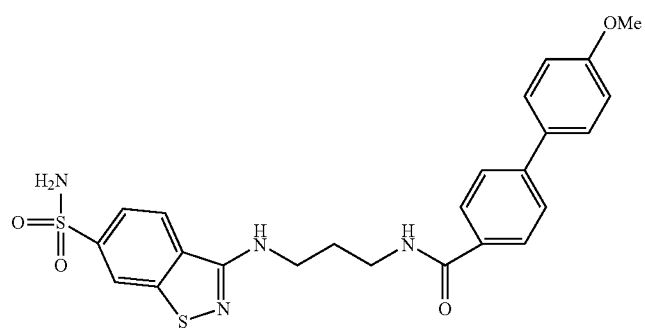 |
| 403 | 4-butoxy-N-(3-(5-phenylbenzo[d]isothiazol-3-ylamino)propyl)benzamide | 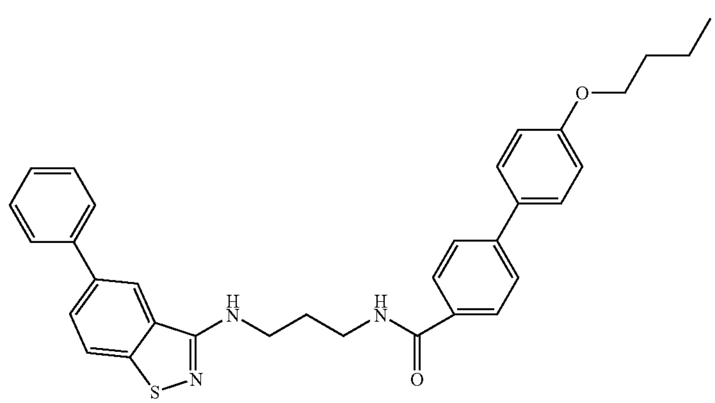 |

TABLE 2-continued

| Entry | Name | Structure |
|---|---|---|
| 404 | N$^1$-(5-bromobenzo[d]isothiazol-3-yl)-N$^3$-((4'-methoxybiphenyl-4-yl)methyl)propane-1,3-diamine | 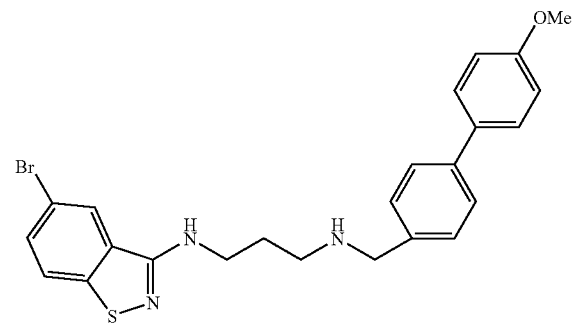 |
| 405 | 4'-methoxy-N-(3-(5-phenylbenzo[d]isothiazol-3-ylamino)propyl)biphenyl-4-carboxamide | 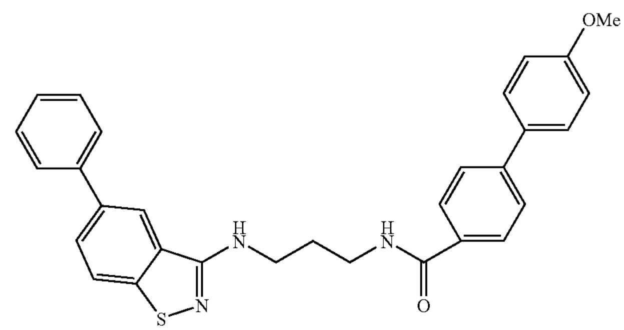 |
| 406 | 4'-methoxy-N-(3-(5-(4-methoxyphenyl)benzo[d]isothiazol-3-ylamino)propyl)biphenyl-4-carboxamide | 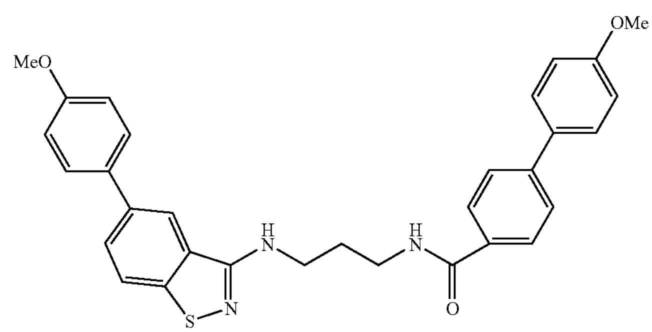 |
| 407 | N-(3-(5-(2-fluoro-3-methoxyphenyl)benzo[d]isothiazol-3-ylamino)propyl)-4'-methoxybiphenyl-4-carboxamide | 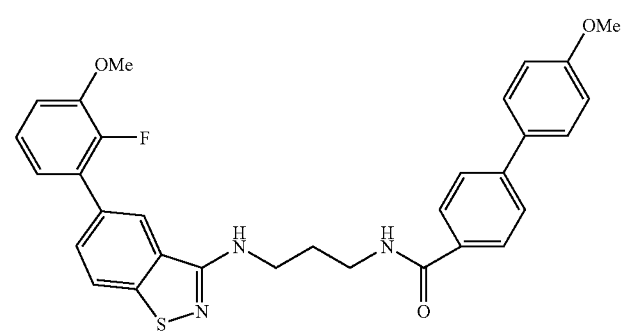 |

TABLE 2-continued

| Entry | Name | Structure |
|---|---|---|
| 408 | N-(3-(5-(3,5-difluorophenyl)benzo[d]isothiazol-3-ylamino)propyl)-4'-methoxybiphenyl-4-carboxamide | 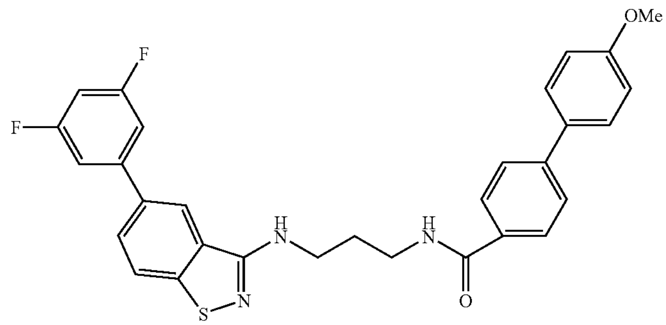 |
| 409 | N-(3-(5-(4-isopropoxyphenyl)benzo[d]isothiazol-3-ylamino)propyl)-4'-methoxybiphenyl-4-carboxamide | 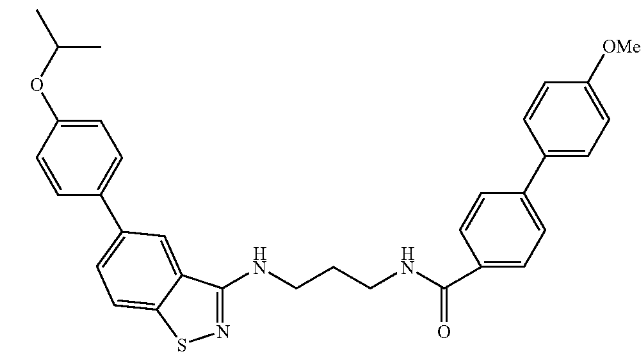 |
| 410 | $N^1$-((4'-methoxybiphenyl-4-yl)methyl)-$N^3$-(5-(4-methoxyphenyl)benzo[d]isothiazol-3-yl)propane-1,3-diamine | 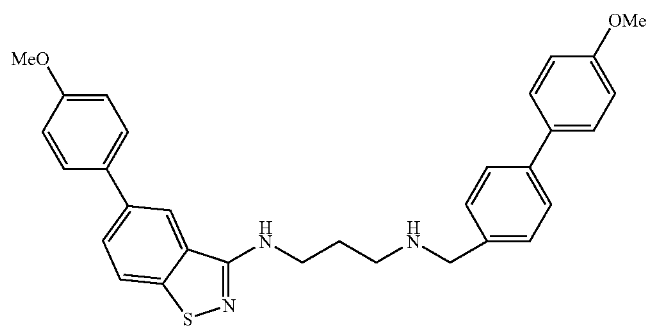 |
| 411 | $N^1$-(5-(3,5-difluorophenyl)benzo[d]isothiazol-3-yl)-N-((4'-methoxybiphenyl-4-yl)methyl)propane-1,3-diamine | 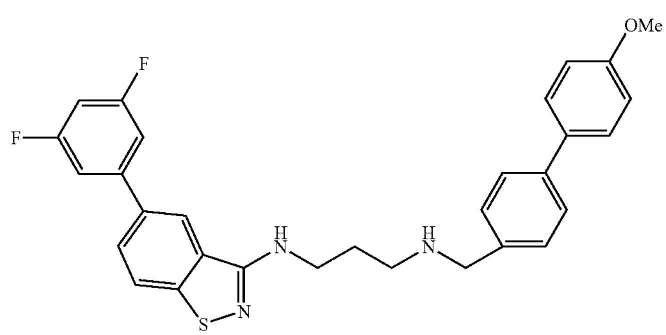 |
| 412 | N-(2-(benzo[d]isothiazol-3-ylamino)ethyl)-1-methyl-1H-indole-2-carboxamide | 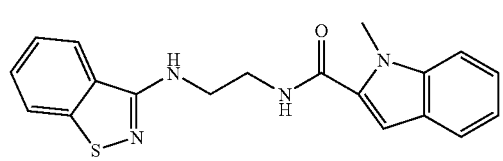 |

TABLE 2-continued

| Entry | Name | Structure |
|---|---|---|
| 413 | N-(2-(benzo[d]isothiazol-3-ylamino)ethyl)-3-phenyl-1H-pyrazole-5-carboxamide | 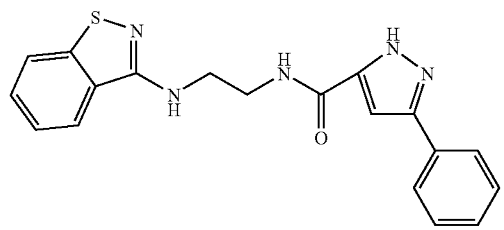 |
| 414 | N-(2-(benzo[d]isothiazol-3-ylamino)ethyl)-3-formylbenzamide | 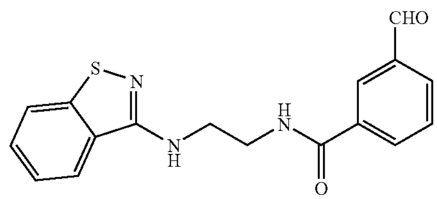 |
| 415 | N-(2-(benzo[d]isothiazol-3-ylamino)ethyl)-4-formylbenzamide | 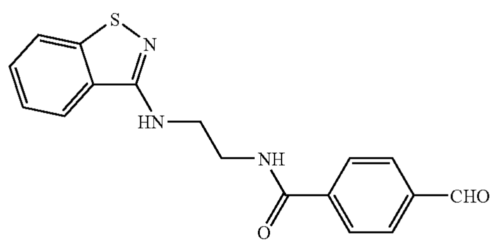 |
| 416 | N-(2-(benzo[d]isothiazol-3-ylamino)ethyl)-3-(hydroxymethyl)benzamide | 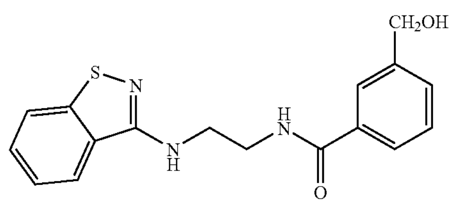 |
| 417 | $N^1,N^2$-di(benzo[d]isothiazol-3-yl)ethane-1,2-diamine | 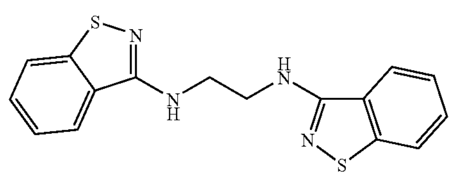 |
| 418 | $N^1$-(2-(benzo[d]isothiazol-3-ylamino)ethyl)-$N^4$-propylterephthalamide | 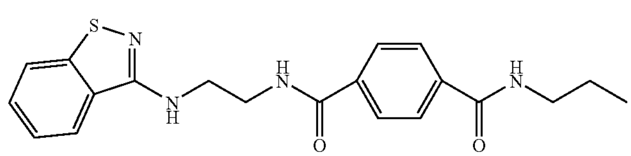 |
| 419 | N-(3-(benzo[d]isothiazol-3-ylamino)propyl)-6-bromopicolinamide | 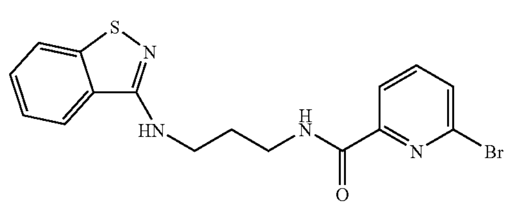 |

TABLE 2-continued

| Entry | Name | Structure |
|---|---|---|
| 420 | N-(3-(benzo[d]isothiazol-3-ylamino)propyl)-6-fluoropicolinamide | 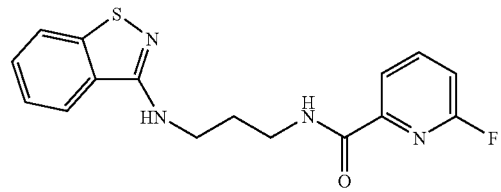 |
| 421 | 4-butyl-N-(2-(5-chlorobenzo[d]isothiazol-3-ylamino)ethyl)benzamide | 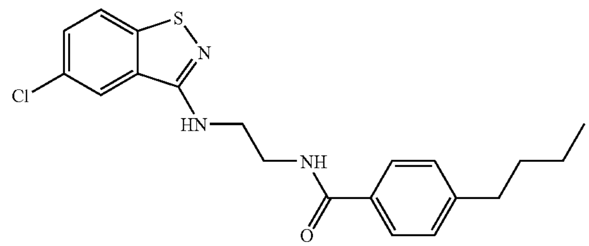 |
| 422 | $N^1$-(2-(benzo[d]isothiazol-3-ylamino)ethyl)-$N^4$-butylterephthalamide | 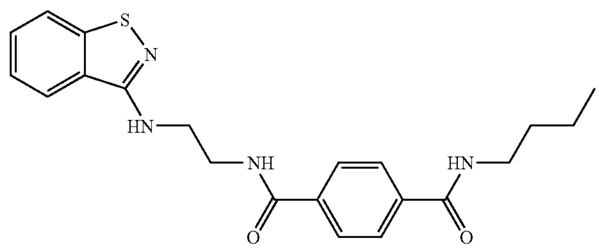 |
| 423 | N-(2-(5-chlorobenzo[d]isothiazol-3-ylamino)ethyl)-4-(pentyloxy)benzamide | 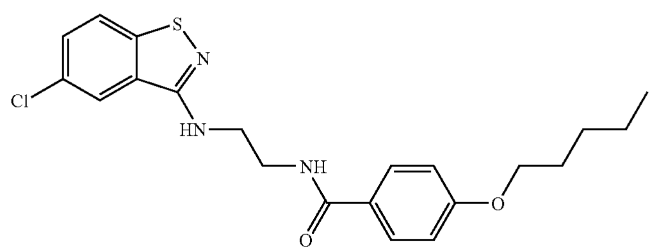 |
| 424 | tert-butyl 3-(2-(5-chlorobenzo[d]isothiazol-3-ylamino)ethylcarbamoyl)piperidine-1-carboxylate | 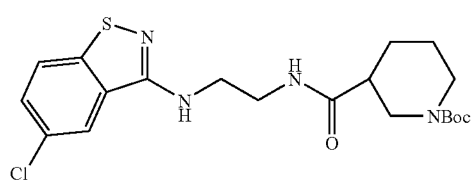 |
| 425 | (S)-tert-butyl 2-(2-(5-chlorobenzo[d]isothiazol-3-ylamino)ethylamino)-2-oxo-1-phenylethylcarbamate | 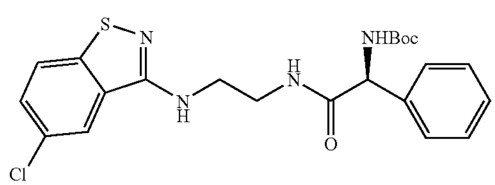 |
| 426 | $N^1$-(2-(benzo[d]isothiazol-3-ylamino)ethyl)-$N^4$-isopropylterephthalamide | 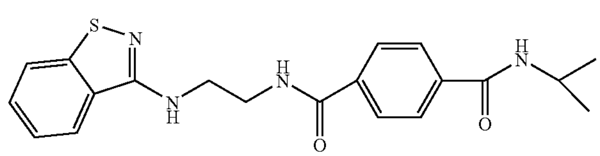 |

TABLE 2-continued

| Entry | Name | Structure |
|---|---|---|
| 427 | N[1]-(2-(benzo[d]isothiazol-3-ylamino)ethyl)-N[4]-cyclopropylterephthalamide | 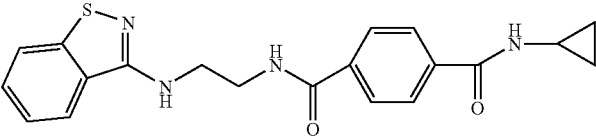 |
| 428 | N[1]-(2-(benzo[d]isothiazol-3-ylamino)ethyl)-N[3]-propylisophthalamide | 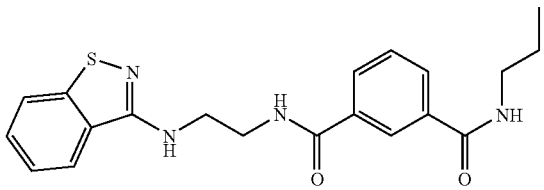 |
| 429 | N[1]-(2-(benzo[d]isothiazol-3-ylamino)ethyl)-N[3]-butylisophthalamide | 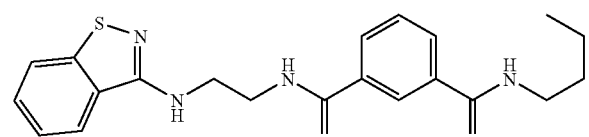 |
| 430 | N[1]-(2-(benzo[d]isothiazol-3-ylamino)ethyl)-N -isopropylisophthalamide | 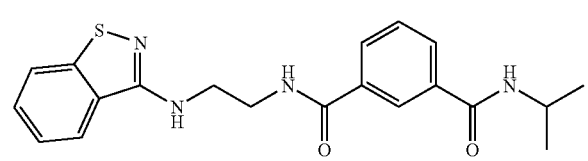 |
| 431 | N[1]-(2-(benzo[d]isothiazol-3-ylamino)ethyl)-N[3]-cyclopropylisophthalamide | 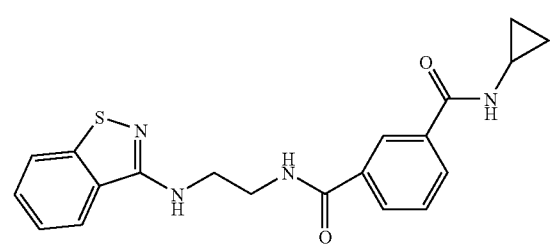 |
| 432 | N-(2-(5-chlorobenzo[d]isothiazol-3-ylamino)ethyl)-5-methoxy-1H-indole-2-carboxamide | 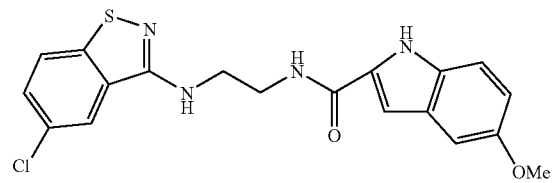 |
| 433 | N-(3-(benzo[d]isothiazol-3-ylamino)propyl)-6-nitrobenzo[b]thiophene-2-carboxamide | 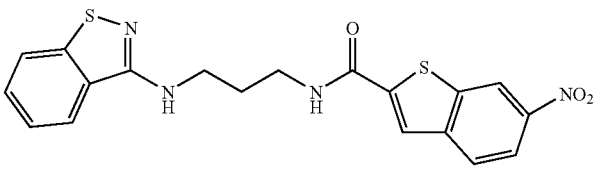 |
| 434 | N[1],N[3]-di(benzo[d]isothiazol-3-yl)propane-1,3-diamine | 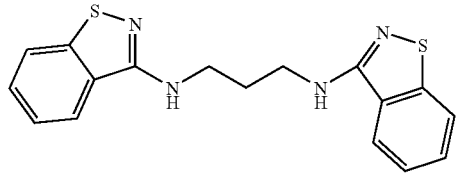 |

TABLE 2-continued

| Entry | Name | Structure |
|---|---|---|
| 435 | N-(3-(benzo[d]isothiazol-3-ylamino)propyl)-7-methoxybenzofuran-2-carboxamide | 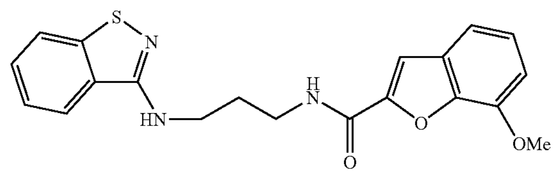 |
| 436 | N-(3-(benzo[d]isothiazol-3-ylamino)propyl)-5-chlorobenzofuran-2-carboxamide | 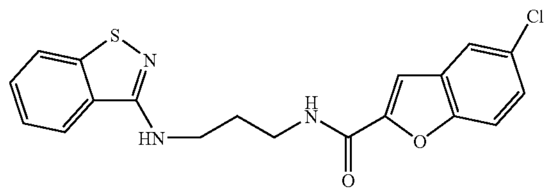 |
| 437 | N-(3-(benzo[d]isothiazol-3-ylamino)propyl)-5-methoxybenzofuran-2-carboxamide | 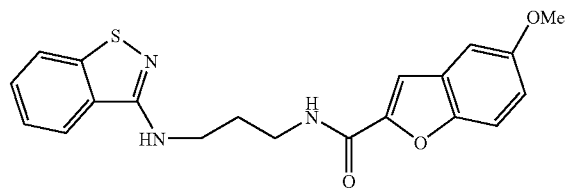 |
| 438 | N-(3-(benzo[d]isothiazol-3-ylamino)propyl)-6-(2,4-dimethoxyphenyl)picolinamide | 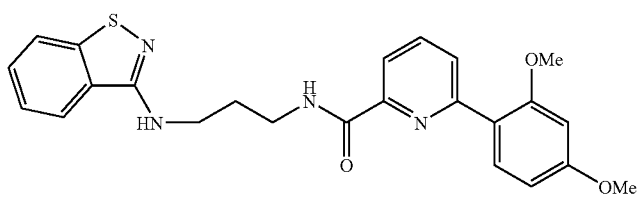 |
| 439 | N-(3-(benzo[d]isothiazol-3-ylamino)propyl)-6-nitrobenzofuran-2-carboxamide | 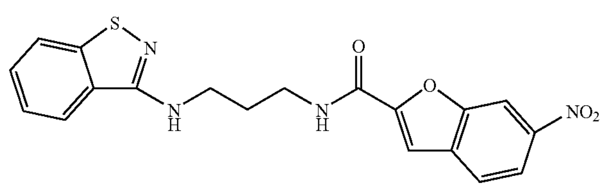 |
| 440 | N-(3-(benzo[d]isothiazol-3-ylamino)propyl)-6-(4-(methylsulfonyl)phenyl)picolinamide | 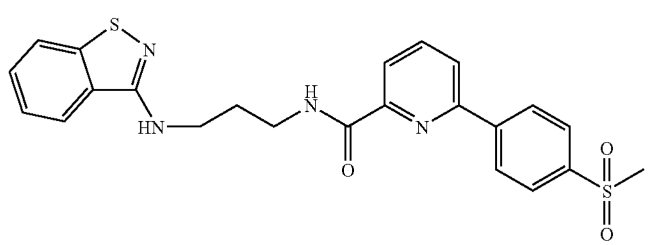 |
| 441 | N-(2-(benzo[d]isothiazol-3-ylamino)ethyl)-4-(3-methyl-5-oxo-4,5-dihydropyrazol-1-yl)benzamide | 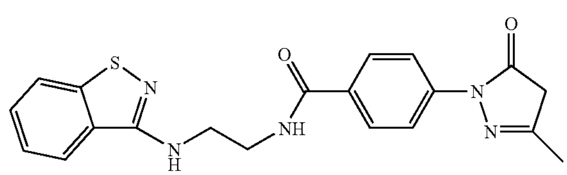 |
| 442 | N-(3-(benzo[d]isothiazol-3-ylamino)propyl)-6-(2-(pyridin-2-yl)ethylamino)picolinamide | 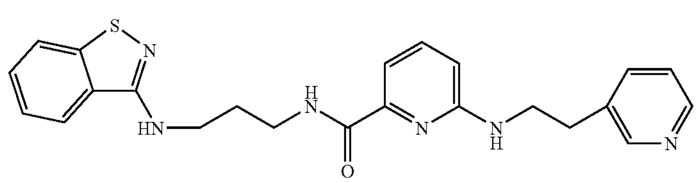 |

TABLE 2-continued

| Entry | Name | Structure |
|---|---|---|
| 443 | N-(3-(benzo[d]isothiazol-3-ylamino)propyl)-6-bromonicotinamide | 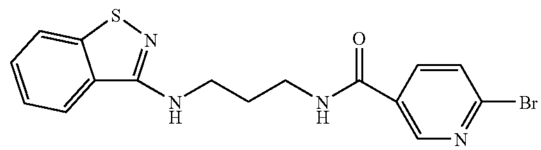 |
| 444 | N-(3-(benzo[d]isothiazol-3-ylamino)propyl)-5-bromo-1H-indole-2-carboxamide | 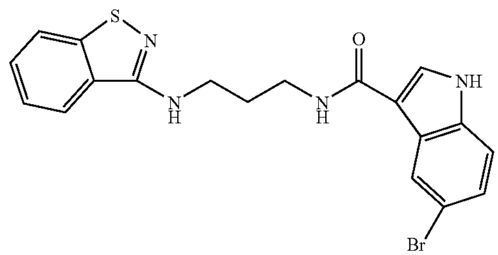 |
| 445 | N-(3-(benzo[d]isothiazol-3-ylamino)propyl)-5-bromobenzo[b]thiophene-2-carboxamide | 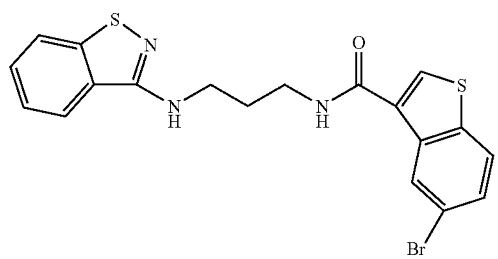 |
| 446 | 6-amino-N-(3-(benzo[d]isothiazol-3-ylamino)propyl)benzofuran-2-carboxamide | 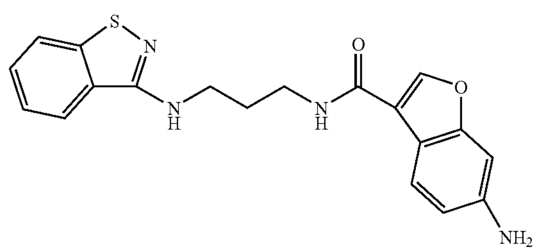 |
| 447 | N-(3-(benzo[d]isothiazol-3-ylamino)propyl)-6-(3-(dimethylamino)propylamino)picolin-amide | 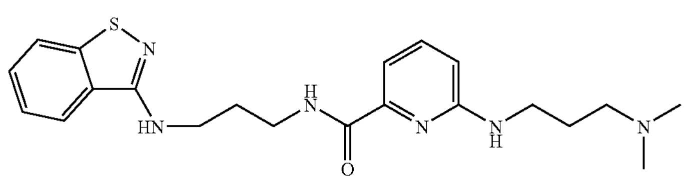 |
| 448 | N-(3-(benzo[d]isothiazol-3-ylamino)propyl)-6-(butylamino)picolinamide | 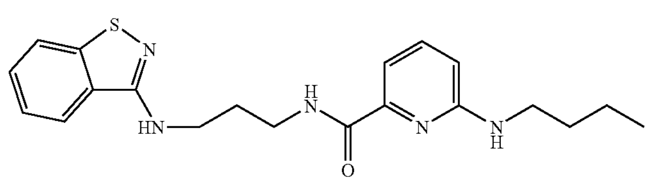 |
| 449 | N-(3-(benzo[d]isothiazol-3-ylamino)propyl)-1H-benzo[d]imidazole-5-carboxamide | 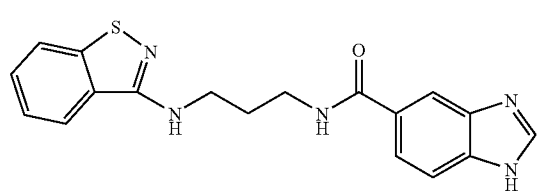 |

TABLE 2-continued

| Entry | Name | Structure |
|---|---|---|
| 450 | N-(3-(benzo[d]isothiazol-3-ylamino)propyl)-1H-indole-5-carboxamide | 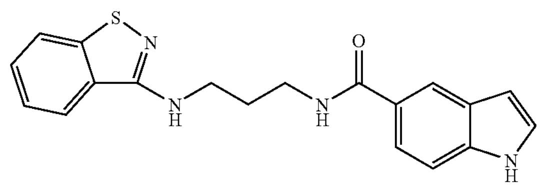 |
| 451 | N-(3-(benzo[d]isothiazol-3-ylamino)propyl)-6-hydroxynicotinamide | 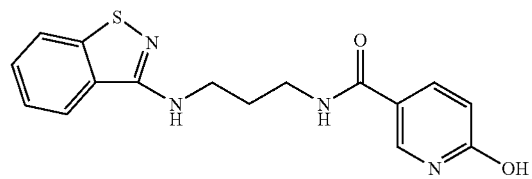 |
| 452 | N-(3-(benzo[d]isothiazol-3-ylamino)propyl)-5-chloro-6-hydroxynicotinamide | 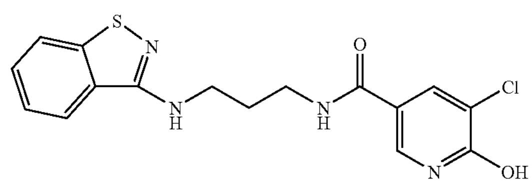 |
| 453 | N-(3-(benzo[d]isothiazol-3-ylamino)propyl)-5-pentanamidobenzofuran-2-carboxamide | 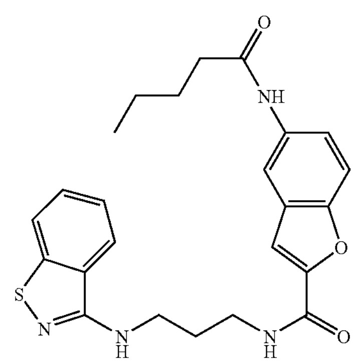 |
| 454 | N-(3-(benzo[d]isothiazol-3-ylamino)propyl)-5-butyramidobenzofuran-2-carboxamide | 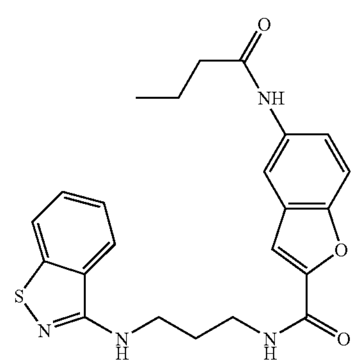 |

TABLE 2-continued

| Entry | Name | Structure |
|---|---|---|
| 455 | N-(3-(benzo[d]isothiazol-3-ylamino)propyl)-5-(3-propylureido)benzofuran-2-carboxamide | 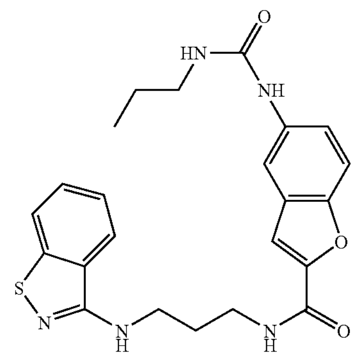 |
| 456 | N-(3-(benzo[d]isothiazol-3-ylamino)propyl)-5-pentanamidobenzo[b]thiophene-2-carboxamide | 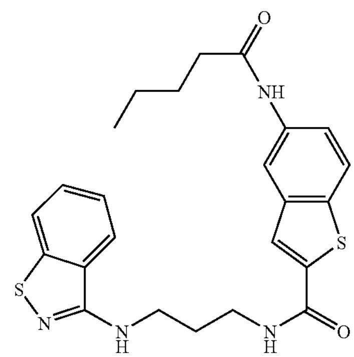 |
| 457 | N-(3-(benzo[d]isothiazol-3-ylamino)propyl)-5-butyramidobenzo[b]thiophene-2-carboxamide | 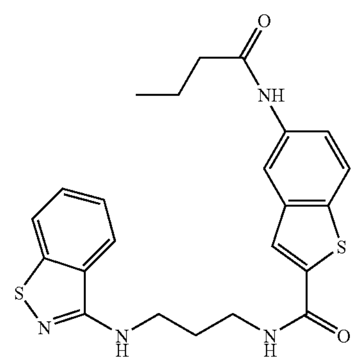 |

TABLE 2

| Entry | Name | Structure |
|---|---|---|
| 458 | N-(3-(benzo[d]isothiazol-3-ylamino)propyl)-5-(3-propylureido)benzo[b]thiophene-2-carboxamide | 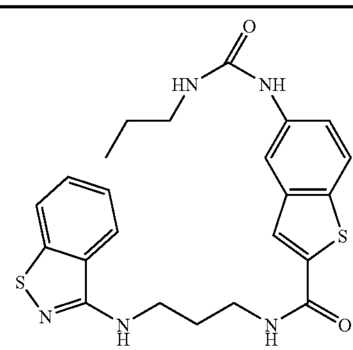 |

TABLE 2-continued

| Entry | Name | Structure |
|---|---|---|
| 459 | 5-amino-N-(3-(benzo[d]isothiazol-3-ylamino)propyl)benzo[b]thiophene-2-carboxamide | 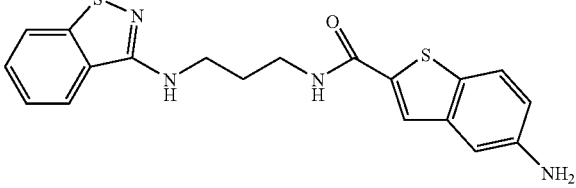 |
| 461 | N-(3-(7-chlorobenzo[d]isothiazol-3-ylamino)propyl)-4'-methoxybiphenyl-4-carboxamide | 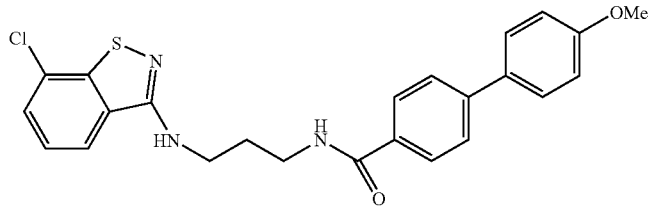 |
| 462 | N-(3-(benzo[d]isothiazol-3-ylamino)propyl)-5-(4-chlorophenyl)furan-2-carboxamide | 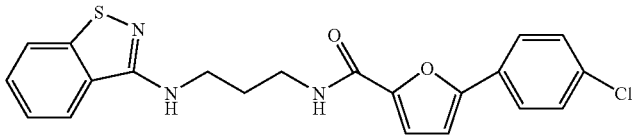 |
| 463 | N-(3-(benzo[d]isothiazol-3-ylamino)propyl)-5-(2,4-dichlorophenyl)furan-2-carboxamide | 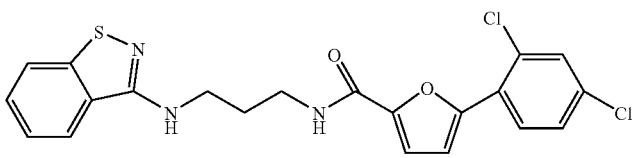 |
| 464 | N-(3-(benzo[d]isothiazol-3-ylamino)propyl)-5-(4-methoxyphenyl)furan-2-carboxamide | 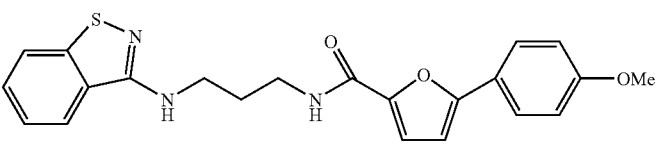 |
| 465 | N-(3-(benzo[d]isothiazol-3-ylamino)propyl)-3-(4-methoxyphenyl)-1H-pyrazole-5-carboxamide | 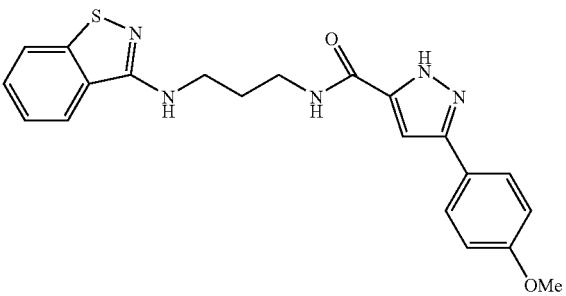 |
| 466 | N-(3-(benzo[d]isothiazol-3-ylamino)propyl)-5-(2-nitrophenyl)furan-2-carboxamide | 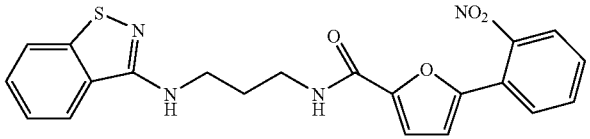 |
| 467 | N-(3-(benzo[d]isothiazol-3-ylamino)propyl)-5-(3-nitrophenyl)furan-2-carboxamide | 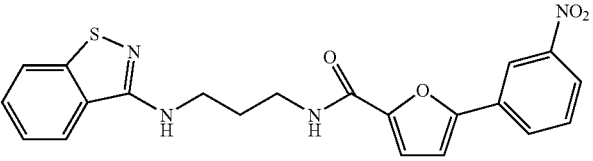 |

TABLE 2-continued

| Entry | Name | Structure |
|---|---|---|
| 468 | N-(3-(benzo[d]isothiazol-3-ylamino)propyl)-5-(4-nitrophenyl)furan-2-carboxamide | 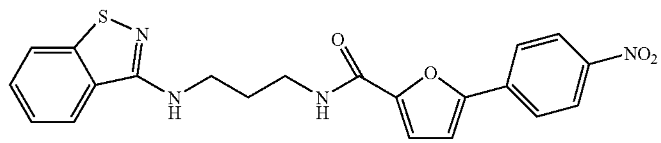 |
| 469 | N-(3-(benzo[d]isothiazol-3-ylamino)propyl)-5-(2-(trifluoromethyl)phenyl)furan-2-carboxamide | 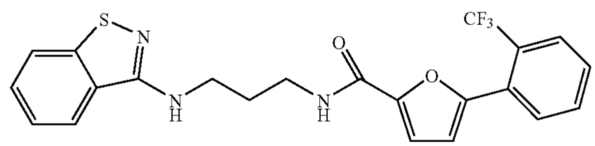 |
| 470 | N-(3-(benzo[d]isothiazol-3-ylamino)propyl)-5-(3-(trifluoromethyl)phenyl)furan-2-carboxamide | 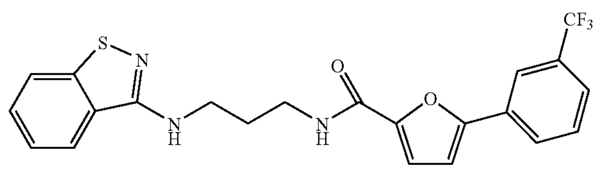 |
| 471 | 4'-methoxy-N-(3-(6-(trifluoromethyl)benzo[d]isothiazol-3-ylamino)propyl)biphenyl-4-carboxamide | 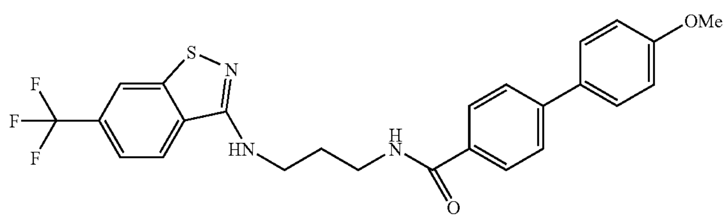 |
| 472 | $N^1$-((4'-methoxybiphenyl-4-yl)methyl)-$N^3$-(6-(trifluoromethyl)benzo[d]isothiazol-3-yl)propane-1,3-diamine | 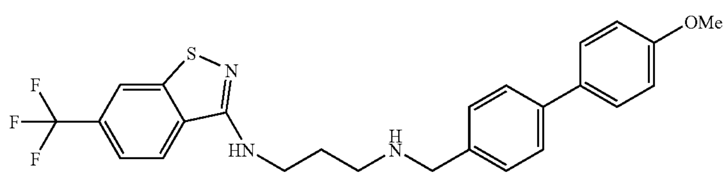 |
| 475 | $N^1$-(5-methoxybenzo[d]isothiazol-3-yl)-$N^3$-((4'-methoxybiphenyl-4-yl)methyl)propane-1,3-diamine | 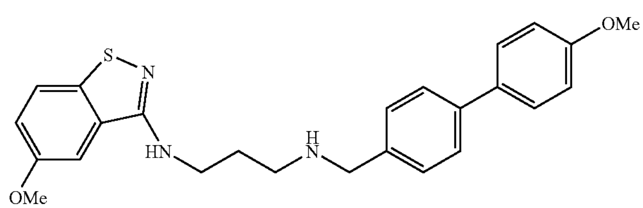 |
| 476 | 4'-methoxy-N-(3-(5-methoxybenzo[d]isothiazol-3-ylamino)propyl)biphenyl-4-carboxamide | 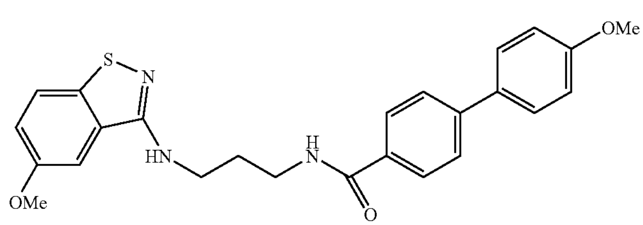 |

TABLE 2-continued

| Entry | Name | Structure |
|---|---|---|
| 477 | N¹-(7-chlorobenzo[d]isothiazol-3-yl)-N³-((4'-methoxybiphenyl-4-yl)methyl)propane-1,3-diamine | 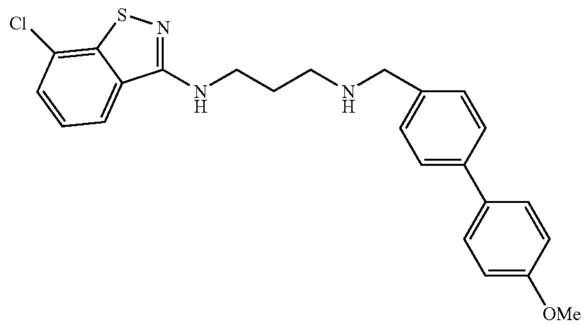 |
| 478 | N¹-((4'-methoxybiphenyl-4-yl)methyl)-N³-(5-(trifluoromethyl)benzo[d]isothiazol-3-yl)propane-1,3-diamine | 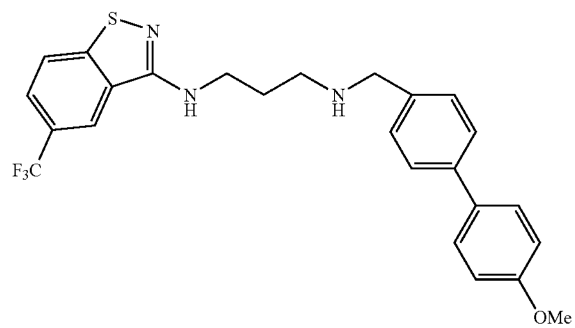 |
| 479 | N¹-(benzo[d]isothiazol-3-yl)-N³-((5-(2-chlorophenyl)furan-2-yl)methyl)propane-1,3-diamine | 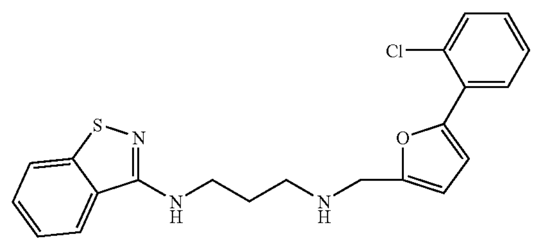 |
| 480 | N¹-(benzo[d]isothiazol-3-yl)-N³-((5-(4-chlorophenyl)furan-2-yl)methyl)propane-1,3-diamine | 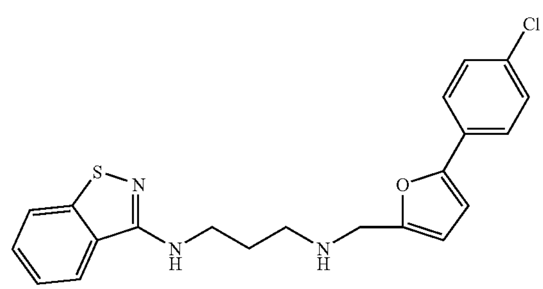 |
| 481 | N¹-(2,2'-bithiophen-5-ylmethyl)-N³-(benzo[d]isothiazol-3-yl)propane-1,3-diamine | 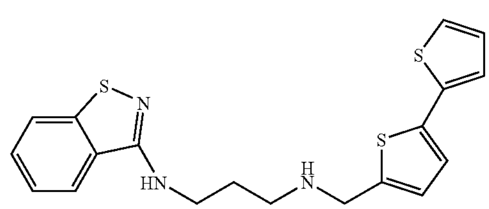 |

TABLE 2-continued

| Entry | Name | Structure |
|---|---|---|
| 482 | N¹-(benzo[d]isothiazol-3-yl-N³-((5-(3-(trifluoromethyl)phenyl)furan-2-yl)methyl)propane-1,3-diamine | 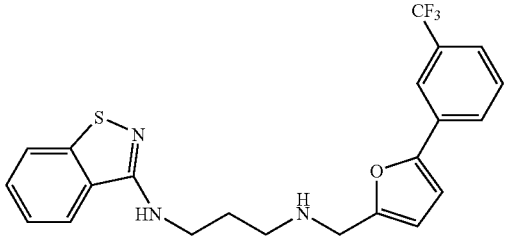 |
| 483 | N-(3-(4-chlorobenzo[d]isothiazol-3-ylamino)propyl)-4'-methoxybiphenyl-4-carboxamide | 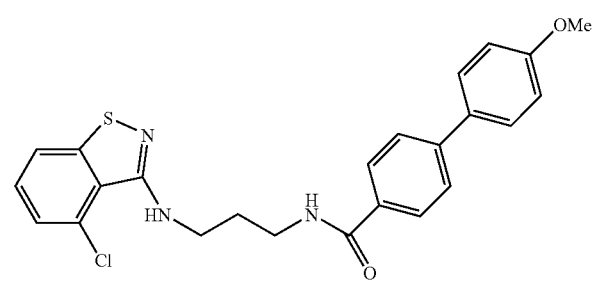 |
| 484 | N¹-(4-chlorobenzo[d]isothiazol-3-yl)-N³-((4'-methoxybiphenyl-4-yl)methyl)propane-1,3-diamine | 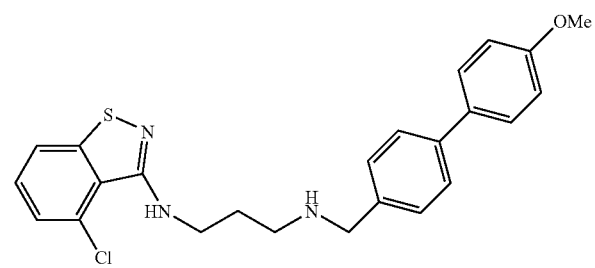 |
| 485 | N-(3-(benzo[d]isothiazol-3-ylamino)propyl)-5-bromothiophene-2-carboxamide | 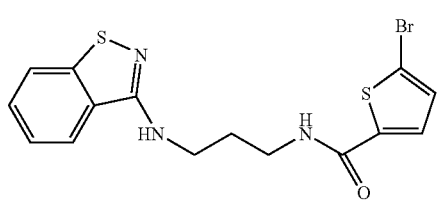 |
| 486 | N-(3-(benzo[d]isothiazol-3-ylamino)propyl)-5-phenylthiophene-2-carboxamide | 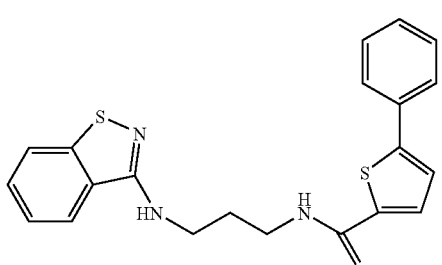 |
| 487 | N-(3-(benzo[d]isothiazol-3-ylamino)propyl)-5-(3-(trifluoromethyl)phenyl)thiophene-2-carboxamide | 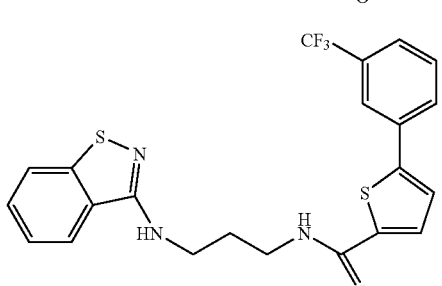 |

TABLE 2-continued

| Entry | Name | Structure |
|---|---|---|
| 488 | N-(3-(benzo[d]isothiazol-3-ylamino)propyl)-5-(4-(trifluoromethyl)phenyl)thiophene-2-carboxamide | 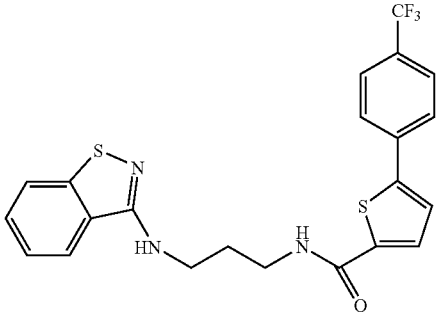 |
| 489 | N-(3-(benzo[d]isothiazol-3-ylamino)propyl)-5-(4-(methylsufonyl)phenyl)thiophene-2-carboxamide | 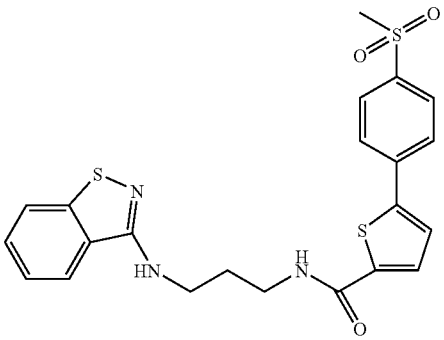 |
| 490 | N-(3-(benzo[d]isothiazol-3-ylamino)propyl)-5-(3-chlorophenyl)thiophene-2-carboxamide | 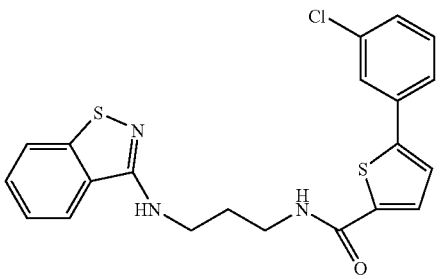 |
| 491 | N-(3-(benzo[d]isothiazol-3-ylamino)propyl)-5-(3-cyanophenyl)thiophene-2-carboxamide | 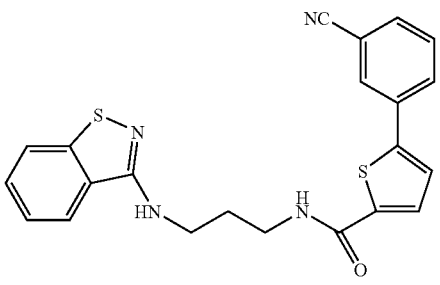 |
| 492 | N-(3-(benzo[d]isothiazol-3-ylamino)propyl)-5-(4-methoxyphenyl)thiophene-2-carboxamide | 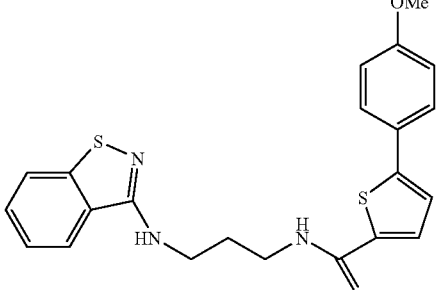 |

TABLE 2-continued

| Entry | Name | Structure |
|---|---|---|
| 493 | N¹-(benzo[d]isothiazol-3-yl)-N³-((4'-methoxybiphenyl-4-yl)methyl)-N³-methylpropane-1,3-diamine | 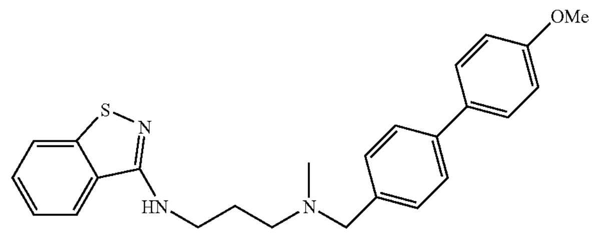 |
| 494 | N¹-(5-chlorobenzo[d]isothiazol-3-yl)-N³-((4'-methoxybiphenyl-4-yl)methyl)propane-1,3-diamine | 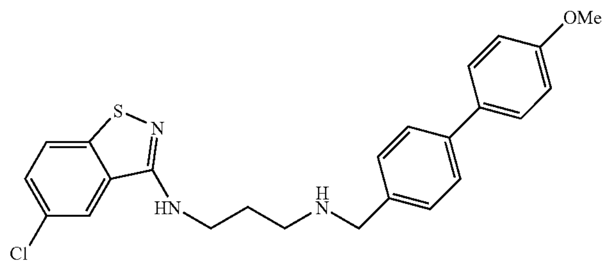 |
| 495 | N-(3-(benzo[d]isothiazol-3-ylamino)propyl)-5-(pyridin-3-yl)thiophene-2-carboxamide | 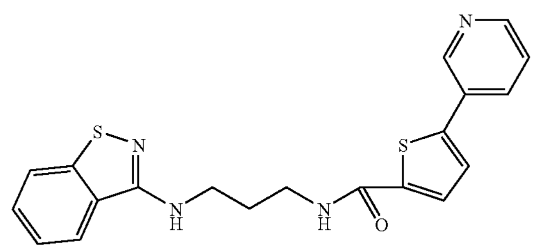 |
| 496 | N-(3-(benzo[d]isothiazol-3-ylamino)propyl)-5-nitrothiophene-2-carboxamide | 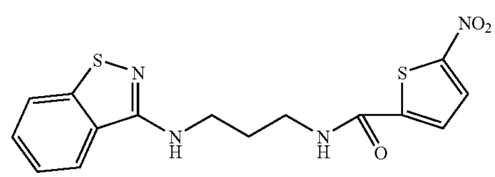 |
| 497 | N-(3-(benzo[d]isothiazol-3-ylamino)propyl)-4-bromothiophene-2-carboxamide | 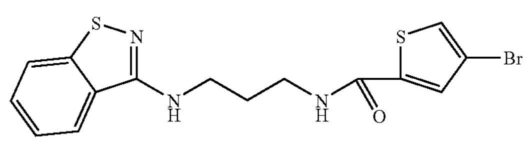 |
| 498 | N-(3-(7-fluorobenzo[d]isothiazol-3-ylamino)propyl)-4'-methoxybiphenyl-4-carboxamide | 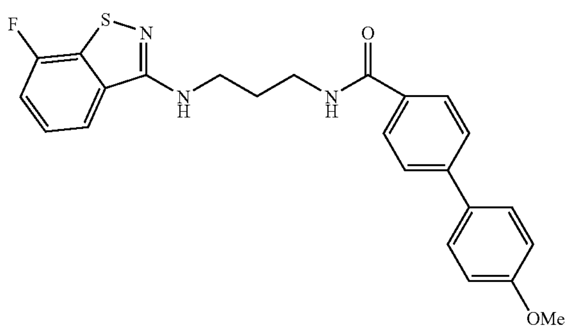 |

TABLE 2-continued

| Entry | Name | Structure |
|---|---|---|
| 499 | N¹-(7-fluorobenzo[d]isothiazol-3-yl)-N³-((4'-methoxybiphenyl-4-yl)methyl)propane-1,3 diamine | 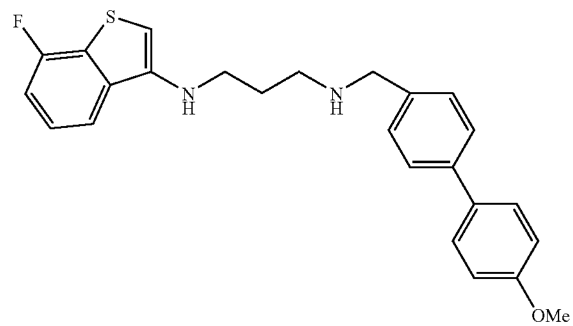 |
| 500 | 5-amino-N-(3-(benzo[d]isothiazol-3-ylamino)propyl)thiophene-2-carboxamide | 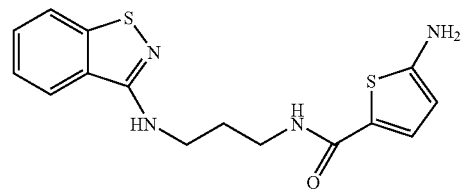 |
| 501 | N¹-(5,6-dimethoxybenzo[d]isothiazol-3-yl)-N³-((4'-methoxybiphenyl-4-yl)methyl)propane-1,3-diamine | 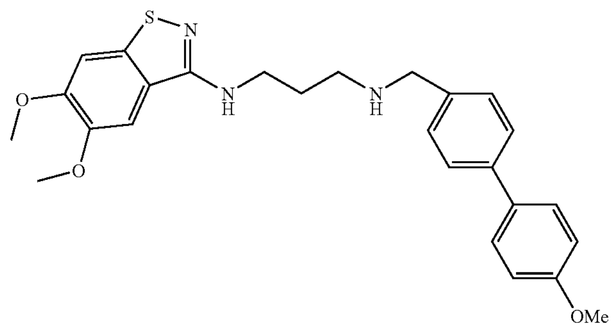 |
| 502 | N-(3-(5,6-dimethoxybenzo[d]isothiazol-3-ylamino)propyl)-4'-methoxybiphenyl-4-carboxamide | 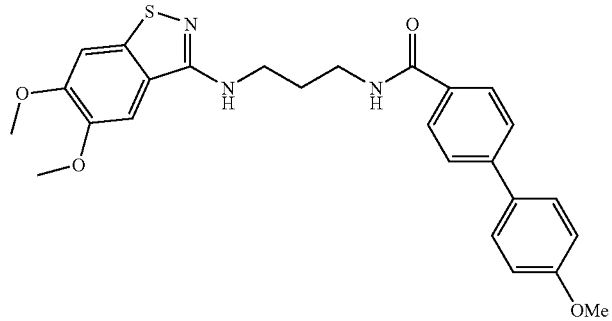 |
| 503 | 4'-methoxy-N-(3-(4-(trifluoromethyl)benzo[d]isothiazol-3-ylamino)propyl)biphenyl-4-carboxamide | 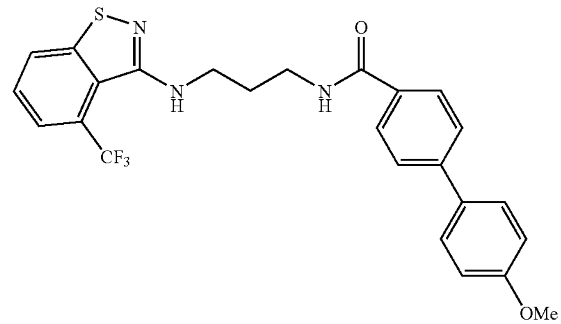 |

TABLE 2-continued

| Entry | Name | Structure |
|---|---|---|
| 504 | N¹-((4'-methoxybiphenyl-4-yl)methyl)-N³-(4-(trifluoromethyl)benzo[d]isothiazol-3-yl)propane-1,3-diamine | 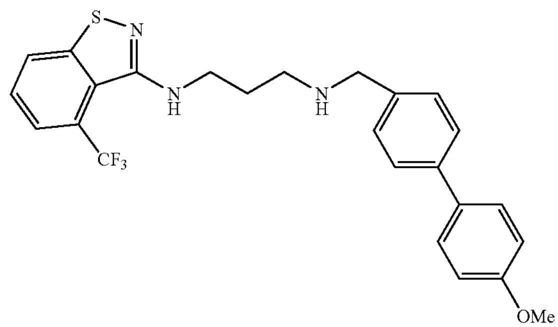 |
| 505 | N¹-(4-methoxybenzo[d]isothiazol-3-yl)-N³-((4'-methoxybiphenyl-4-yl)methyl)propane-1,3-diamine | 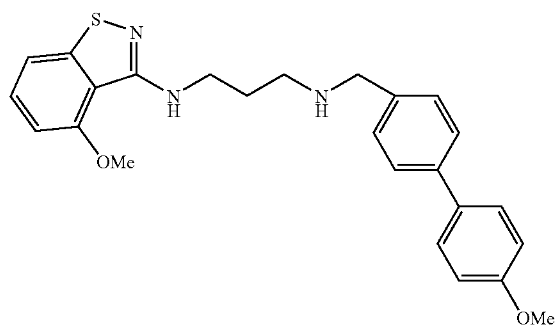 |
| 506 | N-(3-benzo[d]isothiazol-3-ylamino)propyl)-2-(4-bromophenyl)acetamide | 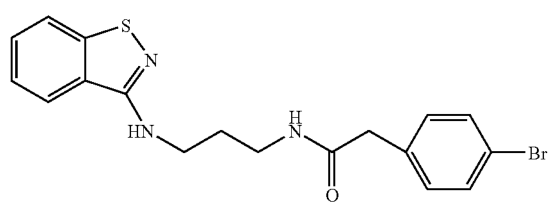 |
| 507 | N-(3-benzo[d]isothiazol-3-ylamino)propyl)-2-(4'-methoxybiphenyl-4-yl)acetamide | 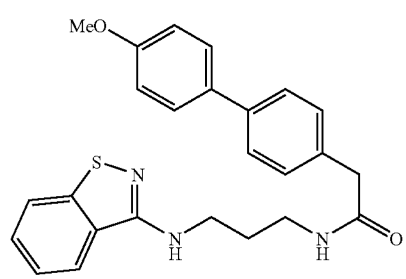 |
| 508 | N-(3-benzo[d]isothiazol-3-ylamino)propyl)-2-(4'-(trifluoromethyl)biphenyl-4-yl)acetamide | 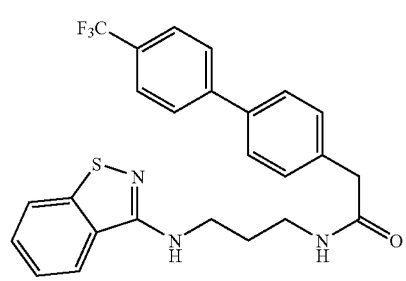 |

TABLE 2-continued

| Entry | Name | Structure |
|---|---|---|
| 509 | 3-(3-aminopropylamino)-N-tert-butylbenzo[d]isothiazole-4-sulfonamide | 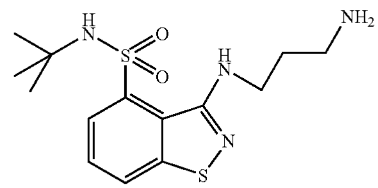 |
| 510 | 3-(3-aminopropylamino)-N-tert-butylbenzo[d]isothiazole-7-sulfonamide | 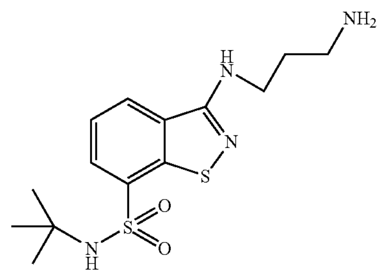 |
| 511 | 3-(3-aminopropylamino)-N-tert-butylbenzo[d]isothiazole-6-sulfonamide | 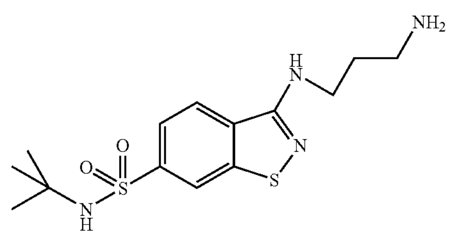 |
| 512 | N-(3-(4-(N-tert-butylsulfamoyl)benzo[d]isothiazol-3-ylamino)propyl)-4-iodobenzamide | 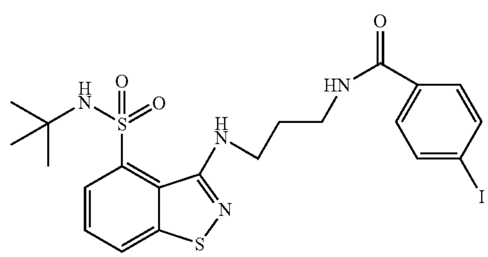 |
| 513 | N-(3-(7-(N-tert-butylsulfamoyl)benzo[d]isothiazol-3-ylamino)propyl)-4-iodobenzamide | 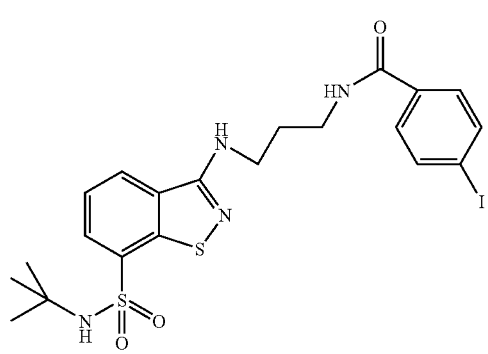 |

TABLE 2-continued

| Entry | Name | Structure |
|---|---|---|
| 514 | N-(3-(6-(N-tert-butylsulfamoyl)benzo[d]isothiazol-3-ylamino)propyl)-4-iodobenzamide | 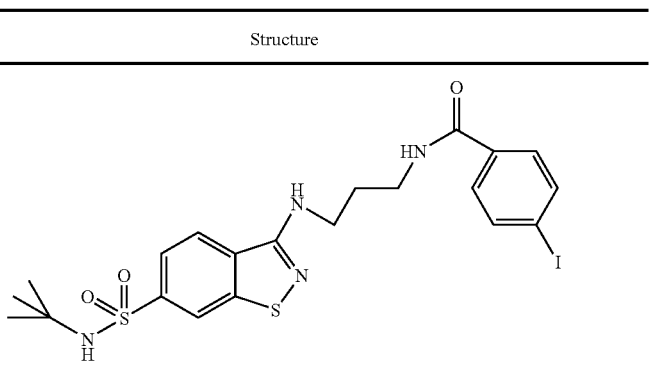 |
| 515 | N-(3-(5-bromobenzo[d]isothiazol-3-ylamino)propyl)-4'-methoxybiphenyl-4-carboxamide | 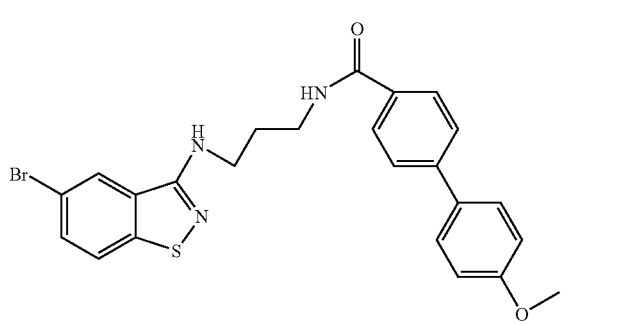 |
| 516 | N-(3-benzo[d]isothiazol-3-ylamino)propyl)-N-((4'-methoxybiphenyl-4-yl)methyl)acetamide | 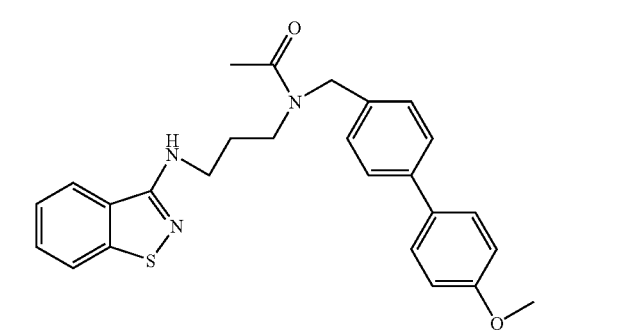 |
| 517 | N-(3-benzo[d]isothiazol-3-ylamino)propyl)-N-((4'-methoxybiphenyl-4-yl)methyl)-5-((3aS,4S,6aR)-2-oxo-hexahydro-1H-thieno[3,4-d]imidazol-4-yl)pentanamide | 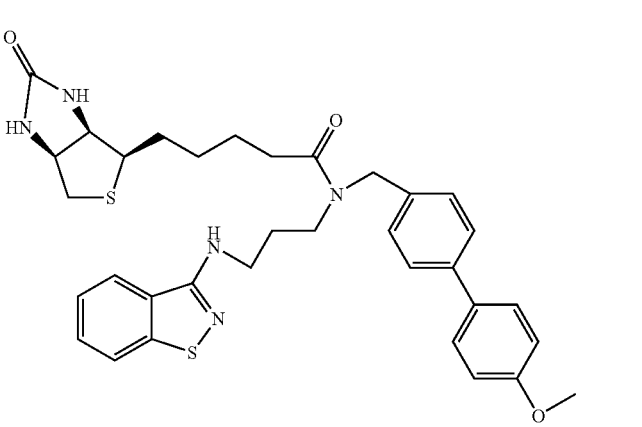 |

TABLE 2-continued

| Entry | Name | Structure |
|---|---|---|
| 518 | 4'-methoxy-N-(3-(5-(N-(4-methoxybenzyl)sulfamoyl)benzo[d]isothiazol-3-ylamino)propyl)biphenyl-4-carboxamide | 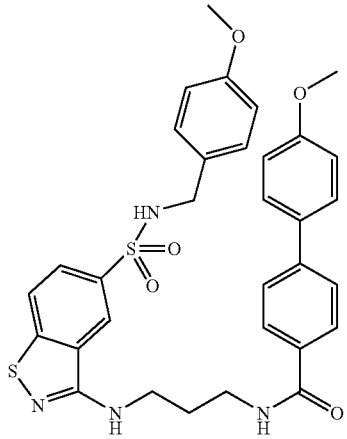 |
| 519 | 4'-methoxy-N-(3-(5-(N-methylsulfamoyl)benzo[d]isothiazol-3-ylamino)propyl)biphenyl-4-carboxamide | 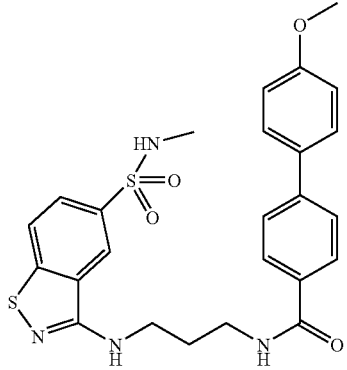 |
| 520 | 5-bromo-N-(3-(5-(N-phenylsulfamoyl)benzo[d]isothiazol-3-ylamino)propyl)thiophene-2-carboxamide | 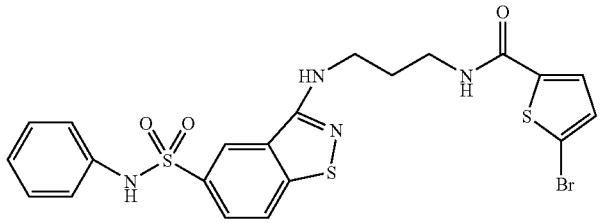 |
| 521 | 4-iodo-N-(3-(5-(N-phenylsulfamoyl)benzo[d]isothiazol-3-ylamino)propyl)benzamide | 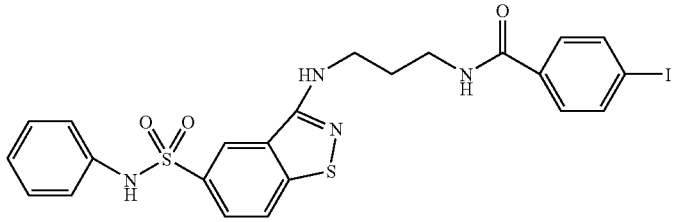 |
| 522 | 5-chloro-N-(3-(5-(N-phenylsulfamoyl)benzo[d]isothiazol-3-ylamino)propyl)thiophene-2-carboxamide | 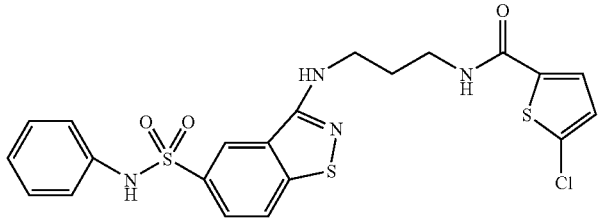 |

TABLE 2-continued

| Entry | Name | Structure |
|---|---|---|
| 523 | 4'-methoxy-N-(3-(5-(N-phenylsulfamoyl)benzo[d]isothiazol-3-ylamino)propyl)biphenyl-4-carboxamide | 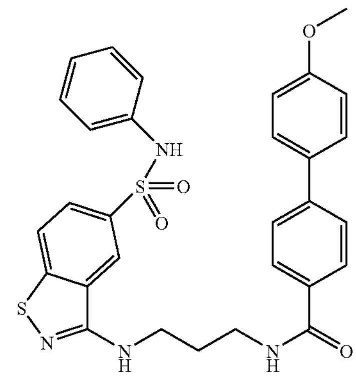 |
| 524 | N-(3-(isothiazolo[5,4-b]pyridin-3-ylamino)propyl)-2-methoxybenzamide | 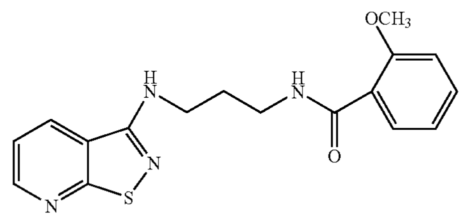 |
| 525 | N-(3-(isothiazolo[5,4-b]pyridin-3-ylamino)propyl)-4-methoxybenzamide | 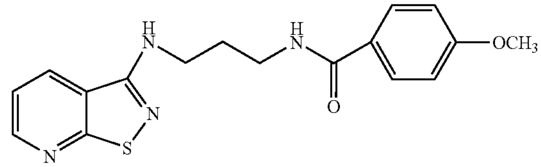 |
| 526 | N-(3-(isothiazolo[5,4-b]pyridin-3-ylamino)propyl)-3,5-dimethoxybenzamide | 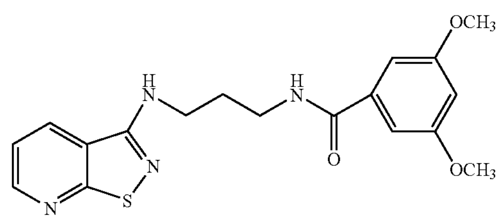 |
| 527 | N-(3-(isothiazolo[5,4-b]pyridin-3-ylamino)propyl)-2-(trifluoromethoxy)benzamide | 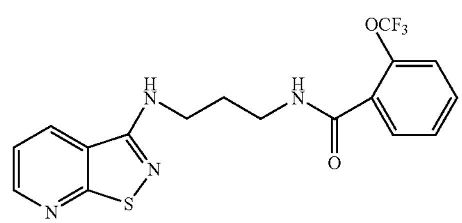 |
| 528 | N-(3-(isothiazolo[5,4-b]pyridin-3-ylamino)propyl)-3-methoxybenzamide | 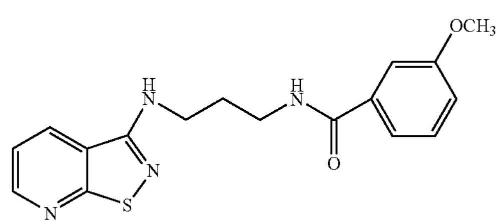 |

TABLE 2-continued

| Entry | Name | Structure |
|---|---|---|
| 529 | 2-fluoro-N-(3-(isothiazolo[5,4-b]pyridin-3-ylamino)propyl)-6-(trifluoromethyl)benzamide | 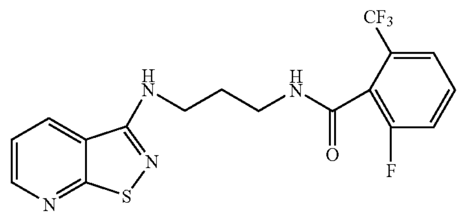 |
| 530 | N-(3-(isothiazolo[5,4-b]pyridin-3-ylamino)propyl)-3-(trifluoromethoxy)benzamide | 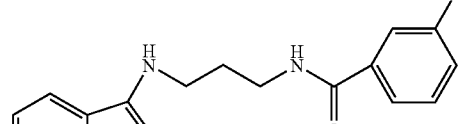 |
| 531 | 2-chloro-N-(3-(isothiazolo[5,4-b]pyridin-3-ylamino)propyl)nicotinamide | 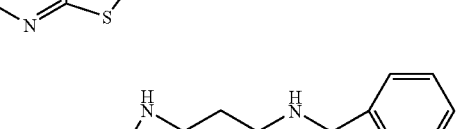 |
| 532 | 6-chloro-N-(3-(isothiazolo[5,4-b]pyridin-3-ylamino)propyl)nicotinamide | 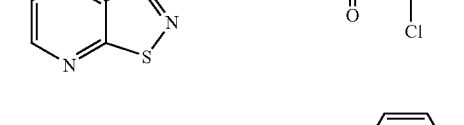 |
| 533 | 4-hexyl-N-(3-(isothiazolo[5,4-b]pyridin-3-ylamino)propyl)benzamide | 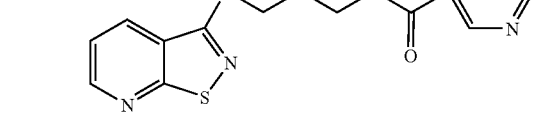 |
| 534 | N-(3-(isothiazolo[5,4-b]pyridin-3-ylamino)propyl)-2,3-dihydrobenzo[b][1,4]dioxine-2-carboxamide | 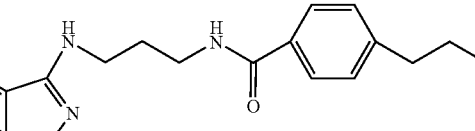 |
| 535 | 3-(2-chloro-6-fluorophenyl)-N-(3-(isothiazolo[5,4-b]pyridin-3-ylamino)propyl)-5-methylisoxazole-4-carboxamide | 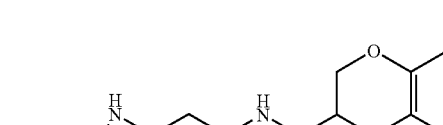 |

TABLE 2-continued

| Entry | Name | Structure |
|---|---|---|
| 536 | N-(3-(isothiazolo[5,4-b]pyridin-3-ylamino)propyl)-1-(4-(trifluoromethyl)pyrimidin-2-yl)piperidine-4-carboxamide | 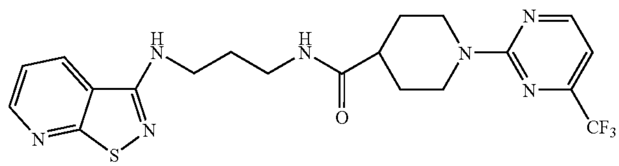 |
| 537 | N-(3-(isothiazolo[5,4-b]pyridin-3-ylamino)propyl)benzofuran-2-carboxamide | 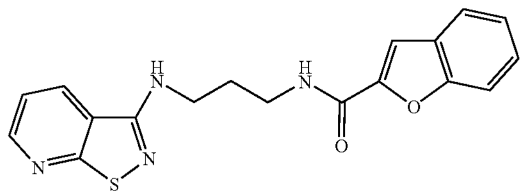 |
| 538 | N-(3-(isothiazolo[5,4-b]pyridin-3-ylamino)propyl)-4-(methylsulfonyl)benzamide | 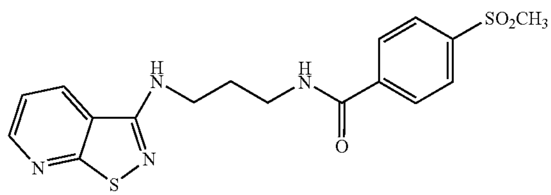 |
| 539 | N-(3-(isothiazolo[5,4-b]pyridin-3-ylamino)propyl)-2-(trifluoromethyl)benzenesulfonamide | 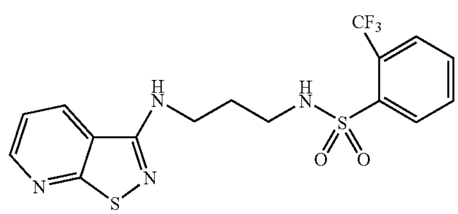 |
| 540 | 3-iodo-N-(3-(isothiazolo[5,4-b]pyridin-3-ylamino)propyl)benzamide | 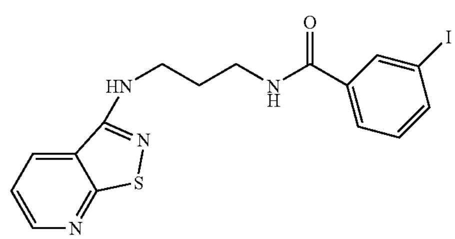 |
| 541 | N-(3-(isothiazolo[5,4-b]pyridin-3-ylamino)propyl)-3-(naphthalen-2-yl)benzamide | 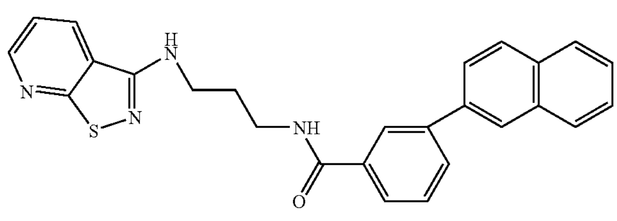 |
| 542 | N-(3-(isothiazolo[5,4-b]pyridin-3-ylamino)propyl)-3',4'-dimethylbiphenyl-3-carboxamide | 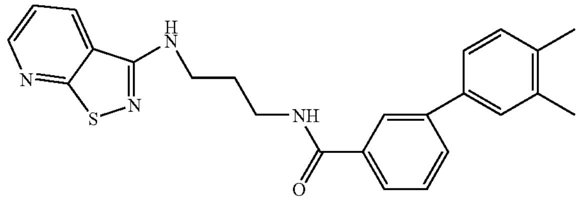 |

TABLE 2-continued

| Entry | Name | Structure |
|---|---|---|
| 543 | 2,6-dichloro-N-(3-(isothiazolo[5,4-b]pyridin-3-ylamino)propyl)benzamide | 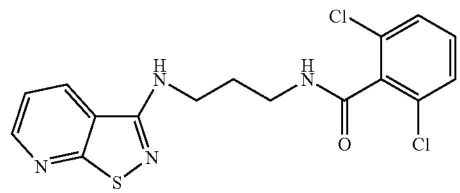 |
| 544 | N-(3-(isothiazolo[5,4-b]pyridin-3-ylamino)propyl)-6-methyl-4-oxo-4H-chromene-2-carboxamide | 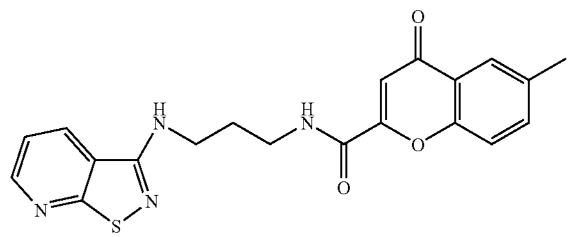 |
| 545 | 4-hexyl-N-(3-(isothiazolo[4,5-b]pyridin-3-ylamino)propyl)benzamide | 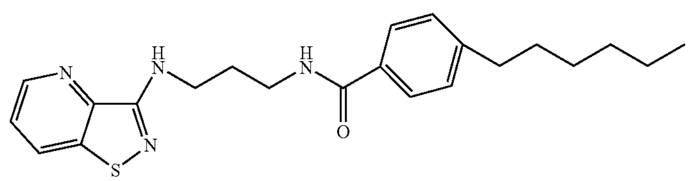 |
| 546 | N-(3-(isothiazolo[4,5-b]pyridin-3-ylamino)propyl)-3-(trifluoromethyl)benzenesulfonamide | 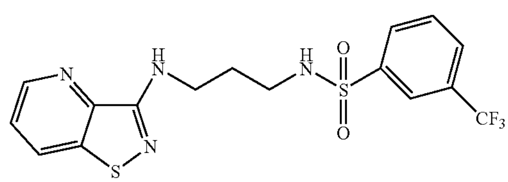 |
| 547 | 3-iodo-N-(3-(isothiazolo[4,5-b]pyridin-3-ylamino)propyl)benzamide | 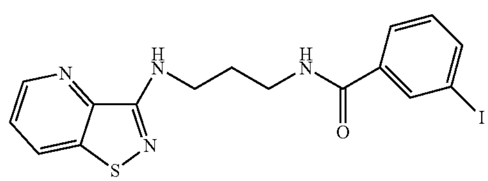 |
| 548 | N-(3-(4-methylbenzo[d]isothiazol-3-ylamino)propyl)-3-(trifluoromethyl)benzenesulfonamide | 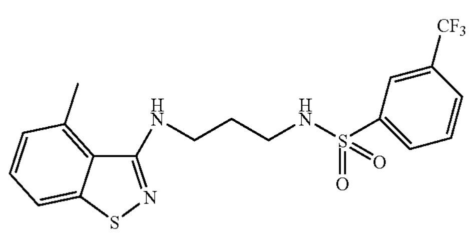 |
| 549 | $N^1$-(isothiazolo[4,5-b]pyridin-3-yl)-$N^3$-((4'-methoxybiphenyl-4-yl)methyl)propane-1,3-diamine | 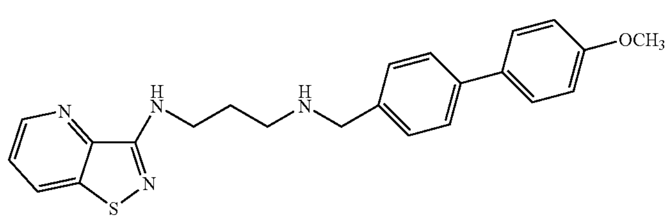 |

TABLE 2-continued

| Entry | Name | Structure |
|---|---|---|
| 550 | N-(3-(isothiazolo[4,5-b]pyridin-3-ylamino)propyl)-N-((4'-methoxybiphenyl-4-yl)methyl)-1,2-dimethyl-1H-imidazole-4-sulfonamide | 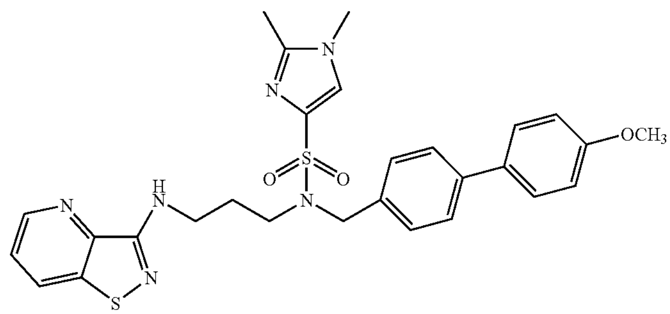 |
| 551 | methyl 5-(N-(3-(isothiazolo[4,5-b]pyridin-3-ylamino)propyl)-N-((4'-methoxybiphenyl-4-yl)methyl)sulfamoyl)-1-methyl-1H-pyrrole-2-carboxylate | 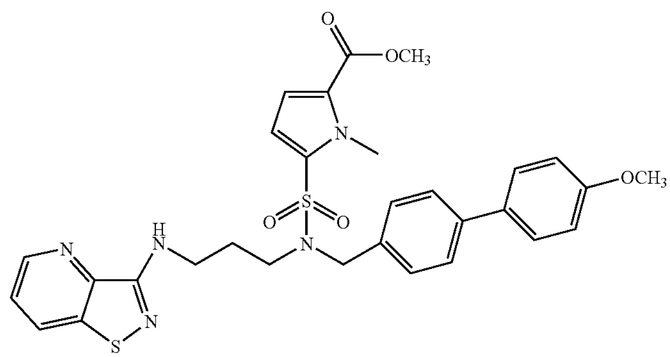 |
| 552 | 2-cyano-N-(3-(isothiazolo[4,5-b]pyridin-3-ylamino)propyl)-N-((4'-methoxybiphenyl-4-yl)methyl)acetamide | 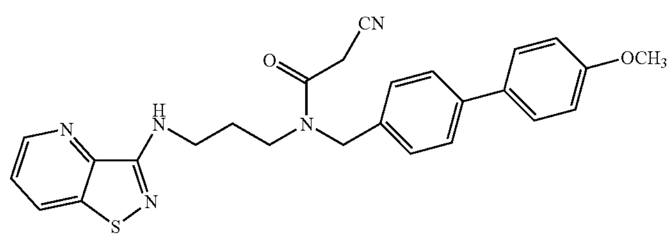 |
| 553 | $N^1$-(isothiazolo[5,4-b]pyridin-3-yl)-$N^3$-((4'-methoxybiphenyl-4-yl)methyl)propane-1,3-diamine | 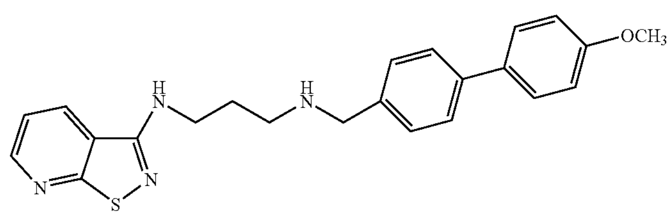 |
| 554 | N-(3-(isothiazolo[5,4-b]pyridin-3-ylamino)propyl)-N-((4'-methoxybiphenyl-4-yl)methyl)-1,2-dimethyl-1H-imidazole-4-sulfonamide | 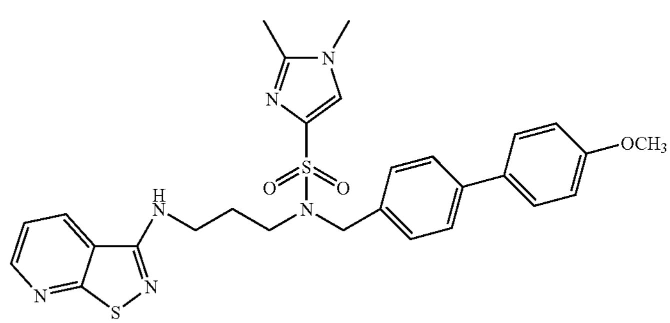 |

TABLE 2-continued

| Entry | Name | Structure |
|---|---|---|
| 555 | methyl 5-(N-(isothiazolo[5,4-b]pyridin-3-ylamino)propyl)-N-((4'-methoxybiphenyl-4-yl)methyl)sulfamoyl)-1-methyl-1H-pyrrole-2-carboxylate | 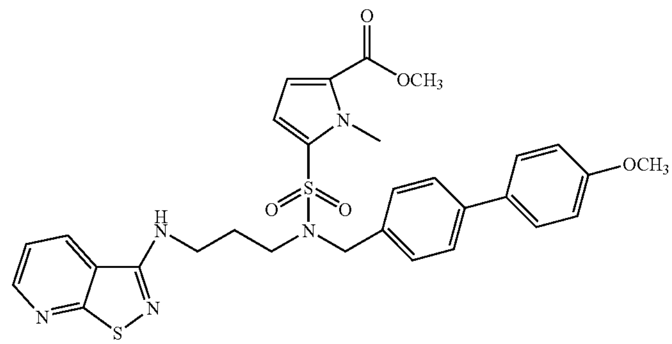 |
| 556 | 2-cyano-N-(3-(isothiazolo[5,4-b]pyridin-3-ylamino)propyl)-N-((4'-methoxybiphenyl-4-yl)methyl)acetamide | 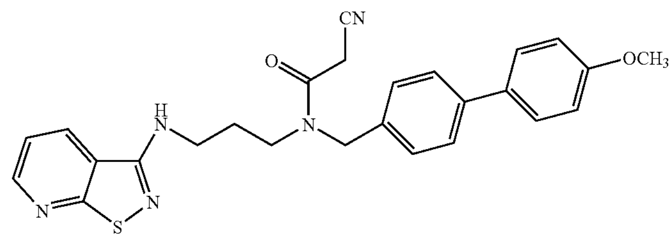 |

Another aspect of the invention, embodiment [0131], is a pharmaceutical composition comprising the compound according to any one of embodiments [0096]-[0129] and a pharmaceutically acceptable carrier.

Another aspect of the invention, embodiment [0132], is a metabolite of the compound or the pharmaceutical composition according to any one of embodiments [0096]-[0129].

Another aspect of the invention, embodiment [0133], is a method of inhibiting replication or proliferation of a hepatitis C ("HC") virion, comprising contacting an HCV replication complex with an amount of the compound according to embodiment [0096], including the compounds in Table 1, effective to inhibit replication of the HC virion.

In one example, embodiment [0134], the method is according to embodiment [0132], which is practiced in vitro.

In another example, embodiment [0134], the method is according to aspect [0132], which is practiced in vivo.

Another aspect of the invention, embodiment [0136], is a method of treating or preventing an HCV infection, comprising administering to a subject an amount of a compound according to embodiment [0096] including the compounds in Table 1, effective to treat or prevent an HCV infection.

In one example, embodiment [0137], the method is according to embodiment [0136], wherein the subject is a human.

In another example, embodiment [0138], the method is according to embodiment [0136], wherein the compound is administered in an amount of 0.1 mg/kg to 200 mg/kg.

In another example, embodiment [0139], the method is according to embodiment [0136], wherein the compound is administered in an amount of 10 mg/kg to 100 mg/kg.

In another example, embodiment [0140], the method is according to embodiment [0137], wherein the compound is administered orally.

In another example, embodiment [0141], the method is according to embodiment [0137], wherein the compound is administered by injection.

In another example, embodiment [0142], the method is according to embodiment [0137], which is practiced therapeutically in a subject having an HCV infection.

In another example, embodiment [0143], the method is according to embodiment [0137], which is practiced prophylactically in a subject at risk of developing an HCV infection.

Synthesis of Compounds

Starting materials useful for preparing compounds of the invention and intermediates thereof are commercially available or can be prepared by well-known synthetic methods (see, e.g., Harrison et al., "Compendium of Synthetic Organic Methods", Vols. 1-8, John Wiley and Sons, 1971-1996; "Beilstein Handbook of Organic Chemistry," Beilstein Institute of Organic Chemistry, Frankfurt, Germany; Feiser et al., "Reagents for Organic Synthesis," Volumes 1-21, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, $5^{th}$ Ed. 2001; Larock "Comprehensive Organic Transformations," VCH Publishers, 1989; Paquette, "Encyclopedia of Reagents for Organic Synthesis," John Wiley & Sons, 1995). Other methods for synthesizing the compounds described herein and/or starting materials are either described in the art or will be readily apparent to the skilled artisan. Alternatives to the reagents and/or protecting groups illustrated in the schemes below may be found in the references provided above and in other compendiums well known to the skilled artisan. Guidance for selecting suitable protecting groups can be found, for example, in Greene & Wuts, "Protective Groups in Organic Synthesis," $3^{rd}$. Ed., Wiley Interscience, 1999. Accordingly, the synthetic methods and strategy presented herein are illustrative rather than comprehensive.

The compounds encompassed by the instant application can be synthesized by methods known to one of ordinary skill in the art. Compounds of the invention generally may be prepared by methods illustrated in Schemes 1-2; however, the schemes and their corresponding description are not intended to be limiting. One of ordinary skill in the art would recognize that functionality of compounds according to formula I can be introduced at various stages of the synthesis of the compounds and likewise protecting groups can be used in such synthetic strategies.

Referring to Scheme 1, the synthesis of compounds according to formula I can be performed via an appropriately substituted benzoisothiazole derivative 1, for example with a leaving group at it's three-position (designated $LG^1$). An example of 1 would be 3-chlorobenzo[d]isothiazole, which can be made, for example, by reaction of benzo[d]isothiazol-3(2H)-one with phosphoryl trichloride. Combination of 1 with, for example, a bis-functional nucleophile 2, gives intermediate 3. Bis-functional nucleophile 2 either contains functionality to form $L^1$ (as defined in relation to formula I herein) or is converted to $L^1$ subsequent to the aforementioned bond forming reaction to form 3. Once formed, 3 is then for example acylated with the appropriate acylating agent (in this example containing leaving group $LG^2$) to form compounds of the invention according to formula I. Again the $Nu^2$ in intermediate 3 either contains functionality to form $L^2$ (as defined in relation to formula I herein) or is converted to $L^2$ subsequent to the aforementioned bond forming reaction to form compounds according to formula I (e.g. where B is —C(=O)—). Of course, other electrophiles such as sulfonyl halides, isocyanates, carbamoyl halides and the like can be used in the latter step to make compounds according to formula I as well.

One of ordinary skill in the art would understand that this description is rather simplified and that particular groups may have to be protected and de-protected, or otherwise converted during the synthesis described. For example if $Nu^1$ and $Nu^2$ of reagent 2 are of differing reactivity (or the same reactivity), one or the other may have to be protected or its reactivity ameliorated in order to effect efficient regiochemical selectivity in the addition reaction described.

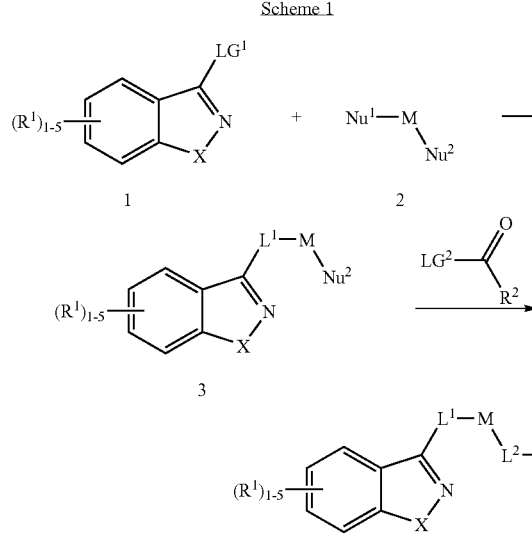

Scheme 1

Referring to Scheme 2, the order of synthesis may be different than that described in relation to Scheme 1. For example, an intermediate 4 may be synthesized and added to starting material 1 to give compounds according to formula I (e.g. where B is —C(=O)—).

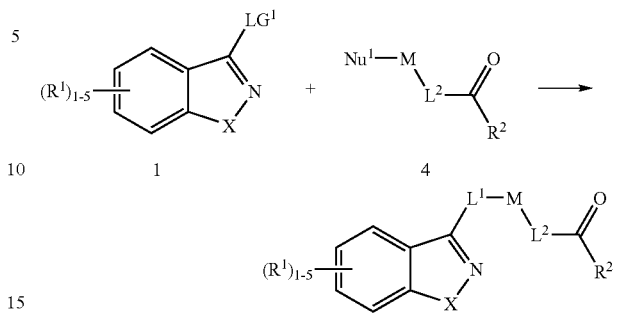

Scheme 2

As mentioned, compounds of the invention may bear suitably protected functional groups at any suitable stage in their synthesis. This protecting group may be introduced or removed at any stage in the synthetic sequence to afford a compound of the invention or a key intermediate along the synthetic pathway. The choice of a suitable protecting group and its introduction or removal is a well-established practice in synthetic organic chemistry.

The following abbreviations and terms have the indicated meanings throughout:

TABLE 3

| Abbreviation | Meaning |
|---|---|
| Ac | acetyl |
| ACN | acetonitrile |
| ATP | adenosine triphosphate |
| BNB | 4-bromomethyl-3-nitrobenzoic acid |
| b.p. | boiling point |
| Boc | t-butyloxy carbonyl or t-Boc |
| br | broad |
| Bu | butyl |
| °C. | degrees Celsius |
| c- | cyclo |
| CBZ | CarboBenZoxy = benzyloxycarbonyl |
| d | doublet |
| dd | doublet of doublet |
| dt | doublet of triplet |
| DBU | Diazabicyclo[5.4.0]undec-7-ene |
| DCM | dichloromethane = methylene chloride = $CH_2Cl_2$ |
| DCE | dichloroethylene |
| DEAD | diethyl azodicarboxylate |
| DIC | diisopropylcarbodiimide |
| DIEA | N,N-diisopropylethyl amine |
| DMAP | 4-N,N-dimethylaminopyridine |
| DMF | N,N-dimethylfonamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | ethyl |
| Fmoc | 9-fluorenylmethoxycarbonyl |
| g | gram(s) |
| GC | gas chromatography |
| H or hr | hour(s) |
| HATU | O-(7-Azabenzotriazol-1-yl)-1,1,3,3-tetramethyluronium hexafluorophosphate |
| HMDS | hexamethyldisilazane |
| HOAc | acetic acid |
| HOBt | 1-hydroxybenzotriazole |
| HPLC | high performance liquid chromatography |
| IR | Infrared spectroscopy |
| L | liter(s) |
| LC-MS | Liquid Chromatography-Mass Spectrometer |
| M | molar or molarity |
| m | multiplet |
| MS | Mass Spectrometry |

TABLE 3-continued

| Abbreviation | Meaning |
| --- | --- |
| mesyl | methanesulfonyl |
| mg | milligram(s) |
| MHz | megahertz (frequency) |
| Min | minute(s) |
| mL | milliliter(s) |
| mM | millimolar |
| mmol | millimole(s) |
| mol | mole(s) |
| m.p. | melting point |
| MS | Mass Spectrometry |
| MTBE | methyl t-butyl ether |
| N | normal or normality |
| NBS | N-bromosuccinimide |
| NCS | N-chlorosuccinimide |
| NIS | N-iodosuccinimide |
| nM | nanomolar |
| NMMO | N-methylmorpholine oxide |
| NMR | nuclear magnetic resonance spectroscopy |
| PEG | polyethylene glycol |
| Ph | phenyl |
| PhOH | phenol |
| PfP | pentafluorophenol |
| PfPy | pentafluoropyridine |
| PPTS | Pyridinium p-toluenesulfonate |
| Py | pyridine |
| PyBroP | bromo-tris-pyrrolidino-phosphonium hexafluorophosphate |
| q | quartet |
| RT | Room temperature |
| Sat'd | saturated |
| s | singlet |
| SEM-Cl | chloromethyl 2-trimethylsilylethyl ether |
| s- | secondary |
| t- | tertiary |
| T or tr | triplet |
| TBDMS | t-butyldimethylsilyl |
| TBDPS | t-butyldiphenylsilyl |
| TES | triethylsilane |
| TFA | trifluoroacetic acid |
| THF | tetrahydrofuran |
| TMOF | trimethyl orthoformate |
| TMS | trimethylsilyl |
| tosyl | p-toluenesulfonyl |
| Trt | triphenylmethyl |
| μL | microliter(s) |
| μM | Micromole(s) or micromolar |
| UV | ultraviolet spectroscopy |
| UV-vis | ultraviolet-visible spectroscopy |

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. Generally, the synthetic examples are presented graphically as an overall reaction path with corresponding description below. All references cited herein are incorporated by reference in their entirety.

Melting Point Methods: Melting points were obtained on an Electrothermal IA9100 series digital melting point apparatus. All Melting points are uncorrected.

Elemental Analysis: Elemental analysis was performed by Desert Analytics, Tucson, Ariz.

NMR Methods: NMR spectra were obtained on a 300 MHz Varian Mercury system.

Microwave Methods: Microwave reactions were carried out in the Personal Chemistry, SmithCreator microwave.

LC-MS Methods

General: LC-MS was performed on a Waters Micromass ZQ instrument with electrospray ionization. The HPLC component was a Waters Model 2690 Separation module coupled to a Waters Model 996 photodiode array detector.

Method Y: This method utilized a 2.1×150 mm Agilent ZorbaY 5 μM C-18 reversed phase column with a flow rate of 0.3 mL/min and a gradient of 5-100% acetonitrile with water containing 0.05% formic acid over 15 min, then continuing for 5 min with 100% acetonitrile.

Method Z: This method utilized a 2.1×5 mm Agilent ZorbaY 5 μM C-18 reversed phase column with a flow rate of 0.5 mL/min and a gradient of 5-100% acetonitrile with water containing 0.1% formic acid over 8 min, then continuing for 2 min with 100% acetonitrile.

Method A: LC-MS was performed on a Waters Micromass ZMD instrument with electrospray ionization. This method utilized a 2.1×5 mm Agilent Zorbax 5 μM C-18 reversed phase column with a flow rate of 0.3 mL/min and a gradient of 10-100% acetonitrile with water containing 0.05% formic acid over 10 min, then continuing for 8 min with 100% acetonitrile.

Method B: This method utilized a 2.1×5 mm Agilent Zorbax 5 μM C-18 reversed phase column with a flow rate of 0.8 mL/min and a gradient of 5-95% acetonitrile with water containing 0.05% formic acid over 5 min, then continuing for 2 min with 95% acetonitrile.

Method C: This method utilized a 2.0×75 mm Phenomonex Luna 5 μM C-18 reversed phase column with a flow rate of 0.45 mL/min and a gradient of 5-100% acetonitrile with water containing 0.1% formic acid over 8 min, then continuing for 2 min with 100% acetonitrile.

Method D: This method utilized a 3.0×100 mm Phenomonex Gemini 5 μM C-18 reversed phase column with a flow rate of 1.5 mL/min and a gradient of 5-100% acetonitrile with water containing 0.1% formic acid over 8 min, then continuing for 2 min with 100% acetonitrile Method E: This method utilized a 2.1×5 mm Agilent ZorbaY 5 μM C-18 reversed phase column with a flow rate of 0.8 mL/min and a gradient of 5-95% acetonitrile with water containing 0.1% formic acid over 6 min, then continuing for 2 min with 100% acetonitrile.

Example 1

Synthesis of N-(2-(Benzo[d]isothiazol-3-ylamino)ethyl)picolinamide

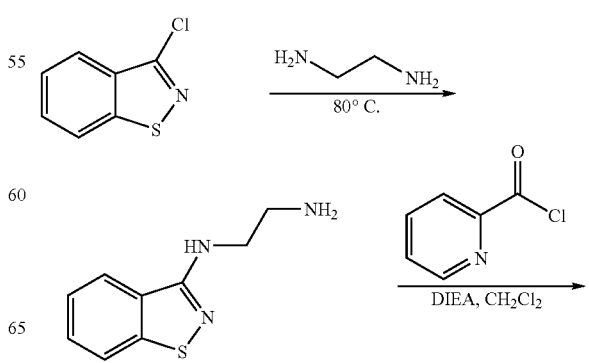

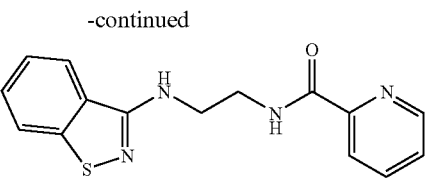

N[1]-(Benzo[d]isothiazol-3-yl)ethane-1,2-diamine. Ethylenediamine (45 mL) was heated to 80° C. A room temperature solution of 3-chlorobenzo[d]isothiazole (12 g, 70.7 mmol) in ethylenediamine (5 mL) was added to the heated ethylenediamine dropwise. The resulting solution was heated at 80° C. for 3 h. The reaction mixture was cooled to room temperature and water (75 mL) was added. The aqueous mixture was extracted with ethyl acetate twice and the ethyl acetate layers were separated. The combined organic layers were dried over anhydrous sodium sulfate, filtered and the filtrate concentrated under reduced pressure to yield N[1]-(benzo[d]isothiazol-3-yl)ethane-1,2-diamine as a light yellow solid (8 g).

$^1$H-NMR (300 MHz, CDCl$_3$): 7.79-7.64 (m, 2H), 7.52 (t, 1H), 7.34 (t, 1H), 5.60 (broad s, 1H), 3.62 (t, 2H), 3.08 ppm (t, 2H).

N-(2-(Benzo[d]isothiazol-3-ylamino)ethyl)picolinamide. N[1]-(Benzo[d]isothia-zol-3-yl)ethane-1,2-diamine (104 mg, 0.54 mmol) was dissolved in anhydrous dichloromethane (3 mL) with diisopropylethylamine (220 µL, 1.3 mmol). The solution was cooled on an ice-water bath and then a solution of 2-picolinoyl chloride hydrochloride (101 mg, 1.2 molar equivalents) in dichloromethane (0.5 mL) was added dropwise. The reaction mixture was allowed to stir for 2.5 h while warming to room temperature. The solution was diluted with dichloromethane, washed with saturated sodium bicarbonate solution, then dried over anhydrous sodium sulfate, filtered and the filtrate concentrated under reduced pressure to yield N-(2-(benzo[d]isothiazol-3-ylamino)ethyl)picolinamide as a yellow solid. $^1$H NMR (300 MHz, CDCl$_3$): 8.52 (d, 1H), 8.50 (broad s, 1H), 8.19 (d, 1H), 7.81 (m, 1H), 7.72 (t, 2H), 7.32-7.46 (m, 3H), 5.88 (broad s, 1H), 3.87 ppm (m, 4H). MW=299 confirmed by LC-MS, t$_r$=11.46 min (Method Y) MH$^+$=300.

Example 2

Synthesis of N-(2-(Benzo[d]isothiazol-3-ylamino)ethyl)-1-(3,5-dichlorobenzoyl)piperidine-3-carboxamide

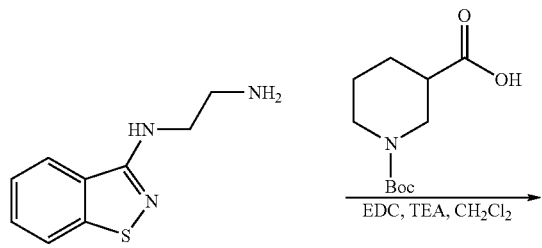

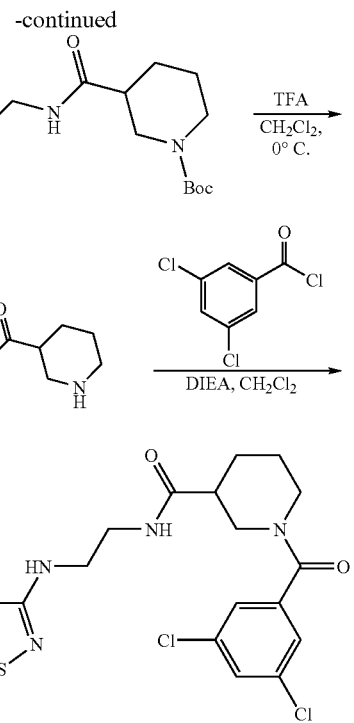

tert-Butyl 3-(2-(Benzo[d]isothiazol-3-ylamino)ethylcarbamoyl)piperidine-1-carboxylate. A mixture of N[1]-(benzo[d]isothiazol-3-yl)ethane-1,2-diamine (600 mg, 3.11 mmol), 1-(tert-butoxycarbonyl)piperidine-3-carboxylic acid (854 mg, 3.7 mmol), 1-(3-dimethylaminopropyl)-3-ethylcarbodiimide hydrochloride (585 mg, 3.7 mmol) and triethylamine (577 µL, 3.7 mmol) in dichloromethane (40 mL) was allowed to stir at room temperature overnight. The reaction mixture was washed successively with 1N aqueous hydrochloric acid, saturated sodium bicarbonate solution and water, then dried over anhydrous sodium sulfate, filtered and the filtrate concentrated under reduced pressure. Purification by flash column chromatography, on silica gel, eluting with a mixture of 25% ethyl acetate in hexanes gave fractions that were combined and concentrated under reduced pressure to yield tert-butyl 3-(2-(benzo[d]isothiazol-3-ylamino)ethylcarbamoyl)piperidine-1-carboxylate as a white solid, (325 mg). $^1$H NMR (300 MHz, DMSO-d$_6$): 8.1 (m, 2H), 7.92 (m, 3H), 7.9 (d, 1H), 7.5 (m, 1H), 7.3 (m, 1H), 3.9 (m, 2H), 3.5 (m, 2H), 3.3 (m, 2H), 2.8 (m, 2H), 2.2 (m, 1H), 1.8 (m, 1H), 1.6 (m, 3H), 1.3 ppm (s, 9H). MW=405 confirmed by LC-MS, t$_r$=3.81 min (Method B) MH$^+$=406.

N-(2-(Benzo[d]isothiazol-3-ylamino)ethyl)piperidine-3-carboxamide. A solution of tert-butyl 3-(2-(benzo[d]isothiazol-3-ylamino)ethylcarbamoyl)piperidine-1-carboxylate (360 mg, 0.89 mmol) in trifluoroacetic acid (2 mL) and dichloromethane (2 mL) was cooled to 0° C. and stirred for 2 h. The reaction mixture was then concentrated under reduced pressure and lyophilized to yield N-(2-(benzo[d]isothiazol-3-ylamino)ethyl)piperidine-3-carboxamide as a yellow oil (265 mg). MW=304 confirmed by LC-MS, t$_r$=2.39 min (Method B) MH$^+$=305.

N-(2-(Benzo[d]isothiazol-3-ylamino)ethyl)-1-(3,5-dichlorobenzoyl)piperidine-3-carboxamide. N-(2-(Benzo[d]isothiazol-3-ylamino)ethyl)piperidine-3-carboxamide (75 mg, 0.24 mmol) was dissolved in anhydrous dichloromethane (5 mL) with diisopropylethylamine (38 µL, 0.27 mmol). The solution was cooled on an ice-water bath and then a solution of 3,5-dichlorobenzoyl chloride (57 mg, 0.27 mmol) in dichloromethane (0.5 mL) was added dropwise. The reaction mixture was allowed to stir overnight while warming to room temperature. The solution was washed with saturated sodium bicarbonate solution and brine, then dried over anhydrous sodium sulfate, filtered and the filtrate concentrated under reduced pressure. Purification by column chromatography, on silica gel, eluting with a mixture of 25% ethyl acetate in hexanes and selected fractions were combined and concentrated under reduced pressure to yield N-(2-(benzo[d]isothiazol-3-ylamino)ethyl)-1-(3,5-dichlorobenzoyl)piperidine-3-carboxamide (23 mg). $^1$H NMR (300 MHz, CDCl$_3$): 7.8 (m, 1H), 7.5 (m, 1H), 7.3 (m, 2H), 7.1 (m, 1H), 6.3 (m, 1H), 3.7 (m, 4H), 3.3 (m, 2H), 2.5 (m, 1H), 1.8 (m, 1H), 1.6 (m, 3H) 1.1 ppm (m, 1H). MW=477 confirmed by LC-MS, t$_r$=3.93 min (Method Y) MH$^+$=478.

Example 3

Synthesis of N-(3-(Benzo[d]isothiazol-3-ylamino)propyl)-4-chlorobenzamide

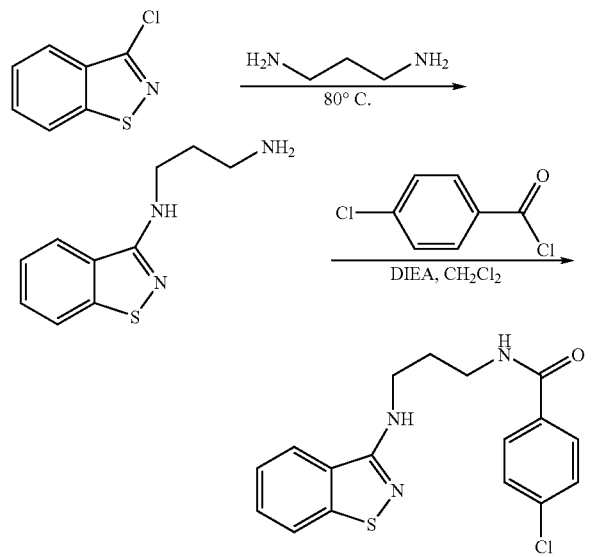

N$^1$-(Benzo[d]isothiazol-3-yl)propane-1,3-diamine. 3-Chlorobenzo[d]isothia-zole (300 mg, 3.0 mmol) was dissolved in propane-1,3-diamine (3 mL) and heated at 80° C. for 3 h. The reaction mixture was cooled to room temperature, poured into water and extracted with ethyl acetate. The organic extract was dried over anhydrous sodium sulfate, filtered and the filtrate concentrated under reduced pressure to yield N$^1$-(benzo[d]isothiazol-3-yl)propane-1,3-diamine as a yellow solid, (530 mg). $^1$H NMR (300 MHz, CDCl$_3$): 7.8 (m, 1H), 7.7 (m, 1H), 7.5 (m, 2H), 7.3 (m, 1H), 3.7 (m, 2H), 2.9 (t, 2H), 1.9 ppm (m, 2H).

N-(3-(Benzo[d]isothiazol-3-ylamino)propyl)-4-chlorobenzamide. N$^1$-(Benzo[d]isothiazol-3-yl)propane-1,3-diamine (100 mg, 0.48 mmol) was dissolved in anhydrous dichloromethane (5 mL) with diisopropylethylamine (92 μL, 0.53 mmol). The solution was cooled on an ice-water bath and then a solution of 4-chlorobenzoyl chloride (68 μL, 0.53 mmol) in dichloromethane (0.5 mL) was added dropwise. The reaction mixture was allowed to stir for 2 h while warming to room temperature. The solution was washed with water, then dried over anhydrous sodium sulfate, filtered and the filtrate concentrated under reduced pressure. Purification by column chromatography, on silica gel, eluting with a mixture of 20% ethyl acetate in hexanes and selected fractions were combined and concentrated under reduced pressure to yield N-(3-(benzo[d]isothiazol-3-ylamino)propyl)-4-chlorobenzamide as a white solid, (73 mg). $^1$H NMR (300 MHz, DMSO-d$_6$): 8.6 (broad s, 1H), 8.1 (d, 1H), 7.8 (m, 3H), 7.4 (m, 5H), 3.5 (m, 2H), 3.3 (m, 2H), 1.9 ppm (m, 2H). MW=346 confirmed by LC-MS, t$_r$=3.97 min (Method B) MH$^+$=347.

Example 4

N-(2-(Benzo[d]isothiazole-(1,1-dioxo)-3-ylamino)ethyl-4-chlorobenzamide

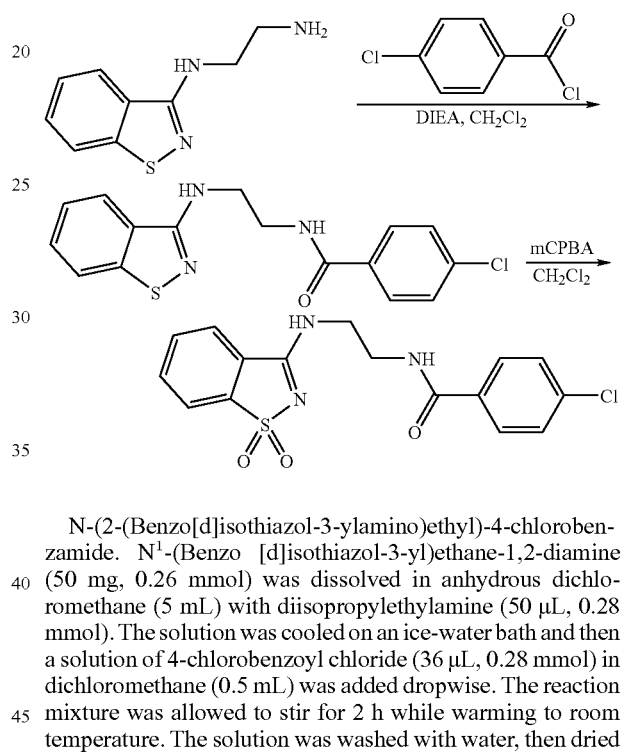

N-(2-(Benzo[d]isothiazol-3-ylamino)ethyl)-4-chlorobenzamide. N$^1$-(Benzo [d]isothiazol-3-yl)ethane-1,2-diamine (50 mg, 0.26 mmol) was dissolved in anhydrous dichloromethane (5 mL) with diisopropylethylamine (50 μL, 0.28 mmol). The solution was cooled on an ice-water bath and then a solution of 4-chlorobenzoyl chloride (36 μL, 0.28 mmol) in dichloromethane (0.5 mL) was added dropwise. The reaction mixture was allowed to stir for 2 h while warming to room temperature. The solution was washed with water, then dried over anhydrous sodium sulfate, filtered and the filtrate concentrated under reduced pressure. Purification by column chromatography, on silica gel, eluting with a mixture of 25% ethyl acetate in hexanes, and selected fractions were combined and concentrated under reduced pressure to yield N-(2-(benzo[d]isothiazol-3-ylamino)ethyl)-4-chlorobenzamide as a white solid, (50 mg). $^1$H NMR (300 MHz, DMSO-d$_6$): 8.7 (broad s, 1H), 8.1 (d, 1H), 7.9 (m, 3H), 7.5 (m, 4H), 7.4 (m, 1H), 3.6 ppm (m, 4H). MW=332 confirmed by LC-MS, t$_r$=3.89 min (Method B) MH$^+$=333.

N-(2-(Benzo[d]isothiazole-(1,1-dioxo)-3-ylamino)ethyl-4-chlorobenzamide. 3-Chloroperoxybenzoic acid (31 mg, 1.8 mmol) was added to a solution of N-(2-(benzo[d]isothiazol-3-ylamino)ethyl)-4-chlorobenzamide (30 mg, 0.9 mmol) in anhydrous dichloromethane (10 mL) and allowed to stir at room temperature overnight. A white precipitate formed and was collected by vacuum filtration. This precipitate was purified by column chromatography, on silica gel, eluting with a mixture of 2% methanol in dichloromethane and selected fractions were combined and concentrated under reduced pressure to yield N-(2-(benzo[d]isothiazole-(1,1-dioxo)-3- ylamino)ethyl-4-chlorobenzamide as a white solid (25 mg). $^1$H NMR (300 MHz, DMSO-$d_6$): 9.6 (m, 1H), 8.8 (m, 1H), 8.1 (m, 1H), 7.9 (m, 1H), 7.8 (m, 3H), 7.5 (m, 1H), 3.7 (m, 2H), 3.5 ppm (m, 2H). MW=364 confirmed by LC-MS, $t_r$=10.51 min (Method Y) MH$^+$=365.

Example 5

Synthesis of $N^2$-(2-(Benzo[d]isothiazol-3-ylamino)ethyl)-N5-methylpyridine-2,5-dicarboxamide

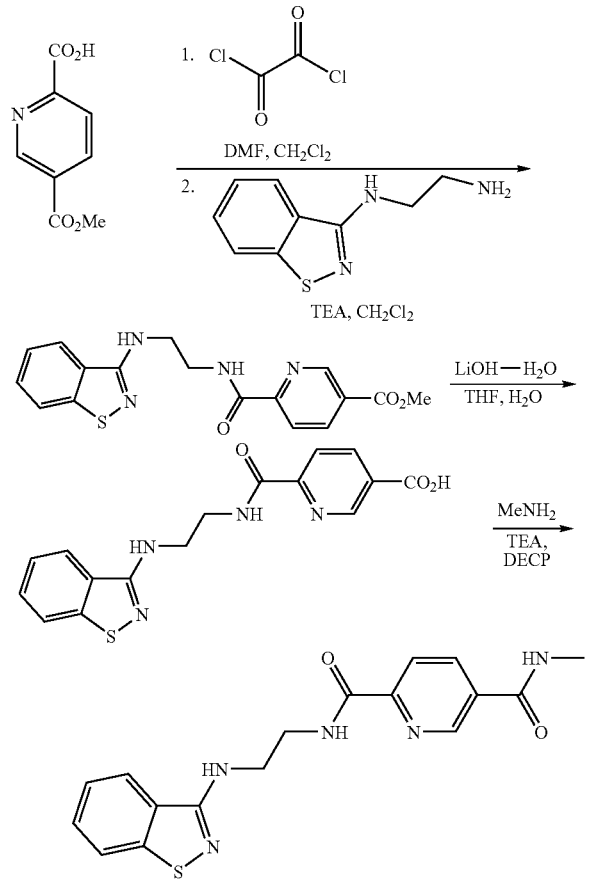

Methyl 6-(2-(Benzo[d]isothiazol-3-ylamino)ethylcarbamoyl)nicotinate. 5-(Methoxycarbonyl)picolinic acid (390 mg, 2.2 mmol), was dissolved in anhydrous dichloromethane. Several drops of dimethylformamide were added, followed by oxalyl chloride (0.23 mL, 1.2 mmol). After 1.5 h at room temperature the reaction mixture was concentrated under reduced pressure. The residue was dissolved in dichloromethane (10 mL) and added to a solution of $N^1$-(benzo[d]isothiazol-3-yl)ethane-1,2-diamine (300 mg, 1.6 mmol) in anhydrous dichloromethane with triethylamine (420 µL, 3.0 mmol). After 4 h, the reaction was diluted with dichloromethane and washed with saturated sodium bicarbonate solution, then dried over anhydrous sodium sulfate and concentrated under reduced pressure. The crude product was purified by flash column chromatography, on silica gel, eluting with a mixture of 2% methanol in dichloromethane and selected fractions were combined and concentrated under reduced pressure. Trituration with boiling dichloromethane and methanol removed impurities and gave methyl 6-(2-(benzo[d]isothiazol-3-ylamino)ethylcarbamoyl)nicotinate (255 mg) as a pale yellow solid. $^1$H NMR (300 MHz, CDCl$_3$): 9.11 (m, 1H), 8.55 (broad s, 1H), 8.40 (m, 1H), 8.24 (d, 1H), 7.68-7.76 (m, 2H), 7.42 (t, 1H), 7.32 (t, 1H), 3.98 (s, 3H), 3.88 ppm (m, 4H). MW=356 confirmed by LC-MS, $t_r$=12.06 min (Method Y) MH$^+$=357.

6-(2-(Benzo[d]isothiazol-3-ylamino)ethylcarbamoyl)nicotinic Acid. Methyl 6-(2(benzo[d]isothiazol-3-ylamino)ethylcarbamoyl)nicotinate (211 mg, 0.6 mmol) was dissolved in a mixture of tetrahydrofuran (5 mL) and water (0.5 mL) and treated with lithium hydroxide monohydrate (100 mg, 2.4 mmol). The reaction mixture was stirred at room temperature overnight. The tetrahydrofuran was removed under vacuum and the residue was diluted with water. Dropwise addition of 50% aqueous hydrochloric acid gave a white solid, which was collected by vacuum filtration and dried to yield 6-(2-(benzo[d]isothiazol-3-ylamino)ethylcarbamoyl)nicotinic acid (130 mg) as a white solid. $^1$H NMR (300 MHz, CDCl3/DMSO-$d_6$): 9.02 (m, 1H), 8.83 (broad s, 1H), 8.32 (m, 1H), 8.10 (d, 1H), 7.95 (d, 1H), 7.68 (d, 1H), 7.39 (t, 1H), 7.25 (t, 1H), 3.71 ppm (m, 4H). MW=342 confirmed by LC-MS, $t_r$=10.56 min (Method Y) MH$^+$=343

$N^2$-(2-(Benzo[d]isothiazol-3-ylamino)ethyl)-N5-methylpyridine-2,5-dicarbox-amide. A mixture of 6-(2-(benzo[d]isothiazol-3-ylamino)ethylcarbamoyl)nicotinic acid (62 mg, 0.13 mmol), diethyl cyanophosphonate (21 µL, 0.14 mmol), methylamine (2.0M soln in THF, 15 µL, 0.14 mmol) and triethylamine (20 µL, 0.14 mmol) in dichloromethane (5 mL) was allowed to stir at room temperature overnight. The solution was washed with water, then dried over anhydrous sodium sulfate, filtered and the filtrate concentrated under reduced pressure. Purification by column chromatography, on silica gel, eluting with a mixture of 30% ethyl acetate in hexanes, and selected fractions were combined and concentrated under reduced pressure to yield $N^2$-(2-(benzo[d]isothiazol-3-ylamino)ethyl)-N5-methylpyridine-2,5-dicarboxamide as a white solid, (50 mg). $^1$H NMR (300 MHz, DMSO-$d_6$): 9.16 (broad s, 1H), 8.99 (s, 1H), 8.79 (m, 1H), 8.37 (d, 1H), 8.23 (t, 2H), 7.91 (d, 1H), 7.58 (s, 1H), 7.49 (t, 1H), 7.39 (t, 1H), 3.61 (m, 3H), 3.34 ppm (m, 4H). MW=355 confirmed by LC-MS, $t_r$=2.98 min (Method B) MH$^+$=356.

Example 6

Synthesis of (S)-N-(2-(Benzo[d]isothiazol-3-ylamino)ethyl)-2-phenyl-2-(phenylsulfonamido)acetamide

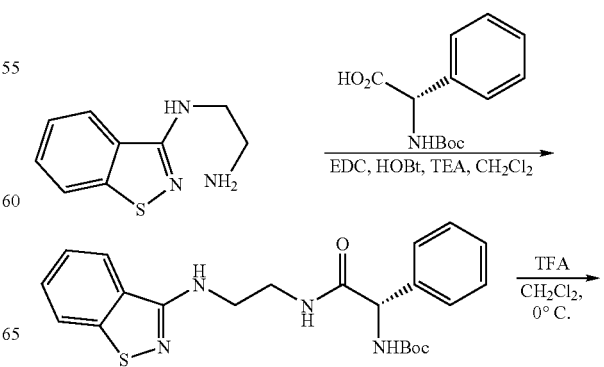

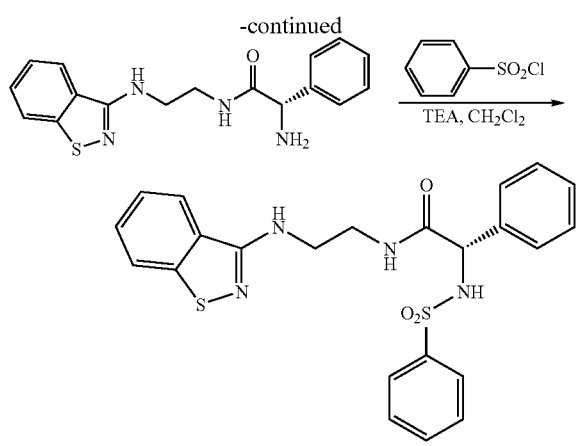

(S)-tert-Butyl 2-(2-(Benzo[d]isothiazol-3-ylamino)ethylamino)-2-oxo-1-phenylethylcarbamate. A mixture of N¹-(benzo[d]isothiazol-3-yl)ethane-1,2-diamine (600 mg, 3.1 mmol), N α (t-butoxycarbonyl)phenylglycine (850 mg, 3.4 mmol), 1-(3-dimethylaminopropyl)-3-ethylcarbodiimide hydrochloride (650 mg, 3.4 mmol), 1-hydroxybenzotriazole (520 mg, 3.4 mmol) and triethylamine (950 µL, 6.8 mmol) in dichloromethane (50 mL) was allowed to stir at room temperature overnight. The reaction mixture was washed successively with 1N aqueous hydrochloric acid, saturated sodium bicarbonate solution and water, then dried over anhydrous sodium sulfate, filtered and the filtrate concentrated under reduced pressure. Purification by flash column chromatography, on silica gel, eluting with a mixture of 30% ethyl acetate in hexanes and selected fractions were combined and concentrated under reduced pressure to give (S)-tert-butyl 2-(2-(benzo[d]isothiazol-3-ylamino)ethylamino)-2-oxo-1-phenylethylcarbamate (720 mg) as a white solid. ¹H NMR (300 MHz, CDCl₃): 7.78 (d, 1H), 7.61 (d, 1H), 7.49 (t, 1H), 7.30 (t, 1H), 7.21 (m, 2H), 7.18 (m, 2H), 6.95 (t, 1H), 5.66 (m, 2H), 5.10 (broad s, 1H), 3.62 (m, 4H), 1.39 ppm (s, 9H). MW=427 confirmed by LC-MS, $t_r$=13.38 min (Method Y) MH⁺=428.

(S)-2-Amino-N-(2-(benzo[d]isothiazol-3-ylamino)ethyl)-2-phenylacetamide, Trifluoroacetate Salt. A solution of (S)-tert-butyl 2-(2-(benzo[d]isothiazol-3-ylamino)ethylamino)-2-oxo-1-phenylethylcarbamate (720 mg, 1.7 mmol) in trifluoroacetic acid (5 mL) and dichloromethane (5 mL) was cooled to 0° C. and stirred for 4 h. The reaction mixture was then concentrated under reduced pressure and lyophilized to yield (S)-2-amino-N-(2-(benzo[d]isothiazol-3-ylamino)ethyl)-2-phenylacetamide,trifluoroacetate salt (550 mg) as a yellow solid. ¹H NMR (300 MHz, CDCl₃): 8.38 (m, 1H), 7.97 (d, 1H), 7.61 (d, 1H), 7.42 (m, 2H), 7.37 (t, 1H), 7.22 (m, 3H), 5.04 (s, 1H), 3.58 (m, 2H), 3.37 ppm (m, 2H). MW=326 confirmed by LC-MS, $t_r$=7.64 min (Method B) MH⁺=327.

(S)-N-(2-(Benzo[d]isothiazol-3-ylamino)ethyl)-2-phenyl-2-(phenylsulfon-amido) acetamide. (S)-2-amino-N-(2-(benzo[d]isothiazol-3-ylamino)ethyl)-2-phenyl-acetamide trifluoroacetate salt (100 mg, 0.31 mmol) was dissolved in anhydrous dichloromethane (5 mL) with triethylamine (52 µL, 0.37 mmol). The solution was cooled on an ice-water bath and then a solution of benzenesulfonyl chloride (47 µL, 0.37 mmol) in dichloromethane (0.5 mL) was added dropwise. The reaction mixture was allowed to stir overnight while warming to room temperature. The solution was diluted with dichloromethane, washed with saturated sodium bicarbonate solution, then dried over anhydrous sodium sulfate, filtered and the filtrate concentrated under reduced pressure. Purification by column chromatography, on silica gel, eluting with a mixture of 30% ethyl acetate in hexanes, and selected fractions were combined and concentrated under reduced pressure to yield (S)-N-(2-(benzo[d]isothiazol-3-ylamino)ethyl)-2-phenyl-2-(phenylsulfonamido)acetamide (26 mg) as a white solid. ¹H NMR (300 MHz, CDCl₃): 7.78 (d, 1H), 7.70 (t, 3H), 7.48 (m, 2H), 7.38 (q, 3H), 7.10 (m, 5H), 6.00 (d, 1H), 5.90 (broad s, 1H), 4.78 (d, 1H), 3.63 (broad s, 2H), 3.52 ppm (m, 2H). MW=467 confirmed by LC-MS, $t_r$=3.94 min (Method B) MH⁺=468.

Example 7

Synthesis of N-(2-(5-acetamidobenzo[d]isothiazol-3-ylamino)ethyl)picolinamide

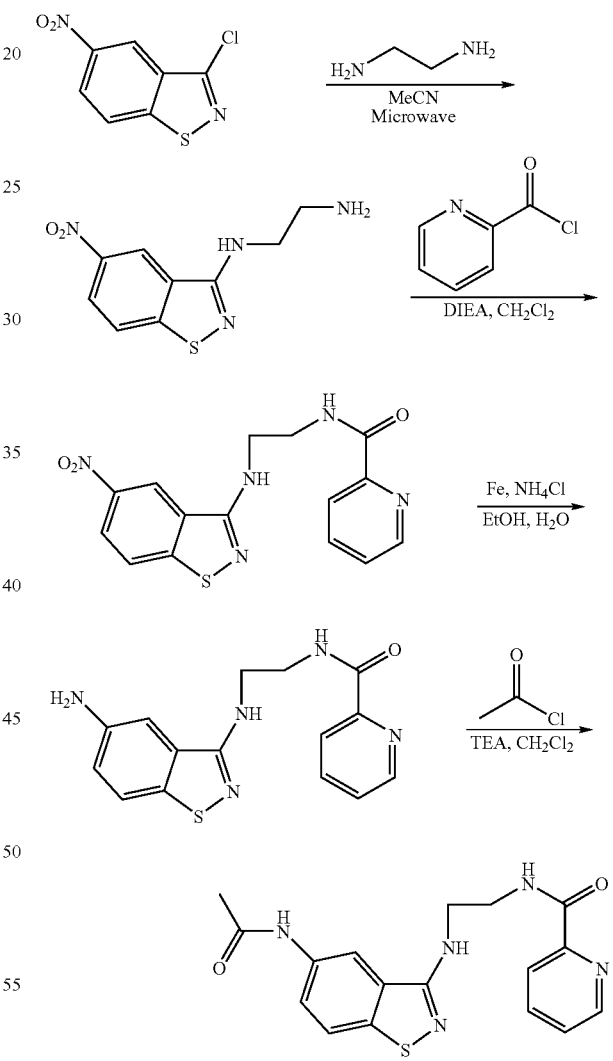

N¹-(5-Nitrobenzo[d]isothiazol-3-yl)ethane-1,2-diamine. Ethylenediamine (1.5 mL, 24 mmol) was added dropwise to a solution of 3-chloro-5-nitrobenzo[d]isothiazole (250 mg, 1.2 mmol) in acetonitrile (1 mL). The reaction mixture was microwaved at 120° C. for 10 min. The reaction mixture was concentrated under reduced pressure. The resulting residue was diluted with water and the aqueous mixture was extracted with ethyl acetate. The organic extract was concentrated

243 under reduced pressure and the crude product was purified by column chromatography, on silica gel, eluting with a mixture of 2% methanol in dichloromethane and selected fractions were combined and concentrated under reduced pressure to yield $N^1$-(5-nitrobenzo[d]isothiazol-3-yl)ethane-1,2-diamine (100 mg) as a yellow solid.

N-(2-(5-Nitrobenzo[d]isothiazol-3-ylamino)ethyl)picolinamide. $N^1$-(5-Nitrobenzo[d]isothiazol-3-yl)ethane-1,2-diamine (92 mg, 0.38 mmol) was dissolved in anhydrous dichloromethane (5 mL) with diisopropylethylamine (148 µL, 1.3 mmol). The solution was cooled on an ice-water bath and a solution of 2-picolinoyl chloride hydrochloride (76 mg, 2.7 mmol) in dichloromethane (0.5 mL) was added dropwise. The reaction mixture was allowed to stir for 2.5 h while warming to room temperature. The solution was diluted with dichloromethane, washed with saturated sodium bicarbonate solution, then dried over anhydrous sodium sulfate, filtered and the filtrate concentrated under reduced pressure to yield N-(2-(5-nitrobenzo[d]isothiazol-3-ylamino)ethyl)picolinamide (100 mg) as a yellow solid. $^1$H NMR (300 MHz, CDCl$_3$): 8.58 (m, 1H), 8.40 (m, 1H), 8.22 (d, 1H), 7.83 (t, 1H), 7.45 (m, 2H), 7.40 (m, 2H), 3.80 (m, 2H), 3.60 ppm (m, 2H). MW=343 confirmed by LC-MS, $t_r$=11.59 min (Method Y) MH$^+$=344.

N-(2-(5-Aminobenzo[d]isothiazol-3-ylamino)ethyl)picolinamide. A mixture of N-(2-(5-nitrobenzo[d]isothiazol-3-ylamino)ethyl)picolinamide (100 mg, 0.29 mmol), iron powder (100 mg, 1.75 mmol) and ammonium chloride (31 mg, 0.29 mmol) in ethanol (5 mL) and water (2.5 mL) was allowed to stir at room temperature for 15 min. The mixture was then heated at 80° C. for 20 min. The reaction mixture was cooled to room temperature and passed through a plug of Celite. The filtrate was concentrated under reduced pressure and the resulting residue was diluted with water. The aqueous solution was extracted several times with ethyl acetate and then concentrated under reduced pressure. Purification by column chromatography, on silica gel, eluting with a mixture of 2% methanol in dichloromethane, and selected fractions were combined and concentrated under reduced pressure to yield N-(2-(5-aminobenzo[d]isothiazol-3-ylamino)ethyl)picolinamide (95 mg) as a pale yellow solid. $^1$H NMR (300 MHz, CDCl$_3$): 8.56 (d, 1H), 8.25 (d, 1H), 8.20 (d, 2H), 7.80 (t, 1H), 7.40 (m, 1H), 7.18 (d, 1H), 6.01 (s, 1H), 5.98 (d, 1H), 4.80 (broad s, 1H), 3.70 (m, 2H), 3.40 (m, 2H). MW=313 confirmed by LC-MS, $t_r$=9.21 min (Method Y) MH$^+$=314.

N-(2-(5-Acetamidobenzo[d]isothiazol-3-ylamino)ethyl) picolinamide. N-(2-(5-Aminobenzo[d]isothiazol-3-ylamino) ethyl)picolinamide (95 mg, 0.30 mmol) was dissolved in anhydrous dichloromethane (5 mL) with triethylamine (50 µL, 0.36 mmol). The solution was cooled on an ice-water bath and a solution of acetyl chloride (26 µL, 0.36 mmol) in dichloromethane (0.5 mL) was added dropwise. The reaction mixture was allowed to stir for 2.5 h while warming to room temperature. The solution was diluted with dichloromethane, washed with saturated sodium bicarbonate solution, then dried over anhydrous sodium sulfate, filtered and the filtrate concentrated under reduced pressure to yield N-(2-(5-acetamidobenzo[d]isothiazol-3-ylamino)ethyl) picolinamide as a white solid. $^1$H NMR (300 MHz, CDCl$_3$): 8.48 (d, 1H), 8.30 (s, 1H), 8.20 (d, 1H), 7.80 (t, 1H), 7.52 (s, 1H), 7.42 (m, 1H), 7.31 (d, 1H), 7.18 (s, 1H), 6.82 (d, 1H), 3.70 (m, 2H), 3.50 (m, 2H), 2.20 ppm (s, 3H). MW=355 confirmed by LC-MS, $t_r$=9.35 min (Method Y) MH$^+$=356.

244

Example 8

Synthesis of N-(2-(Benzo[d]isothiazol-3-ylamino) ethyl)-4-morpholinopicolinamide

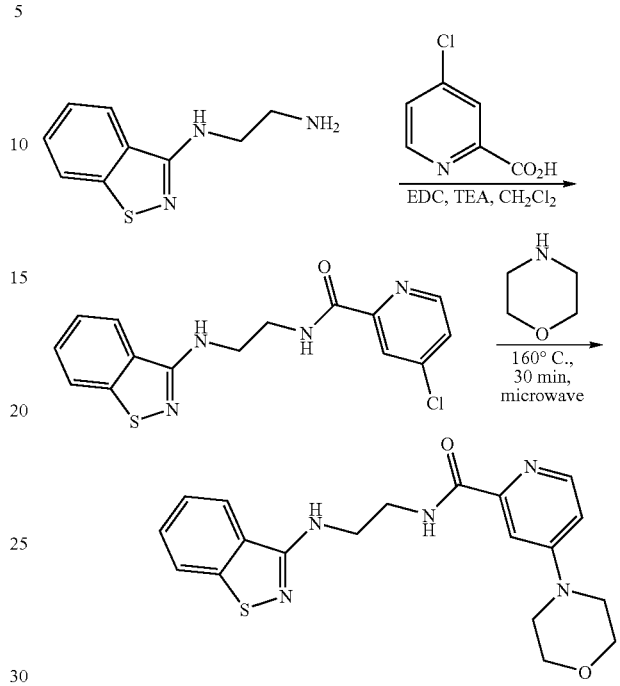

N-(2-(Benzo[d]isothiazol-3-ylamino)ethyl)-4-chloropicolinamide. A mixture of $N^1$-(benzo[d]isothiazol-3-yl) ethane-1,2-diamine (100 mg, 0.52 mmol), 4-chloropicolinic acid (90 mg, 0.57 mmol), 1-(3-dimethylaminopropyl)-3-ethylcarbodiimide hydrochloride (98 mg, 0.57 mmol) and triethylamine (174 µL, 1.1 mmol) in dichloromethane (5 mL) was allowed to stir at room temperature overnight. The reaction mixture was washed successively with 1N aqueous hydrochloric acid, saturated sodium bicarbonate solution and water, then dried over anhydrous sodium sulfate, filtered and the filtrate concentrated under reduced pressure. Purification by flash column chromatography, on silica gel, eluting with a mixture of 1% methanol in dichloromethane and selected fractions were combined and concentrated under reduced pressure to give N-(2-(benzo[d]isothiazol-3-ylamino)ethyl)-4-chloropicolinamide (50 mg) as a white solid. $^1$H NMR (300 MHz, CDCl$_3$): 8.66 (broad s, 1H), 8.41 (d, 1H), 8.20 (s, 1H), 7.78 (t, 2H), 7.65-7.38 (m, 3H), 5.95 (broad s, 1H), 3.84 ppm (m, 4H). MW=333 confirmed by LC-MS, $t_r$=12.38 min (Method Y) MH$^+$=334.

N-(2-(Benzo[d]isothiazol-3-ylamino)ethyl)-4-morpholinopicolinamide. A mixture of N-(2-(benzo[d]isothiazol-3-ylamino)ethyl)-4-chloropicolinamide (50 mg) in morpholine (1 mL) was microwaved at 160° C. for 30 min. The reaction mixture was diluted with dichloromethane and washed with saturated sodium bicarbonate solution and water. The organic layer was dried over anhydrous sodium sulfate, filtered and the filtrate concentrated under reduced pressure. Purification by flash column chromatography, on silica gel, eluting with a mixture of 1% methanol in dichloromethane and selected fractions were combined and concentrated under reduced pressure to give N-(2-(benzo[d]isothiazol-3-ylamino)ethyl)-4-morpholinopicolinamide as a white solid. $^1$H NMR (300 MHz, DMSO-d$_6$): 8.80 (broad s, 1H), 8.20 (m, 1H), 8.10 (m, 1H), 7.91 (m, 1H), 7.30-7.60 (m, 3H), 7.00 (m, 1H), 3.60-3.80 (m, 4H), 3.30 ppm (m, 8H). MW=383 confirmed by LC-MS, $t_r$=8.06 min (Method Y) MH$^+$=384.

Example 9

Synthesis of 4-Butoxy-N-(3-(5-phenylbenzo[d]isothiazol-3-ylamino)propyl) Benzamide

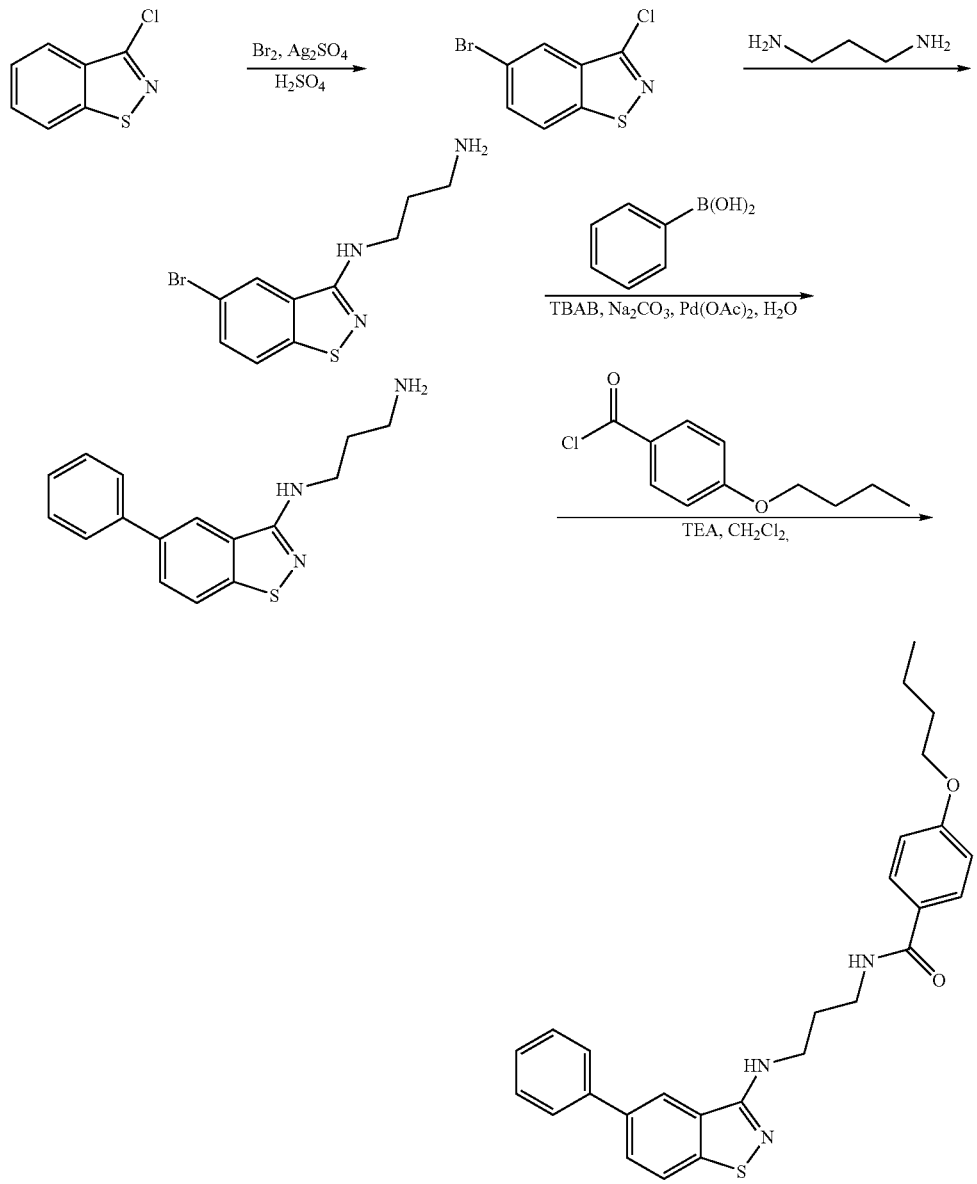

was dissolved in propylene diamine (20 mL) and allowed to stir at room temperature for 1 h, followed by heating at 80° C. for 30 min. The mixture was diluted with ethyl acetate. This organic solution was successively washed with water and Synthesis of 5-Bromo-3-chlorobenzo [d]isothiazole. 3-Chlorobenzo[d]isothiazole (10 g, 59.0 mmol) was added to a solution of bromine (3.2 mL, 62.0 mmol) and silver sulfate (19.6 g, 63.0 mmol) in sulfuric acid (200 mL). The resulting brown mixture was allowed to stir at room temperature for 2h under nitrogen. The color slowly faded to pale yellow as a white precipitate formed. The precipitate was collected by vacuum filtration and triturated with hexanes to yield 5-bromo-3-chlorobenzo[d]isothiazole as a white solid (3.8 g). $^1$H NMR (300 MHz, CDCl$_3$): 8.18 (s, 1H), 7.8 (d, 1H), 7.64 ppm (d, 1H).

Synthesis of N$^1$-(5-Bromobenzo[d]isothiazol-3-yl)propane-1,3-diamine. 5-Bromo-3-chlorobenzo[d]isothiazole brine, then dried over anhydrous sodium sulfate, filtered and concentrated under reduced pressure. The resulting residue was triturated with hexanes to provide N$^1$-(5-bromobenzo[d]isothiazol-3-yl)propane-1,3-diamine (2.4 g). $^1$H NMR (300 MHz, DMSO-d$_6$): 8.4 (s, 1H), 7.84 (d, 1H), 7.59 (d, 1H), 7.2 (t, 1H), 3.35 (q, 2H), 2.53 (t, 2H), 1.62-1.81 ppm (m, 2H).

Synthesis of N$^1$-(5-Phenylbenzo[d]isothiazol-3-yl)propane-1,3-diamine. A mixture of N$^1$-(5-bromobenzo[d]isothiazol-3-yl)propane-1,3-diamine (100 mg, 0.35 mmol), phenylboronic acid (43 mg, 0.35 mmol), tetrabutylammonium bromide (115 mg, 0.35 mmol), sodium carbonate (110 mg, 1.05 mmol) and palladium (II) acetate (1 mg) in water (3 mL) was microwaved at 150° C. for 5 min. The reaction was diluted with methylene chloride and the mixture was washed successively with aqueous sodium bicarbonate and brine, dried over anhydrous sodium sulfate, filtered and concentrated under reduced pressure. The resulting product, N$^1$-(5-Phenylbenzo[d]isothiazol-3-yl)propane-1,3-diamine, was carried forward without further purification. MW=238 confirmed by LC-MS, t$_r$=2.73 min (Method B) MH$^+$=237-239

(d, 2H), 4.00 (t, 2H), 3.50 (q, 2H), 3.39 (q, 2H), 1.90-2.00 (m, 2H), 1.62-1.78 (m, 2H), 1.40-1.49 (m, 2H), 0.96 ppm (t, 3H).

Example 10

Synthesis of N$^1$-(5-Bromobenzo[d]isothiazol-3-yl)-N$^3$-((4'-methoxybiphenyl-4-yl)methyl)propane-1,3-diamine

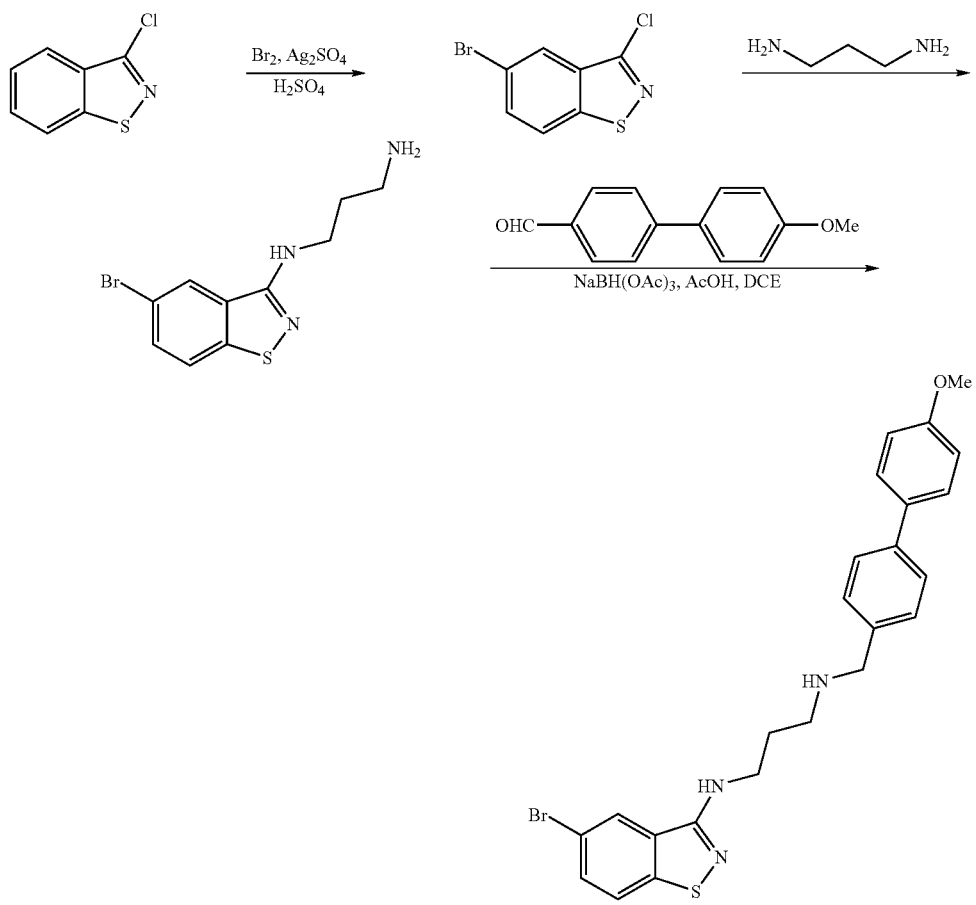

Synthesis of 4-Butoxy-N-(3-(5-phenylbenzo [d]isothiazol-3-ylamino)propyl) Benzamide. The crude N$^1$-(5-Phenylbenzo[d]isothiazol-3-yl)propane-1,3-diamine mixture (~100 mg, 0.20 mmol) was dissolved in anhydrous methylene chloride with triethylamine (0.3 mL, 0.24 mmol). The mixture was cooled in an ice-bath under nitrogen, then a solution of 4-butoxybenzoyl chloride (51 mg, 0.24 mmol) was added dropwise. After the addition was completed the ice-bath was removed and the mixture was stirred at room temperature overnight. The reaction mixture was diluted with methylene chloride and then washed successively with saturated sodium bicarbonate solution and brine. The organic solution was dried over anhydrous sodium sulfate, filtered and concentrated under reduced pressure. The resulting residue was purified by prep-scale reverse phase high performance liquid chromatography to yield 4-butoxy-N-(3-(5-phenylbenzo[d]isothiazol-3-ylamino)propyl) benzamide (13 mg). $^1$H NMR (300 MHz, DMSO-d$_6$): 8.23 (s, 1H), 8.17 (t, 1H), 7.98 (d, 1H), 7.76-7.82 (m, 4H), 7.50 (t, 3H), 7.37-7.40 (m, 1H), 6.97

Synthesis of 5-Bromo-3-chlorobenzo[d]isothiazole. 3-Chlorobenzo[d]isothiazole (10 g, 59.0 mmol) was added to a solution of bromine (3.2 mL, 62.0 mmol) and silver sulfate (19.6 g, 63.0 mmol) in sulfuric acid (200 mL). The resulting brown mixture was allowed to stir at room temperature for 2 h under nitrogen. The color slowly faded to pale yellow as a white precipitate formed. The precipitate was collected by vacuum filtration and triturated with hexanes to yield 5-bromo-3-chlorobenzo[d]isothiazole as a white solid (3.8 g). $^1$H NMR (300 MHz, CDCl$_3$): 8.18 (s, 1H), 7.8 (d, 1H), 7.64 ppm (d, 1H).

Synthesis of N$^1$-(5-Bromobenzo[d]isothiazol-3-yl)propane-1,3-diamine. 5-Bromo-3-chlorobenzo[d]isothiazole was dissolved in propylene diamine (20 mL) and allowed to stir at room temperature for 1 h, followed by heating at 80° C. for 30 min. The mixture was diluted with ethyl acetate. This organic solution was successively washed with water and brine, then dried over anhydrous sodium sulfate, filtered and concentrated under reduced pressure. The resulting residue was triturated with hexanes to provide N¹-(5-bromobenzo[d]isothiazol-3-yl)propane-1,3-diamine (2.4 g). ¹H NMR (300 MHz, DMSO-d₆): 8.4 (s, 1H), 7.84 (d, 1H), 7.59 (d, 1H), 7.2 (t, 1H), 3.35 (q, 2H), 2.53 (t, 2H), 1.81 ppm (m, 2H).

Synthesis of N¹-(5-Bromobenzo[d]isothiazol-3-yl)-N³-((4'-methoxybiphenyl-4-yl)methyl)propane-1,3-diamine. N¹-(5-Bromobenzo[d]isothiazol-3-yl)propane-1,3-diamine solid. MW=482 confirmed by LC-MS, t$_r$=3.24 min (Method B) MH⁺=481-483.

Example 11

Synthesis of N-(3-(Benzo[d]isothiazol-3-ylamino)propyl)-N-((4'-methoxybiphenyl-4-yl)methyl)-2-(pyrrolidin-2-yl) Acetamide

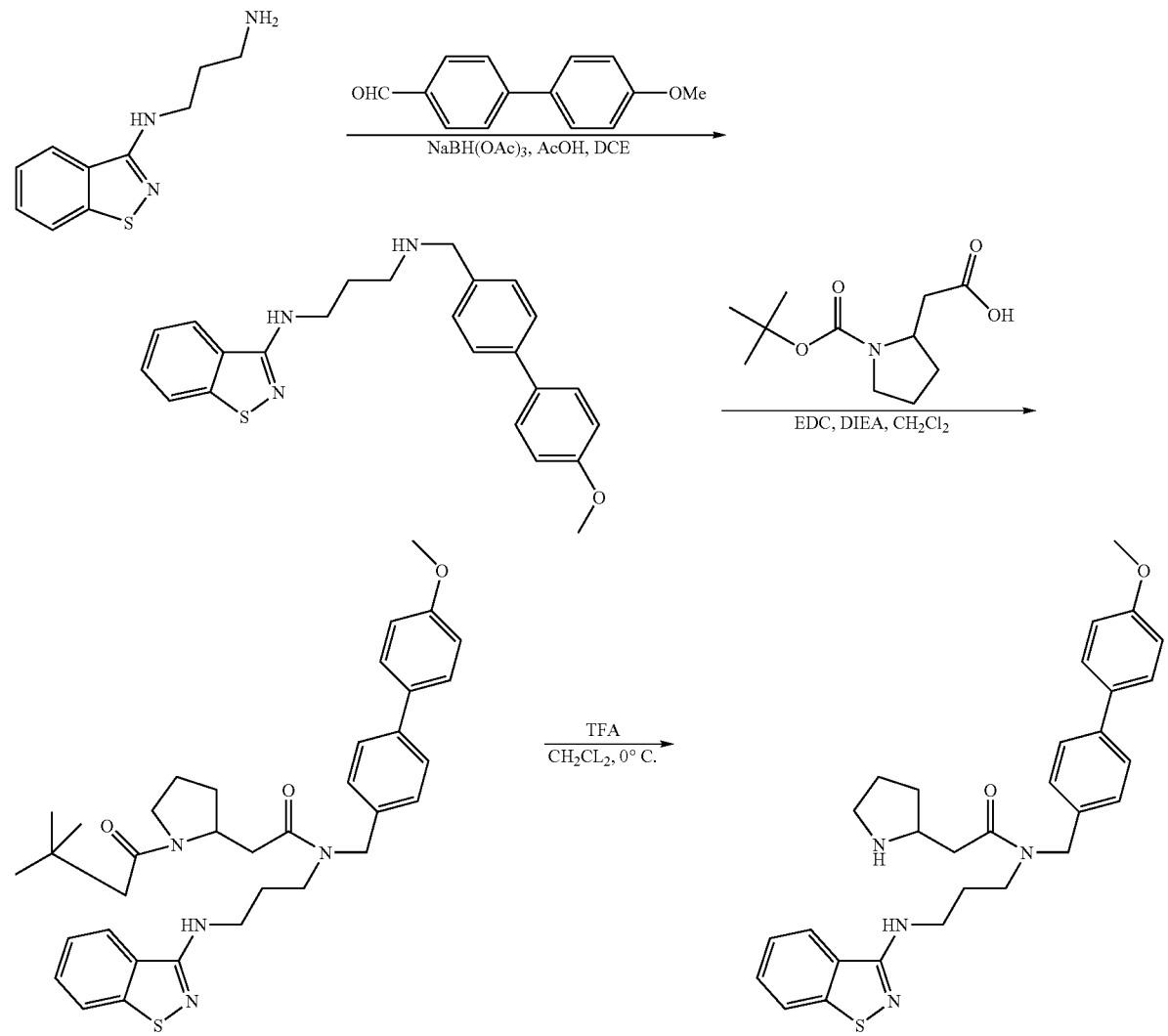

(190 mg, 0.66 mmol) and 4'-methoxybiphenyl-4-carbaldehyde (140 mg, 0.66 mmol) were combined in 1,2-dichloroethane (30 mL) and treated with sodium triacetoxyborohydride (280 mg, 1.32 mmol) and acetic acid (one drop). The mixture was sonicated at room temperature for 18 h. The reaction was diluted with ethyl acetate and then washed with water, brine and saturated sodium bicarbonate solution. The organic solution was dried over anhydrous sodium sulfate, filtered and concentrated under reduced pressure. The resulting residue was purified by flash column chromatography, on silica gel, eluting with 98:2 methylene chloride:methanol to yield N¹-(5-bromobenzo[d]isothiazol-3-yl)-N³-((4'-methoxybiphenyl-4-yl)methyl)propane-1,3-diamine (130 mg) as a yellow Synthesis of N¹-(Benzo[d]isothiazol-3-yl)-N³-((4'-methoxybiphenyl-4-yl)methyl)propane-1,3-diamine. N¹-(Benzo[d]isothiazol-3-yl)propane-1,3-diamine (600 mg, 2.8 mmol) and 4'-methoxy-biphenyl-4-carboxaldehyde (614 mg, 2.8 mmol) were combined in 1,2-dichloroethane (20 mL) and treated with sodium triacetoxyborohydride (1.2 g, 5.7 mmol) and acetic acid (160 µL, 5.6 mmol). The mixture was stirred at room temperature overnight. The reaction was quenched by addition of saturated aqueous sodium bicarbonate solution. The crude product was extracted with ethyl acetate (2×50 mL). The organic extract was dried over anhydrous sodium sulfate, filtered and concentrated under reduced pressure. The resulting residue was purified by column chromatography, on silica gel, eluting with 98:2 methylene chloride: methanol to yield N¹-(benzo[d]isothiazol-3-yl)-N³-((4'-methoxybiphenyl-4-yl)methyl)propane-1,3-diamine (330 mg) as a light yellow foam. $^1$H NMR (CDCl$_3$): 7.80 (d, 1H), 7.75 (d, 1H), 7.25-7.45 (m, 8H), 6.90 (d, 2H), 3.95 (s, 2H), 3.85 (s, 3H), 3.70 (t, 2H), 3.00 (t, 2H), 2.30-2.40 ppm (m, 2H).

Synthesis of tert-Butyl 2-(2-((3-(Benzo[d]isothiazol-3-ylamino)propyl)((4'-methoxybiphenyl-4-yl)methyl)amino)-2-oxoethyl)pyrrolidine-1-carboxylate. N$^1$-(Benzo[d]isothiazol-3-yl)-N$^3$-((4'-methoxybiphenyl-4-yl)methyl)propane-1,3-diamine (100 mg, 0.25 mmol), 2-carboxymethyl-pyrrolidine-1-carboxylic acid tert-butyl ester (68 mg, 0.34 mmol), and 1-(3-dimethylaminopropyl)-3-ethylcarboduimide hydrochloride (58 mg, 0.30 mmol) were dissolved in anhydrous methylene chloride (10 mL). Diisopropylethylamine (52 µL, mmol) added to the mixture. The reaction was allowed to stir overnight at room temperature. The solution was washed with water, then dried over anhydrous sodium sulfate and concentrated under reduced pressure. Purification by column chromatography, on silica gel, eluting with a mixture of 3:1 hexanes:ethyl acetate yielded tert-butyl 2-(2-((3-(benzo[d]isothiazol-3-ylamino)propyl)((4'-methoxybiphenyl-4-yl)methyl)amino)-2-oxoethyl)pyrrolidine-1-carboxylate as a solid (30 mg). $^1$H NMR (300 MHz, CDCl$_3$): 7.90-7.95 (m, 1H), 7.75-7.85 (m, 1H), 7.35-7.55 (m, 6H), 7.19-7.25 (m, 2H), 6.95-7.00 m, 2H), 4.90-5.00 (m, 1H), 4.55-4.65 (m, 2H), 4.19-4.25 (m, 1H), 3.85 (s, 3H), 3.55-3.65 (m, 2H), 3.30-3.35 (m, 2H), 3.10-3.19 (m, 1H), 2.35-2.45 (m, 1H), 2.05-2.15 (m, 1H), 1.80-1.90 (m, 4H), 1.50 ppm (s, 9H). MW=615 confirmed by LC-MS, $t_r$=5.12 min (Method B) MH$^+$=614-616.

Synthesis of N-(3-(Benzo[d]isothiazol-3-ylamino)propyl)-N-((4'-methoxybiphenyl-4-yl)methyl)-2-(pyrrolidin-2-yl) Acetamide. tert-Butyl 2-(2-((3-(benzo[d]isothiazol-3-ylamino)propyl)((4'-methoxybiphenyl-4-yl)methyl)amino)-2-oxoethyl)pyrrolidine-1-carboxylate (20 mg, 0.033 mmol) was dissolved in methylene chloride (0.5 mL) and cooled in an ice-bath. A cooled solution of trifluoroacetic acid (1.0 mL) in methylene chloride (1.0 mL) was added to the mixture, dropwise. The reaction was allowed to stir for 3 h at 0° C. The solution was concentrated under reduced pressure to yield N-(3-(benzo[d]isothiazol-3-ylamino)propyl)-N-((4'-methoxybiphenyl-4-yl)methyl)-2-(pyrrolidin-2-yl) acetamide (22 mg) as a solid. $^1$H NMR (300 MHz, CDCl$_3$): 8.15-8.20 (m, 1H), 7.45-7.70 (m, 6H), 7.15-7.20 (m, 2H), 6.90-6.95 (m, 2H), 4.60-4.75 (m, 1H), 4.45-4.55 (m, 1H), 3.95-4.10 (m, 2H), 3.85 (s, 3H), 3.60-3.75 (m, 2H), 3.35-3.45 (m,2H), 3.15-3.25 (m, 2H), 2.75-2.85 (m,1H), 1.90-2.00 ppm (m, 1H). MW=515 confirmed by LC-MS, $t_r$=4.50 min (Method B) MH$^+$=514-516.

Example 12

Synthesis of N$^1$-(Isothiazolo[5,4-b]pyrazin-3-yl)-N$^3$-((4'-methoxybiphenyl-4-yl)methyl)propane-1,3-diamine

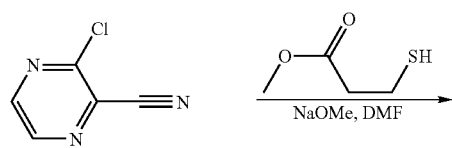

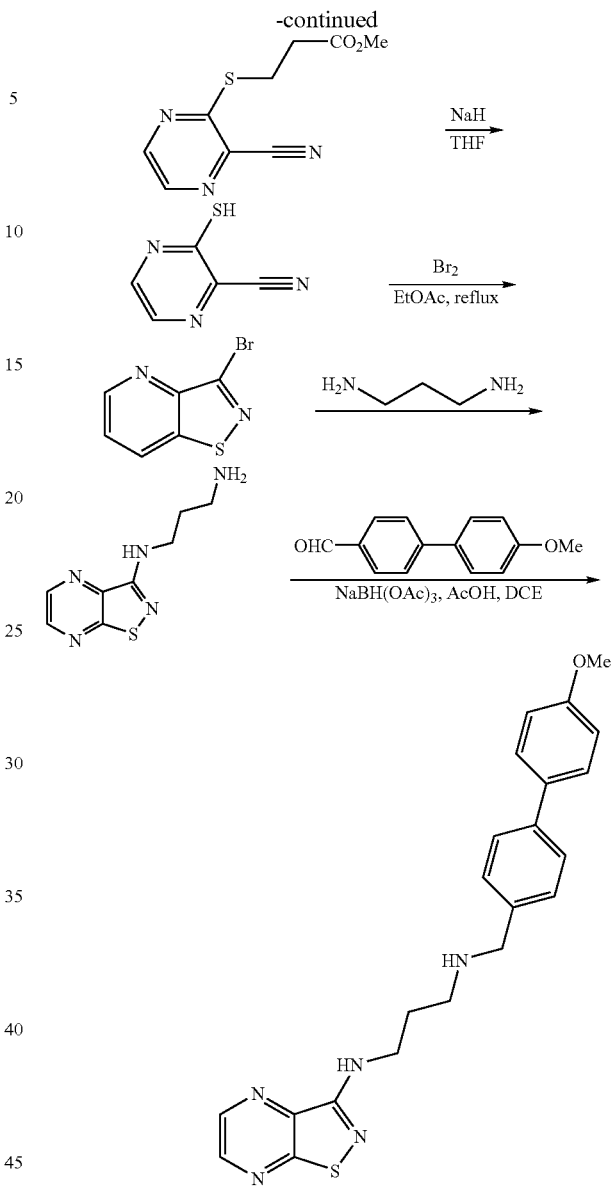

Synthesis of Methyl 3-(3-Cyanopyrazin-2-ylthio)propanoate. To a solution of 2-chloro-3-cyanopyrazine (9.9 g, 73.8 mmol) and methyl 3-mercaptopropionate (9.36 mL, 84.5 mmol) in anhydrous dimethylformamide (40 mL) cooled to 4° C. was added solid sodium methoxide (4.7 g, 87.0 mmol). The reaction mixture was allowed to warm to room temperature overnight. The mixture was poured into water and extracted twice with ethyl acetate. The combined organic layers were washed once saturated aqueous sodium bicarbonate solution, five times with brine, then dried over anhydrous sodium sulfate, filtered and concentrated under reduced pressure. Purification by column chromatography, on silica gel, eluting with a mixture of 7:3 hexanes:ethyl acetate gave methyl 3-(3-cyanopyrazin-2-ylthio)propanoate (7.2 g) as a pale yellow liquid. $^1$H NMR (300 MHz, CDCl$_3$): 8.51 (d, 1H), 8.32 (d, 1H), 3.72 (s, 3H), 3.50 (t, 2H), 2.79 ppm (t, 2H). MW=223 confirmed by LC-MS, $t_r$=11.11 min (Method Y) MH$^+$=221-225.

Synthesis of 3-Mercaptopyrazine-2-carbonitrile. To a solution of methyl 3-(3-cyanopyrazin-2-ylthio)propanoate (1.56 g, 6.96 mmol) in anhydrous tetrahydrofuran at room temperature was added 60% sodium hydroxide suspension (0.34 g, 8.4 mmol). Vigorous hydrogen evolution was observed. After 1 h at room temperature there appeared to be no reaction, the reaction temperature was raised to 50° C. for 6 h, whereupon the starting material was consumed by TLC. The reaction was quenched by the addition ice, followed by 5% aqueous citric acid. The mixture was extracted with ethyl acetate. The organic layer was washed with saturated aqueous sodium bicarbonate solution, dried over anhydrous sodium sulfate, filtered and concentrated under reduced pressure to yield 3-mercaptopyrazine-2-carbonitrile (1.1 g) as an orange solid. MW=137 confirmed by LC-MS, $t_r$=4.79 min (Method Y) MH$^+$=136-138.

Synthesis of 3-Bromoisothiazolo[5,4-b]pyrazine. Crude 3-mercaptopyrazine-2-carbonitrile (1.1 g, 8.0 mmol) was dissolved in ethyl acetate (30 mL) and treated with bromine (0.46 mL, 8.8 mmol). The reaction mixture was heated to reflux. As soon as the bromine was added, the mixture became homogeneous but after several minutes a precipitate began to form. After 90 min the reaction mixture was cooled to room temperature and then partitioned between ethyl acetate and saturated aqueous sodium bicarbonate solution. The organic layer was dried over anhydrous sodium sulfate, filtered and concentrated under reduced pressure to yield 3-bromoisothiazolo[5,4-b]pyrazine as a pale orange solid. MW=215 confirmed by LC-MS, $t_r$=10.34 min (Method Y) MH$^+$=214-216.

Synthesis of N$^1$-(Isothiazolo[5,4-b]pyrazin-3-yl)propane-1,3-diamine. To a solution of 3-bromoisothiazolo[5,4-b]pyrazine in methanol (25 mL) was added 1,3-diaminopropane (6 mL). The reaction mixture was stirred at room temperature for 15 min, then heated to 50° C. After 1 h, the starting material was consumed as judged by LC-MS. The reaction mixture was concentrated under reduced pressure and then partitioned between ethyl acetate and brine. The aqueous layer was back-extracted twice with ethyl acetate and once with methylene chloride. The combined organic layers were washed with brine and dried over anhydrous sodium sulfate and filtered. Concentration under reduced pressure gave N$^1$-(isothiazolo[5,4-b]pyrazin-3-yl)propane-1,3-diamine (410 mg) as a yellow solid. $^1$H NMR (300 MHz, CDCl$_3$-DMSO-d$_6$): 8.62 (d, 1H), 8.54 (d, 1H), 2.66 (m, 4H), 2.49 (br s, 2H), 1.51 ppm (m, 2H). MW=209 confirmed by LC-MS, $t_r$=2.51 min (Method Y) MH$^+$=208-210.

Synthesis of N$^1$-(Isothiazolo[5,4-b]pyrazin-3-yl)-N$^3$-((4'-methoxybiphenyl-4-yl)methyl)propane-1,3-diamine. N$^1$-(Isothiazolo[5,4-b]pyrazin-3-yl)propane-1,3-diamine (410 mg, 1.96 mmol) and 4'-methoxybiphenyl-4-carbaldehyde (410 mg, 1.96 mmol) were combined in 1,2-dichloroethane (8 mL) and treated with sodium triacetoxyborohydride (506 mg, 2.35 mmol). The mixture was shaken at room temperature for 3 h. The reaction was diluted with methylene chloride, quenched with water and the layers were separated. The organic solution was dried over anhydrous sodium sulfate, filtered and concentrated under reduced pressure. The resulting residue was purified by flash column chromatography, on silica gel, eluting with methylene chloride:methanol to yield N$^1$-(isothiazolo[5,4-b]pyrazin-3-yl)-N$^3$-((4'-methoxybiphenyl-4-yl)methyl)propane-1,3-diamine (100 mg) as a yellow solid. $^1$H NMR (300 MHz, DMSO-d$_6$): 8.79 (d, 1H), 8.72 (d, 1H), 7.90 (t, 1H), 7.54 (m, 4H), 7.40 (d, 2H), 6.98 (d, 2H), 3.82 (s, 2H), 3.80 (s, 3H), 3.48 (t, 2H), 2.70 (m, 3H), 1.85 ppm (m, 2H). MW=405 confirmed by LC-MS, $t_r$=9.59 min (Method Y) MH$^+$=404-406.

Example 13

Synthesis of 4'-Methoxy-N-(3-(5-(N-(4-methoxybenzyl)sulfamoyl)benzo[d]isothiazol-3-ylamino)propyl)biphenyl-4-carboxamide

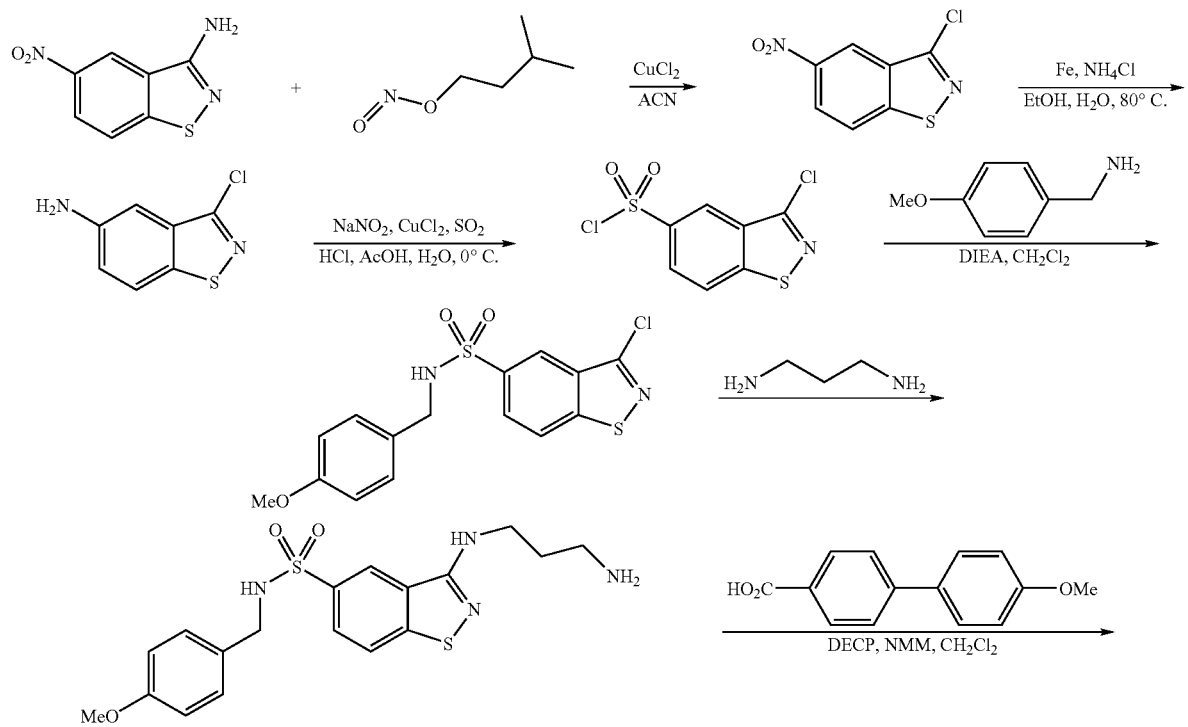

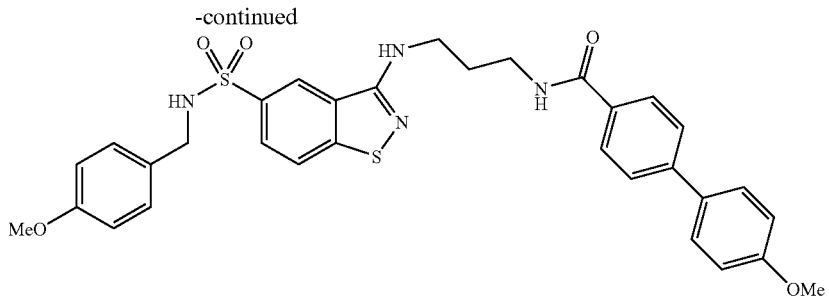

Synthesis of 3-Chloro-5-nitrobenzo[d]isothiazole. To a warm solution (65° C.) of copper (II) chloride (anhydrous, 1.65 g, 12.3 mmol), isoamyl nitrite (2.1 mL, 15.6 mmol) in anhydrous acetonitrile (80 mL), a solution of 3-amino-5-nitrobenzo[d]isothiazole (2.0 g, 10.2 mmol) in acetonitrile (20 mL) was added dropwise. A significant amount of precipitate appeared followed by evolution of nitrogen gas. The resulting brown reaction mixture was allowed to stir at 65° C. for 1 h after which time it was poured into 20% HCl aqueous solution, neutralized to pH 8 with solid sodium bicarbonate and extracted with methylene chloride. The combined organic layers were then dried over anhydrous magnesium sulfate, filtered and concentrated to give 2.8 g of a brown solid. Purification by column chromatography, on silica gel, eluting with 1:9 ethyl acetate:hexanes provided 3-chloro-5-nitrobenzo[d]isothiazole (0.85 g) as a yellow solid. $^1$H NMR (300 MHz, CDCl$_3$): 8.74 (dd, 1H), 8.26 (dd, 1H), 7.88 ppm (dd, 1H). MW=214 confirmed by LC-MS, $t_r$=13.37 min (Method Y) MH$^+$=215.

Synthesis of 3-Chlorobenzo[d]isothiazol-5-amine. A solution of 3-chloro-5-nitrobenzo[d]isothiazole (4.53 g, 21.1 mmol), iron (7.2 g, 129 mmol) and ammonium chloride (2.4 g, 45 mmol) in ethanol/water (2:1, 270 mL) is allowed to stir at 80° C. for 1.5 h. The resulting dark reaction mixture was filtered through Celite while still hot and concentrated under reduced pressure to give a brown solid, which was dissolved in ethyl acetate and washed with saturated aqueous sodium bicarbonate solution and brine. The resulting organic layer was dried over anhydrous magnesium sulfate, filtered and concentrated under reduced pressure to give a brown solid which was triturated with hexanes to provide 3-chlorobenzo[d]isothiazol-5-amine (3.7 g) as a yellow solid. $^1$H NMR (300 MHz, CDCl$_3$): 7.57 (dd, 1H), 6.99 (dd, 1H), 6.66 ppm (dd, 1H). MW=184 confirmed by LC-MS, $t_r$=10.41 min (Method Y) MH$^+$=185.

Synthesis of 3-Chlorobenzo[d]isothiazole-5-sulfonyl Chloride. To a solution of 3-chlorobenzo[d]isothiazol-5-amine (3.7 g, 20 mmol) in concentrated hydrochloric acid (37 mL) at 0° C. was added a solution of sodium nitrite (1.52 g, 22 mol) in water (10 mL). The reaction mixture was allowed to stir at 0° C. for 2 h, after which time a pre-cooled solution of acetic acid (30 mL) and copper II chloride (1.48 g, 11 mmol) saturated with SO$_2$ gas was added. The resulting reaction mixture was then allowed to warm to room temperature over 2.5 h, poured into an Erlenmeyer flask containing ice/water (200 mL) and extracted with ethyl acetate. The organic layer was then dried over anhydrous magnesium sulfate, filtered and concentrated under reduced pressure to give 3-chlorobenzo[d]isothiazole-5-sulfonyl chloride (4.9 g). MW=268 confirmed by LC-MS, $t_r$=4.15 min (Method B) MH$^+$=269.

Synthesis of 3-Chloro-N-(4-methoxybenzyl)benzo[d]isothiazole-5-sulfonamide. To a solution of 3-chlorobenzo[d]isothiazole-5-sulfonyl chloride (90 mg, 0.33 mmol) in methylene chloride (2 mL), diisopropylethylamine (142 μL, 0.82 mmol) and 4-methoxybenzylamine (85 μL, 0.65 mmol) were added at room temperature. After stirring for 6 h, the reaction mixture was diluted with methylene chloride (20 mL) and washed with 10% HCl aqueous solution and brine. The organic layer was then dried over anhydrous magnesium sulfate, filtered and concentrated under reduced pressure to give a brown residue. Purification by column chromatography, on silica gel, eluting with 2:8 ethyl acetate:hexanes provided 3-chloro-N-(4-methoxybenzyl)benzo-[d]isothiazole-5-sulfonamide (55 mg). $^1$H NMR (300 MHz, CDCl$_3$): 8.22 (dd, 1H), 7.82 (dd, 1H), 7.75 (dd, 1H), 7.10 (d, 2H), 6.73 (d, 2H), 5.06 (t, 1H), 4.18 (d, 2H), 3.73 ppm (s, 3H). MW=368 confirmed by LC-MS, $t_r$=13.39 min (Method Y) MH$^+$=369.

Synthesis of 3-(3-Aminopropylamino)-N-(4-methoxybenzyl)benzo[d]isothiazole-5-sulfonamide. A solution of 3-chloro-N-(4-methoxybenzyl)benzo[d]isothiazole-5-sulfonamide (52 mg, 0.1 mmol) in 1,3-diaminopropane (1 mL) was allowed to stir at room temperature for 80 min. The dark brown reaction mixture was then poured over water (10 mL) and extracted with ethyl acetate. The combined organic layer was dried over anhydrous magnesium sulfate, filtered and concentrated under reduced pressure to give 3-(3-aminopropylamino)-N-(4-methoxybenzyl)benzo[d]isothiazole-5-sulfonamide (57 mg) as an orange oil. $^1$H NMR (300 MHz, CD$_3$OD): 8.22 (dd,1H), 7.54 (dd, 1H), 7.29 (dd, 1H), 7.04 (d, 2H), 6.64 (d, 2H), 4.00 (s, 2H), 3.64 (s, 3H), 3.36 (t, 2H), 2.82 (d, 2H), 1.94-2.02 ppm (m, 2H). MW=406 confirmed by LC-MS, $t_r$=7.95 min (Method Y) MH$^+$=407.

Synthesis of 4'-Methoxy-N-(3-(5-(N-(4-methoxybenzyl)sulfamoyl)benzo[d]isothiazol-3-ylamino)propyl)biphenyl-4-carboxamide. To a solution of 4'-methoxybiphenyl-4-carboxylic acid (34 mg, 0.1 mmol) in methylene chloride (1 mL), diethyl cyanophosphonate (23 μL, 0.2 mmol) and 4-methylmorpholine (34 μL, 0.3 mmol) were added at room temperature and allowed to stir for 15 min. A solution of 3-(3-aminopropylamino)-N-(4-methoxybenzyl)benzo[d]isothiazole-5-sulfonamide (57 mg, 0.1 mmol) in methylene chloride (1 mL) was then added and the resulting reaction mixture was allowed to stir for 7 h. Upon diluting the reaction mixture with methylene chloride (20 mL) and 10% HCl aqueous solution, a precipitate was observed, filtered and air-dried to provide 4'-methoxy-N-(3-(5-(N-(4-methoxybenzyl)sulfamoyl)-benzo[d]isothiazol-3-ylamino)propyl)biphenyl-4-carboxamide (13 mg). $^1$H NMR (300 MHz, DMSO-d$_6$): 9.01 (br s, 1H), 8.58 (t, 1H), 8.47 (d, 1H), 7.88-7.91 (m, 3H), 7.70 (d, 2H), 7.66 (d, 2H), 7.50 (dd, 1H), 7.34 (d, 1H), 7.13 (d, 2H), 7.03 (d, 2H), 6.78 (d, 2H), 3.88 (d, 2H), 3.80 (s, 3H), 3.67 (s, 3H), 3.42-3.48 (m, 2H), 3.31 (m, 2H), 2.00-2.09 ppm (m, 2H). MW=616 confirmed by LC-MS, $t_r$=13.65 min (Method Y) $MH^+$=617.

Example 14a

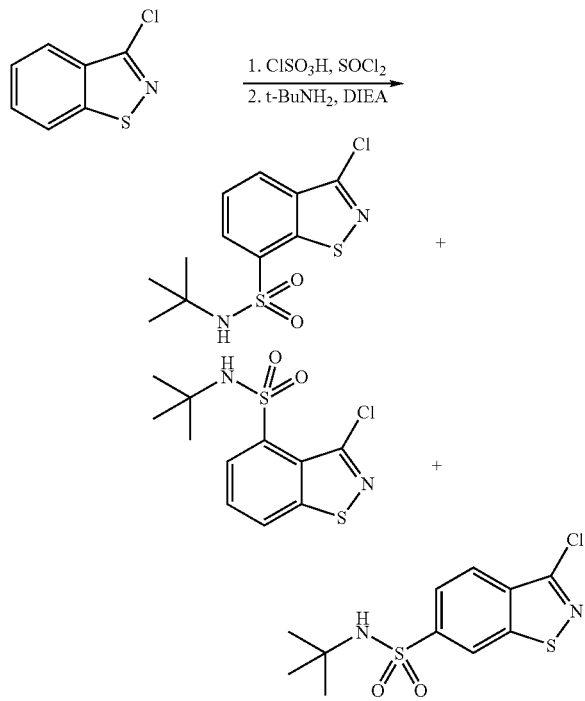

Synthesis of N-tert-Butyl-3-chlorobenzo[d]isothiazole-6-sulfonamide. Step 1: A solution of 3-chlorobenzo[d]isothiazole (1.0 g, 5.9 mmol) in chlorosulfonic acid (2 mL) was heated at 150° C. for 2.5 h. The resulting reaction mixture was then cooled to room temperature and thionyl chloride (0.9 mL, 12.3 mmol) was added. The resulting yellow solution was heated at 150° C. for 2 h, allowed to cool to room temperature and poured over ice. The aqueous reaction mixture was then extracted with ethyl acetate, dried over anhydrous magnesium sulfate, filtered and concentrated under reduced pressure to give a pale yellow oil which crystallized into an off-white solid upon standing at −20° C. (1.43 g). MW=267 confirmed by LC-MS, $t_r$=4.17 min (Method B) $MH^+$=268.

Step 2: A solution of the solid obtained from Step 1 (1.43 g, 5.3 mmol) in methylene chloride (15 mL) was treated with diisopropylethylamine (1.4 mL, 8.0 mmol) and t-butylamine (0.93 mL, 8.8 mmol) at room temperature. The resulting reaction mixture was then allowed to stir at room temperature overnight. The reaction was worked up by diluting with methylene chloride (20 mL) and extracted with 10% HCl aqueous solution and brine. The resulting organic layer was then dried over anhydrous magnesium sulfate, filtered and concentrated under reduced pressure to give a yellow oil. Purification by column chromatography, on silica gel, eluting with methylene chloride, followed by 5% acetonitrile/methylene chloride provided three products: N-tert-butyl-3-chlorobenzo[d]isothiazole-6-sulfonamide (311 mg). $^1$H NMR (300 MHz, $CDCl_3$): 8.61 (d, 1H), 8.12 (dd, 1H), 8.05 (d, 1H), 1.29 ppm (s, 9H). MW=304 confirmed by LC-MS, $t_r$=13.69 min (Method Y) $MH^+$=305.

N-t-butyl-3-chlorobenzo[d]isothiazole-7-sulfonamide (272 mg), $^1$H NMR (300 MHz, $CDCl_3$): 7.92 (dd,1H), 7.85 (dd, 1H), 7.51 (t, 1H), 1.50 ppm (s, 9H). $^{13}$C NMR ($CDCl_3$): 143.47, 136.51, 134.83, 127.46, 126.85, 114.43, 106.83, 67.32, 28.56. MW=304 confirmed by LC-MS, $t_r$=13.62 min (Method Y) $MH^+$=305.

N-t-Butyl-3-chlorobenzo[d]isothiazole-4-sulfonamide (297 mg), $^1$H NMR (300 MHz, $CDCl_3$): 8.23 (dd, 1H), 8.14 (dd, 1H), 7.70 (t, 1H), 1.27 ppm (s, 9H). MW=304 confirmed by LC-MS, $t_r$=14.10 min (Method Y) $MH^+$=305.

Example 14

Synthesis of N-(3-(6(N-tert-Butylsulfamoyl)benzo[d]isothiazol-3-ylamino)propyl)-4'-methoxybiphenyl-4-carboxamide

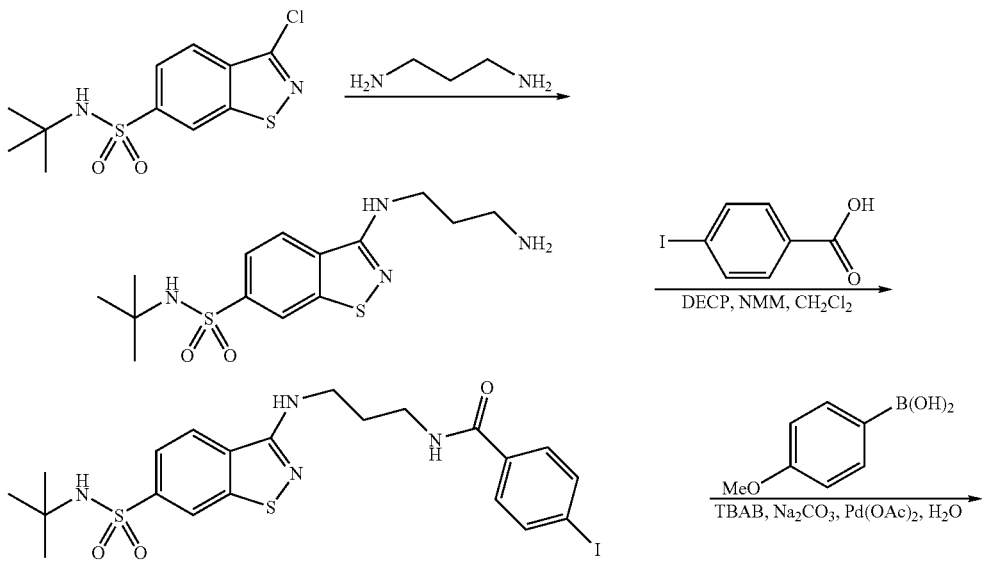

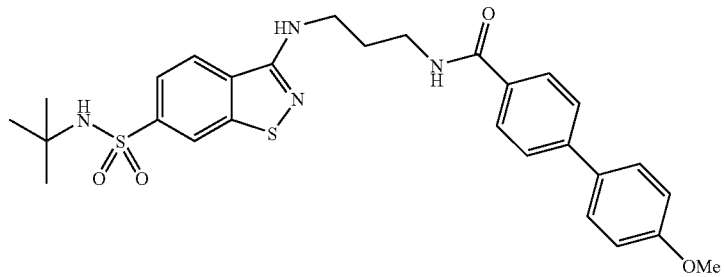

After the synthesis of N-tert-Butyl-3-chlorobenzo[d]isothiazole-6-sulfonamide as described in Example 14a, the title compound was synthesized as follows.

Synthesis of 3-(3-Aminopropylamino)-N-tert-butylbenzo[d]isothiazole-6-sulfonamide. A solution of N-tert-butyl-3-chlorobenzo[d]isothiazole-6-sulfonamide (278 mg, 0.9 mmol) in 1,3-diaminopropane (1 mL) was allowed to stir at room temperature for 3.5 h. The reaction mixture was then poured over water (10 mL), extracted with ethyl acetate and the combined organic layers were dried over anhydrous magnesium sulfate, filtered and concentrated under reduced pressure to give, upon trituration with ethyl ether, 3-(3-aminopropylamino)-N-t-butylbenzo[d]isothiazole-6-sulfonamide (242 mg). $^1$H NMR (300 MHz, CD$_3$OD): 8.54 (dd, 1H), 7.95 (d, 1H), 7.94 (d, 1H), 3.58 (t, 2H), 2.80 (t, 2H), 1.91 (q, 2H), 1.20 ppm (s, 9H). MW=342 confirmed by LC-MS, t$_r$=8.14 min (Method Y) MH$^+$=343.

Synthesis of N-(3-(6-(N-tert-Butylsulfamoyl)benzo[d]isothiazol-3-ylamino)propyl)-4-iodobenzamide. To a solution of 4-iodobenzoic acid (181 mg, 0.7 mmol) in methylene chloride (2 mL), diethyl cyanophosphonate (115 μL, 0.8 mmol) and 4-methylmorpholine (160 μL, 1.5 mmol) were added at room temperature and allowed to stir for 15 min. A solution of 3-(3-aminopropylamino)-N-tert-butylbenzo[d]isothiazole-6-sulfonamide (238 mg, 0.7 mmol) in methylene chloride (4 mL) was then added and the resulting reaction mixture was allowed to stir overnight. The reaction mixture with diluted with methylene chloride (20 mL), washed with 10% HCl aqueous solution and brine, dried over anhydrous magnesium sulfate, filtered and concentrated under reduced pressure. Purification by column chromatography, on silica gel, eluting with 1:1 ethyl acetate:hexanes provided N-(3-(6-(N-tert-butylsulfamoyl)benzo[d]isothiazol-3-ylamino)propyl)-4-iodobenzamide (252 mg). $^1$H NMR (300 MZh, CDCl$_3$): 8.47 (d, 1H), 7.96 (dd, 1H), 7.86 (d, 1H), 7.82 (d, 2H), 7.60 (d, 2H), 7.37 (t, 1H), 6.19 (br s, 1H), 4.98 (s, 1H), 3.75 (t, 2H), 3.60 (dd, 2H), 2.02 (q, 2H), 1.29 ppm (s, 9H). $^{13}$C NMR (CDCl$_3$): 167.25, 159.79, 154.96, 139.87, 138.01, 134.16, 128.91, 126.28, 121.54, 121.19, 98.76, 55.46, 43.08, 40.33, 37.32, 30.66, 30.06. MW=572 confirmed by LC-MS, t$_r$=14.28 min (Method Y) MH$^+$=573.

Synthesis of N-(3-(6-(N-tert-Butylsulfamoyl)benzo[d]isothiazol-3-ylamino)propyl)-4'-methoxybiphenyl-4-carboxamide. A mixture of N-(3-(6-(N-tert-butylsulfamoyl)benzo[d]isothiazol-3-ylamino)propyl)4-iodobenzamide (50 mg, 0.09 mmol), 4-methoxyphenylboronic acid (14 mg, 0.09 mmol), tetrabutylammonium bromide (29 mg, 0.09 mmol), sodium carbonate (29 mg, 0.27 mmol) and palladium (II) acetate (1 mg) in water (3 mL) was microwaved at 160° C. for 5 min. The reaction was diluted with methylene chloride and the mixture was washed successively with aqueous sodium bicarbonate and brine, dried over anhydrous sodium sulfate, filtered and concentrated under reduced pressure. Purification by column chromatography, on silica gel, eluting with 98:2 methylene chloride:methanol yielded N-(3-(6-(N-tert-butylsulfamoyl)benzo[d]isothiazol-3-ylamino)propyl)-4'-methoxybiphenyl-4-carboxamide (17 mg), as a white solid. $^1$H NMR (300 MHz, DMSO-d$_6$): 8.70 (s, 1H), 8.52 (t, 1H), 8.10 (d, 1H), 7.86 (d, 2H), 7.81 (t, 1H), 7.68 (t, 3H), 7.52-7.60 (m, 2H), 6.97-7.08 (m, 2H), 3.80 (s, 3H), 3.49-3.57 (m, 4H), 1.95 (t, 2H), 1.12 ppm (s, 9H). MW=553 confirmed by LC-MS, t$_r$=4.30 min (Method B) MH$^+$=554.

Example 15

Synthesis of N-(3-(4-(N-tert-Butylsulfamoyl)benzo[d]isothiazol-3-ylamino)propyl)-4'-methoxybiphenyl-4-carboxamide

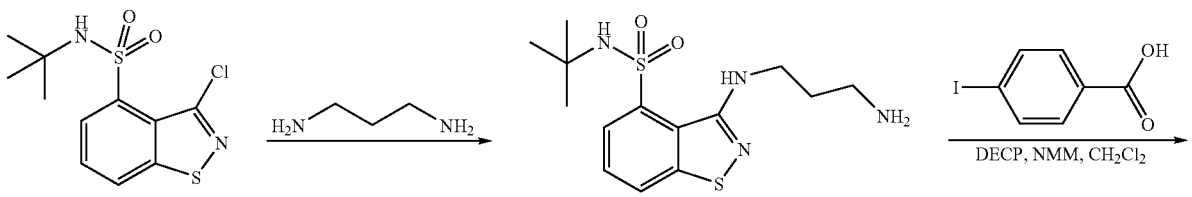

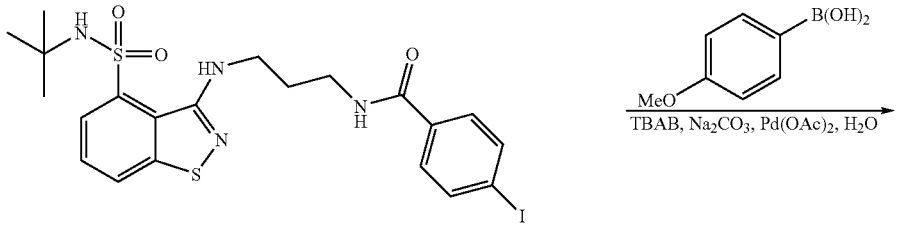

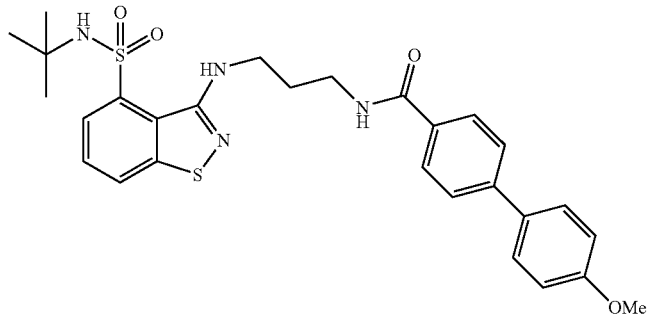

After the synthesis of N-t-Butyl-3-chlorobenzo[d]isothiazole-4-sulfonamide as described in Example 14a, the title compound was synthesized as follows.

Synthesis of 3-(3-Aminopropylamino)-N-tert-butylbenzo[d]isothiazole-4-sulfonamide. A solution of N-tert-butyl-3-chlorobenzo[d]isothiazole-4-sulfonamide (280 mg, 0.92 mmol) in 1,3-diaminopropane (1 mL) was allowed to stir at room temperature for 2.5 h. The reaction mixture was then poured over water (10 mL), extracted with ethyl acetate and the combined organic layers was dried over anhydrous magnesium sulfate, filtered and concentrated under reduced pressure to give, upon trituration with ethyl ether, 3-(3-aminopropylamino)-N-tert-butylbenzo[d]isothiazole-4-sulfonamide (257 mg) as an off-white solid. $^1$H NMR (300 MHz, CD$_3$OD): 8.02 (d, 1H), 7.85 (d, 1H), 7.70 (t, 1H), 3.74 (t, 2H), 3.02 (t, 2H), 1.87-1.95 (m, 2H), 1.24 ppm (s, 9H). MW=342 confirmed by LC-MS, $t_r$=8.22 min (Method Y) MH$^+$=343.

Synthesis of N-(3-(4-(N-tert-Butylsulfamoyl)benzo[d]isothiazol-3-ylamino)propyl)-4-iodobenzamide. To a solution of 4-iodobenzoic acid (210 mg, 0.8 mmol) in methylene chloride (2 mL), diethyl cyanophosphonate (120 μL, 0.8 mmol) and 4-methylmorpholine (172 μL, 1.6 mmol) were added at room temperature and allowed to stir for 15 min. A solution of 3-(3-aminopropylamino)-N-tert-butylbenzo[d]isothiazole-4-sulfonamide (243 mg, 0.7 mmol) in methylene chloride (4 mL) was then added and the resulting reaction mixture was allowed to stir overnight. The reaction mixture with diluted with methylene chloride (20 mL), washed with 10% HCl aqueous solution and brine, dried over anhydrous magnesium sulfate, filtered and concentrated under reduced pressure. Purification by column chromatography, on silica gel, eluting with 1:1 ethyl acetate:hexanes, followed by 7:3 ethyl acetate:hexanes provided N-(3-(4-(N-tert-butylsulfamoyl)benzo[d]isothiazol-3-ylamino)propyl)-4-iodobenzamide (365 mg) as a yellow foam. $^1$H NMR (300 MHz, CDCl$_3$): 8.01 (dd, 1H), 7.96 (dd, 1H), 7.80 (d, 2H), 7.59 (d, 2H), 7.43-7.49 (m, 2H), 6.10 (t, 1H), 4.98 (s, 1H), 3.71 (dd, 2H), 3.59 (dd, 2H), 1.92-2.00 (m, 2H), 1.25 ppm (s, 9H). MW=572 confirmed by LC-MS, $t_r$=13.85 min (Method Y) MH$^+$=573.

Synthesis of N-(3-(4-(N-tert-Butylsulfamoyl)benzo[d]isothiazol-3-ylamino)propyl)-4'-methoxybiphenyl-4-carboxamide. A mixture of N-(3-(4-(N-tert-butylsulfamoyl)benzo[d]isothiazol-3-ylamino)propyl)-4-iodobenzamide (50 mg, 0.09 mmol), 4-methoxyphenylboronic acid (14 mg, 0.09 mmol), tetrabutylammonium bromide (29 mg, 0.09 mmol), sodium carbonate (29 mg, 0.27 mmol) and palladium (II) acetate (1 mg) in water (3 mL) was microwaved at 160° C. for 5 min. The reaction was diluted with methylene chloride and the mixture was washed successively with aqueous sodium bicarbonate and brine, dried over anhydrous sodium sulfate, filtered and concentrated under reduced pressure. Purification by column chromatography, on silica gel, eluting with 98:2 methylene chloride:methanol yielded N-(3-(4-(N-tert-Butylsulfamoyl)benzo[d]isothiazol-3-ylamino)propyl)-4'-methoxybiphenyl-4-carboxamide (22 mg), as a white solid. $^1$H NMR (300 MHz, DMSO-d$_6$)-8.53 (t, 1H), 8.32 (d, 1H), 7.98 (d, 1H), 7.88-7.92 (m, 2H), 7.51-7.70 (m, 5H), 7.00 (d, 2H), 3.80 (s, 3H), 3.38-3.51 (m, 4H), 1.93 (t, 2H), 1.10 ppm (s, 9H). MW=553 confirmed by LC-MS, $t_r$=4.18 min (Method B) MH$^+$=554.

Example 16

Synthesis of N-(3-(7-(N-tert-Butylsulfamoyl)benzo[d]isothiazol-3-ylamino)propyl)-4'-methoxybiphenyl-4-carboxamide

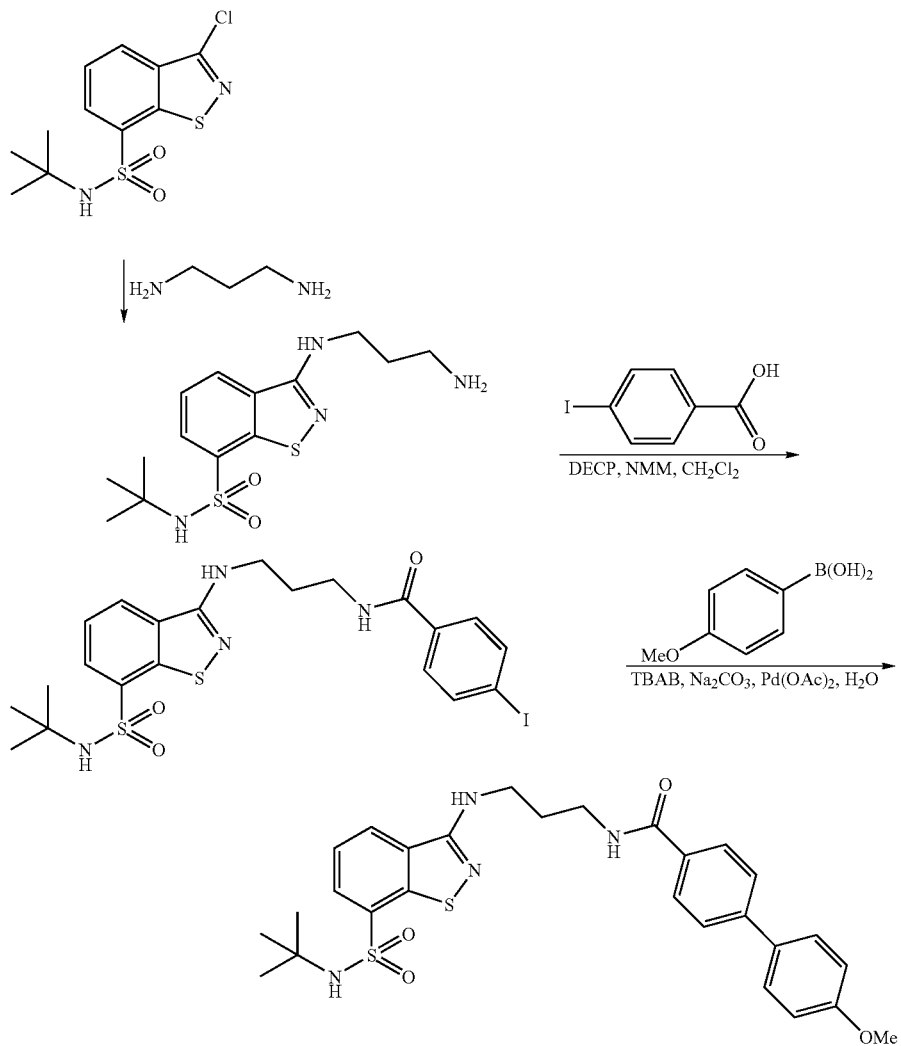

After the synthesis of N-t-butyl-3-chlorobenzo[d]isothiazole-7-sulfonamide as described in Example 14a, the title compound was synthesized as follows.

Synthesis of 3-(3-Aminopropylamino)-N-tert-butylbenzo[d]isothiazole-7-sulfonamide. A solution of N-tert-butyl-3-chlorobenzo[d]isothiazole-7-sulfonamide (260 mg, 0.85 mmol) in 1,3-diaminopropane (1 mL) was allowed to stir at room temperature for 3h. The dark brown reaction mixture was then poured over water (10 mL), extracted with ethyl acetate and the combined organic layers were dried over anhydrous magnesium sulfate, filtered and concentrated under reduced pressure to give 3-(3-aminopropylamino)-N-tert-butylbenzo[d]isothiazole-7-sulfonamide (271 mg) as a pale yellow solid. $^1$H NMR (300 MHz, CD$_3$OD): 8.17 (dd, 1H), 8.01 (dd, 1H), 7.55 (t, 1H), 3.58 (t, 2H), 2.81 (t, 2H), 1.86-1.95 (m, 2H), 1.17 ppm (s, 9H). MW=342 confirmed by LC-MS, $t_r$=7.95 min (Method Y) MH$^+$=343.

Synthesis of N-(3-(7-(N-tert-Butylsulfamoyl)benzo[d]isothiazol-3-ylamino)propyl)-4-iodobenzamide. To a solution of 4-iodobenzoic acid (270 mg, 0.8 mmol) in methylene chloride (2 mL), diethyl cyanophosphonate (130 μL, 0.9 mmol) and 4-methylmorpholine (182 μL, 1.7 mmol) were added at room temperature and allowed to stir for 15 min. A solution of 3-(3-aminopropylamino)-N-t-butylbenzo[d]isothiazole-7-sulfonamide (270 mg, 0.8 mmol) in methylene chloride (4 mL) was then added and the resulting reaction mixture was allowed to stir overnight. The reaction mixture with diluted with methylene chloride (20 mL), washed with 10% HCl aqueous solution and brine, dried anhydrous magnesium sulfate, filtered and concentrated under reduced pressure. Purification by column chromatography, on silica gel, eluting with 6:4 ethyl acetate:hexanes provided N-(3-(7-(N-tert-butylsulfamoyl)benzo[d]isothiazol-3-ylamino)propyl)-4-iodobenzamide (355 mg). $^1$H NMR (300 MHz, CDCl$_3$): 8.01 (dd, 1H), 7.96 (d, 1H), 7.78 (d, 2H), 7.59 (d, 2H), 7.53 (t, 1H), 7.44 (t, 1H), 6.15 (t, 1H), 5.09 (s, 1H), 3.70 (dd, 2H), 3.57 (dd, 2H), 1.90-1.99 (m, 2H), 1.24 ppm (s, 9H). MS (m/z): 573 (M+H)$^+$ confirmed by LC-MS, $t_r$=13.92 min (Method Y) MW=572 confirmed by LC-MS, $t_r$=13.92 min (Method Y) MH$^+$=573.

Synthesis of N-(3-(7-(N-tert-Butylsulfamoyl)benzo[d]isothiazol-3-ylamino)propyl)-4'-methoxybiphenyl-4-carboxamide. A mixture of N-(3-(7-(N-tert-butylsulfamoyl)benzo[d]isothiazol-3-ylamino)propyl)-4-iodobenzamide (50 mg, 0.09 mmol), 4-methoxyphenylboronic acid (14 mg, 0.09 mmol), tetrabutylammonium bromide (29 mg, 0.09 mmol), sodium carbonate (29 mg, 0.27 mmol) and palladium (II) acetate (1 mg) in water (3 mL) was microwaved at 160° C. for 5 min. The reaction was diluted with methylene chloride and the mixture was washed successively with aqueous sodium bicarbonate and brine, dried over anhydrous sodium sulfate, filtered and concentrated under reduced pressure. Purification by column chromatography, on silica gel, eluting with 98:2 methylene chloride:methanol yielded N-(3-(7-(N-tert-Butylsulfamoyl)benzo[d]isothiazol-3-ylamino)propyl)-4'-methoxybiphenyl-4-carboxamide (14 mg), as a white solid. $^1$H NMR (300 MHz, DMSO-$d_6$): 8.50 (t, 1H), 8.32 (d, 1H), 7.83-7.99 (m, 3H), 7.50-7.71 (m, 5H), 7.03 (d, 2H), 4.80 (s, 3H), 3.38-3.51 (m, 4H), 1.93 (t, 2H), 1.10 ppm (s, 9H). MW=533 confirmed by LC-MS, $t_r$=4.30 min (Method B) MH$^+$=554.

Example 17

Synthesis of N-(3-(Isothiazolo[5,4-b]pyridin-3-ylamino)propyl)-4-methoxybenzamide

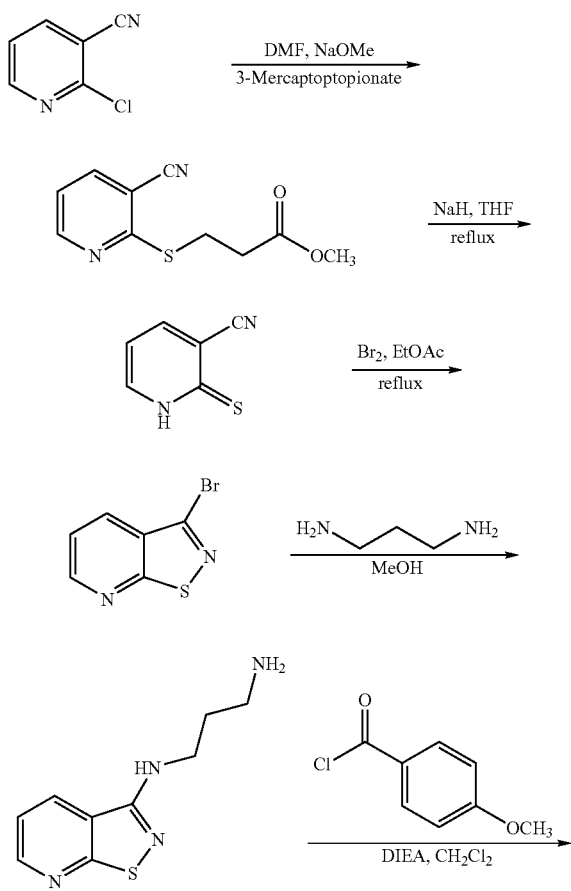

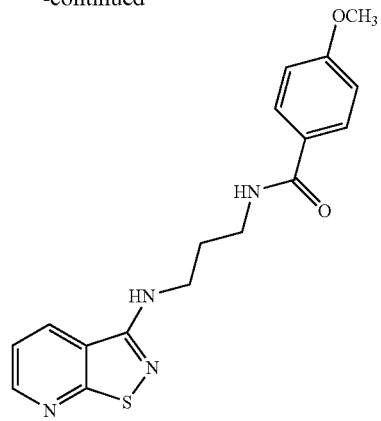

Synthesis of Methyl 3-(3-Cyanopyridin-2-ylthio)propanoate. A mixture of anhydrous N,N-dimethylformamide (30 ml), sodium methoxide (0.54 g, 10 mmol), methyl 3-mercaptopropionate (1.20 g, 10 mmol) and 2-chloro-3-cyanopyridine (1.38 g, 10 mmol) was stirred at room temperature for 1 h. The reaction mixture was poured into water (200 ml), the product filtered, washed with water and recrystallized from ethyl acetate/hexanes to yield methyl 3-(3-cyanopyridin-2-ylthio)propanoate (1.60 g). mp 101-102° C. as heavy colorless prisms. $^1$H NMR (300 MHz, CDCl$_3$): 8.45 (dd, 1H), 7.02 (dd, 1H), 3.68 (s, 3H), 3.49 (t, 2H), 2.78 ppm (t, 2H).

Synthesis of 2-Thioxo-1,2-dihydropyridine-3-carbonitrile. A mixture of methyl 3-(3-cyanopyridin-2-ylthio)propanoate (1.5 g, 6.8 mmol), sodium hydride (0.36 g, 15 mmol) and tetrahydrofuran (30 ml) was heated at reflux for 5 h. The reaction was quenched by the addition of ethanol (5 ml). The solvents removed under reduced pressure and the residue was treated with water (50 ml). The ph was adjusted to 6 and the mixture was filtered to yield 2-thioxo-1,2-dihydropyridine-3-carbonitrile (0.64 g). An analytically pure sample was prepared by recrystallisation from ethanol, yellow needles, mp 243-246° C. (lit. mp 248-250° C.). $^1$H NMR (DMSO-$d_6$): 14.30 (br s, exchangeable, 1H), 8.12 (dd, 1H), 7.94 (dd, 1H), 6.86 ppm (dd, 1H). MW=136 confirmed by LC-MS, $t_r$=5.27 min (Method C) MH$^+$=137.

Synthesis of 3-Bromoisothiazolo[5,4-b]pyridine. To a solution of 2-thioxo-1,2-dihydropyridine-3-carbonitrile (2.1 g, 15.44 mmol) in ethyl acetate (50 mL), bromine (5.9 g, 37.11 mmol) was added drop wise at 0° C. The reaction mixture was allowed to warm to room temperature and then refluxed for 3 h. The reaction mixture was concentrated under reduced pressure. Trituration with hexanes:methylene chloride (1:1) mixture gave 3-bromoisothiazolo[5,4-b]pyridine, as light brown solid which was carried forward without further purification. MW=215 confirmed by LC-MS, $t_r$=16.08 min (Method Y) MH$^+$=216.

Synthesis of N$^1$-(Isothiazolo[5,4-b]pyridin-3-yl)propane-1,3-diamine. A mixture of 3-bromoisothiazolo[5,4-b]pyridine (1.9 g, 8.8 mmol), and 1, 3-diaminopropane (6.7 g, 90 mmol) in methanol (10 ml) was heated at 64° C. for 1.5 hours. The reaction mixture was cooled to room temperature and concentrated under reduced pressure. The crude reaction mixture was diluted with ethyl acetate and washed successively with saturated aqueous sodium bicarbonate solution and brine. The organic layer was dried over anhydrous sodium sulfate, filtered and concentrated under reduced pressure. Lyophilization of the crude sample in acetonitrile/water mixture yielded N$^1$-(isothiazolo[5,4-b]pyridin-3-yl)propane- 1,3-diamine. $^1$H NMR (300 MHz, DMSO-d$_6$): 8.68 (d, 1H), 8.53 (d, 1H), 7.73 (br s, 1H), 7.40 (dd, 1H), 3.46 (dd, 2H), 2.85 (t, 2H), 1.75 (t, 2H), 1.45 ppm (t, 2H). MW=208 confirmed by LC-MS, t$_r$=5.55 min (Method Y) MH$^+$=209.

Synthesis of N-(3-(Isothiazolo[5,4-b]pyridin-3-ylamino)propyl)-4-methoxybenzamide. N$^1$-(Isothiazolo[5,4-b]pyridin-3-yl)propane-1,3-diamine (100 mg, 0.48 mmol) was dissolved in anhydrous methylene chloride with diisopropylethylamine (0.23 mL, 1.34 mmol). The mixture was cooled in an ice-bath under nitrogen and a solution of 4-methoxybenzoyl chloride (98 mg, 0.58 mmol) in methylene chloride (5 mL) was added drop-wise. After the addition was completed the ice-bath was removed and the mixture was stirred at room temperature overnight. The reaction mixture was diluted with methylene chloride and then washed successively with saturated sodium bicarbonate solution and brine. The organic solution was dried over anhydrous sodium sulfate, filtered and concentrated under reduced pressure. The resulting residue was purified by prep-scale reverse phase high performance liquid chromatography to yield N-(3-(isothiazolo[5,4-b]pyridin-3-ylamino)propyl)-4-methoxybenzamide (54 mg). $^1$H NMR (300 MHz, DMSO-d$_6$): 8.68 (d, 1H), 8.55 (t, 1H), 8.45 (d, 1H), 8.18 (s, 1H), 7.82-7.85 (m, 2H), 7.41 (dd, 1H), 7.26-7.36 (m, 2H), 3.95 (s, 3H), 3.40-3.42 (dd, 2H), 3.39-3.40 (dd, 2H), 1.82-1.95 ppm (m, 2H). MW=342 confirmed by LC-MS, t$_r$=10.82 min (Method Y) MH$^+$=343.

Example 18

Synthesis of N-(3-(isothiazolo[5,4-b]pyridin-3-ylamino)propyl)-N-((4'-methoxybiphenyl-4-yl)methyl)-1,2-dimethyl-1H-imidazole-4-sulfonamide

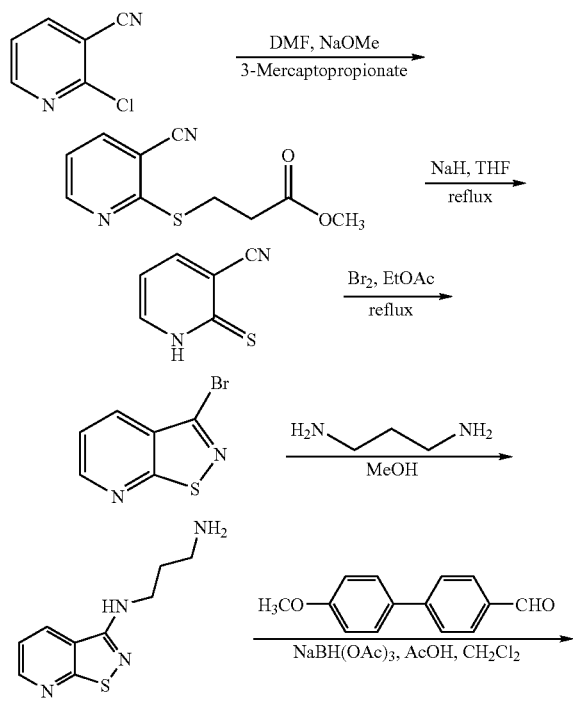

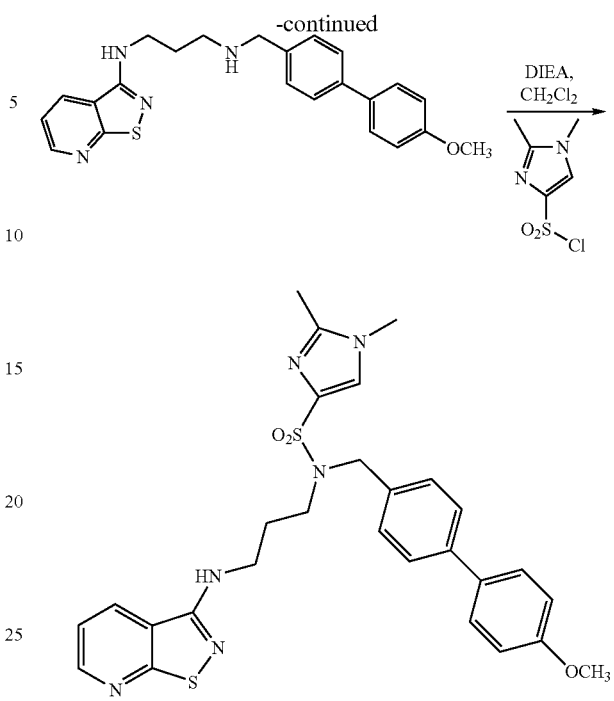

Synthesis of Methyl 3-(3-Cyanopyridin-2-ylthio)propanoate. A mixture of anhydrous N,N-dimethylformamide (30 ml), sodium methoxide (0.54 g, 10 mmol), methyl 3-mercaptopropionate (1.20 g, 10 mmol) and 2-chloro-3-cyanopyridine (1.38 g, 10 mmol) was stirred at room temperature for 1 h. The reaction mixture was poured into water (200 ml), the product filtered, washed with water and recrystallized from ethyl acetate/hexanes to yield methyl 3-(3-cyanopyridin-2-ylthio)propanoate (1.60 g). mp 101-102° C. as heavy colorless prisms. $^1$H NMR (300 MHz, CDCl$_3$): 8.45 (dd, 1H), 7.02 (dd, 1H), 3.68 (s, 3H), 3.49 (t, 2H), 2.78 ppm (t, 2H).

Synthesis of 2-Thioxo-1,2-dihydropyridine-3-carbonitrile. A mixture of methyl 3-(3-cyanopyridin-2-ylthio)propanoate (1.5 g, 6.8 mmol), sodium hydride (0.36 g, 15 mmol) and tetrahydrofuran (30 ml) was heated at reflux for 5 h. The reaction was quenched by the addition of ethanol (5 ml). The solvents removed under reduced pressure and the residue was treated with water (50 ml). The ph was adjusted to 6 and the mixture was filtered to yield 2-thioxo-1,2-dihydropyridine-3-carbonitrile (0.64 g). An analytically pure sample was prepared by recrystallisation from ethanol, yellow needles, mp 243-246° C. (lit. mp 248-250° C.). $^1$H NMR (DMSO-d$_6$): 14.30 (br s, exchangeable, 1H), 8.12 (dd, 1H), 7.94 (dd, 1H), 6.86 ppm (dd, 1H). MW=136 confirmed by LC-MS, t$_r$=5.27 min (Method C) MH$^+$=137.

Synthesis of 3-Bromoisothiazolo[5,4-b]pyridine. To a solution of 2-thioxo-1,2-dihydropyridine-3-carbonitrile (2.1 g, 15.44 mmol) in ethyl acetate (50 mL), bromine (5.9 g, 37.11 mmol) was added drop wise at 0° C. The reaction mixture was allowed to warm to room temperature and then refluxed for 3 h. The reaction mixture was concentrated under reduced pressure. Trituration with hexanes:methylene chloride (1:1) mixture gave 3-bromoisothiazolo[5,4-b]pyridine, as light brown solid which was carried forward without further purification. MW=215 confirmed by LC-MS, t$_r$=16.08 min (Method Y) MH$^+$=216.

Synthesis of N¹-(Isothiazolo[5,4-b]pyridin-3-yl)propane-1,3-diamine. A mixture of 3-bromoisothiazolo[5,4-b]pyridine (1.9 g, 8.8 mmol), and 1,3-diaminopropane (6.7 g, 90 mmol) in methanol (10 ml) was heated at 64° C. for 1.5 hours. The reaction mixture was cooled to room temperature and concentrated under reduced pressure. The crude reaction mixture was diluted with ethyl acetate and washed successively with saturated aqueous sodium bicarbonate solution and brine. The organic layer was dried over anhydrous sodium sulfate, filtered and concentrated under reduced pressure. Lyophilization of the crude sample in acetonitrile/water mixture yielded N¹-(isothiazolo[5,4-b]pyridin-3-yl)propane-1,3-diamine. ¹H NMR (300 MHz, DMSO-$d_6$): 8.68 (d, 1H), 8.53 (d, 1H), 7.73 (br s, 1H), 7.40 (dd, 1H), 3.46 (dd, 2H), 2.85 (t, 2H), 1.75 (t, 2H), 1.45 ppm (t, 2H). MW=208 confirmed by LC-MS, $t_r$=5.55 min (Method Y) MH⁺=209.

Synthesis of N¹-(Isothiazolo[5,4-b]pyridin-3-yl)-N³-((4'-methoxybiphenyl-4-yl)methyl)propane-1,3-diamine. A mixture of N¹-(isothiazolo[5,4-b]pyridin-3-yl)propane-1,3-diamine (1.20 g, 5.77 mmol), 4'-methoxybiphenyl-4-carbaldehyde (1.22 g, 5.77 mmol), sodium triacetoxyborohydride (2.50 g, 11.8 mmol) and acetic acid (one drop) was taken up in methylene chloride (25 mL) and stirred overnight at room temperature under argon. The crude reaction mixture was concentrated under reduced pressure, diluted with ethyl acetate and washed successively with saturated aqueous sodium bicarbonate solution and brine. The organic layer was dried over anhydrous sodium sulfate, filtered and concentrated under reduced pressure. Purification by column chromatography, on silica gel, eluting with 95:5 methylene chloride:methanol yielded N¹-(isothiazolo[5,4-b]pyridin-3-yl)-N³-((4'-methoxybiphenyl-4-yl)methyl)propane-1,3-diamine. ¹H NMR (300 MHz, CD₃OD): 8.66-8.68 (d, 1H), 8.40-8.45 (d, 1H), 7.33-7.45 (m, 7H), 6.96 (s, 1H), 6.93 (s, 3.83 (s, 2H), 3.80 (s, 3H), 3.58-3.63 (t, 2H), 2.78-2.83 (t, 2H), 1.96-2.00 ppm (t, 2H). MW=405 confirmed by LC-MS, $t_r$=9.08 min (Method Y) MH⁺=406.

Synthesis of N-(3-(Isothiazolo[5,4-b]pyridin-3-ylamino)propyl)-N-((4'-methoxybiphenyl-4-yl)methyl)-1,2-dimethyl-1H-imidazole-4-sulfonamide. N¹-(Isothiazolo[5,4-b]pyridin-3-yl)-N³-((4'-methoxybiphenyl-4-yl)methyl)propane-1,3-diamine (100 mg, 0.25 mmol) was dissolved in anhydrous methylene chloride with diisopropylethylamine (0.11 mL, 0.63 mmol). The mixture was cooled in an ice-bath under nitrogen and a solution of 1,2-dimethylimidazole-4-sulfonyl chloride (58.4 mg, 0.30 mmol) in methylene chloride (5 mL) was added dropwise. After the addition was completed the ice-bath was removed and the mixture was stirred at room temperature overnight. The reaction mixture was diluted with methylene chloride and then washed successively with saturated sodium bicarbonate solution and brine. The organic solution was dried over anhydrous sodium sulfate, filtered and concentrated under reduced pressure. The resulting residue was purified by prep-scale reverse phase high performance liquid chromatography to yield N-(3-(isothiazolo[5,4-b]pyridin-3-ylamino)propyl)-N-((4'-methoxybiphenyl-4-yl)methyl)-1,2-dimethyl-1H-imidazole-4-sulfonamide (45 mg). ¹H NMR (300 MHz, DMSO-$d_6$): 8.64-8.66 (d, 1H), 8.45-8.50 (d, 1H), 7.52-7.75 (m, 8H), 7.28 (s, 1H), 6.95 (s, 1H), 6.82 (s, 1H), 3.99 (s, 2H), 3.89 (s, 3H), 3.55-3.65 (m, 5H), 2.88-2.90 (t, 2H), 2.50 (s, 3H), 1.99-2.10 ppm (t, 2H). MW=563 confirmed by LC-MS, $t_r$=4.31 min (Method E) MH⁺=564.

Example 19

Synthesis of 4-Hexyl-N-(3-(isothiazolo[4,5-b]pyridin-3-ylamino)propyl)benzamide

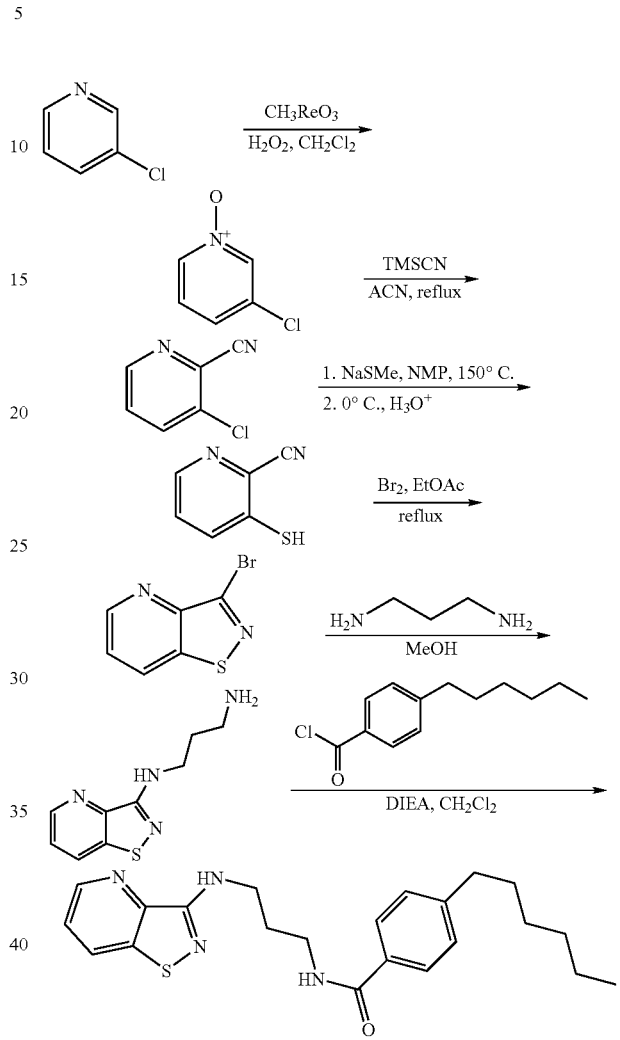

Synthesis of 3-Chloropyridine 1-Oxide. A mixture of 3-chloropyridine (2.30 g, 20.30 mmol), and methyl rhenium trioxide (25 mg, 0.1 mmol) in methylene chloride (10 mL) was treated with 30% aqueous hydrogen peroxide (5 mL, 50 mmol) and stirred for 6 h at room temperature. The biphasic reaction mixture was then treated with a catalytic amount of manganese (IV) oxide (5 mg) and stirred until oxygen evolution ceased. Following phase separation, the aqueous layer was extracted with methylene chloride, and the combined organic layers were dried over anhydrous sodium sulfate, filtered and concentrated under reduced pressure to give 3-chloropyridine 1-oxide (2.50 g) as a solid. mp 56-58° C. (Lit. 59-60° C.). ¹H NMR (300 MHz, C₆D₆): 7.80-8.40 (m, 2H), 6.50-6.80 ppm (m, 2H). ¹³C NMR (300 MHz, C₆D₆): 138.79, 137.76, 132.85, 125.46, 123.41. MW=130 confirmed by LC-MS, $t_r$=0.38 min (Method E) MH⁺=131.

Synthesis of 3-Chloropicolinonitrile. A mixture of 3-chloropyridine-N-oxide (2.12 g, 16.30 mmol), trimethylsilyl(acetonitrile) (3.25 g, 32.80 mmol), triethylamine (3.30 g, 32.60 mmol) and acetonitrile (10 mL) was heated at reflux for 6 h. After concentration under reduced pressure, the resulting residue was basified with aqueous sodium carbonate (3N) and extracted with methylene chloride. The combined organic layers were dried over anhydrous sodium sulfate, filtered and concentrated under reduced pressure to give 3-chloropicolinonitrile (1.90 g). The crude product was carried forward without further purification. MW=139 confirmed by LC-MS, $t_r$=2.33 min (Method E) MH$^+$=140.

Synthesis of 3-Mercaptopicolinonitrile. A mixture of 3-chloro-2-cyanopyridine (2.50 g, 18.05 mmol), and sodium thiomethoxide (3.60 g, 51.40 mmol) in 1-methyl-2-pyrrolidinone (25 mL) was heated at 140° C. overnight. The reaction mixture was cooled to 0° C. and quenched with 50% aqueous HCl. A light brown precipitate formed and the reaction was cooled for 1 h while stirring. The light brown solid was collected by vacuum filtration and dried under reduced pressure overnight to provide 3-mercaptopicolinonitrile (1.05 g). The crude product was used carried forward without further purification. MW=136 confirmed by LC-MS, $t_r$=1.85 min (Method E) MH$^+$=137.

Synthesis of 3-Bromoisothiazolo[4,5-b]pyridine. To a solution of 3-mercaptopicolinonitrile (1.05 g, 7.72 mmol) in ethyl acetate (30 mL), bromine (3.00 g, 18.90 mmol) was added dropwise at 0° C. The reaction mixture was allowed to warm to room temperature and then refluxed for 3 h. The reaction mixture was concentrated under reduced pressure. Trituration with hexanes:methylene chloride (1:1 mixture) gave 3-bromoisothiazolo[4,5-b]pyridine, as light brown solid which was carried forward without further purification. MW=215 confirmed by LC-MS, $t_r$=15.89 min (Method Y) MH$^+$=216.

Synthesis of N$^1$-(Isothiazolo[4,5-b]pyridin-3-yl)propane-1,3-diamine. 3-Bromoisothiazolo[4,5-b]pyridine (1.90 g, 8.8 mmol) and 1,3-diaminopropane (6.70 g, 90 mmol) in methanol (15 ml) was heated at 64° C. for 1.5 hours. The reaction mixture was cooled to room temperature and concentrated under reduced pressure. The crude reaction mixture was diluted with ethyl acetate and washed successively with saturated aqueous sodium bicarbonate solution and brine. The organic solution was dried over anhydrous sodium sulfate, filtered and concentrated under reduced pressure. Lyophilization of the crude sample in acetonitrile/water yielded N$^1$-(isothiazolo[4,5-b]pyridin-3-yl)propane-1,3-diamine. $^1$H NMR (300 MHz, DMSO-d$_6$): 8.55 (d, 1H), 8.05 (d, 1H), 7.32 (dd, 1H), 6.25 (br s, 1H), 3.65 (m, 2H), 2.85 (t, 2H), 1.85 (t, 2H), 1.45 ppm (br s, 2H). MW=208 confirmed by LC-MS, $t_r$=5.91 min (Method Y) MH$^+$=209.

Synthesis of 4-Hexyl-N-(3-(isothiazolo[4,5-b]pyridin-3-ylamino)propyl)benzamide. N$^1$-(Isothiazolo[4,5-b]pyridin-3-yl)propane-1,3-diamine (200 mg, 0.96 mmol) was dissolved in anhydrous methylene chloride with diisopropylethylamine (0.46 mL, 2.70 mmol). The mixture was cooled in an ice-bath under nitrogen and a solution of 4-methoxybenzoyl chloride (0.26 mL, 1.20 mmol) in methylene chloride (5 mL) was added dropwise. After the addition was completed the ice-bath was removed and the mixture was stirred at room temperature overnight. The reaction mixture was diluted with methylene chloride and then washed successively with saturated sodium bicarbonate solution and brine. The organic solution was dried over anhydrous sodium sulfate, filtered and concentrated under reduced pressure. The resulting residue was purified by prep-scale reverse phase high performance liquid chromatography to yield hexyl-N-(3-(isothiazolo[4,5-b]pyridin-3-ylamino)propyl)benzamide (160 mg). $^1$H NMR (300 MHz, DMSO-d$_6$): 8.66 (d, 1H), 8.50 (t, 1H), 8.40 (d, 1H), 8.10 (s, 1H), 7.75-7.80 (m, 4H), 7.41 (dd, 1H), 7.25 (m, 2H), 3.85 (t, 2H), 3.45-3.46 (dd, 2H), 2.88 (dd, 2H), 1.70-1.75 (m, 3H), 1.35-1.48 (m, 5H), 0.98-1.05 ppm (t, 3H). MW=397 confirmed by LC-MS, $t_r$=5.06 min (Method E) MH$^+$=398.

Example 20

Synthesis of N-(3-(4-Methylbenzo[d]isothiazol-3-ylamino)propyl)-3-(trifluoromethyl)benzenesulfonamide

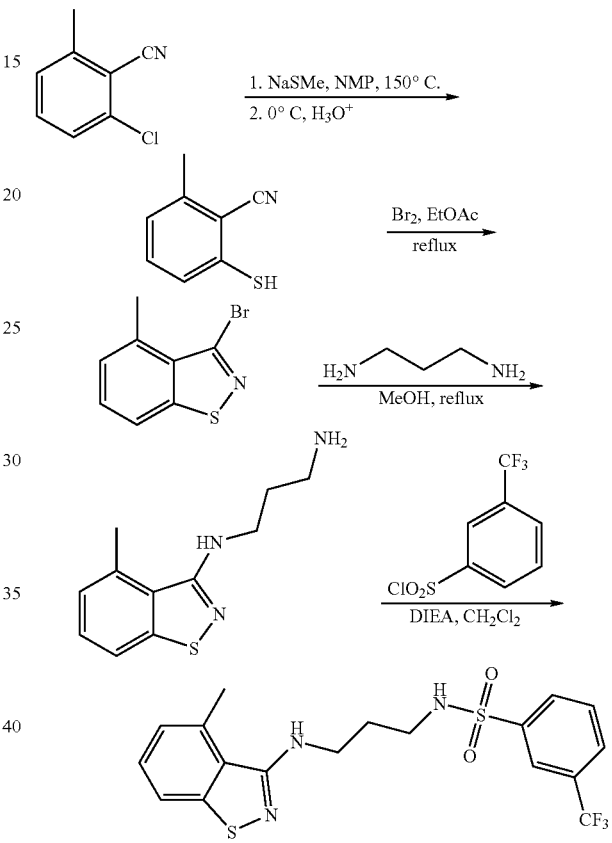

Synthesis of 2-Mercapto-6-methylbenzonitrile. A mixture of 2-chloro-6-methylbenzonitrile (3.00 g, 19.80 mmol), and sodium thiomethoxide (2.91 g, 41.58 mmol) in 1-methyl-2-pyrrolidinone (25 mL) was heated at 140° C. overnight. The reaction mixture was cooled to 0° C. and quenched with 50% aqueous HCl. A light yellow precipitate formed and the reaction was cooled for 1 h while stirring. The yellow solid was collected by vacuum filtration, washed with ice-cold water and dried under reduced pressure overnight to provide 2-mercapto-6-methylbenzonitrile (1.0 g). The crude product was carried forward without further purification. MW=149 confirmed by LC-MS, $t_r$=2.98 min (Method E) MH$^+$=150.

Synthesis of 3-Bromo-4-methylbenzo[d]isothiazole. To a solution of 2-mercapto-6-methylbenzonitrile (1.00 g, 6.71 mmol) in ethyl acetate (10 mL), bromine (1.05 g, 6.60 mmol) was added dropwise at 0° C. The reaction mixture was allowed to stir at 0° C. for 3 h. The reaction mixture was then allowed to warm to room temperature, followed by heating at reflux for 3 h. The reaction mixture was concentrated under reduced pressure. Crystallization of the crude mixture with hexanes gave 3-bromo-4-methylbenzo[d]isothiazole (2.7 g), which was carried forward without further purification. MW=228 confirmed by LC-MS, $t_r$=6.82 min (Method E) MH$^+$=229.

Synthesis of N$^1$-(4-Methylbenzo[d]isothiazol-3-yl)propane-1,3-diamine. 3-Bromo-4-methylbenzo[d]isothiazole (2.70 g, 11.84 mmol), and 1,3-diaminopropane (10.0 g, 135 mmol) in methanol (15 ml) was heated at 64° C. for 1.5 h. The reaction mixture was cooled to room temperature and concentrated under reduced pressure. The crude reaction mixture was diluted with ethyl acetate and washed successively with saturated aqueous sodium bicarbonate solution and brine. The organic solution was dried over anhydrous sodium sulfate, filtered and concentrated under reduced pressure. Lyophilization of the crude sample in acetonitrile/water yielded N$^1$-(4-methylbenzo[d]isothiazol-3-yl)propane-1,3-diamine sample. $^1$H NMR (300 MHz, DMSO-d$_6$): 7.70 (d, 1H), 7.30 (t, 1H), 7.15 (dd, 1H), 6.58 (t, 1H), 3.47 (t, 2H), 2.96 (t, 2H), 2.73 (s, 3H), 1.92 (t, 2H), 1.56 ppm (m, 2H). MW=221 confirmed by LC-MS, $t_r$=2.30 min (Method E) MH$^+$=222.

Synthesis of N-(3-(4-Methylbenzo[d]isothiazol-3-ylamino)propyl)-3-(trifluoromethyl)benzenesulfonamide. N$^1$-(4-methylbenzo[d]isothiazol-3-yl)propane-1,3-diamine (100 mg, 0.45 mmol) was dissolved in anhydrous methylene chloride with diisopropylethylamine (0.12 mL, 0.63 mmol). The mixture was cooled in an ice-bath under nitrogen and a solution of 3-trifluoromethylbenzenesulfonyl chloride (0.09 mL, 0.54 mmol) in methylene chloride (5 mL) was added drop-wise. After the addition was completed the ice-bath was removed and the mixture was stirred at room temperature overnight. The reaction mixture was diluted with dichloromethane and then washed successively with saturated sodium bicarbonate solution and brine. The organic solution was dried over anhydrous sodium sulfate, filtered and concentrated under reduced pressure. The resulting residue was purified by prep-scale reverse phase high performance liquid chromatography to yield N-(3-(4-methylbenzo[d]isothiazol-3-ylamino)propyl)-3-(trifluoromethyl)benzenesulfonamide (23 mg). $^1$H NMR (300 MHz, DMSO-d$_6$): 7.75 (d, 1H), 7.30 (m, 2H), 7.25 (m, 2H), 6.92 (t, 1H), 6.28 (t, 1H), 3.22 (t, 2H), 2.98 (t, 2H), 2.81 (s, 3H), 2.15 (t, 2H), 1.80 ppm (m, 2H). MW=429 confirmed by LC-MS, $t_r$=3.92 min (Method E) MH$^+$=430.

Example 21

Synthesis of N$^1$-(4-Chlorobenzo[d]isothiazol-3-yl)-N$^3$-((4'-methoxybiphenyl-4-yl)methyl)propane-1,3-diamine

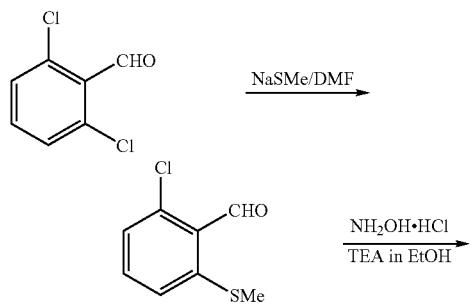

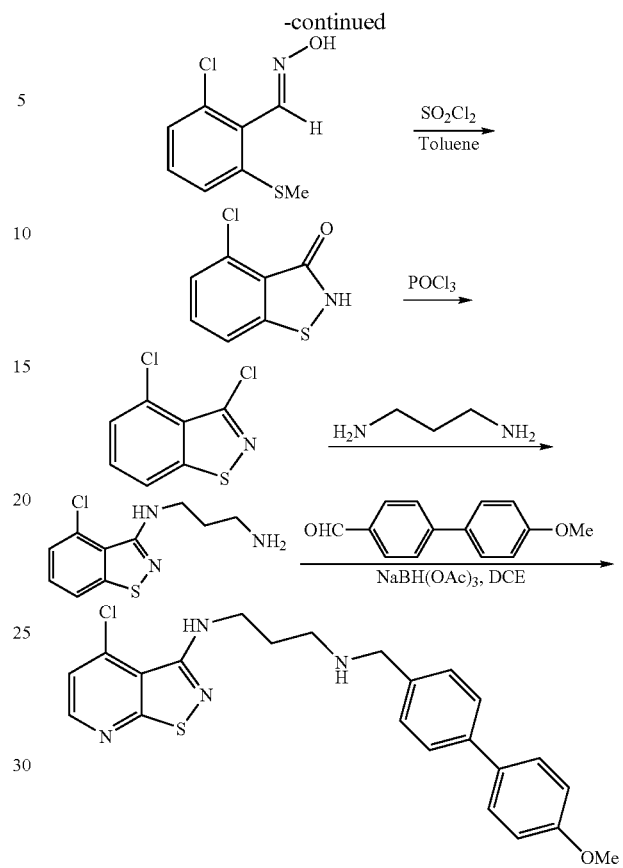

Synthesis of 2-Chloro-6-(methylthio)benzaldehyde. To a solution of 2,6-dichlorobenzaldehyde (20 g, 114.28 mmol) in N,N-dimethylformamide (200 ml), sodium thiomethoxide (8.81 g, 125.7 mmol) was added at 0° C. The reaction mixture was allowed to warm to room temperature overnight, then poured into water. A yellow precipitate was collected by vacuum filtration and dried to afford 2-chloro-6-(methylthio)benzaldehyde (11. g), as a light yellow solid. (This method is general for other 2-haloaldehydes). $^1$H NMR (300 MHz, CDCl$_3$): 10.6 (s, 1H), 7.4 (t, 1H), 7.2 (dd, 2H), 2.4 ppm (s, 3H). MW=187 confirmed by LC-MS, $t_r$=13.18 min (Method Y) MH$^+$=188.

Synthesis of (E)-2-Chloro-6-(methylthio)benzaldehyde Oxime. 6-Chloro-2-(methylthio)benzaldehyde (11.6 g, 75.16 mmol), and hydroxylamine hydrochloride (5.75 g, 82.86 mmol) were combined in ethanol (100 ml). Diethylamide (11.5 ml, 82.86 mmol) was slowly added to the solution and it was allowed to stir at room temperature overnight. After the completion of the reaction, the reaction mixture was concentrated under reduced pressure, diluted with ethyl acetate and then washed successively with water and saturated aqueous sodium bicarbonate solution. The organic layer was dried over anhydrous sodium sulfate, filtered and concentrated under reduced pressure to yield (E)-2-chloro-6-(methylthio) benzaldehyde oxime (12.37 g) as a white solid. (This method is general for other 2-(methythio)benzaldehydes). $^1$H NMR (300 MHz, DMSO-d$_6$): 11.62 (s, 1H), 8.22 (s, 1H), 7.20-7.40 (m, 3H), 2.41 ppm (s, 3H). MW=202 confirmed by LC-MS, $t_r$=3.58 min (Method B) MH$^+$=203.

Synthesis of 4-Chlorobenzo [d]isothiazol-3(2H)-one. (E)-2-Chloro-6-(methylthio)benzaldehyde oxime (12.37 g) was dissolved in toluene (35 mL). Sulfuryl chloride (5.4 ml, 66.24 mmol) was added, dropwise to the solution at 0° C., followed by heating at 80° C. for 1 h. After the completion of the reaction, the reaction mixture was cooled to room temperature and a white precipitate formed. The solid was collected by vacuum filtration, washed with toluene and air dried to 4-chlorobenzo[d]isothiazol-3(2H)-one (6 g). (This method is general for other 2-(methylthio) benzaldehyde oximes.) $^1$H NMR (300 MHz, DMSO-$d_6$): 7.90 (t, 1H), 7.55 (t, 1H), 7.41 ppm (d, 1H). MW=186 confirmed by LC-MS, $t_r$=2.38 min (Method B) MH$^+$=187.

Synthesis of 3,4-Dichlorobenzo[d]isothiazole. Phosphorus oxychloride was added slowly to 4-chlorobenzo[d]isothiazol-3(2H)-one (2.34 g). The reaction mixture was heated at reflux overnight. After normal aqueous work-up, the product was purified by column chromatography, on silica gel, eluted with a mixture of 5% ethyl acetate in hexanes to provide 3,4-dichlorobenzo[d]isothiazole. (This method can be used to 1,2-benzisothiozal-3-ones). 1H NMR (300 MHz, DMSO-$d_6$): 8.23-8.31 (m, 1H), 7.62 ppm (d, 2H). MW=204 confirmed by LC-MS, $t_r$=2.38 min (Method B) MH$^+$=205.

Synthesis of N$^1$-(4-Chlorobenzo[d]isothiazol-3-yl)propane-1,3-diamine. 3,4-Dichlorobenzo[d]isothiazole (2.5 g, 12.25 mmol) was dissolved in propylene diamine (20 mL) and allowed to stir at room temperature for 1 h, followed by heating at 80° C. for 30 min. The mixture was diluted with ethyl acetate. This organic solution was successively washed with water and brine, then dried over anhydrous sodium sulfate, filtered and concentrated under reduced pressure to provide N$^1$-(4-chlorobenzo[d]isothiazol-3-yl)propane-1,3-diamine (2.66 g). The product was carried forward without characterization.

Synthesis of N$^1$-(4-Chlorobenzo [d]isothiazol-3-yl)-N$^3$-((4'-methoxybiphenyl-4-yl)methyl)propane-1,3-diamine. N$^1$-(4-Chlorobenzo[d]isothiazol-3-yl)propane-1,3-diamine (100 mg, 0.41 mmol) and 4'-methoxybiphenyl-4-carbaldehyde (88 mg, 0.41 mmol) were combined in 1,2-dichloroethane (2 mL) and treated with sodium triacetoxyborohydride (123 mg, 0.58 mmol). The mixture was sonicated at room temperature for 18 h. The reaction was diluted with ethyl acetate and then washed with water, brine and saturated sodium bicarbonate solution. The organic solution was dried over anhydrous sodium sulfate, filtered and concentrated under reduced pressure. The resulting residue was purified by flash column chromatography, on silica gel, eluting with 98:2 methylene chloride:methanol to yield N$^1$-(5-bromobenzo[d]isothiazol-3-yl)-N 3-((4'-methoxybiphenyl-4-yl)methyl)propane-1,3-diamine (50 mg) as a white solid. $^1$H NMR (300 MHz, CDCl$_3$): 7.60 (dd, 1H), 7.44-7.50 (m, 4H), 7.38 (d, 2H), 7.35 (t, 1H), 7.20 (dd, 1H), 3.62 (t, 2H), 2.91 (t, 2H), 1.98-2.02 ppm (m, 2H). MW=438 confirmed by LC-MS, $t_r$=7.98 min (Method D) MH$^+$=437-439.

Exemplary Compounds of the Invention

The following compounds are representative examples of the invention. The compounds identified below were prepared by methods outlined or otherwise described throughout the specification, or using methods within the skill of ordinary artisans. Each of the compounds was, at a minimum, identified by LC-MS using one of the aforementioned methods.

TABLE 4

1. N-(2-(Benzo[d]isothiazole-3-ylamino)ethyl-4-chlorobenzamide
MW = 331 confirmed by LC-MS, $t_r$ = 3.89 min (Method B) MH$^+$ = 329-333
2. N-(2-(Benzo[d]isothiazol-3-ylamino)ethyl)picolinamide
MW = 299 confirmed by LC-MS, $t_r$ = 11.46 min (Method Y) MH$^+$ = 300
3. tert-Butyl 3-(2-(Benzo[d]isothiazol-3-ylamino)ethylcarbamoyl) piperidine-1-carboxylate
MW = 405 confirmed by LC-MS, $t_r$ = 3.81 min (Method B) MH$^+$ = 406
4. (S)-tert-Butyl 2-(2-(Benzo[d]isothiazol-3-ylamino)ethylamino)-2-oxo-1-phenylethylcarbamate
MW = 427 confirmed by LC-MS, $t_r$ = 13.35 min (Method Y) MH$^+$ = 428
5. (S)-tert-Butyl 1-(2-(Benzo[d]isothiazol-3-ylamino)ethylamino)-3-methyl-1-oxobutan-2-ylcarbamate
MW = 392 confirmed by LC-MS, $t_r$ = 12.78 min (Method Y) MH$^+$ = 393
6. N-(2-(Benzo[d]isothiazol-3-ylamino)ethyl)piperidine-3-carboxamide
MW = 304 confirmed by LC-MS, $t_r$ = 7.07 min (Method Y) MH$^+$ = 305
7. (S)-2-Amino-N-(2-(benzo[d]isothiazol-3-ylamino)ethyl)-2-phenylacetamide
MW = 326 confirmed by LC-MS, $t_r$ = 8.48 min (Method Y) MH$^+$ = 327
8. (S)-2-Amino-N-(2-(benzo[d]isothiazol-3-ylamino)ethyl)-3-methylbutanamide
MW = 292 confirmed by LC-MS, $t_r$ = 7.56 min (Method Y) MH$^+$ = 293
9. N-(2-(Benzo[d]isothiazol-3-ylamino)ethyl)-3-methylpicolinamide
MW = 312 confirmed by LC-MS, $t_r$ = 11.52 min (Method Y) MH$^+$ = 313
10. N-(2-(Benzo[d]isothiazol-3-ylamino)ethyl)-3-benzoylpicolinamide
MW = 402 confirmed by LC-MS, $t_r$ = 12.80 min (Method Y) MH$^+$ = 403
11. Methyl 6-(2-(Benzo[d]isothiazol-3-ylamino)ethylcarbamoyl)nicotinate
MW = 356 confirmed by LC-MS, $t_r$ = 12.06 min (Method Y) MH$^+$ = 357
12. N-(2-(Benzo[d]isothiazol-3-ylamino)ethyl)-6-methylpicolinamide
MW = 312 confirmed by LC-MS, $t_r$ = 12.05 min (Method Y) MH$^+$ = 313
13. N-(2-(Benzo[d]isothiazol-3-ylamino)ethyl)-6-bromopicolinamide
MW = 376 confirmed by LC-MS, $t_r$ = 12.61 min (Method Y) MH$^+$ = 377
14. 6-(2-(Benzo[d]isothiazol-3-ylamino)ethylcarbamoyl)nicotinic Acid
MW = 343 confirmed by LC-MS, $t_r$ = 10.56 min (Method Y) MH$^+$ = 344
15. N-(2-(Benzo[d]isothiazol-3-ylamino)ethyl)quinoline-2-carboxamide
MW = 348 confirmed by LC-MS, $t_r$ = 13.14 min (Method Y) MH$^+$ = 349
16. Methyl 6-(2-(Benzo[d]isothiazol-3-ylamino)ethylcarbamoyl)picolinate
MW = 356 confirmed by LC-MS, $t_r$ = 10.99 min (Method Y) MH$^+$ = 357
17. 6-(2-(Benzo[d]isothiazol-3-ylamino)ethylcarbamoyl)picolinic Acid
MW = 342 confirmed by LC-MS, $t_r$ = 10.10 min (Method Y) MH$^+$ = 343
18. N-(2-(Benzo[d]isothiazol-3-ylamino)ethyl)-4-methoxybenzamide
MW = 327 confirmed by LC-MS, $t_r$ = 11.52 min (Method Y) MH$^+$ = 328
19. N-(2-(Benzo[d]isothiazol-3-ylamino)ethyl)-3-chlorobenzamide
MW = 332 confirmed by LC-MS, $t_r$ = 12.04 min (Method Y) MH$^+$ = 330-334
20. N-(2-(Benzo[d]isothiazol-3-ylamino)ethyl)-2-(1H-indol-3-yl)acetamide
MW = 350 confirmed by LC-MS, $t_r$ = 11.10 min (Method Y) MH$^+$ = 351

TABLE 4-continued

21. N-(2-(Benzo[d]isothiazol-3-ylamino)ethyl)-2,6-dichlorobenzamide
MW = 366 confirmed by LC-MS, $t_r$ = 12.14 min (Method Y) MH$^+$ = 364-368
22. N-(2-(Benzo[d]isothiazol-3-ylamino)ethyl)furan-2-carboxamide
MW = 287 confirmed by LC-MS, $t_r$ = 10.97 min (Method Y) MH$^+$ = 289
23. N$^2$-(2-(Benzo[d]isothiazol-3-ylamino)ethyl)-N5-methylpyridine-2,5-dicarboxamide
MW = 355 confirmed by LC-MS, $t_r$ = 2.98 min (Method B) MH$^+$ = 356
24. (S)-N-(2-(Benzo[d]isothiazol-3-ylamino)ethyl)-2-phenyl-2-(phenylsulfonamido)acetamide
MW = 366 confirmed by LC-MS, $t_r$ = 3.94 min (Method B) MH$^+$ = 367
25. (S)-2-Acetamido-N-(2-(benzo[d]isothiazol-3-ylamino)ethyl)-2-phenylacetamide
MW = 368 confirmed by LC-MS, $t_r$ = 10.11 min (Method Y) MH$^+$ = 369
26. (S)-N-(2-(2-(Benzo[d]isothiazol-3-ylamino)ethylamino)-2-oxo-1-phenylethyl)picolinamide
MW = 432 confirmed by LC-MS, $t_r$ = 3.88 min (Method B) MH$^+$ = 433
27. (S)-N-(2-(2-(Benzo[d]isothiazol-3-ylamino)ethylamino)-2-oxo-1-phenylethyl)pivalamide
MW = 411 confirmed by LC-MS, $t_r$ = 12.69 min (Method B) MH$^+$ = 412
28. (S)-N-(2-(2-(Benzo[d]isothiazol-3-ylamino)ethylamino)-2-oxo-1-phenylethyl)-2,2,2-trifluoroacetamide
MW = 422 confirmed by LC-MS, $t_r$ = 12.95 min (Method Y) MH$^+$ = 423
29. (S)-N-(2-(2-(Benzo[d]isothiazol-3-ylamino)ethylamino)-2-oxo-1-phenylethyl)-4-methoxybenzamide
MW = 461 confirmed by LC-MS, $t_r$ = 12.64 min (Method Y) MH$^+$ = 462
30. (S)-N-(2-(2-(Benzo[d]isothiazol-3-ylamino)ethylamino)-2-oxo-1-phenylethyl)butyramide
MW = 397 confirmed by LC-MS, $t_r$ = 11.46 min (Method Y) MH$^+$ = 398
31. (S)-N-(2-(2-(Benzo[d]isothiazol-3-ylamino)ethylamino)-2-oxo-1-phenylethyl)cyclopentanecarboxamide
MW = 423 confirmed by LC-MS, $t_r$ = 12.43 min (Method Y) MH$^+$ = 424
32. (S)-N-(2-(2-(Benzo[d]isothiazol-3-ylamino)ethylamino)-2-oxo-1-phenylethyl)furan-3-carboxamide
MW = 420 confirmed by LC-MS, $t_r$ = 3.92 min (Method B) MH$^+$ = 421
33. N-(2-(Benzo[d]isothiazol-3-ylamino)ethyl)-2,3-dihydrobenzo[b][1,4]dioxine-2-carboxamide
MW = 355 confirmed by LC-MS, $t_r$ = 12.64 min (Method Y) MH$^+$ = 356
34. N-(2-(2-(Benzo[d]isothiazol-3-ylamino)ethylamino)-2-oxoethyl)benzamide
MW = 354 confirmed by LC-MS, $t_r$ = 10.11 min (Method Y) MH$^+$ = 355
35. N-(2-(Benzo[d]isothiazol-3-ylamino)ethyl)benzo[b]thiophene-2-carboxamide
MW = 353 confirmed by LC-MS, $t_r$ = 13.38 min (Method Y) MH$^+$ = 354
36. N-(2-(Benzo[d]isothiazol-3-ylamino)ethyl)-4-(1H-pyrrol-1-yl)benzamide
MW = 362 confirmed by LC-MS, $t_r$ = 13.05 min (Method Y) MH$^+$ = 363
37. N-(2-(Benzo[d]isothiazol-3-ylamino)ethyl)-5-methoxy-1H-indole-2-carboxamide
MW = 366 confirmed by LC-MS, $t_r$ = 12.13 min (Method Y) MH$^+$ = 367
38. N-(2-(Benzo[d]isothiazol-3-ylamino)ethyl)-3H-benzo[d][1,2,3]triazole-5-carboxamide
MW = 338 confirmed by LC-MS, $t_r$ = 9.43 min (Method Y) MH$^+$ = 339
39. N-(2-(Benzo[d]isothiazol-3-ylamino)ethyl)-2-oxo-2-(thiophen-2-yl)acetamide
MW = 331 confirmed by LC-MS, $t_r$ = 12.42 min (Method Y) MH$^+$ = 332
40. tert-Butyl 4-(2-(Benzo[d]isothiazol-3-ylamino)ethylcarbamoyl)piperidine-1-carboxylate
MW = 405 confirmed by LC-MS, $t_r$ = 12.39 min (Method Y) MH$^+$ = 406
41. N-(2-(Benzo[d]isothiazol-3-ylamino)ethyl)-2-methoxynicotinamide
MW = 328 confirmed by LC-MS, $t_r$ = 11.30 min (Method Y) MH$^+$ = 329
42. N-(2-(Benzo[d]isothiazol-3-ylamino)ethyl)thiophene-2-carboxamide
MW = 303 confirmed by LC-MS, $t_r$ = 11.70 min (Method Y) MH$^+$ = 304
43. tert-Butyl 2-(2-(Benzo[d]isothiazol-3-ylamino)ethylcarbamoyl)indoline-1-carboxylate
MW = 439 confirmed by LC-MS, $t_r$ = 13.73 min (Method Y) MH$^+$ = 440
44. N-(2-(Benzo[d]isothiazol-3-ylamino)ethyl)-3-chloro-2-methylbenzamide
MW = 346 confirmed by LC-MS, $t_r$ = 12.77 min (Method Y) MH$^+$ = 344-348
45. N-(2-(Benzo[d]isothiazol-3-ylamino)ethyl)pyrazine-2-carboxamide
MW = 299 confirmed by LC-MS, $t_r$ = 9.90 min (Method Y) MH$^+$ = 300
46. N-(2-(Benzo[d]isothiazol-3-ylamino)ethyl)-4-methylnicotinamide
MW = 312 confirmed by LC-MS, $t_r$ = 8.60 min (Method Y) MH$^+$ = 313
47. N-(2-(Benzo[d]isothiazol-3-ylamino)ethyl)quinoline-3-carboxamide
MW = 348 confirmed by LC-MS, $t_r$ = 11.23 min (Method Y) MH$^+$ = 349
48. (R)-tert-Butyl 2-(2-(Benzo[d]isothiazol-3-ylamino)ethylamino)-2-oxo-1-phenylethylcarbamate
MW = 427 confirmed by LC-MS, $t_r$ = 13.38 min (Method Y) MH$^+$ = 428
49. (S)-tert-Butyl 1-(2-(Benzo[d]isothiazol-3-ylamino)ethylamino)-1-oxo-3-phenylpropan-2-ylcarbamate
MW = 441 confirmed by LC-MS, $t_r$ = 13.32 min (Method Y) MH$^+$ = 442
50. (S)-tert-Butyl 1-(2-(Benzo[d]isothiazol-3-ylamino)ethylamino)-3-(4-hydroxyphenyl)-1-oxopropan-2-ylcarbamate
MW = 457 confirmed by LC-MS, $t_r$ = 11.48 min (Method Y) MH$^+$ = 458
51. N-(2-(Benzo[d]isothiazol-3-ylamino)ethyl)-4-chloropicolinamide
MW = 333 confirmed by LC-MS, $t_r$ = 12.38 min (Method Y) MH$^+$ = 331-335
52. N-(2-(Benzo[d]isothiazol-3-ylamino)ethyl)quinoline-8-carboxamide
MW = 348 confirmed by LC-MS, $t_r$ = 11.85 min (Method Y) MH$^+$ = 349
53. (R)-2-Amino-N-(2-(benzo[d]isothiazol-3-ylamino)ethyl)-2-phenylacetamide
MW = 326 confirmed by LC-MS, $t_r$ = 7.90 min (Method Y) MH$^+$ = 327
54. N-(2-(Benzo[d]isothiazol-3-ylamino)ethyl)piperidine-4-carboxamide
MW = 304 confirmed by LC-MS, $t_r$ = 6.29 min (Method Y) MH$^+$ = 305
55. N-(2-(Benzo[d]isothiazol-3-ylamino)ethyl)isoquinoline-1-carboxamide
MW = 348 confirmed by LC-MS, $t_r$ = 12.41 min (Method Y) MH$^+$ = 349
56. N-(2-(Benzo[d]isothiazol-3-ylamino)ethyl)-4,5-dichloroisothiazole-3-carboxamide
MW = 373 confirmed by LC-MS, $t_r$ = 13.68 min (Method Y) MH$^+$ = 371-375

TABLE 4-continued 57. (R)-Benzyl 1-(2-(Benzo[d]isothiazol-3-ylamino)ethylamino)-1-oxo-3-phenylpropan-2-ylcarbamate
MW = 475 confirmed by LC-MS, $t_r$ = 13.85 min (Method Y) $MH^+$ = 476
58. (S)-N-(1-(2-(Benzo[d]isothiazol-3-ylamino)ethylamino)-1-oxo-3-phenylpropan-2-yl)benzamide
MW = 445 confirmed by LC-MS, $t_r$ = 12.78 min (Method Y) $MH^+$ = 446
59. (S)-2-Acetamido-N-(2-(benzo[d]isothiazol-3-ylamino)ethyl)-3-phenylpropanamide
MW = 382 confirmed by LC-MS, $t_r$ = 10.77 min (Method Y) $MH^+$ = 383
60. (S)-Benzyl 1-(2-(Benzo[d]isothiazol-3-ylamino)ethylamino)-1-oxo-3-phenylpropan-2-ylcarbamate
MW = 475 confirmed by LC-MS, $t_r$ = 13.89 min (Method Y) $MH^+$ = 476
61. (S)-Benzyl 2-(2-(Benzo[d]isothiazol-3-ylamino)ethylamino)-2-oxo-1-phenylethylcarbamate
MW = 461 confirmed by LC-MS, $t_r$ = 13.29 min (Method Y) $MH^+$ = 462
62. tert-Butyl 6-(2-(Benzo[d]isothiazol-3-ylamino)ethylcarbamoyl)pyridin-2-ylcarbamate
MW = 414 confirmed by LC-MS, $t_r$ = 13.99 min (Method Y) $MH^+$ = 415
63. N-(2-(Benzo[d]isothiazol-3-ylamino)ethyl)-5-morpholinopicolinamide
MW = 383 confirmed by LC-MS, $t_r$ = 8.06 min (Method Y) $MH^+$ = 384
64. 6-Amino-N-(2-(benzo[d]isothiazol-3-ylamino)ethyl)picolinamide
MW = 313 confirmed by LC-MS, $t_r$ = 8.60 min (Method Y) $MH^+$ = 314
65. N-(2-(Benzo[d]isothiazol-3-ylamino)ethyl)-4-(4-methylpiperazin-1-yl)picolinamide
MW = 397 confirmed by LC-MS, $t_r$ = 5.84 min (Method Y) $MH^+$ = 398
66. N-(2-(6-Nitrobenzo[d]isothiazol-3-ylamino)ethyl)picolinamide
MW = 343 confirmed by LC-MS, $t_r$ = 11.59 min (Method Y) $MH^+$ = 344
67. N-(2-(6-Aminobenzo[d]isothiazol-3-ylamino)ethyl)picolinamide
MW = 313 confirmed by LC-MS, $t_r$ = 9.21 min (Method Y) $MH^+$ = 314
68. N-(2-(6-Acetamidobenzo[d]isothiazol-3-ylamino)ethyl)picolinamide
MW = 355 confirmed by LC-MS, $t_r$ = 9.35 min (Method Y) $MW^+$=356
69. N-(2-(Benzo[d]isothiazol-3-ylamino)ethyl)-4-(4-phenylpiperazin-1-yl)picolinamide
MW = 459 confirmed by LC-MS, $t_r$ = 10.65 min (Method Y) $MH^+$ = 460
70. N-(2-(Benzo[d]isothiazol-3-ylamino)ethyl)-5-methyl-1H-indole-2-carboxamide
MW = 350 confirmed by LC-MS, $t_r$ = 13.01 min (Method Y) $MH^+$ = 351
71. N-(2-(Benzo[d]isothiazol-3-ylamino)ethyl)-5-fluoro-1H-indole-2-carboxamide
MW = 354 confirmed by LC-MS, $t_r$ = 12.76 min (Method Y) $MH^+$ = 355
72. N-(2-(Benzo[d]isothiazol-3-ylamino)ethyl)-5-chloro-1H-indole-2-carboxamide
MW = 371 confirmed by LC-MS, $t_r$ = 13.56 min (Method Y) $MH^+$369-373
73. N-(2-(Benzo[d]isothiazol-3-ylamino)ethyl)-5,6-dimethoxy-1H-indole-2-carboxamide
MW = 396 confirmed by LC-MS, $t_r$ = 11.22 min (Method Y) $MH^+$ = 394-398
74. N-(2-(Benzo[d]isothiazol-3-ylamino)ethyl)-5-(benzyloxy)-1H-indole-2-carboxamide
MW = 443 confirmed by LC-MS, $t_r$ = 14.23 min (Method Y) $MH^+$ = 444
75. N-(2-(Benzo[d]isothiazol-3-ylamino)ethyl)-2-(1-methyl-1H-indol-3-yl)acetamide
MW = 364 confirmed by LC-MS, $t_r$ = 12.23 min (Method Y) $MH^+$ = 365
76. N-(2-(Benzo[d]isothiazol-3-ylamino)ethyl)-7-nitro-1H-indole-2-carboxamide
MW = 381 confirmed by LC-MS, $t_r$ = 13.21 min (Method Y) $MH^+$ = 382
77. N-(2-(Benzo[d]isothiazol-3-ylamino)ethyl)-1-methyl-1H-pyrrole-2-carboxamide
MW = 300 confirmed by LC-MS, $t_r$ = 11.63 min (Method Y) $MH^+$ = 301
78. N-(2-(Benzo[d]isothiazol-3-ylamino)ethyl)-5-hydroxy-1H-indole-2-carboxamide
MW = 352 confirmed by LC-MS, $t_r$ = 10.35 min (Method Y) $MH^+$ = 353
79. N-(2-(Benzo[d]isothiazol-3-ylamino)ethyl)-1H-indole-2-carboxamide
MW = 336 confirmed by LC-MS, $t_r$ = 12.35 min (Method Y) $MH^+$ = 337
80. N-(2-(Benzo[d]isothiazol-3-ylamino)ethyl)nicotinamide
MW = 298 confirmed by LC-MS, $t_r$ = 8.18 min (Method Y) $MH^+$ = 299
81. N-(2-(Benzo[d]isothiazol-3-ylamino)ethyl)-4-(trifluoromethyl)benzamide
MW = 365 confirmed by LC-MS, $t_r$ = 4.11 min (Method B) $MH^+$ = 366
82. N-(2-(Benzo[d]isothiazol-3-ylamino)ethyl)-4-methylbenzamide
MW = 311 confirmed by LC-MS, $t_r$ = 3.77 min (Method B) $MH^+$ = 312
83. N-(2-(Benzo[d]isothiazol-3-ylamino)ethyl)benzamide
MW = 297 confirmed by LC-MS, $t_r$ = 3.48 min (Method B) $MH^+$ = 298
84. N-(2-(Benzo[d]isothiazol-3-ylamino)ethyl)-2-phenoxypropanamide
MW = 341 confirmed by LC-MS, $t_r$ = 3.73 min (Method B) $MH^+$ = 342
85. N-(2-(Benzo[d]isothiazol-3-ylamino)ethyl)-2-(4-methoxyphenyl)acetamide
MW = 341 confirmed by LC-MS, $t_r$ = 3.45 min (Method B) $MH^+$ = 342
86. N-(2-(Benzo[d]isothiazol-3-ylamino)ethyl)-2-(4-chlorophenyl)acetamide
MW = 346 confirmed by LC-MS, $t_r$ = 3.73 min (Method B) $MH^+$ = 344-348
87. N-(2-(Benzo[d]isothiazol-3-ylamino)ethyl)-1H-indole-3-carboxamide
MW = 336 confirmed by LC-MS, $t_r$ = 11.28 min (Method Y) $MH^+$ = 337
88. N-(2-(Benzo[d]isothiazole-(1,1-dioxo)-3-ylamino)ethyl-4-chlorobenzamide
MW = 364 confirmed by LC-MS, $t_r$ = 10.51 min (Method Y) $MH^+$ = 362-366
89. N-(2-(Benzo[d]isothiazol-3-ylamino)ethyl)-2,4-dichlorobenzamide
MW = 366 confirmed by LC-MS, $t_r$ = 3.93 min (Method B) $MH^+$ = 64-368
90. N-(2-(Benzo[d]isothiazol-3-ylamino)ethyl)benzofuran-2-carboxamide
MW = 337 confirmed by LC-MS, $t_r$ = 3.83 min (Method B) $MH^+$ = 338
91. N-(2-(Benzo[d]isothiazol-3-ylamino)ethyl)-4-methyl-5-phenylisoxazole-3-carboxamide
MW = 378 confirmed by LC-MS, $t_r$ = 3.73 min (Method B) $MH^+$ = 379
92. N-(2-(Benzo[d]isothiazol-3-ylamino)ethyl)-6,6-dimethyl-4-oxo-5,6-dihydro-4H-pyran-2-carboxamide
MW = 345 confirmed by LC-MS, $t_r$ = 3.35 min (Method B) $MH^+$ = 346
93. N-(2-(Benzo[d]isothiazol-3-ylamino)ethyl)-3,4-dimethoxybenzamide
MW = 357 confirmed by LC-MS, $t_r$ = 3.31 min (Method B) $MH^+$ = 358
94. N-(2-(Benzo[d]isothiazol-3-ylamino)ethyl)-3,5-dichlorobenzamide
MW = 366 confirmed by LC-MS, $t_r$ = 4.35 min (Method B) $MH^+$ = 364-368

TABLE 4-continued

95. N-(3-(Benzo[d]isothiazol-3-ylamino)propyl)-4-chlorobenzamide
MW = 345 confirmed by LC-MS, $t_r$ = 3.97 min (Method B) MH$^+$ = 343-347
96. N-(2-(Benzo[d]isothiazol-3-ylamino)ethyl)-1H-indazole-3-carboxamide
MW = 337 confirmed by LC-MS, $t_r$ = 3.44 min (Method B) MH$^+$ = 338
97. N-(3-(Benzo[d]isothiazol-3-ylamino)propyl)picolinamide
MW = 312 confirmed by LC-MS, $t_r$ = 3.41 min (Method B) MH$^+$ = 313
98. (S)-tert-Butyl 2-(3-(Benzo[d]isothiazol-3-ylamino)propylamino)-2-oxo-1-phenylethylcarbamate
MW = 441 confirmed by LC-MS, $t_r$ = 4.11 min (Method B) MH$^+$ = 442
99. 6-Acetamido-N-(2-(benzo[d]isothiazol-3-ylamino)ethyl)picolinamide
MW = 355 confirmed by LC-MS, $t_r$ = 3.09 min (Method B) MH$^+$ = 356
100. N-(2-(Benzo[d]isothiazol-3-ylamino)ethyl)imidazo[1,2-a]pyridine-2-carboxamide
MW = 337 confirmed by LC-MS, $t_r$ = 9.63 min (Method Y) MH$^+$ = 338
101. (S)-2-Amino-N-(3-(benzo[d]isothiazol-3-ylamino)propyl)-2-phenylacetamide
MW = 340 confirmed by LC-MS, $t_r$ = 2.76 min (Method B) MH$^+$ = 341
102. tert-Butyl 2-(2-(Benzo[d]isothiazol-3-ylamino)ethylcarbamoyl)pyrrolidine-1-carboxylate
MW = 391 confirmed by LC-MS, $t_r$ = 3.57 min (Method B) MH$^+$ = 392
103. tert-Butyl 2-(2-(Benzo[d]isothiazol-3-ylamino)ethylcarbamoyl)piperidine-1-carboxylate
MW = 405 confirmed by LC-MS, $t_r$ = 13.93 min (Method Y) MH$^+$ = 406
104. 1-Acetyl-N-(2-(benzo[d]isothiazol-3-ylamino)ethyl)pyrrolidine-2-carboxamide
MW = 332 confirmed by LC-MS, $t_r$ = 2.65 min (Method B) MH$^+$ = 333
105. N-(2-(Benzo[d]isothiazol-3-ylamino)ethyl)-1-picolinoylpyrrolidine-2-carboxamide
MW = 395 confirmed by LC-MS, $t_r$ = 2.89 min (Method B) MH$^+$ = 396
106. N-(2-(Benzo[d]isothiazol-3-ylamino)ethyl)-1-(3,5-dichlorobenzoyl)pyrrolidine-2-carboxamide
MW = 463 confirmed by LC-MS, $t_r$ = 3.91 min (Method B) MH$^+$ = 461-465
107. N-(2-(Benzo[d]isothiazol-3-ylamino)ethyl)-1-picolinoylpiperidine-2-carboxamide
MW = 410 confirmed by LC-MS, $t_r$ = 3.14 min (Method B) MH$^+$ = 411
108. N-(2-(Benzo[d]isothiazol-3-ylamino)ethyl)-1-(3,5-dichlorobenzoyl)piperidine-2-carboxamide
MW = 477 confirmed by LC-MS, $t_r$ = 4.26 min (Method B) MH$^+$ = 475-479
109. N-(2-(Benzo[d]isothiazol-3-ylamino)ethyl)-1-(3,5-dichlorobenzoyl)piperidine-3-carboxamide
MW = 477 confirmed by LC-MS, $t_r$ = 3.93 min (Method B) MH$^+$ = 475-479
110. N-(2-(Benzo[d]isothiazol-3-ylamino)ethyl)-5-nitropicolinamide
MW = 343 confirmed by LC-MS, $t_r$ = 11.97 min (Method Y) MH$^+$ = 344
111. 1-Acetyl-N-(2-(benzo[d]isothiazol-3-ylamino)ethyl)piperidine-2-carboxamide
MW = 346 confirmed by LC-MS, $t_r$ = 9.79 min (Method Y) MH$^+$347
112. 1-Acetyl-N-(2-(benzo[d]isothiazol-3-ylamino)ethyl)piperidine-3-carboxamide
MW = 346 confirmed by LC-MS, $t_r$ = 2.91 min (Method B) MH$^+$ = 347
113. N-(2-(Benzo[d]isothiazol-3-ylamino)ethyl)-1-picolinoylpiperidine-3-carboxamide
MW = 410 confirmed by LC-MS, $t_r$ = 2.99 min (Method B) MH$^+$ = 411
114. 5-Amino-N-(2-(benzo[d]isothiazol-3-ylamino)ethyl)picolinamide
MW = 313 confirmed by LC-MS, $t_r$ = 2.94 min (Method B) MH$^+$ = 314
115. N-(2-(Benzo[d]isothiazol-3-ylamino)ethyl)-4,6-dichloro-1H-indole-2-carboxamide
MW = 405 confirmed by LC-MS, $t_r$ = 4.51 min (Method B) MH$^+$ = 403-407
116. N-(2-(Benzo[d]isothiazol-3-ylamino)ethyl)-1-(biphenylcarbonyl)piperidine-3-carboxamide
MW = 485 confirmed by LC-MS, $t_r$ = 4.21 min (Method B) MH$^+$ = 486
117. N-(2-(Benzo[d]isothiazol-3-ylamino)ethyl)-1-(2-(2,2,2-trifluoroacetyl)-1,2,3,4-tetrahydroisoquinolin-7-ylsulfonyl)piperidine-3-carboxamide
MW = 596 confirmed by LC-MS, $t_r$ = 13.26 min (Method Y) MH$^+$ = 597
118. tert-Butyl 1-(3-(2-(Benzo[d]isothiazol-3-ylamino)ethylcarbamoyl)piperidin-1-yl)-1-oxo-3-phenylpropan-2-ylcarbamate
MW = 552 confirmed by LC-MS, $t_r$ = 3.98 min (Method B) MH$^+$ = 553
119. tert-Butyl 2-(3-(2-(Benzo[d]isothiazol-3-ylamino)ethylcarbamoyl)piperidin-1-yl)-2-oxo-1-phenylethylcarbamate
MW = 538 confirmed by LC-MS, $t_r$ = 13.12 min (Method Y) MH$^+$ = 539
220. N-(3-(benzo[d]isothiazol-3-ylamino)propyl)-3-methoxybenzenesulfonamide
MW = 377 confirmed by LC-MS, $t_r$ = 12.81 (Method Y)
221. N-(3-(benzo[d]isothiazol-3-ylamino)propyl)-4-bromo-2,5-difluorobenzenesulfonamide
MW = 461 confirmed by LC-MS, $t_r$ = 14.28 (Method Y)
222. N-(3-(benzo[d]isothiazol-3-ylamino)propyl)-5-bromothiophene-2-sulfonamide
MW = 431 confirmed by LC-MS, $t_r$ = 13.79 (Method Y)
223. N-(3-(benzo[d]isothiazol-3-ylamino)propyl)-4-(4-chlorophenoxy)benzenesulfonamide
MW = 473 confirmed by LC-MS, $t_r$ = 15.5 (Method Y)
224. 6-(3-(benzo[d]isothiazol-3-ylamino)propylamino)nicotinonitrile
MW = 309 confirmed by LC-MS, $t_r$ = 12.41 (Method Y)
225. methyl 2-(3-(benzo[d]isothiazol-3-ylamino)propylamino)-4-(trifluoromethyl)pyrimidine-5-carboxylate
MW = 411 confirmed by LC-MS, $t_r$ = 14.58 (Method Y)
226. N$^1$-(benzo[d]isothiazol-3-yl)-N$^3$-(5-chloropyridin-2-yl)propane-1,3-diamine
MW = 318 confirmed by LC-MS, $t_r$ = 10.77 (Method Y)
227. N$^1$-(benzo[d]isothiazol-3-yl)-N$^3$-(4-methylpyridin-2-yl)propane-1,3-diamine
MW = 298 confirmed by LC-MS, $t_r$ = 8.47 (Method Y)
228. N$^1$-(benzo[d]isothiazol-3-yl)-N$^3$-(5-(trifluoromethyl)pyridin-2-yl)propane-1,3-diamine
MW = 352 confirmed by LC-MS, $t_r$ = 13.37 (Method Y)
229. 2-(3-(benzo[d]isothiazol-3-ylamino)propylamino)isonicotinonitrile
MW = 309 confirmed by LC-MS, $t_r$ = 11.38 (Method Y)
230. N$^1$-(benzo[d]isothiazol-3-yl)-N$^3$-(6-chloropyridin-2-yl)propane-1,3-diamine
MW = 318 confirmed by LC-MS, $t_r$ = 14.57 (Method Y)
231. N$^1$-(benzo[d]isothiazol-3-yl)-N$^3$-(4-(trifluoromethyl)pyridin-2-yl)propane-1,3-diamine
MW = 352 confirmed by LC-MS, $t_r$ = 12.55 (Method Y)

TABLE 4-continued

232. N-(3-(benzo[d]isothiazol-3-ylamino)propyl)-3-(2-hydroxy-3-morpholinopropoxy)benzamide
MW = 470 confirmed by LC-MS, $t_r$ = 8.69 (Method Y)
233. N-(3-(benzo[d]isothiazol-3-ylamino)propyl)-3-(2-hydroxy-3-(4-(3-methoxyphenyl)piperazin-1-yl)propoxy)benzamide
MW = 575 confirmed by LC-MS, $t_r$ = 10.75 (Method Y)
234. N-(3-(benzo[d]isothiazol-3-ylamino)propyl)-4-fluorobenzamide
MW = 329 confirmed by LC-MS, $t_r$ = 12.43 (Method Y)
235. N-(3-(benzo[d]isothiazol-3-ylamino)propyl)-4-(pyridin-4-ylmethoxy)benzamide
MW = 418 confirmed by LC-MS, $t_r$ = 9.80 (Method Y)
236. N-(3-(benzo[d]isothiazol-3-ylamino)propyl)-4-(3-methoxybenzyloxy)benzamide
MW = 447 confirmed by LC-MS, $t_r$ = 14.27 (Method Y)
237. N-(3-(benzo[d]isothiazol-3-ylamino)propyl)-4-(3,4-dimethoxybenzyloxy)benzamide
MW = 477 confirmed by LC-MS, $t_r$ = 14.99 (Method Y)
238. 2-(4-(3-(benzo[d]isothiazol-3-ylamino)propylcarbamoyl)phenoxy)acetic acid
MW = 385 confirmed by LC-MS, $t_r$ = 10.29 (Method Y)
239. tert-butyl 2-(4-(3-(benzo[d]isothiazol-3-ylamino)propylcarbamoyl)phenoxy)acetate
MW = 441 confirmed by LC-MS, $t_r$ = 14.03 (Method Y)
240. N-(3-(benzo[d]isothiazol-3-ylamino)propyl)-N-methyl-2-(trifluoromethyl)benzenesulfonamide
MW = 429 confirmed by LC-MS, $t_r$ = 14.44 (Method Y)
241. $N^1$-(isothiazolo[5,4-b]pyrazin-3-yl)-$N^3$-((4'-methoxybiphenyl-4-yl)methyl)propane-1,3-diamine
MW = 405 confirmed by LC-MS, $t_r$ = 9.59 (Method Y)
242. N-(3-(benzo[d]isothiazol-3-ylamino)propyl)-3-nitrobenzenesulfonamide
MW = 392 confirmed by LC-MS, $t_r$ = 12.93 (Method Y)
243. methyl 2-(N-(3-(benzo[d]isothiazol-3-ylamino)propyl)sulfamoyl)benzoate
MW = 405 confirmed by LC-MS, $t_r$ = 13.01 (Method Y)
244. methyl 5-(N-(3-(benzo[d]isothiazol-3-ylamino)propyl)sulfamoyl)furan-2-carboxylate
MW = 396 confirmed by LC-MS, $t_r$ = 12.39 (Method Y)
245. N-(3-(benzo[d]isothiazol-3-ylamino)propyl)-4-(trifluoromethyl)benzenesulfonamide
MW = 415 confirmed by LC-MS, $t_r$ = 14.07 (Method Y)
246. N-(3-(benzo[d]isothiazol-3-ylamino)propyl)-3,5-bis(trifluoromethyl)benzenesulfonamide
MW = 483 confirmed by LC-MS, $t_r$ = 14.83 (Method Y)
247. N-(5-(N-(3-(benzo[d]isothiazol-3-ylamino)propyl)sulfamoyl)-4-methylthiazol-2-yl)acetamide
MW = 425 confirmed by LC-MS, $t_r$ = 10.66 (Method Y)
248. N-(3-(benzo[d]isothiazol-3-ylamino)propyl)-1,2-dimethyl-1H-imidazole-4-sulfonamide
MW = 365 confirmed by LC-MS, $t_r$ = 9.74 (Method Y)
249. N-(3-(benzo[d]isothiazol-3-ylamino)propyl)quinoline-8-sulfonamide
MW = 398 confirmed by LC-MS, $t_r$ = 12.67 (Method Y)
250. N-(3-(benzo[d]isothiazol-3-ylamino)propyl)-2,3,4-trifluorobenzenesulfonamide
MW = 402 confirmed by LC-MS, $t_r$ = 13.48 (Method Y)
251 N-(3-(benzo[d]isothiazol-3-ylamino)propyl)-4-methoxybenzenesulfonamide
MW = 377 confirmed by LC-MS, $t_r$ = 12.52 (Method Y)
252. N-(3-(benzo[d]isothiazol-3-ylamino)propyl)-2-(2,2,2-trifluoroacetyl)-1,2,3,4-tetrahydroisoquinoline-7-sulfonamide
MW = 498 confirmed by LC-MS, $t_r$ = 13.35 (Method Y)
253. N-(3-(benzo[d]isothiazol-3-ylamino)propyl)-2-bromo-4,6-difluorobenzenesulfonamide
MW = 461 confirmed by LC-MS, $t_r$ = 13.63 (Method Y)
254. N-(3-(benzo[d]isothiazol-3-ylamino)propyl)-N-benzyl-2-(trifluoromethyl)benzenesulfonamide
MW = 505 confirmed by LC-MS, $t_r$ = 16.10 (Method Y)
255. N-(3-(benzo[d]isothiazol-3-ylamino)propyl)-N-((4'-methoxybiphenyl-4-yl)methyl)-2-morpholinoacetamide
MW = 530 confirmed by LC-MS, $t_r$ = 10.56 (Method Y)
256. N-(3-(benzo[d]isothiazol-3-ylamino)propyl)-N-((4'-methoxybiphenyl-4-yl)methyl)-2-(4-phenylpiperazin-1-yl)acetamide
MW = 605 confirmed by LC-MS, $t_r$ = 12.95 (Method Y)
257. N-(3-(benzo[d]isothiazol-3-ylamino)propyl)-2-(isopropylamino)-N-((4'-methoxybiphenyl-4-yl)methyl)acetamide
MW = 502 confirmed by LC-MS, $t_r$ = 11.22 (Method Y)
258. 4-((3-(benzo[d]isothiazol-3-ylamino)propylamino)methyl)-N-(4-methoxyphenyl)benzenesulfonamide
MW = 482 confirmed by LC-MS, $t_r$ = 9.39 (Method Y)
259. $N^1$-(benzo[d]isothiazol-3-yl)-$N^3$-(4-(morpholinosulfonyl)benzyl)propane-1,3-diamine
MW = 447 confirmed by LC-MS, $t_r$ = 7.89 (Method Y)
260. $N^1$-(benzo[d]isothiazol-3-yl)-$N^3$-(4-(pyrrolidin-1-ylsulfonyl)benzyl)propane-1,3-diamine
MW = 430 confirmed by LC-MS, $t_r$ = 8.30 (Method Y)
261. N-(3-(benzo[d]isothiazol-3-ylamino)propyl)-2,5-dimethoxybenzenesulfonamide
MW = 407 confirmed by LC-MS, $t_r$ = 12.72 (Method Y)
262. N-(3-(benzo[d]isothiazol-3-ylamino)propyl)-4-bromo-2-chlorobenzenesulfonamide
MW = 459 confirmed by LC-MS, $t_r$ = 14.59 (Method Y)
263. N-(3-(benzo[d]isothiazol-3-ylamino)propyl)-4-bromo-2-(trifluoromethyl)benzenesulfonamide
MW = 493 confirmed by LC-MS, $t_r$ = 15.00 (Method Y)
264. N-(3-(benzo[d]isothiazol-3-ylamino)propyl)-3,4-dimethoxybenzenesulfonamide
MW = 407 confirmed by LC-MS, $t_r$ = 11.98 (Method Y)
265. N-(3-(benzo[d]isothiazol-3-ylamino)propyl)-4-bromo-3-methylbenzenesulfonamide
MW = 439 confirmed by LC-MS, $t_r$ = 14.48 (Method Y)
266. N-(3-(benzo[d]isothiazol-3-ylamino)propyl)-3-(trifluoromethoxy)benzenesulfonamide
MW = 431 confirmed by LC-MS, $t_r$ = 14.35 (Method Y)
267. N-(3-(benzo[d]isothiazol-3-ylamino)propyl)-4-bromo-2,6-dichlorobenzenesulfonamide
MW = 494 confirmed by LC-MS, $t_r$ = 15.25 (Method Y)

TABLE 4-continued

268. N-(3-(benzo[d]isothiazol-3-ylamino)propyl)-3-bromobenzenesulfonamide
MW = 425 confirmed by LC-MS, $t_r$ = 13.75 (Method Y)
269. N-(3-(benzo[d]isothiazol-3-ylamino)propyl)-4-bromo-3-(trifluoromethyl)benzenesulfonamide
MW = 493 confirmed by LC-MS, $t_r$ = 14.88 (Method Y)
270. N-(3-(benzo[d]isothiazol-3-ylamino)propyl)-N-((4'-methoxybiphenyl-4-yl)methyl)-2-
(trifluoromethyl)benzenesulfonamide
MW = 573 confirmed by LC-MS, $t_r$ = 16.95 (Method Y)
271. N-(2-(benzo[d]isothiazol-3-ylamino)ethyl)-4-chlorobenzenesulfonamide
MW = 367 confirmed by LC-MS, $t_r$ = 3.94 (Method B)
272. $N^1$-(benzo[d]isothiazol-3-yl)-$N^2$-(pyridin-2-ylmethyl)ethane-1,2-diamine
MW = 284 confirmed by LC-MS, $t_r$ = 2.49 (Method B)
273. N-(3-(benzo[d]isothiazol-3-ylamino)propyl)-4-propylbenzamide
MW = 353 confirmed by LC-MS, $t_r$ = 4.22 (Method B)
274. N-(3-(benzo[d]isothiazol-3-ylamino)propyl)-4-hexylbenzamide
MW = 395 confirmed by LC-MS, $t_r$ = 5.05 (Method B)
275. $N^1$-(benzo[d]isothiazol-3-yl)-$N^3$-(3-methoxypyridin-2-yl)propane-1,3-diamine
MW = 314 confirmed by LC-MS, $t_r$ = 8.16 (Method Y)
276. $N^1$-(benzo[d]isothiazol-3-yl)-$N^3$-(3-(trifluoromethyl)pyridin-2-yl)propane-1,3-diamine
MW = 352 confirmed by LC-MS, $t_r$ = 4.38 (Method B)
277. 2-(3-(benzo[d]isothiazol-3-ylamino)propylamino)nicotinonitrile
MW = 309 confirmed by LC-MS, $t_r$ = 3.67 (Method B)
278. $N^1$-(benzo[d]isothiazol-3-yl)-$N^3$-(3-methylpyridin-2-yl)propane-1,3-diamine
MW = 298 confirmed by LC-MS, $t_r$ = 2.52 (Method B)
279. N-(2-(benzo[d]isothiazol-3-ylamino)ethyl)-5-butylpicolinamide
MW = 354 confirmed by LC-MS, $t_r$ = 4.28 (Method B)
280. 3-(benzo[d]isothiazol-3-ylamino)-2-(4-butylbenzamido)propanoic acid
MW = 397 confirmed by LC-MS, $t_r$ = 14.2 (Method Y)
281. $N^1$-(benzo[d]isothiazol-3-yl)-$N^3$-(6-methylpyridin-2-yl)propane-1,3-diamine
MW = 298 confirmed by LC-MS, $t_r$ = 2.19 (Method B)
282. $N^1$-(benzo[d]isothiazol-3-yl)-$N^3$-(5-methoxypyridin-2-yl)propane-1,3-diamine
MW = 314 confirmed by LC-MS, $t_r$ = 2.46 (Method B)
283. $N^1$-(benzo[d]isothiazol-3-yl)-$N^3$-(6-methoxypyridin-2-yl)propane-1,3-diamine
MW = 314 confirmed by LC-MS, $t_r$ = 3.15 (Method B)
284. methyl 6-(3-(benzo[d]isothiazol-3-ylamino)propylamino)-4-(trifluoromethyl)nicotinate
MW = 410 confirmed by LC-MS, $t_r$ = 4.07 (Method B)
285. N-(3-(benzo[d]isothiazol-3-ylamino)propyl)-3-butoxy-4-methoxybenzamide
MW = 413 confirmed by LC-MS, $t_r$ = 4.04 (Method B)
286. N-(3-(benzo[d]isothiazol-3-ylamino)propyl)-3-(cyclopentyloxy)-4-methoxybenzamide
MW = 425 confirmed by LC-MS, $t_r$ = 4.02 (Method B)
287. $N^1$-(benzo[d]isothiazol-3-yl)-$N^3$-(4-bromobenzyl)propane-1,3-diamine
MW = 376 confirmed by LC-MS, $t_r$ = 3.04 (Method B)
288. $N^1$-(benzo[d]isothiazol-3-yl)-$N^3$-(4-butylbenzyl)propane-1,3-diamine
MW = 353 confirmed by LC-MS, $t_r$ = 3.56 (Method B)
289. N-(3-(benzo[d]isothiazol-3-ylamino)propyl)-4-bromobenzamide
MW = 390 confirmed by LC-MS, $t_r$ = 3.89 (Method B)
290. N-(3-(benzo[d]isothiazol-3-ylamino)propyl)-4-(propylamino)benzamide
MW = 368 confirmed by LC-MS, $t_r$ = 3.76 (Method B)
291. $N^1$-(benzo[d]isothiazol-3-yl)-$N^3$-((4'-methoxybiphenyl-4-yl)methyl)propane-1,3-diamine
MW = 403 confirmed by LC-MS, $t_r$ = 5.16 (Method B)
292. $N^1$-(benzo[d]isothiazol-3-yl)-$N^3$-((3',4'-dimethoxybiphenyl-4-yl)methyl)propane-1,3-diamine
MW = 433 confirmed by LC-MS, $t_r$ = 3.06 (Method B)
293. N-(3-(benzo[d]isothiazol-3-ylamino)propyl)-N-(4-butylbenzyl)picolinamide
MW = 458 confirmed by LC-MS, $t_r$ = 4.83 (Method B)
294. $N^1$-(benzo[d]isothiazol-3-yl)-$N^3$-((5'-chloro-2'-methoxybiphenyl-4-yl)methyl)propane-1,3-
diamine
MW = 437 confirmed by LC-MS, $t_r$ = 3.76 (Method B)
295. $N^1$-(benzo[d]isothiazol-3-yl)-$N^3$-(4-butylphenyl)propane-1,3-diamine
MW = 339 confirmed by LC-MS, $t_r$ = 3.96 (Method B)
296. N-(3-(benzo[d]isothiazol-3-ylamino)propyl)-4-(4-ethylpiperazin-1-yl)benzamide
MW = 423 confirmed by LC-MS, $t_r$ = 3.91 (Method C)
297. N-(3-(benzo[d]isothiazol-3-ylamino)propyl)-4-(pyridin-2-ylmethylamino)benzamide
MW = 417 confirmed by LC-MS, $t_r$ = 2.68 (Method B)
298. N-(3-(benzo[d]isothiazol-3-ylamino)propyl)-4-(isopropylamino)benzamide
MW = 368 confirmed by LC-MS, $t_r$ = 3.6 (Method B)
299. $N^1$-(benzo[d]isothiazol-3-yl)-$N^3$-(3-bromobenzyl)propane-1,3-diamine
MW = 376 confirmed by LC-MS, $t_r$ = 2.8 (Method B)
300. $N^1$-(benzo[d]isothiazol-3-yl)-$N^3$-((4'-methoxybiphenyl-3-yl)methyl)propane-1,3-diamine
MW = 403 confirmed by LC-MS, $t_r$ = 2.98 (Method B)
301. $N^1$-(benzo[d]isothiazol-3-yl)-$N^3$-((4',5'-dimethoxybiphenyl-3-yl)methyl)propane-1,3-diamine
MW = 433 confirmed by LC-MS, $t_r$ = 2.79 (Method B)
302. $N^1$-(benzo[d]isothiazol-3-yl)-$N^3$-((3'-chloro-6'-methoxybiphenyl-3-yl)methyl)propane-1,3-
diamine
MW = 437 confirmed by LC-MS, $t_r$ = 3.32 (Method B)
303. 2-((3-(benzo[d]isothiazol-3-ylamino)propylamino)methyl)-4-bromophenol
MW = 392 confirmed by LC-MS, $t_r$ = 2.59 (Method B)
304. 5-((3-(benzo[d]isothiazol-3-ylamino)propylamino)methyl)-2-methoxyphenol
MW = 343 confirmed by LC-MS, $t_r$ = 2.34 (Method B)
305. 3-butoxy-N-(2-(5-chlorobenzo[d]isothiazol-3-ylamino)ethyl)-4-methoxybenzamide
MW = 433 confirmed by LC-MS, $t_r$ = 4.29 (Method B)

TABLE 4-continued

306. $N^1$-(benzo[d]isothiazol-3-yl)-$N^3$-(1-benzylpiperidin-3-yl)propane-1,3-diamine
MW = 380 confirmed by LC-MS, $t_r$ = 2.17 (Method B)
307. tert-butyl 4-(3-(benzo[d]isothiazol-3-ylamino)propylamino)piperidine-1-carboxylate
MW = 390 confirmed by LC-MS, $t_r$ = 3.05 (Method B)
308. $N^1$-(benzo[d]isothiazol-3-yl)-$N^3$-(pyridin-3-ylmethyl)propane-1,3-diamine
MW = 298 confirmed by LC-MS, $t_r$ = 2.05 (Method B)
309. $N^1$-(benzo[d]isothiazol-3-yl)-$N^3$-(pyridin-2-ylmethyl)propane-1,3-diamine
MW = 298 confirmed by LC-MS, $t_r$ = 2.43 (Method B)
310. 3-butoxy-4-methoxy-N-(2-(5-(propylamino)benzo[d]isothiazol-3-ylamino)ethyl)benzamide
MW = 456 confirmed by LC-MS, $t_r$ = 3.98 (Method B)
311. 5-((benzo[d]isothiazol-3-ylamino)methyl)-3-(4-iodophenyl)imidazolidine-2,4-dione
MW = 464 confirmed by LC-MS, $t_r$ = 10.33 (Method C)
312. $N^1$-(benzo[d]isothiazol-3-yl)-$N^3$-((4'-methoxybiphenyl-2-yl)methyl)propane-1,3-diamine
MW = 403 confirmed by LC-MS, $t_r$ = 3.18 (Method B)
313. $N^1$-(benzo[d]isothiazol-3-yl)-$N^3$-((3',4'-dimethoxybiphenyl-2-yl)methyl)propane-1,3-diamine
MW = 433 confirmed by LC-MS, $t_r$ = 3.13 (Method B)
314. N-(3-(benzo[d]isothiazol-3-ylamino)propyl)-N-((4'-methoxybiphenyl-4-yl)methyl)morpholine-4-carboxamide
MW = 516 confirmed by LC-MS, $t_r$ = 4.45 (Method B)
315. 1-(3-(benzo[d]isothiazol-3-ylamino)propyl)-1-((4'-methoxybiphenyl-4-yl)methyl)-3,3-dimethylurea
MW = 474 confirmed by LC-MS, $t_r$ = 4.54 (Method B)
316. N-(3-(benzo[d]isothiazol-3-ylamino)propyl)-N-((4'-methoxybiphenyl-4-yl)methyl)-1,2-dimethyl-1H-imidazole-4-sulfonamide
MW = 561 confirmed by LC-MS, $t_r$ = 4.32 (Method B)
317. methyl 5-(N-(3-(benzo[d]isothiazol-3-ylamino)propyl)-N-((4'-methoxybiphenyl-4-yl)methyl)sulfamoyl)-1-methyl-1H-pyrrole-2-carboxylate
MW = 604 confirmed by LC-MS, $t_r$ = 4.93 (Method B
318. tert-butyl 2-(2-((3-(benzo[d]isothiazol-3-ylamino)propyl)((4'-methoxybiphenyl-4-yl)methyl)amino)-2-oxoethyl)pyrrolidine-1-carboxylate
MW = 614 confirmed by LC-MS, $t_r$ = 5.12 (Method B)
319. N-(3-(benzo[d]isothiazol-3-ylamino)propyl)-2-cyano-N-((4'-methoxybiphenyl-4-yl)methyl)acetamide
MW = 470 confirmed by LC-MS, $t_r$ = 4.32 (Method B)
320. N-(3-(benzo[d]isothiazol-3-ylamino)propyl)-N-((4'-methoxybiphenyl-4-yl)methyl)-2-(pyrrolidin-2-yl)acetamide
MW = 514 confirmed by LC-MS, $t_r$ = 4.57 (Method B)
321. 4-butyl-N-{3-[(1-oxido-1,2-benzisothiazol-3-yl)amino]propyl}benzamide
MW = 369 confirmed by LC-MS, $t_r$ = 6.72 (Method C)
322. 4-butyl-N-{3-[(1,1-dioxido-1,2-benzisothiazol-3-yl)amino]propyl}benzamide
MW = 385 confirmed by LC-MS, $t_r$ = 7.25 (Method C)
323. N-[(4'-methoxybiphenyl-4-yl)methyl]-N'-(1-oxido-1,2-benzisothiazol-3-yl)propane-1,3-diamine
MW = 419 confirmed by LC-MS, $t_r$ = 2.9 (Method B)
324. N-(1,1-dioxido-1,2-benzisothiazol-3-yl)-N'-[(4'-methoxybiphenyl-4-yl)methyl]propane-1,3-diamine
MW = 435 confirmed by LC-MS, $t_r$ = 3.24 (Method B)
325. N-(3-(benzo[d]isothiazol-3-ylamino)propyl)-4-iodobenzenesulfonamide
MW = 473 confirmed by LC-MS, $t_r$ = 4.14 (Method B)
326. $N^1$-(benzo[d]isothiazol-3-yl)-$N^3$-(2-(trifluoromethyl)benzyl)propane-1,3-diamine
MW = 365 confirmed by LC-MS, $t_r$ = 5.07 (Method C)
327. $N^1$-(benzo[d]isothiazol-3-yl)-$N^3$-(2-(benzyloxy)-4,5-dimethoxybenzyl)propane-1,3-diamine
MW = 463 confirmed by LC-MS, $t_r$ = 3.7 (Method B)
328. $N^1$-(benzo[d]isothiazol-3-yl)-$N^3$-(3-(benzyloxy)benzyl)propane-1,3-diamine
MW = 403 confirmed by LC-MS, $t_r$ = 3.8 (Method B)
329. $N^1$-(benzo[d]isothiazol-3-yl)-$N^3$-((2-phenyl-1H-imidazol-4-yl)methyl)propane-1,3-diamine
MW = 363 confirmed by LC-MS, $t_r$ = 2.69 (Method B)
330. $N^1$-(benzo[d]isothiazol-3-yl)-$N^3$-((2-phenyl-1H-indol-3-yl)methyl)propane-1,3-diamine
MW = 413 confirmed by LC-MS, $t_r$ = 6.88 (Method C)
331. N-(3-(benzo[d]isothiazol-3-ylamino)propyl)-4'-methoxybiphenyl-4-sulfonamide
MW = 454 confirmed by LC-MS, $t_r$ = 4.25 (Method B)
332. N-(3-(benzo[d]isothiazol-3-ylamino)propyl)-3',4'-dimethoxybiphenyl-4-sulfonamide
MW = 484 confirmed by LC-MS, $t_r$ = 4 (Method B)
333. N-(3-(benzo[d]isothiazol-3-ylamino)propyl)-4'-(trifluoromethoxy)biphenyl-4-sulfonamide
MW = 507 confirmed by LC-MS, $t_r$ = 4.71 (Method B)
334. methyl 4'-(N-(3-(benzo[d]isothiazol-3-ylamino)propyl)sulfamoyl)biphenyl-4-carboxylate
MW = 481 confirmed by LC-MS, $t_r$ = 4.2 (Method B)
335. N-(3-(benzo[d]isothiazol-3-ylamino)propyl)-2'-(trifluoromethoxyl)biphenyl-4-sulfonamide
MW = 491 confirmed by LC-MS, $t_r$ = 4.53 (Method B)
336. $N^1$-(benzo[d]isothiazol-3-yl)-$N^3$-((4'-(trifluoromethoxy)biphenyl-4-yl)methyl)propane-1,3-diamine
MW = 457 confirmed by LC-MS, $t_r$ = 6.04 (Method C)
337. $N^1$-(benzo[d]isothiazol-3-yl)-$N^3$-(benzofuran-2-ylmethyl)propane-1,3-diamine
MW = 337 confirmed by LC-MS, $t_r$ = 4.73 (Method C)
338. $N^1$-(benzo[d]isothiazol-3-yl)-$N^3$-(4-(pyrrolidin-1-yl)benzyl)propane-1,3-diamine
MW = 366 confirmed by LC-MS, $t_r$ = 5.21 (Method C)
339. N-(3-(benzo[d]isothiazol-3-ylamino)propyl)-N-((4'-methoxybiphenyl-4-yl)methyl)-2-(methylsulfonyl)acetamide
MW = 523 confirmed by LC-MS, $t_r$ = 7.18 (Method C)

TABLE 4-continued

340. N-{3-[(1,1-dioxido-1,2-benzisothiazol-3-yl)amino]propyl}-N-[(4'-methoxybiphenyl-4-yl)methyl]-1,2-dimethyl-1H-imidazole-4-sulfonamide
MW = 593 confirmed by LC-MS, $t_r$ = 3.68 (Method B)
341. N-(3-(benzo[d]isothiazol-3-ylamino)propyl)-2-(1H-imidazol-1-yl)-N-((4'-methoxybiphenyl-4-yl)methyl)acetamide
MW = 511 confirmed by LC-MS, $t_r$ = 5.34 (Method C)
342. N-(3-(benzo[d]isothiazol-3-ylamino)propyl)-N-((4'-methoxybiphenyl-4-yl)methyl)picolinamide
MW = 508 confirmed by LC-MS, $t_r$ = 4.59 (Method B)
343. $N^1$-(benzo[d]isothiazol-3-yl)-$N^3$-(3-methoxybenzyl)propane-1,3-diamine
MW = 327 confirmed by LC-MS, $t_r$ = 2.76 (Method B)
344. N-(3-(benzo[d]isothiazol-3-yl(methyl)amino)propyl)-3-methoxy-N-methylbenzenesulfonamide
MW = 405 confirmed by LC-MS, $t_r$ = 4.6 (Method B)
345. N-(3-(benzo[d]isothiazol-3-yl(methyl)amino)propyl)-N-methyl-2-(trifluoromethyl)benzenesulfonamide
MW = 443 confirmed by LC-MS, $t_r$ = 4.77 (Method B))
346. 1-(4-((3-(benzo[d]isothiazol-3-ylamino)propylamino)methyl)phenyl)pyrrolidin-2-one
MW = 380 confirmed by LC-MS, $t_r$ = 4.03 (Method C)
347. $N^1$-(benzo[d]isothiazol-3-yl)-$N^3$-((4'-methoxybiphenyl-4-yl)methyl)-$N^1$,$N^3$-dimethylpropane-1,3-diamine
MW = 431 confirmed by LC-MS, $t_r$ = 5.48 (Method C)
348. (R)-N-(2-(2-(benzo[d]isothiazol-3-ylamino)ethylamino)-2-oxo-1-phenylethyl)-4-chlorobenzamide
MW = 465 confirmed by LC-MS, $t_r$ = 4.23 (Method B)
349. N-(2-(benzo[d]isothiazol-3-ylamino)ethyl)-2,4-difluorobenzamide
MW = 333 confirmed by LC-MS, $t_r$ = 3.57 (Method B)
350. N-(2-(benzo[d]isothiazol-3-ylamino)ethyl)-2,5-difluorobenzamide
MW = 333 confirmed by LC-MS, $t_r$ = 3.57 (Method B)
351. N-(2-(benzo[d]isothiazol-3-ylamino)ethyl)-2-(trifluoromethyl)benzamide
MW = 365 confirmed by LC-MS, $t_r$ = 3.61 (Method B)
352. N-(2-(benzo[d]isothiazol-3-ylamino)ethyl)-5-fluoro-2-(trifluoromethyl)benzamide
MW = 383 confirmed by LC-MS, $t_r$ = 3.71 (Method B)
353. N-(2-(benzo[d]isothiazol-3-ylamino)ethyl)-3-fluoro-5-(trifluoromethyl)benzamide
MW = 383 confirmed by LC-MS, $t_r$ = 4.13 (Method B)
354. N-(2-(benzo[d]isothiazol-3-ylamino)ethyl)-2-fluoro-4-(trifluoromethyl)benzamide
MW = 383 confirmed by LC-MS, $t_r$ = 3.99 (Method B)
355. N-(2-(benzo[d]isothiazol-3-ylamino)ethyl)-3-fluoro-4-(trifluoromethyl)benzamide
MW = 383 confirmed by LC-MS, $t_r$ = 4.07 (Method B)
356. N-(2-(benzo[d]isothiazol-3-ylamino)ethyl)-2,4-bis(trifluoromethyl)benzamide
MW = 433 confirmed by LC-MS, $t_r$ = 4.09 (Method B)
357. N-(2-(benzo[d]isothiazol-3-ylamino)ethyl)-2,5-bis(trifluoromethyl)benzamide
MW = 433 confirmed by LC-MS, $t_r$ = 4.09 (Method B)
358. N-(2-(benzo[d]isothiazol-3-ylamino)ethyl)-2-fluoro-6-(trifluoromethyl)benzamide
MW = 383 confirmed by LC-MS, $t_r$ = 3.64 (Method B)
359. N-(2-(benzo[d]isothiazol-3-ylamino)ethyl)-3,4-difluorobenzamide
MW = 333 confirmed by LC-MS, $t_r$ = 3.68 (Method B)
360. N-(2-(benzo[d]isothiazol-3-ylamino)ethyl)-4'-methoxybiphenyl-4-carboxamide
MW = 403 confirmed by LC-MS, $t_r$ = 4.09 (Method B)
361. N-(2-(benzo[d]isothiazol-3-ylamino)ethyl)-3',4'-dimethoxybiphenyl-4-carboxamide
MW = 433 confirmed by LC-MS, $t_r$ = 13.10 (Method Y)
362. N-(2-(benzo[d]isothiazol-3-ylamino)ethyl)-5'-chloro-2'-methoxybiphenyl-4-carboxamide
MW = 438 confirmed by LC-MS, $t_r$ = 15.30 (Method Y)
363. N-(2-(benzo[d]isothiazol-3-ylamino)ethyl)-2'-isopropoxy-5'-methylbiphenyl-4-carboxamide
MW = 445 confirmed by LC-MS, $t_r$ = 4.76 (Method B)
364. N-(2-(benzo[d]isothiazol-3-ylamino)ethyl)-2',3'-dimethoxybiphenyl-4-carboxamide
MW = 433 confirmed by LC-MS, $t_r$ = 14.22 (Method Y)
365. N-(2-(benzo[d]isothiazol-3-ylamino)ethyl)-2'-methoxy-5'-methylbiphenyl-4-carboxamide
MW = 417 confirmed by LC-MS, $t_r$ = 4.36 (Method B)
366. N-(2-(benzo[d]isothiazol-3-ylamino)ethyl)-4'-methoxy-2'-methylbiphenyl-4-carboxamide
MW = 417 confirmed by LC-MS, $t_r$ = 4.32 (Method B)
367. N-(2-(benzo[d]isothiazol-3-ylamino)ethyl)-5'-fluoro-2'-propoxybiphenyl-4-carboxamide
MW = 449 confirmed by LC-MS, $t_r$ = 4.65 (Method B)
368. N-(3-(benzo[d]isothiazol-3-ylamino)propyl)-4'-fluoro-6'-methoxybiphenyl-3-carboxamide
MW = 435 confirmed by LC-MS, $t_r$ = 4.35 (Method B)
369. N-(3-(benzo[d]isothiazol-3-ylamino)propyl)-5',6'-dimethoxybiphenyl-3-carboxamide
MW = 447 confirmed by LC-MS, $t_r$ = 4.15 (Method B)
370. N-(2-(benzo[d]isothiazol-3-ylamino)ethyl)-3',4'-dimethoxybiphenyl-3-carboxamide
MW = 433 confirmed by LC-MS, $t_r$ = 3.82 (Method B)
371. N-(2-(benzo[d]isothiazol-3-ylamino)ethyl)-4'-methoxybiphenyl-3-carboxamide
MW = 403 confirmed by LC-MS, $t_r$ = 4.06 (Method B)
372. N-(2-(benzo[d]isothiazol-3-ylamino)ethyl)-3',4'-dimethylbiphenyl-3-carboxamide
MW = 401 confirmed by LC-MS, $t_r$ = 4.58 (Method B)
373. N-(2-(benzo[d]isothiazol-3-ylamino)ethyl)-3-(naphthalen-2-yl)benzamide
MW = 423 confirmed by LC-MS, $t_r$ = 4.59 (Method B)
374. N-(2-(benzo[d]isothiazol-3-ylamino)ethyl)-3-(quinolin-8-yl)benzamide
MW = 424 confirmed by LC-MS, $t_r$ = 3.60 (Method B)
375. N-(2-(benzo[d]isothiazol-3-ylamino)ethyl)-3-(quinolin-3-yl)benzamide
MW = 424 confirmed by LC-MS, $t_r$ = 3.60 (Method B)

TABLE 4-continued

376. N-(3-(benzo[d]isothiazol-3-ylamino)propyl)-6'-isopropoxybiphenyl-3-carboxaimde
MW = 445 confirmed by LC-MS, $t_r$ = 4.66 (Method B)
377. N-(2-(benzo[d]isothiazol-3-ylamino)ethyl)-2'-isopropoxybiphenyl-4-carboxamide
MW = 431 confirmed by LC-MS, $t_r$ = 4.53 (Method B)
378. N-(3-(benzo[d]isothiazol-3-ylamino)propyl)-4'-methoxybiphenyl-3-carboxamide
MW = 417 confirmed by LC-MS, $t_r$ = 4.21 (Method B)
379. 1-(3-(benzo[d]isothiazol-3-ylamino)propyl)-3-(4-butylphenyl)urea
MW = 382 confirmed by LC-MS, $t_r$ = 4.93 (Method Z)
380. N-(3-(benzo[d]isothiazol-3-ylamino)propyl)-3-(6-chloropyridin-3-yl)benzamide
MW = 423 confirmed by LC-MS, $t_r$ = 3.90 (Method B)
381. N-(3-(benzo[d]isothiazol-3-ylamino)propyl)-3'-ethoxy-6'-methylbiphenyl-3-carboxamide
MW = 445 confirmed by LC-MS, $t_r$ = 4.61 (Method B)
382. N-(3-(benzo[d]isothiazol-3-ylamino)propyl)-3',6'-dimethoxybiphenyl-3-carboxamide
MW = 447 confirmed by LC-MS, $t_r$ = 4.15 (Method B)
383. N-(3-(benzo[d]isothiazol-3-ylamino)propyl)-4'-fluoro-6'-propoxybiphenyl-3-carboxamide
MW = 463 confirmed by LC-MS, $t_r$ = 4.73 (Method B)
384 N-(3-(benzo[d]isothiazol-3-ylamino)propyl)-6'-methoxybiphenyl-3-carboxamide
MW = 417 confirmed by LC-MS, $t_r$ = 4.20 (Method B)
385. N-(2-(benzo[d]isothiazol-3-ylamino)ethyl)-2'-hydroxybiphenyl-4-carboxamide
MW = 389 confirmed by LC-MS, $t_r$ = 3.66 (Method B)
386. N-(3-(benzo[d]isothiazol-3-ylamino)propyl)-3-iodobenzamide
MW = 437 confirmed by LC-MS, $t_r$ = 4.12 (Method B)
387. 1-(3-(benzo[d]isothiazol-3-ylamino)propyl)-3-(4-iodophenyl)urea
MW = 452 confirmed by LC-MS, $t_r$ = 4.00 (Method B)
388. N-(3-(benzo[d]isothiazol-3-ylamino)propyl)-3-(6-methoxypyridin-3-yl)benzamide
MW = 418 confirmed by LC-MS, $t_r$ = 3.96 (Method B)
389. 1-(3-(benzo[d]isothiazol-3-ylamino)propyl)-3-(2'-isopropoxybiphenyl-4-yl)urea
MW = 460 confirmed by LC-MS, $t_r$ = 4.49 (Method B)
390. tert-butyl 4-(3-benzo[d]isothiazol-3-ylamino)propylcarbamoyl)phenyl)-5,6-dihydropyridine-1(2H)-carboxylate
MW = 492 confirmed by LC-MS, $t_r$ = 4.45 (Method B)
391. N-(3-(benzo[d]isothiazol-3-ylamino)propyl)-3,5-diethoxybenzamide
MW = 399 confirmed by LC-MS, $t_r$ = 4.16 (Method B)
392. 1-(3-(benzo[d]isothiazol-3-ylamino)propyl)-3-(2'-isopropoxy-5'-methylbiphenyl-4-yl)urea
MW = 474 confirmed by LC-MS, $t_r$ = 4.71 (Method B)
393. 1-(3-(benzo[d]isothiazol-3-ylamino)propyl)-3-(4'-fluoro-2'-methoxybiphenyl-4-yl)urea
MW = 450 confirmed by LC-MS, $t_r$ = 4.21 (Method B)
394. N-(3-(benzo[d]isothiazol-3-ylamino)propyl)-3-(1,2,3,6-tetrahydropyridin-4-yl)benzamide
MW = 392 confirmed by LC-MS, $t_r$ = 2.51 (Method B)
395. 1-(3-(benzo[d]isothiazol-3-ylamino)propyl)-3-(2'-methoxybiphenyl-4-yl)urea
MW = 432 confirmed by LC-MS, $t_r$ = 4.13 (Method B)
396. N-(3-(benzo[d]isothiazol-3-ylamino)propyl)-3-bromo-4-hydroxybenzamide
MW = 406 confirmed by LC-MS, $t_r$ = 3.33 (Method B)
397. N-(3-(benzo[d]isothiazol-3-ylamino)propyl)-3-bromo-4-(2-morpholinoethoxy)benzamide
MW = 519 confirmed by LC-MS, $t_r$ = 2.65 (Method B)
398. N-(3-(4-(N-tert-butylsulfamoyl)benzo[d]isothiazol-3-ylamino)propyl)-4'-methoxybiphenyl-4-carboxamide
MW = 553 confirmed by LC-MS, $t_r$ = 4.18 (Method B)
399. N-(3-(6-(N-tert-butylsulfamoyl)benzo[d]isothiazol-3-ylamino)propyl)-4'-methoxybiphenyl-4-carboxamide
MW = 553 confirmed by LC-MS, $t_r$ = 4.30 (Method B)
400. N-(3-(7-(tert-butylsulfonyl)benzo[d]isothiazol-3-ylamino)propyl)-4'-methoxybiphenyl-4-carboxamide
MW = 538 confirmed by LC-MS, $t_r$ = 4.18 (Method B)
401. 4'-methoxy-N-(3-(4-sulfamoylbenzo[d]isothiazol-3-ylamino)propyl)biphenyl-4-carboxamide
MW = 496 confirmed by LC-MS, $t_r$ = 3.55 (Method B)
402. 4'-methoxy-N-(3-(6-sulfamoylbenzo[d]isothiazol-3-ylamino)propyl)biphenyl-4-carboxamide
MW = 496 confirmed by LC-MS, $t_r$ = 3.63 (Method B)
403. 4-butoxy-N-(3-(5-phenylbenzo[d]isothiazol-3-ylamino)propyl)benzamide
MW = 459 confirmed by LC-MS, $t_r$ = 5.05 (Method B)
404. $N^1$-(5-bromobenzo[d]isothiazol-3-yl)-$N^3$-((4'-methoxybiphenyl-4-yl)methyl)propane-1,3-diamine
MW = 482 confirmed by LC-MS, $t_r$ = 3.24 (Method B)
405. 4'-methoxy-N-(3-(5-phenylbenzo[d]isothiazol-3-ylamino)propyl)biphenyl-4-carboxamide
MW = 493 confirmed by LC-MS, $t_r$ = 4.88 (Method B)
406. 4'-methoxy-N-(3-(5-(4-methoxyphenyl)benzo[d]isothiazol-3-ylamino)propyl)biphenyl-4-carboxamide
MW = 523 confirmed by LC-MS, $t_r$ = 4.81 (Method B)
407. N-(3-(5-(2-fluoro-3-methoxyphenyl)benzo[d]isothiazol-3-ylamino)propyl)-4'-methoxybiphenyl-4-carboxamide
MW = 541 confirmed by LC-MS, $t_r$ = 4.78 (Method B)
408. N-(3-(5-(3,5-difluorophenyl)benzo[d]isothiazol-3-ylamino)propyl)-4'-methoxybiphenyl-4-carboxamide
MW = 529 confirmed by LC-MS, $t_r$ = 5.03 (Method B)
409. N-(3-(5-(4-isopropoxyphenyl)benzo[d]isothiazol-3-ylamino)propyl)-4'-methoxybiphenyl-4-carboxamide
MW = 552 confirmed b LC-MS, $t_r$ = 5.21 (Method B)

TABLE 4-continued

410. $N^1$-((4'-methoxybiphenyl-4-yl)methyl)-$N^3$-(5-(4-methoxyphenyl)benzo[d]isothiazol-3-yl)propane-1,3-diamine
MW = 509 confirmed by LC-MS, $t_r$ = 4.80 (Method B)
411. $N^1$-(5-(3,5-difluorophenyl)benzo[d]isothiazol-3-yl)-$N^3$-((4'-methoxybiphenyl-4-yl)methyl)propane-1,3-diamine
MW = 515 confirmed by LC-MS, $t_r$ = 4.86 (Method B)
412. N-(2-(benzo[d]isothiazol-3-ylamino)ethyl)-1-methyl-1H-indole-2-carboxamide
MW = 350 confirmed by LC-MS, $t_r$ = 13.55 (Method Y)
413. N-(2-(benzo[d]isothiazol-3-ylamino)ethyl)-3-phenyl-1H-pyrazole-5-carboxamide
MW = 363 confirmed by LC-MS, $t_r$ = 11.76 (Method Y)
414. N-(2-(benzo[d]isothiazol-3-ylamino)ethyl)-3-formylbenzamide
MW = 325 confirmed by LC-MS, $t_r$ = 11.19 (Method Y)
415. N-(2-(benzo[d]isothiazol-3-ylamino)ethyl)-4-formylbenzamide
MW = 325 confirmed by LC-MS, $t_r$ = 11.13 (Method Y)
416. N-(2-(benzo[d]isothiazol-3-ylamino)ethyl)-3-(hydroxymethyl)benzamide
MW = 327 confirmed by LC-MS, $t_r$ = 10.25 (Method Y)
417. $N^1$,$N^2$-di(benzo[d]isothiazol-3-yl)ethane-1,2-diamine
MW = 326 confirmed by LC-MS, $t_r$ = 14.23 (Method Y)
418 $N^1$-(2-(benzo[d]isothiazol-3-ylamino)ethyl)-$N^4$-propylterephthalamide
MW = 182 confirmed by LC-MS, $t_r$ = 11.16 (Method Y)
419. N-(3-(benzo[d]isothiazol-3-ylamino)propyl)-6-bromopicolinamide
MW = 391 confirmed by LC-MS, $t_r$ = 13.10 (Method Y)
420. N-(3-(benzo[d]isothiazol-3-ylamino)propyl)-6-fluoropicolinamide
MW = 330 confirmed by LC-MS, $t_r$ = 12.38 (Method Y)
421. 4-butyl-N-(2-(5-chlorobenzo[d]isothiazol-3-ylamino)ethyl)benzamide
MW = 388 confirmed by LC-MS, $t_r$ = 16.44 (Method Y)
422. $N^1$-(2-(benzo[d]isothiazol-3-ylamino)ethyl)-$N^4$-butylterephthalamide
MW = 397 confirmed by LC-MS, $t_r$ = 11.93 (Method Y)
423. N-(2-(5-chlorobenzo[d]isothiazol-3-ylamino)ethyl)-4-(pentyloxy)benzamide
MW = 418 confirmed by LC-MS, $t_r$ = 16.69 (Method Y)
424. tert-butyl 3-(2-(5-chlorobenzo[d]isothiazol-3-ylamino)ethylcarbamoyl)piperidine-1-carboxylate
MW = 439 confirmed by LC-MS, $t_r$ = 14.31 (Method Y)
425. (S)-tert-butyl 2-(2-(5-chlorobenzo[d]isothiazol-3-ylamino)ethylamino)-2-oxo-1-phenylethylcarbamate
MW = 461 confirmed by LC-MS, $t_r$ = 14.71 (Method Y)
426. $N^1$-(2-(benzo[d]isothiazol-3-ylamino)ethyl)-$N^4$-isopropylterephthalamide
MW = 382 confirmed by LC-MS, $t_r$ = 3.10 (Method B))
427. $N^1$-(2-(benzo[d]isothiazol-3-ylamino)ethyl)-$N^4$-cyclopropylterephthalamide
MW = 380 confirmed by LC-MS, $t_r$ = 6.83 (Method D)
428. $N^1$-(2-(benzo[d]isothiazol-3-ylamino)ethyl)-$N^3$-propylisophthalamide
MW = 382 confirmed by LC-MS, $t_r$ = 3.18 (Method B)
429. $N^1$-(2-(benzo[d]isothiazol-3-ylamino)ethyl)-$N^3$-butylisophthalamide
MW = 397 confirmed by LC-MS, $t_r$ = 3.43 (Method B)
430. $N^1$-(2-(benzo[d]isothiazol-3-ylamino)ethyl)-$N^3$-isopropylisophthalamide
MW = 382 confirmed by LC-MS, $t_r$ = 6.81 (Method D)
431. $N^1$-(2-(benzo[d]isothiazol-3-ylamino)ethyl)-$N^3$-cyclopropylisophthalamide
MW = 380 confirmed by LC-MS, $t_r$ = 10.93 (Method Y)
432. N-(2-(5-chlorobenzo[d]isothiazol-3-ylamino)ethyl)-5-methoxy-1H-indole-2-carboxamide
MW = 401 confirmed by LC-MS, $t_r$ = 13.84 (Method Y)
433. N-(3-(benzo[d]isothiazol-3-ylamino)propyl)-6-nitrobenzo[b]thiophene-2-carboxamide
MW = 412 confirmed by LC-MS, $t_r$ = 14.30 (Method Y)
434. $N^1$,$N^3$-di(benzo[d]isothiazol-3-yl)propane-1,3-diamine
MW = 340 confirmed by LC-MS, $t_r$ = 14.73 (Method Y)
435. N-(3-(benzo[d]isothiazol-3-ylamino)propyl)-7-methoxybenzofuran-2-carboxamide
MW = 381 confirmed by LC-MS, $t_r$ = 7.33 (Method D)
436. N-(3-(benzo[d]isothiazol-3-ylamino)propyl)-5-chlorobenzofuran-2-carboxamide
MW = 386 confirmed by LC-MS, $t_r$ = 8.01 (Method D)
437. N-(3-(benzo[d]isothiazol-3-ylamino)propyl)-5-methoxybenzofuran-2-carboxamide
MW = 381 confirmed by LC-MS, $t_r$ = 7.31 (Method D)
438. N-(3-(benzo[d]isothiazol-3-ylamino)propyl)-6-(2,4-dimethoxyphenyl)picolinamide
MW = 449 confirmed by LC-MS, $t_r$ = 15.10 (Method Y)
439. N-(3-(benzo[d]isothiazol-3-ylamino)propyl)-6-nitrobenzofuran-2-carboxamide
MW = 396 confirmed by LC-MS, $t_r$ = 13.55 (Method Y)
440. N-(3-(benzo[d]isothiazol-3-ylamino)propyl)-6-(4-(methylsulfonyl)phenyl)picolinamide
MW = 467 confirmed by LC-MS, $t_r$ = 12.82 (Method Y)
441. N-(2-(benzo[d]isothiazol-3-ylamino)ethyl)-4-(3-methyl-5-oxo-4,5-dihydropyrazol-1-yl)benzamide
MW = 393 confirmed by LC-MS, $t_r$ = 10.89 (Method Y)
442. N-(3-(benzo[d]isothiazol-3-ylamino)propyl)-6-(2-(pyridin-2-yl)ethylamino)picolinamide
MW = 433 confirmed by LC-MS, $t_r$ = 8.78 (Method Y)
443. N-(3-(benzo[d]isothiazol-3-ylamino)propyl)-6-bromonicotinamide
MW = 391 confirmed by LC-MS, $t_r$ = 11.95 (Method Y)
444. N-(3-(benzo[d]isothiazol-3-ylamino)propyl)-5-bromo-1H-indole-2-carboxamide
MW = 429 confirmed by LC-MS, $t_r$ = 14.18 (Method Y)
445. N-(3-(benzo[d]isothiazol-3-ylamino)propyl)-5-bromobenzo[b]thiophene-2-carboxamide
MW = 446 confirmed by LC-MS, $t_r$ = 15.11 (Method Y)
446. 6-amino-N-(3-(benzo[d]isothiazol-3-ylamino)propyl)benzofuran-2-carboxamide
MW = 366 confirmed by LC-MS, $t_r$ = 8.76 (Method Y)

TABLE 4-continued

447. N-(3-(benzo[d]isothiazol-3-ylamino)propyl)-6-(3-(dimethylamino)propylamino)picolinamide
MW = 413 confirmed by LC-MS, $t_r$ = 2.10 (Method B)
448. N-(3-(benzo[d]isothiazol-3-ylamino)propyl)-6-(butylamino)picolinamide
MW = 384 confirmed by LC-MS, $t_r$ = 4.05 (Method B)
449. N-(3-(benzo[d]isothiazol-3-ylamino)propyl)-1H-benzo[d]imidazole-5-carboxamide
MW = 351 confirmed by LC-MS, $t_r$ = 2.20 (Method B)
450. N-(3-(benzo[d]isothiazol-3-ylamino)propyl)-1H-indole-5-carboxamide
MW = 350 confirmed by LC-MS, $t_r$ = 3.29 (Method B)
451. N-(3-(benzo[d]isothiazol-3-ylamino)propyl)-6-hydroxynicotinamide
MW = 328 confirmed by LC-MS, $t_r$ = 2.45 (Method B)
452. N-(3-(benzo[d]isothiazol-3-ylamino)propyl)-5-chloro-6-hydroxynicotinamide
MW = 363 confirmed by LC-MS, $t_r$ = 2.69 (Method B)
453. N-(3-(benzo[d]isothiazol-3-ylamino)propyl)-5-pentanamidobenzofuran-2-carboxamide
MW = 451 confirmed by LC-MS, $t_r$ = 13.01 (Method Y)
454. N-(3-(benzo[d]isothiazol-3-ylamino)propyl)-5-butyramidobenzofuran-2-carboxamide
MW = 437 confirmed by LC-MS, $t_r$ = 12.15 (Method Y)
455. N-(3-(benzo[d]isothiazol-3-ylamino)propyl)-5-(3-propylureido)benzofuran-2-carboxamide
MW = 452 confirmed by LC-MS, $t_r$ = 3.80 (Method B)
456. N-(3-(benzo[d]isothiazol-3-ylamino)propyl)-5-pentanamidobenzo[b]thiophene-2-carboxamide
MW = 467 confirmed by LC-MS, $t_r$ = 13.61 (Method Y)
457. N-(3-(benzo[d]isothiazol-3-ylamino)propyl)-5-butyramidobenzo[b]thiophene-2-carboxamide
MW = 453 confirmed by LC-MS, $t_r$ = 12.75 (Method Y)
458. N-(3-(benzo[d]isothiazol-3-ylamino)propyl)-5-(3-propylureido)benzo[b]thiophene-2-carboxamide
MW = 468 confirmed by LC-MS, $t_r$ = 12.35 (Method Y)
459. 5-amino-N-(3-(benzo[d]isothiazol-3-ylamino)propyl)benzo[b]thiophene-2-carboxamide
MW = 383 confirmed by LC-MS, $t_r$ = 10.03 (Method Y)
461. N-(3-(7-chlorobenzo[d]isothiazol-3-ylamino)propyl)-4'-methoxybiphenyl-4-carboxamide
MW.=452 confirmed by LC-MS, $t_r$ = 15.80 (Method Y)
462. N-(3-(benzo[d]isothiazol-3-ylamino)propyl)-5-(4-chlorophenyl)furan-2-carboxamide
MW = 412 confirmed by LC-MS, $t_r$ = 8.53 (Method D)
463. N-(3-(benzo[d]isothiazol-3-ylamino)propyl)-5-(2,4-dichlorophenyl)furan-2-carboxamide
MW = 446 confirmed by LC-MS, $t_r$ = 9.35 (Method D)
464. N-(3-(benzo[d]isothiazol-3-ylamino)propyl)-5-(4-methoxyphenyl)furan-2-carboxamide
MW = 407 confirmed by LC-MS, $t_r$ = 4.09 (Method B)
465. N-(3-(benzo[d]isothiazol-3-ylamino)propyl)-3-(4-methoxyphenyl)-1H-pyrazole-5-carboxamide
MW = 408 confirmed by LC-MS, $t_r$ = 3.56 (Method B)
466. N-(3-(benzo[d]isothiazol-3-ylamino)propyl)-5-(2-nitrophenyl)furan-2-carboxamide
MW = 422 confirmed by LC-MS, $t_r$ = 3.94 (Method B)
467. N-(3-(benzo[d]isothiazol-3-ylamino)propyl)-5-(3-nitrophenyl)furan-2-carboxamide
MW = 422 confirmed by LC-MS, $t_r$ = 7.78 (Method D)
468. N-(3-(benzo[d]isothiazol-3-ylamino)propyl)-5-(4-nitrophenyl)furan-2-carboxamide
MW = 422 confirmed by LC-MS, $t_r$ = 7.83 (Method D)
469. N-(3-(benzo[d]isothiazol-3-ylamino)propyl)-5-(2-(trifluoromethyl)phenyl)furan-2-carboxamide
MW = 445 confirmed by LC-MS, $t_r$ = 8.33 (Method D)
470. N-(3-(benzo[d]isothiazol-3-ylamino)propyl)-5-(3-(trifluoromethyl)phenyl)furan-2-carboxamide
MW = 445 confirmed by LC-MS, $t_r$ = 8.57 (Method D)
471. 4'-methoxy-N-(3-(6-(trifluoromethyl)benzo[d]isothiazol-3-ylamino)propyl)biphenyl-4-carboxamide
MW = 486 confirmed by LC-MS, $t_r$ = 8.93 (Method D)
472. $N^1$-((4'-methoxybiphenyl-4-yl)methyl)-$N^3$-(6-(trifluoromethyl)benzo[d]isothiazol-3-yl)propane-1,3-diamine
MW = 472 confirmed by LC-MS, $t_r$ = 3.23 (Method B)
475. $N^1$-(5-methoxybenzo[d]isothiazol-3-yl)-$N^3$-((4'-methoxybiphenyl-4-yl)methyl)propane-1,3-diamine
MW = 434 confirmed by LC-MS, $t_r$ = 7.38 (Method D)
476. 4'-methoxy-N-(3-(5-methoxybenzo[d]isothiazol-3-ylamino)propyl)biphenyl-4-carboxamide
MW = 448 confirmed by LC-MS, $t_r$ = 4.24 (Method B)
477. $N^1$-(7-chlorobenzo[d]isothiazol-3-yl)-$N^3$-((4'-methoxybiphenyl-4-yl)methyl)propane-1,3-diamine
MW = 438 confirmed by LC-MS, $t_r$ = 5.55 (Method D)
478. $N^1$-((4'-methoxybiphenyl-4-yl)methyl)-$N^3$-(5-(trifluoromethyl)benzo[d]isothiazol-3-yl)propane-1,3-diamine
MW = 472 confirmed by LC-MS, $t_r$ = 5.63 (Method D)
479. $N^1$-(benzo[d]isothiazol-3-yl)-$N^3$-((5-(2-chlorophenyl)furan-2-yl)methyl)propane-1,3-diamine
MW = 398 confirmed by LC-MS, $t_r$ = 7.89 (Method D)
480. $N^1$-(benzo[d]isothiazol-3-yl)-$N^3$-((5-(4-chlorophenyl)furan-2-yl)methyl)propane-1,3-diamine
MW = 398 confirmed by LC-MS, $t_r$ = 7.94 (Method D)
481. $N^1$-(2,2'-bithiophen-5-ylmethyl)-$N^3$-(benzo[d]isothiazol-3-yl)propane-1,3-diamine
MW = 386 confirmed by LC-MS, $t_r$ = 7.51 (Method D)
482. $N^1$-(benzo[d]isothiazol-3-yl)-$N^3$-((5-(3-(trifluoromethyl)phenyl)furan-2-yl)methyl)propane-1,3-diamine
MW = 431 confirmed by LC-MS, $t_r$ = 8.13 (Method D)
483. N-(3-(4-chlorobenzo[d]isothiazol-3-ylamino)propyl)-4'-methoxybiphenyl-4-carboxamide
MW = 452 confirmed by LC-MS, $t_r$ = 8.84 (Method D)
484. $N^1$-(4-chlorobenzo[d]isothiazol-3-yl)-$N^3$-((4'-methoxybiphenyl-4-yl)methyl)propane-1,3-diamine
MW = 438 confirmed by LC-MS, $t_r$ = 7.98 (Method D)

TABLE 4-continued

485. N-(3-(benzo[d]isothiazol-3-ylamino)propyl)-5-bromothiophene-2-carboxamide
MW = 396 confirmed by LC-MS, $t_r$ = 3.98 (Method B)
486. N-(3-(benzo[d]isothiazol-3-ylamino)propyl)-5-phenylthiophene-2-carboxamide
MW = 394 confirmed by LC-MS, $t_r$ = 8.04 (Method D)
487. N-(3-(benzo[d]isothiazol-3-ylamino)propyl)-5-(3-(trifluoromethyl)phenyl)thiophene-2-carboxamide
MW = 462 confirmed by LC-MS, $t_r$ = 8.69 (Method D)
488. N-(3-(benzo[d]isothiazol-3-ylamino)propyl)-5-(4-(trifluoromethyl)phenyl)thiophene-2-carboxamide
MW = 462 confirmed by LC-MS, $t_r$ = 8.74 (Method D)
489. N-(3-(benzo[d]isothiazol-3-ylamino)propyl)-5-(4-(methylsulfonyl)phenyl)thiophene-2-carboxamide
MW = 472 confirmed by LC-MS, $t_r$ = 6.78 (Method D)
490. N-(3-(benzo[d]isothiazol-3-ylamino)propyl)-5-(3-chlorophenyl)thiophene-2-carboxamide
MW = 428 confirmed by LC-MS, $t_r$ = 8.66 (Method D)
491. N-(3-(benzo[d]isothiazol-3-ylamino)propyl)-5-(3-cyanophenyl)thiophene-2-carboxamide
MW = 419 confirmed by LC-MS, $t_r$ = 7.66 (Method D)
492. N-(3-(benzo[d]isothiazol-3-ylamino)propyl)-5-(4-methoxyphenyl)thiophene-2-carboxamide
MW = 424 confirmed by LC-MS, $t_r$ = 7.96 (Method D)
493. $N^1$-(benzo[d]isothiazol-3-yl)-$N^3$-((4'-methoxybiphenyl-4-yl)methyl)-$N^3$-methylpropane-1,3-diamine
MW = 418 confirmed by LC-MS, $t_r$ = 11.22 (Method Y)
494. $N^1$-(5-chlorobenzo[d]isothiazol-3-yl)-$N^3$-((4'-methoxybiphenyl-4-yl)methyl)propane-1,3-diamine
MW = 438 confirmed by LC-MS, $t_r$ = 11.14 (Method Y)
495. N-(3-(benzo[d]isothiazol-3-ylamino)propyl)-5-(pyridin-3-yl)thiophene-2-carboxamide
MW = 395 confirmed by LC-MS, $t_r$ = 4.76 (Method D)
496. N-(3-(benzo[d]isothiazol-3-ylamino)propyl)-5-nitrothiophene-2-carboxamide
MW = 362 confirmed by LC-MS, $t_r$ = 12.84 (Method Y)
497. N-(3-(benzo[d]isothiazol-3-ylamino)propyl)-4-bromothiophene-2-carboxamide
MW = 396 confirmed by LC-MS, $t_r$ = 13.34 (Method Y)
498. N-(3-(7-fluorobenzo[d]isothiazol-3-ylamino)propyl)-4'-methoxybiphenyl-4-carboxamide
MW = 436 confirmed by LC-MS, $t_r$ = 7.11 (Method D)
499. $N^1$-(7-fluorobenzo[d]isothiazol-3-yl)-$N^3$-((4'-methoxybiphenyl-4-yl)methyl)propane-1,3-diamine
MW = 422 confirmed by LC-MS, $t_r$ = 3.96 (Method D)
500. 5-amino-N-(3-(benzo[d]isothiazol-3-ylamino)propyl)thiophene-2-carboxamide
MW = 332 confirmed by LC-MS, $t_r$ = 10.31 (Method Y)
501. $N^1$-(5,6-dimethoxybenzo[d]isothiazol-3-yl)-$N^3$-((4'-methoxybiphenyl-4-yl)methyl)propane-1,3-diamine
MW = 464 confirmed by LC-MS, $t_r$ = 4.43 (Method B)
502. N-(3-(5,6-dimethoxybenzo[d]isothiazol-3-ylamino)propyl)-4'-methoxybiphenyl-4-carboxamide
MW = 478 confirmed by LC-MS, $t_r$ = 4.13 (Method B)
503. 4'-methoxy-N-(3-(4-(trifluoromethyl)benzo[d]isothiazol-3-ylamino)propyl)biphenyl-4-carboxamide
MW = 486 confirmed by LC-MS, $t_r$ = 6.83 (Method D)
504. $N^1$-((4'-methoxybiphenyl-4-yl)methyl)-$N^3$-(4-(trifluoromethyl)benzo[d]isothiazol-3-yl)propane-1,3-diamine
MW = 472 confirmed by LC-MS, $t_r$ = 5.09 (Method D)
505. $N^1$-(4-methoxybenzo[d]isothiazol-3-yl)-$N^3$-((4'-methoxybiphenyl-4-yl)methyl)propane-1,3-diamine
MW = 434 confirmed by LC-MS, $t_r$ = 5.18 (Method D)
506. N-(3-(benzo[d]isothiazol-3-ylamino)propyl)-2-(4-bromophenyl)acetamide
MW = 404 confirmed by LC-MS, $t_r$ = 13.25 (Method Y)
507. N-(3-(benzo[d]isothiazol-3-ylamino)propyl)-2-(4'-methoxybiphenyl-4-yl)acetamide
MW = 432 confirmed by LC-MS, $t_r$ = 6.53 (Method D)
508. N-(3-(benzo[d]isothiazol-3-ylamino)propyl)-2-(4'-(trifluoromethyl)biphenyl-4-yl)acetamide
MW = 470 confirmed by LC-MS, $t_r$ = 7.36 (Method D)
509. 3-(3-aminopropylamino)-N-tert-butylbenzo[d]isothiazole-4-sulfonamide
MW = 343 confirmed by LC-MS, $t_r$ = 8.22 (Method Y)
510. 3-(3-aminopropylamino)-N-tert-butylbenzo[d]isothiazole-7-sulfonamide
MW = 343 confirmed by LC-MS, $t_r$ = 7.85 (Method Y)
511. 3-(3-aminopropylamino)-N-tert-butylbenzo[d]isothiazole-6-sulfonamide
MW = 343 confirmed by LC-MS, $t_r$ = 8.14 (Method Y)
512. N-(3-(4-(N-tert-butylsulfamoyl)benzo[d]isothiazol-3-ylamino)propyl)-4-iodobenzamide
MW = 573 confirmed by LC-MS, $t_r$ = 13.81 (Method Y)
513. N-(3-(7-(N-tert-butylsulfamoyl)benzo[d]isothiazol-3-ylamino)propyl)-4-iodobenzamide
MW = 573 confirmed by LC-MS, $t_r$ = 13.92 (Method Y)
514. N-(3-(6-(N-tert-butylsulfamoyl)benzo[d]isothiazol-3-ylamino)propyl)-4-iodobenzamide
MW = 573 confirmed by LC-MS, $t_r$ = 14.28 (Method Y)
515. N-(3-(5-bromobenzo[d]isothiazol-3-ylamino)propyl)-4'-methoxybiphenyl-4-carboxamide
MW = 496 confirmed by LC-MS, $t_r$ = 15.71 (Method Y)
516. N-(3-(benzo[d]isothiazol-3-ylamino)propyl)-N-((4'-methoxybiphenyl-4-yl)methyl)acetamide
MW = 446 confirmed by LC-MS, $t_r$ = 15.14 (Method Y)
517. N-(3-(benzo[d]isothiazol-3-ylamino)propyl)-N-((4'-methoxybiphenyl-4-yl)methyl)-5-((3aS,4S,6aR)-2-oxo-hexahydro-1H-thieno[3,4-d]imidazol-4-yl)pentanamide
MW = 630 confirmed by LC-MS, $t_r$ = 13.83 (Method Y)

TABLE 4-continued 518. 4'-methoxy-N-(3-(5-(N-(4-methoxybenzyl)sulfamoyl)benzo[d]isothiazol-3-ylamino)propyl)biphenyl-4-carboxamide
MW = 617 confirmed by LC-MS, $t_r$ = 13.65 (Method Y)
519. 4'-methoxy-N-(3-(5-(N-methylsulfamoyl)benzo[d]isothiazol-3-ylamino)propyl)biphenyl-4-carboxamide
MW = 511 confirmed by LC-MS, $t_r$ = 12.04 (Method Y)
520. 5-bromo-N-(3-(5-(N-phenylsulfamoyl)benzo[d]isothiazol-3-ylamino)propyl)thiophene-2-carboxamide
MW = 551 confirmed by LC-MS, $t_r$ = 12.97 (Method Y)
521. 4-iodo-N-(3-(5-(N-phenylsulfamoyl)benzo[d]isothiazol-3-ylamino)propyl)benzamide
MW = 593 confirmed by LC-MS, $t_r$ = 13.16 (Method Y)
522. 5-chloro-N-(3-(5-(N-phenylsulfamoyl)benzo[d]isothiazol-3-ylamino)propyl)thiophene-2-carboxamide
MW = 507 confirmed by LC-MS, $t_r$ = 12.71 (Method Y)
523. 4'-methoxy-N-(3-(5-(N-phenylsulfamoyl)benzo[d]isothiazol-3-ylamino)propyl)biphenyl-4-carboxamide
MW = 573 confirmed by LC-MS, $t_r$ = 13.62 (Method Y)
524. N-(3-(isothiazolo[5,4-b]pyridin-3-ylamino)propyl)-2-methoxybenzamide
MW = 342 confirmed by LC-MS, $t_r$ = 10.37 (Method Y)
525. N-(3-(isothiazolo[5,4-b]pyridin-3-ylamino)propyl)-4-methoxybenzamide
MW = 342 confirmed by LC-MS, $t_r$ = 10.82 (Method Y)
526. N-(3-(isothiazolo[5,4-b]pyridin-3-ylamino)propyl)-3,5-dimethoxybenzamide
MW = 372 confirmed by LC-MS, $t_r$ = 10.80 (Method Y)
527. N-(3-(isothiazolo[5,4-b]pyridin-3-ylamino)propyl)-2-(trifluoromethoxy)benzamide
MW = 396 confirmed by LC-MS, $t_r$ = 11.87 (Method Y)
528. N-(3-(isothiazolo[5,4-b]pyridin-3-ylamino)propyl)-3-methoxybenzamide
MW = 342 confirmed by LC-MS, $t_r$ = 10.62 (Method Y)
529. 2-fluoro-N-(3-(isothiazolo[5,4-b]pyridin-3-ylamino)propyl)-6-(trifluoromethyl)benzamide
MW = 398 confirmed by LC-MS, $t_r$ = 11.30 (Method Y)
530. N-(3-(isothiazolo[5,4-b]pyridin-3-ylamino)propyl)-3-(trifluoromethoxy)benzamide
MW = 396 confirmed by LC-MS, $t_r$ = 3.91 (Method E)
531. 2-chloro-N-(3-(isothiazolo[5,4-b]pyridin-3-ylamino)propyl)nicotinamide
MW = 348 confirmed by LC-MS, $t_r$ = 2.89 (Method E)
532. 6-chloro-N-(3-(isothiazolo[5,4-b]pyridin-3-ylamino)propyl)nicotinamide
MW = 348 confirmed by LC-MS, $t_r$ = 2.55 (Method E)
533. 4-hexyl-N-(3-(isothiazolo[5,4-b]pyridin-3-ylamino)propyl)benzamide
MW = 397 confirmed by LC-MS, $t_r$ = 5.06 (Method E)
534. N-(3-(isothiazolo[5,4-b]pyridin-3-ylamino)propyl)-2,3-dihydrobenzo[b][1,4]dioxine-2-carboxamide
MW = 370 confirmed by LC-MS, $t_r$ = 11.39 (Method Y)
535. 3-(2-chloro-6-fluorophenyl)-N-(3-(isothiazolo[5,4-b]pyridin-3-ylamino)propyl)-5-methylisoxazole-4-carboxamide
MW = 446 confirmed by LC-MS, $t_r$ = 12.02 (Method Y)
536. N-(3-(isothiazolo[5,4-b]pyridin-3-ylamino)propyl)-1-(4-(trifluoromethyl)pyrimidin-2-yl)piperidine-4-carboxamide
MW = 466 confirmed by LC-MS, $t_r$ = 12.44 (Method Y)
537. N-(3-(isothiazolo[5,4-b]pyridin-3-ylamino)propyl)benzofuran-2-carboxamide
MW = 352 confirmed by LC-MS, $t_r$ = 11.34 (Method Y)
538. N-(3-(isothiazolo[5,4-b]pyridin-3-ylamino)propyl)-4-(methylsulfonyl)benzamide
MW = 390 confirmed by LC-MS, $t_r$ = 2.56 (Method E)
539. N-(3-(isothiazolo[5,4-b]pyridin-3-ylamino)propyl)-2-(trifluoromethyl)benzenesulfonamide
MW = 416 confirmed by LC-MS, $t_r$ = 3.78 (Method E)
540. 3-iodo-N-(3-(isothiazolo[5,4-b]pyridin-3-ylamino)propyl)benzamide
MW = 438 confirmed by LC-MS, $t_r$ = 13.21 (Method Y)
541. N-(3-(isothiazolo[5,4-b]pyridin-3-ylamino)propyl)-3-(naphthalen-2-yl)benzamide
MW = 439 confirmed by LC-MS, $t_r$ = 14.88 (Method Y)
542. N-(3-(isothiazolo[5,4-b]pyridin-3-ylamino)propyl)-3',4'-dimethylbiphenyl-3-carboxamide
MW = 417 confirmed by LC-MS, $t_r$ = 13.99 (Method Y)
543. 2,6-dichloro-N-(3-(isothiazolo[5,4-b]pyridin-3-ylamino)propyl)benzamide
MW = 381 confirmed by LC-MS, $t_r$ = 14.05 (Method Y)
544. N-(3-(isothiazolo[5,4-b]pyridin-3-ylamino)propyl)-6-methyl-4-oxo-4H-chromene-2-carboxamide
MW = 394 confirmed by LC-MS, $t_r$ = 12.82 (Method Y)
545. 4-hexyl-N-(3-(isothiazolo[4,5-b]pyridin-3-ylamino)propyl)benzamide
MW = 397 confirmed by LC-MS, $t_r$ = 14.58 (Method Y)
546. N-(3-(isothiazolo[4,5-b]pyridin-3-ylamino)propyl)-3-(trifluoromethyl)benzenesulfonamide
MW = 416 confirmed by LC-MS, $t_r$ = 11.38 (Method Y)
547. 3-iodo-N-(3-(isothiazolo[4,5-b]pyridin-3-ylamino)propyl)benzamide
MW = 438 confirmed by LC-MS, $t_r$ = 13.18 (Method Y)
548. N-(3-(4-methylbenzo[d]isothiazol-3-ylamino)propyl)-3-(trifluoromethyl)benzenesulfonamide
MW = 429 confirmed by LC-MS, $t_r$ = 3.92 (Method E)
549. $N^1$-(isothiazolo[4,5-b]pyridin-3-yl)-$N^3$-((4'-methoxybiphenyl-4-yl)methyl)propane-1,3-diamine
MW = 410 confirmed by LC-MS, $t_r$ = 6.10 (Method E)
550. N-(3-(isothiazolo[4,5-b]pyridin-3-ylamino)propyl)-N-((4'-methoxybiphenyl-4-yl)methyl)-1,2-dimethyl-1H-imidazole-4-sulfonamide
MW = 452 confirmed by LC-MS, $t_r$ = 16.36 (Method Y)
551. methyl 5-(N-(3-(isothiazolo[4,5-b]pyridin-3-ylamino)propyl)-N-((4'-methoxybiphenyl-4-yl)methyl)sulfamoyl)-1-methyl-1H-pyrrole-2-carboxylate
MW = 430 confirmed by LC-MS, $t_r$ = 15.98 (Method Y)

TABLE 4-continued 552. 2-cyano-N-(3-(isothiazolo[4,5-b]pyridin-3-ylamino)propyl)-N-((4'-methoxybiphenyl-4-yl)methyl)acetamide
MW = 472 confirmed by LC-MS, $t_r$ = 4.51 (Method E)
553. $N^1$-(isothiazolo[5,4-b]pyridin-3-yl)-$N^3$-((4'-methoxybiphenyl-4-yl)methyl)propane-1,3-diamine
MW = 405 confirmed by LC-MS, $t_r$ = 9.08 (Method Y)
554. N-(3-(isothiazolo[5,4-b]pyridin-3-ylamino)propyl)-N-((4'-methoxybiphenyl-4-yl)methyl)-1,2-dimethyl-1H-imidazole-4-sulfonamide
MW = 563 confirmed by LC-MS, $t_r$ = 4.31 (Method E)
555. methyl 5-(N-(3-(isothiazolo[5,4-b]pyridin-3-ylamino)propyl)-N-((4'-methoxybiphenyl-4-yl)methyl)sulfamoyl)-1-methyl-1H-pyrrole-2-carboxylate
MW = 606 confirmed by LC-MS, $t_r$ = 5.05 (Method E)
556. 2-cyano-N-(3-(isothiazolo[5,4-b]pyridin-3-ylamino)propyl)-N-((4'-methoxybiphenyl-4-yl)methyl)acetamide
MW = 472 confirmed by LC-MS, $t_r$ = 4.31 (Method E)

Assays for Modulation of HCV Replication

One measure of inhibition is $K_i$. For compounds with $IC_{50}$'s less than 1 μM, the $K_i$ or $K_d$ is defined as the dissociation rate constant for the interaction of the agent with an HCV gene product. Exemplary compositions have $K_i$'s of, for example, less than about 100 μM, less than about 10 μM, less than about 1 μM, and further for example having $K_i$'s of less than about 100 nM, and still further, for example, less than about 10 nM. The $K_i$ for a compound is determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + K_d) - \sqrt{(E_0 + I_0 + K_d)^2 - 4E_0 I_0}}{2E_0}\right]$$

where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

The compounds of the invention are potent inhibitors of HCV replication and/or proliferation. The activity of the compounds of the invention can be confirmed in in vitro assays suitable for measuring inhibition of viral replication or proliferation. Such assays are well-known in the art. A specific example of a replicon assay suitable for confirming the activity of specific compounds is provided in the Examples section. Alternatively, the activity of the compounds can be confirmed using semi-quantitative Western blot assays utilizing antibodies specific for HCV proteins. Another assay that can be used to confirm the anti-HCV properties of the various compounds of the invention is described in Fournier et al., 1998; J. Gen. Virol. 79(10):2367-2374, the disclosure of which is incorporated by reference. According to this method, HCV-infected hepatocytes can be tested in the presence and absence of a specified test compound and the $IC_{50}$ of the compound determined.

Generally, active compounds are those that exhibit an $IC_{50}$ (e.g., concentration of compound that yields a 50% reduction in replication or a 50% reduction in the amount of measured HCV protein) in the particular assay in the range of about 1 mM or less. Compounds which exhibit an $IC_{50}$, for example, in the range of about 100 μM, 10 μM, 1 μM, 100 nM, 10 nM, 1 nM, or even lower, are particularly useful for as therapeutics or prophylactics to treat or prevent HCV infections. Alternatively, active compounds are those which exhibit an $EC_{50}$ (i.e., the effective concentration of compound that causes 50% reduction of HCV replication) in the range of about 1 mM or less. Compounds which exhibit a lower $EC_{50}$, for example, in the range of about 100 μM, 10 μM, 1 μM, 100 nM, 10 nM, 1 nM, or even lower, are particularly useful for as therapeutics or prophylactics to treat or prevent HCV infections.

Particular Uses and Administration

Owing to their ability to inhibit HCV replication, and/or proliferation, the compounds of the invention and/or compositions thereof can be used in a variety of contexts. For example, the compounds of the invention can be used as controls in in vitro assays to identify additional more or less potent anti HCV compounds. As another example, the compounds of the invention and/or compositions thereof can be used as preservatives or disinfectants in clinical settings to prevent medical instruments and supplies from becoming infected with HCV virus. When used in this context, the compound of the invention and/or composition thereof may be applied to the instrument to be disinfected at a concentration that is a multiple, for example 1x, 2x, 3x, 4x, 5x or even higher, of the measured $IC_{50}$ for the compound.

The compounds of the invention and/or compositions thereof find particular use in the treatment and/or prevention of HCV infections in animals and humans. When used in this context, the compounds may be administered per se, but are typically formulated and administered in the form of a pharmaceutical composition. The exact composition needed will depend upon, among other things, the method of administration and will apparent to those of skill in the art. A wide variety of suitable pharmaceutical compositions are described, for example, in Remington's Pharmaceutical Sciences, 20th ed., 2000.

Formulations suitable for oral administration can consist of (a) liquid solutions, such as an effective amount of the active compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation (aqueous suspensions, dry powders). Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials. Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of HCV infection, the compounds utilized in the pharmaceutical method of the invention are administered to patients diagnosed with HCV infection at dosage levels suitable to achieve therapeutic benefit. By therapeutic benefit is meant that the administration of compound leads to a beneficial effect in the patient over time. For example, therapeutic benefit is achieved when the HCV titer or load in the patient is either reduced or stops increasing. Therapeutic benefit is also achieved if the administration of compound slows or halts altogether the onset of the organ damage or other adverse symptoms that typically accompany HCV infections, regardless of the HCV titer or load in the patient.

The compounds of the invention and/or compositions thereof may also be administered prophylactically in patients that are at risk of developing HCV infection, or who have been exposed to HCV, to prevent the development of HCV infection. For example, the compounds of the invention and/or compositions thereof may be administered to hospital workers accidentally stuck with needles while working with HCV patients to lower the risk of, or avoid altogether, developing an HCV infection.

Initial dosages suitable for administration to humans may be determined from in vitro assays or animal models. For example, an initial dosage may be formulated to achieve a serum concentration that includes the $IC_{50}$ of the particular compound being administered, as measured in an in vitro assay. Alternatively, an initial dosage for humans may be based upon dosages found to be effective in animal models of HCV infection, as is well-known in the art. Exemplary suitable model systems are described in Muchmore, 2001, Immumol. Rev. 183:86-93 and Lanford & Bigger, 2002, Virology 293(i): 1-9 and the references cited therein, the disclosure of which are incorporated herein by reference. As one example, the initial dosage may be in the range of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can also be used. The dosages, however, may be varied depending upon the requirements of the patient, the severity of the condition being treated, and the compound being employed. The size of the dose also will be determined by the existence, nature, and extent of any adverse side-effects that accompany the administration of a particular compound in a particular patient. Determination of the proper dosage for a particular situation is within the skill of the practitioner. Generally, the antiviral treatment is initiated with dosages which are 1×, 2×, or 3× of $EC_{90}$ (i.e. the effective concentration of the compound that reduces HCV replication in cells by 90%) of the compound. Thereafter, the dosage is increased by small increments until the optimum effect under circumstances is reached. For convenience, the total daily dosage may be divided and administered in portions during the day, if desired. The duration of the treatment ranges from weeks to years, depending on the time the sustained virological response is established in the treated subjects.

Combination Therapy

In certain embodiments of the present invention, the compounds of the invention and/or compositions thereof can be used in combination therapy with at least one other therapeutic agent. A compound of the invention and/or composition thereof and the therapeutic agent can act additively or, more preferably, synergistically. In a preferred embodiment, a compound of the invention and/or a composition thereof is administered concurrently with the administration of another therapeutic agent. In another embodiment, a compound of the invention and/or composition thereof is administered prior or subsequent to administration of another therapeutic agent.

In one embodiment, the compounds of the invention and/or compositions thereof can be used in combination therapy with other antiviral agents. In an embodiment, the compounds of the invention and/or compositions thereof can be used in combination therapy with interferon-α. In another embodiment, the compounds of the invention and/or compositions thereof can be used in combination therapy with ribavarin. In another embodiment, the compounds of the invention and/or compositions thereof can be used in combination therapy with ribavarin and interferon-α. In yet another embodiment, the compounds of the invention and/or compositions thereof can be used in combination therapy with PEG-interferon-α. In another embodiment, the compounds of the invention and/ or compositions thereof can be used in combination therapy with PEG-interferon-α and ribavarin.

Inhibition of HCV Translation or Replication

The inhibitory activity of certain exemplary compounds of the invention was confirmed using an HCV replicon assay. The HCV replicon can include such features as the HCV IRES, the HCV 3' untranslated region, selected HCV genes encoding HCV polypeptides, selectable markers, and a reporter gene such as luciferase, GFP, etc. In the assay, actively dividing replicon-comprising cells were seeded at a density of between about 5,000 and 7,500 cells/well onto 96 well plates (about 90 μl of cells per well) and incubated at 37° C. and 5% $CO_2$ for 24 hours. Then, the test compound (in a volume of about 10 μL) was added at various concentrations to each well and the cells were incubated for an additional 24-48 hours. The cells were harvested, and HCV replication or translation was monitored via a reporter assay, e.g., a luciferase reporter assay. The media was aspirated from each cell and Bright-Glo (Pharmacia, Peapack, N.J.) luciferase assay reagents were added to each well according to the manufacturer's instructions. In this assay, the amount of test compound that yielded a 50% reduction in luciferase activity ($IC_{50}$) was determined.

Certain exemplary compounds of the invention were also tested for their ability to inhibit HCV replication using a semi-quantitative Western blot analysis with antibodies specific for certain HCV proteins. In this assay, the amount of test compound that yielded a 50% reduction in the amount of the specified HCV protein($IC_{50}$) was determined.

The results of the Replicon reporter and Western blot assays are provided in Tables 5 and 6, below. The structures of the indicated compounds are provided in Tables 2. In Tables 5 and 6, a value of "A" indicates an $IC_{50}$ of 5 μM or less in the specified assay; a value of "B" indicates an $IC_{50}$ of greater than 5 μM in the specified assay. A number of compounds exhibited $IC_{50}$'s in the Replicon assay of less than 1 μM.

TABLE 5

| Entry | Name | $IC_{50}$ |
|---|---|---|
| 1 | N-(2-(Benzo[d]isothiazole-(1,1-dioxo)-3-ylamino)ethylbenzamide | B |
| 11 | (S)-tert-Butyl 2-(2-(Benzo[d]isothiazol-3-ylamino)ethylamino)-2-oxo-1-phenylethylcarbamate | A |
| 12 | N-(2-(Benzo[d]isothiazol-3-ylamino)ethyl)-3-benzoylpicolinamide | A |
| 13 | N-(2-(Benzo[d]isothiazol-3-ylamino)ethyl)-6-methylpicolinamide | B |
| 14 | N-(2-(Benzo[d]isothiazol-3-ylamino)ethyl)-4-methoxybenzamide | A |
| 18 | (S)-tert-Butyl 1-(2-(Benzo[d]isothiazol-3-ylamino)ethylamino)-3-methyl-1-oxobutan-2-ylcarbamate | A |
| 24 | [N-(2-(Benzo[d]isothiazol-3-ylamino)ethyl)-aminosulfonyl]anisole | B |
| 25 | N-(2-(Benzo[d]isothiazol-3-ylamino)ethyl)picolinamide | A |
| 25 | N-(2-(Benzo[d]isothiazol-3-ylamino)ethyl)furan-2-carboxamide | B |
| 26 | tert-Butyl 3-(2-(Benzo[d]isothiazol-3-ylamino)ethylcarbamoyl) piperidine-1-carboxylate | B |
| 26 | $N^2$-(2-(Benzo[d]isothiazol-3-ylamino)ethyl)-N5-methylpyridine-2,5-dicarboxamide | A |
| 27 | N-(2-(Benzo[d]isothiazol-3-ylamino)ethyl)-6-bromopicolinamide | B |
| 27 | (S)-N-(2-(Benzo[d]isothiazol-3-ylamino)ethyl)-2-phenyl-2-(phenylsulfonamido)acetamide | B |
| 28 | (S)-2-Acetamido-N-(2-(benzo[d]isothiazol-3-ylamino)ethyl)-2-phenylacetamide | A |
| 29 | (S)-N-(2-(2-(Benzo[d]isothiazol-3-ylamino)ethylamino)-2-oxo-1-phenylethyl)picolinamide | A |
| 30 | (S)-N-(2-(2-(Benzo[d]isothiazol-3-ylamino)ethylamino)-2-oxo-1-phenylethyl)pivalamide | B |
| 31 | (S)-N-(2-(2-(Benzo[d]isothiazol-3-ylamino)ethylamino)-2-oxo-1-phenylethyl)-2,2,2-trifluoroacetamide | A |
| 32 | (S)-N-(2-(2-(Benzo[d]isothiazol-3-ylamino)ethylamino)-2-oxo-1-phenylethyl)-4-methoxybenzamide | A |
| 33 | N-(2-(Benzo[d]isothiazol-3-ylamino)ethyl)-3-chlorobenzamide | B |
| 33 | (S)-N-(2-(2-(Benzo[d]isothiazol-3-ylamino)ethylamino)-2-oxo-1-phenylethyl)butyramide | B |
| 34 | (S)-N-(2-(2-(Benzo[d]isothiazol-3-ylamino)ethylamino)-2-oxo-1-phenylethyl)furan-3-carboxamide | B |
| 35 | N-(2-(benzo[d]isothiazol-3-ylamino)ethyl)-4-butylbenzamide | A |
| 36 | N-(2-(Benzo[d]isothiazol-3-ylamino)ethyl)-2,3-dihydrobenzo[b][1,4]dioxine-2-carboxamide | A |
| 37 | N-(2-(2-(Benzo[d]isothiazol-3-ylamino)ethylamino)-2-oxoethyl)benzamide | A |
| 38 | N-(2-(Benzo[d]isothiazol-3-ylamino)ethyl)benzo[b]thiophene-2-carboxamide | B |
| 39 | N-(2-(Benzo[d]isothiazol-3-ylamino)ethyl)-4-(1H-pyrrol-1-yl)benzamide | A |
| 40 | N-(2-(Benzo[d]isothiazol-3-ylamino)ethyl)-5-methoxy-1H-indole-2-carboxamide | A |
| 41 | N-(2-(Benzo[d]isothiazol-3-ylamino)ethyl)-2,6-dichlorobenzamide | B |
| 41 | N-(2-(Benzo[d]isothiazol-3-ylamino)ethyl)-3H-benzo[d][1,2,3]triazole-5-carboxamide | B |
| 42 | N-(2-(Benzo[d]isothiazol-3-ylamino)ethyl)-2-methoxynicotinamide | A |
| 43 | N-(2-(Benzo[d]isothiazol-3-ylamino)ethyl)thiophene-2-carboxamide | A |
| 44 | tert-Butyl 2-(2-(Benzo[d]isothiazol-3-ylamino)ethylcarbamoyl)indoline-1-carboxylate | A |
| 45 | N-(2-(Benzo[d]isothiazol-3-ylamino)ethyl)-3-chloro-2-methylbenzamide | B |
| 46 | N-(2-(Benzo[d]isothiazol-3-ylamino)ethyl)pyrazine-2-carboxamide | B |
| 47 | N-(2-(Benzo[d]isothiazol-3-ylamino)ethyl)-4-methylnicotinamide | A |
| 48 | N-(2-(Benzo[d]isothiazol-3-ylamino)ethyl)quinoline-3-carboxamide | B |
| 49 | (R)-tert-Butyl 2-(2-(Benzo[d]isothiazol-3-ylamino)ethylamino)-2-oxo-1-phenylethylcarbamate | A |

TABLE 5-continued

| Entry | Name | IC$_{50}$ |
|---|---|---|
| 50 | (S)-tert-Butyl 1-(2-(Benzo[d]isothiazol-3-ylamino)ethylamino)-1-oxo-3-phenylpropan-2-ylcarbamate | B |
| 51 | (S)-tert-Butyl 1-(2-(Benzo[d]isothiazol-3-ylamino)ethylamino)-3-(4-hydroxyphenyl)-1-oxopropan-2-ylcarbamate | A |
| 52 | N-(2-(Benzo[d]isothiazol-3-ylamino)ethyl)-4-chloropicolinamide | A |
| 53 | 1-(2-(benzo[d]isothiazol-3-ylamino)ethyl)-3-(2,4-dichlorophenyl)urea | A |
| 54 | N-(2-(Benzo[d]isothiazol-3-ylamino)ethyl)quinoline-8-carboxamide | A |
| 55 | (R)-2-Amino-N-(2-(benzo[d]isothiazol-3-ylamino)ethyl)-2-phenylacetamide | B |
| 56 | N-(2-(Benzo[d]isothiazol-3-ylamino)ethyl)piperidine-4-carboxamide | B |
| 57 | N-(2-(Benzo[d]isothiazol-3-ylamino)ethyl)isoquinoline-1-carboxamide | A |
| 58 | N-(2-(Benzo[d]isothiazol-3-ylamino)ethyl)-4,5-dichloroisothiazole-3-carboxamide | B |
| 59 | (R)-Benzyl 1-(2-(Benzo[d]isothiazol-3-ylamino)ethylamino)-1-oxo-3-phenylpropan-2-ylcarbamate | A |
| 60 | (S)-N-(1-(2-(Benzo[d]isothiazol-3-ylamino)ethylamino)-1-oxo-3-phenylpropan-2-yl)benzamide | A |
| 61 | (S)-2-Acetamido-N-(2-(benzo[d]isothiazol-3-ylamino)ethyl)-3-phenylpropanamide | B |
| 62 | (S)-Benzyl 1-(2-(Benzo[d]isothiazol-3-ylamino)ethylamino)-1-oxo-3-phenylpropan-2-ylcarbamate | B |
| 63 | (S)-Benzyl 2-(2-(Benzo[d]isothiazol-3-ylamino)ethylamino)-2-oxo-1-phenylethylcarbamate | B |
| 64 | tert-Butyl 6-(2-(Benzo[d]isothiazol-3-ylamino)ethylcarbamoyl)pyridin-2-ylcarbamate | A |
| 65 | N-(2-(Benzo[d]isothiazol-3-ylamino)ethyl)-5-morpholinopicolinamide | B |
| 66 | 6-Amino-N-(2-(benzo[d]isothiazol-3-ylamino)ethyl)picolinamide | B |
| 67 | N-(2-(6-Nitrobenzo[d]isothiazol-3-ylamino)ethyl)picolinamide | B |
| 68 | N-(2-(6-Aminobenzo[d]isothiazol-3-ylamino)ethyl)picolinamide | B |
| 69 | N-(2-(6-Acetamidobenzo[d]isothiazol-3-ylamino)ethyl)picolinamide | B |
| 70 | N-(2-(Benzo[d]isothiazole-3-ylamino)ethyl-4-chlorobenzamide | A |
| 70 | N-(2-(Benzo[d]isothiazol-3-ylamino)ethyl)-5-fluoro-1H-indole-2-carboxamide | A |
| 71 | N-(2-(Benzo[d]isothiazol-3-ylamino)ethyl)-2-cyclopropylacetamide | B |
| 71 | N-(2-(Benzo[d]isothiazol-3-ylamino)ethyl)-5-chloro-1H-indole-2-carboxamide | A |
| 72 | N-(2-(Benzo[d]isothiazol-3-ylamino)ethyl)-5,6-dimethoxy-1H-indole-2-carboxamide | A |
| 73 | N-(2-(Benzo[d]isothiazol-3-ylamino)ethyl)piperidine-3-carboxamide | B |
| 73 | N-(2-(Benzo[d]isothiazol-3-ylamino)ethyl)-1H-indole-2-carboxamide | A |
| 74 | (S)-2-Amino-N-(2-(benzo[d]isothiazol-3-ylamino)ethyl)-2-phenylacetamide | B |
| 74 | N-(2-(Benzo[d]isothiazol-3-ylamino)ethyl)nicotinamide | B |
| 75 | (S)-2-Amino-N-(2-(benzo[d]isothiazol-3-ylamino)ethyl)-3-methylbutanamide | B |
| 75 | N-(2-(Benzo[d]isothiazol-3-ylamino)ethyl)-4-methylbenzamide | A |
| 76 | N-(2-(Benzo[d]isothiazol-3-ylamino)ethyl)-3-methylpicolinamide | A |
| 76 | N-(2-(Benzo[d]isothiazol-3-ylamino)ethyl)benzamide | B |
| 77 | Methyl 6-(2-(Benzo[d]isothiazol-3-ylamino)ethylcarbamoyl)nicotinate | B |
| 77 | N-(2-(Benzo[d]isothiazol-3-ylamino)ethyl)-2-phenoxypropanamide | B |
| 78 | 6-(2-(Benzo[d]isothiazol-3-ylamino)ethylcarbamoyl)nicotinic Acid | B |
| 78 | N-(2-(Benzo[d]isothiazol-3-ylamino)ethyl)-2-(4-methoxyphenyl)acetamide | B |
| 79 | N-(2-(Benzo[d]isothiazol-3-ylamino)ethyl)quinoline-2-carboxamide | B |
| 79 | N-(2-(Benzo[d]isothiazol-3-ylamino)ethyl)-2-(4-chlorophenyl)acetamide | A |
| 80 | Methyl 6-(2-(Benzo[d]isothiazol-3-ylamino)ethylcarbamoyl)picolinate | B |
| 80 | N-(2-(Benzo[d]isothiazol-3-ylamino)ethyl)-1H-indole-3-carboxamide | A |
| 81 | 6-(2-(Benzo[d]isothiazol-3-ylamino)ethylcarbamoyl)picolinic Acid | B |
| 81 | N-(2-(Benzo[d]isothiazole-(1,1-dioxo)-3-ylamino)ethyl-4-chlorobenzamide | B |
| 82 | N-(2-(Benzo[d]isothiazol-3-ylamino)ethyl)-2-(1H-indol-3-yl)acetamide | B |
| 82 | N-(2-(Benzo[d]isothiazol-3-ylamino)ethyl)-2,4-dichlorobenzamide | B |
| 83 | N-(2-(Benzo[d]isothiazol-3-ylamino)ethyl)benzofuran-2-carboxamide | A |
| 84 | N-(2-(Benzo[d]isothiazol-3-ylamino)ethyl)-4-methyl-5-phenylisoxazole-3-carboxamide | B |
| 85 | N-(2-(Benzo[d]isothiazol-3-ylamino)ethyl)-6,6-dimethyl-4-oxo-5,6-dihydro-4H-pyran-2-carboxamide | B |
| 86 | N-(2-(Benzo[d]isothiazol-3-ylamino)ethyl)-3,4-dimethoxybenzamide | B |
| 87 | N-(2-(Benzo[d]isothiazol-3-ylamino)ethyl)-3,5-dichlorobenzamide | B |
| 88 | N-(2-(benzo[d]isothiazol-3-ylamino)ethyl)benzo[d]oxazol-2-amine | A |
| 89 | N-(3-(Benzo[d]isothiazol-3-ylamino)propyl)-4-chlorobenzamide | A |
| 90 | N-(2-(Benzo[d]isothiazol-3-ylamino)ethyl)-1H-indazole-3-carboxamide | A |
| 91 | N-(3-(Benzo[d]isothiazol-3-ylamino)propyl)picolinamide | A |
| 92 | (S)-tert-Butyl 2-(3-(Benzo[d]isothiazol-3-ylamino)propylamino)-2-oxo-1-phenylethylcarbamate | A |
| 93 | 6-Acetamido-N-(2-(benzo[d]isothiazol-3-ylamino)ethyl)picolinamide | A |
| 94 | N-(2-(Benzo[d]isothiazol-3-ylamino)ethyl)imidazo[1,2-a]pyridine-2-carboxamide | A |
| 95 | N-(3-(benzo[d]isothiazol-3-ylamino)propyl)benzo[d]oxazol-2-amine | A |
| 96 | (S)-2-Amino-N-(3-(benzo[d]isothiazol-3-ylamino)propyl)-2-phenylacetamide | B |
| 97 | tert-Butyl 2-(2-(Benzo[d]isothiazol-3-ylamino)ethylcarbamoyl)pyrrolidine-1-carboxylate | B |
| 98 | tert-Butyl 2-(2-(Benzo[d]isothiazol-3-ylamino)ethylcarbamoyl)piperidine-1-carboxylate | B |
| 99 | 1-Acetyl-N-(2-(benzo[d]isothiazol-3-ylamino)ethyl)pyrrolidine-2-carboxamide | B |

TABLE 5-continued

| Entry | Name | IC$_{50}$ |
|---|---|---|
| 100 | N-(2-(Benzo[d]isothiazol-3-ylamino)ethyl)-1-picolinoylpyrrolidine-2-carboxamide | B |
| 101 | N-(2-(Benzo[d]isothiazol-3-ylamino)ethyl)-1-(3,5-dichlorobenzoyl)pyrrolidine-2-carboxamide | B |
| 102 | N-(2-(Benzo[d]isothiazol-3-ylamino)ethyl)-1-picolinoylpiperidine-2-carboxamide | A |
| 103 | N-(2-(Benzo[d]isothiazol-3-ylamino)ethyl)-1-(3,5-dichlorobenzoyl)piperidine-2-carboxamide | A |
| 104 | N-(2-(Benzo[d]isothiazol-3-ylamino)ethyl)-1-(3,5-dichlorobenzoyl)piperidine-3-carboxamide | A |
| 105 | N-(2-(Benzo[d]isothiazol-3-ylamino)ethyl)-5-nitropicolinamide | A |
| 106 | 1-Acetyl-N-(2-(benzo[d]isothiazol-3-ylamino)ethyl)piperidine-2-carboxamide | B |
| 107 | 1-Acetyl-N-(2-(benzo[d]isothiazol-3-ylamino)ethyl)piperidine-3-carboxamide | A |
| 108 | N-(2-(Benzo[d]isothiazol-3-ylamino)ethyl)-1-picolinoylpiperidine-3-carboxamide | A |
| 109 | 5-Amino-N-(2-(benzo[d]isothiazol-3-ylamino)ethyl)picolinamide | B |
| 110 | N-(2-(5-(trifluoromethyl)pyrimidin-2-ylamino)ethyl)benzo[d]isothiazol-3-amine | B |
| 111 | N-(2-(Benzo[d]isothiazol-3-ylamino)ethyl)-1-(2-(2,2,2-trifluoroacetyl)-1,2,3,4-tetrahydroisoquinolin-7-ylsulfonyl)piperidine-3-carboxamide | A |
| 112 | (Benzo[d]isothiazol-3-ylamino)ethyl)-[2-benzoyl-3-(pyrimidin-2-yl)]guanidine | B |
| 113 | (2-(benzo[d]isothiazol-3-ylamino)ethyl)-3-(pyrimidin-2-yl)guanidine | A |
| 220 | N-(3-(benzo[d]isothiazol-3-ylamino)propyl)-3-methoxybenzenesulfonamide | A |
| 221 | N-(3-(benzo[d]isothiazol-3-ylamino)propyl)-4-bromo-2,5-difluorobenzenesulfonamide | A |
| 222 | N-(3-(benzo[d]isothiazol-3-ylamino)propyl)-5-bromothiophene-2-sulfonamide | A |
| 223 | N-(3-(benzo[d]isothiazol-3-ylamino)propyl)-4-(4-chlorophenoxy)benzenesulfonamide | A |
| 224 | 6-(3-(benzo[d]isothiazol-3-ylamino)propylamino)nicotinonitrile | A |
| 225 | methyl 2-(3-(benzo[d]isothiazol-3-ylamino)propylamino)-4-(trifluoromethyl)pyrimidine-5-carboxylate | A |
| 226 | N$^1$-(benzo[d]isothiazol-3-yl)-N$^3$-(5-chloropyridin-2-yl)propane-1,3-diamine | A |
| 227 | N$^1$-(benzo[d]isothiazol-3-yl)-N$^3$-(4-methylpyridin-2-yl)propane-1,3-diamine | A |
| 228 | N$^1$-(benzo[d]isothiazol-3-yl)-N$^3$-(5-(trifluoromethyl)pyridin-2-yl)propane-1,3-diamine | A |
| 229 | 2-(3-(benzo[d]isothiazol-3-ylamino)propylamino)isonicotinonitrile | A |
| 230 | N$^1$-(benzo[d]isothiazol-3-yl)-N$^3$-(6-chloropyridin-2-yl)propane-1,3-diamine | A |
| 231 | N$^1$-(benzo[d]isothiazol-3-yl)-N$^3$-(4-(trifluoromethyl)pyridin-2-yl)propane-1,3-diamine | A |
| 232 | N-(3-(benzo[d]isothiazol-3-ylamino)propyl)-3-(2-hydroxy-3-morpholinopropoxy)benzamide | A |
| 233 | N-(3-(benzo[d]isothiazol-3-ylamino)propyl)-3-(2-hydroxy-3-(4-(3-methoxyphenyl)piperazin-1-yl)propoxy)benzamide | A |
| 234 | N-(3-(benzo[d]isothiazol-3-ylamino)propyl)-4-fluorobenzamide | A |
| 235 | N-(3-(benzo[d]isothiazol-3-ylamino)propyl)-4-(pyridin-4-ylmethoxy)benzamide | A |
| 236 | N-(3-(benzo[d]isothiazol-3-ylamino)propyl)-4-(3-methoxybenzyloxy)benzamide | A |
| 237 | N-(3-(benzo[d]isothiazol-3-ylamino)propyl)-4-(3,4-dimethoxybenzyloxy)benzamide | A |
| 238 | 2-(4-(3-(benzo[d]isothiazol-3-ylamino)propylcarbamoyl)phenoxy)acetic acid | B |
| 239 | tert-butyl 2-(4-(3-(benzo[d]isothiazol-3-ylamino)propylcarbamoyl)phenoxy)acetate | A |
| 240 | N-(3-(benzo[d]isothiazol-3-ylamino)propyl)-N-methyl-2-(trifluoromethyl)benzenesulfonamide | A |
| 241 | N$^1$-(isothiazolo[5,4-b]pyrazin-3-yl)-N$^3$-((4'-methoxybiphenyl-4-yl)methyl)propane-1,3-diamine | A |
| 242 | N-(3-(benzo[d]isothiazol-3-ylamino)propyl)-3-nitrobenzenesulfonamide | A |
| 243 | methyl 2-(N-(3-(benzo[d]isothiazol-3-ylamino)propyl)sulfamoyl)benzoate | A |
| 244 | methyl 5-(N-(3-(benzo[d]isothiazol-3-ylamino)propyl)sulfamoyl)furan-2-carboxylate | A |
| 245 | N-(3-(benzo[d]isothiazol-3-ylamino)propyl)-4-(trifluoromethyl)benzenesulfonamide | A |
| 246 | N-(3-(benzo[d]isothiazol-3-ylamino)propyl)-3,5-bis(trifluoromethyl)benzenesulfonamide | A |
| 247 | N-(5-(N-(3-(benzo[d]isothiazol-3-ylamino)propyl)sulfamoyl)-4-methylthiazol-2-yl)acetamide | A |
| 248 | N-(3-(benzo[d]isothiazol-3-ylamino)propyl)-1,2-dimethyl-1H-imidazole-4-sulfonamide | A |
| 249 | N-(3-(benzo[d]isothiazol-3-ylamino)propyl)quinoline-8-sulfonamide | A |
| 250 | N-(3-(benzo[d]isothiazol-3-ylamino)propyl)-2,3,4-trifluorobenzenesulfonamide | A |
| 251 | N-(3-(benzo[d]isothiazol-3-ylamino)propyl)-4-methoxybenzenesulfonamide | A |
| 252 | N-(3-(benzo[d]isothiazol-3-ylamino)propyl)-2-(2,2,2-trifluoroacetyl)-1,2,3,4-tetrahydroisoquinoline-7-sulfonamide | A |
| 253 | N-(3-(benzo[d]isothiazol-3-ylamino)propyl)-2-bromo-4,6-difluorobenzenesulfonamide | A |
| 254 | N-(3-(benzo[d]isothiazol-3-ylamino)propyl)-N-benzyl-2-(trifluoromethyl)benzenesulfonamide | A |
| 255 | N-(3-(benzo[d]isothiazol-3-ylamino)propyl)-N-((4'-methoxybiphenyl-4-yl)methyl)-2-morpholinoacetamide | A |
| 256 | N-(3-(benzo[d]isothiazol-3-ylamino)propyl)-N-((4'-methoxybiphenyl-4-yl)methyl)-2-(4-phenylpiperazin-1-yl)acetamide | A |

TABLE 5-continued

| Entry | Name | IC$_{50}$ |
|---|---|---|
| 257 | N-(3-(benzo[d]isothiazol-3-ylamino)propyl)-2-(isopropylamino)-N-((4'-methoxybiphenyl-4-yl)methyl)acetamide | A |
| 258 | 4-((3-(benzo[d]isothiazol-3-ylamino)propylamino)methyl)-N-(4-methoxyphenyl)benzenesulfonamide | A |
| 259 | N$^1$-(benzo[d]isothiazol-3-yl)-N$^3$-(4-(morpholinosulfonyl)benzyl)propane-1,3-diamine | B |
| 260 | N$^1$-(benzo[d]isothiazol-3-yl)-N$^3$-(4-(pyrrolidin-1-ylsulfonyl)benzyl)propane-1,3-diamine | B |
| 261 | N-(3-(benzo[d]isothiazol-3-ylamino)propyl)-2,5-dimethoxybenzenesulfonamide | A |
| 262 | N-(3-(benzo[d]isothiazol-3-ylamino)propyl)-4-bromo-2-chlorobenzenesulfonamide | A |
| 263 | N-(3-(benzo[d]isothiazol-3-ylamino)propyl)-4-bromo-2-(trifluoromethyl)benzenesulfonamide | A |
| 264 | N-(3-(benzo[d]isothiazol-3-ylamino)propyl)-3,4-dimethoxybenzenesulfonamide | A |
| 265 | N-(3-(benzo[d]isothiazol-3-ylamino)propyl)-4-bromo-3-methylbenzenesulfonamide | A |
| 266 | N-(3-(benzo[d]isothiazol-3-ylamino)propyl)-3-(trifluoromethoxy)benzenesulfonamide | A |
| 267 | N-(3-(benzo[d]isothiazol-3-ylamino)propyl)-4-bromo-2,6-dichlorobenzenesulfonamide | A |
| 268 | N-(3-(benzo[d]isothiazol-3-ylamino)propyl)-3-bromobenzenesulfonamide | A |
| 269 | N-(3-(benzo[d]isothiazol-3-ylamino)propyl)-4-bromo-3-(trifluoromethyl)benzenesulfonamide | A |
| 270 | N-(3-(benzo[d]isothiazol-3-ylamino)propyl)-N-((4'-methoxybiphenyl-4-yl)methyl)-2-(trifluoromethyl)benzenesulfonamide | A |
| 271 | N-(2-(benzo[d]isothiazol-3-ylamino)ethyl)-4-chlorobenzenesulfonamide | A, B |
| 272 | N$^1$-(benzo[d]isothiazol-3-yl)-N$^2$-(pyridin-2-ylmethyl)ethane-1,2-diamine | A, B |
| 273 | N-(3-(benzo[d]isothiazol-3-ylamino)propyl)-4-propylbenzamide | A |
| 274 | N-(3-(benzo[d]isothiazol-3-ylamino)propyl)-4-hexylbenzamide | A |
| 275 | N$^1$-(benzo[d]isothiazol-3-yl)-N$^3$-(3-methoxypyridin-2-yl)propane-1,3-diamine | A |
| 276 | N$^1$-(benzo[d]isothiazol-3-yl)-N$^3$-(3-(trifluoromethyl)pyridin-2-yl)propane-1,3-diamine | A |
| 277 | 2-(3-(benzo[d]isothiazol-3-ylamino)propylamino)nicotinonitrile | A |
| 278 | N$^1$-(benzo[d]isothiazol-3-yl)-N$^3$-(3-methylpyridin-2-yl)propane-1,3-diamine | A |
| 279 | N-(2-(benzo[d]isothiazol-3-ylamino)ethyl)-5-butylpicolinamide | A |
| 280 | 3-(benzo[d]isothiazol-3-ylamino)-2-(4-butylbenzamido)propanoic acid | B |
| 281 | N$^1$-(benzo[d]isothiazol-3-yl)-N$^3$-(6-methylpyridin-2-yl)propane-1,3-diamine | A |
| 282 | N$^1$-(benzo[d]isothiazol-3-yl)-N$^3$-(5-methoxypyridin-2-yl)propane-1,3-diamine | A |
| 283 | N$^1$-(benzo[d]isothiazol-3-yl)-N$^3$-(6-methoxypyridin-2-yl)propane-1,3-diamine | A |
| 284 | methyl 6-(3-(benzo[d]isothiazol-3-ylamino)propylamino)-4-(trifluoromethyl)nicotinate | A |
| 285 | N-(3-(benzo[d]isothiazol-3-ylamino)propyl)-3-butoxy-4-methoxybenzamide | |
| 286 | N-(3-(benzo[d]isothiazol-3-ylamino)propyl)-3-(cyclopentyloxy)-4-methoxybenzamide | A |
| 287 | N$^1$-(benzo[d]isothiazol-3-yl)-N$^3$-(4-bromobenzyl)propane-1,3-diamine | A |
| 288 | N$^1$-(benzo[d]isothiazol-3-yl)-N$^3$-(4-butylbenzyl)propane-1,3-diamine | A |
| 289 | N-(3-(benzo[d]isothiazol-3-ylamino)propyl)-4-bromobenzamide | A |
| 290 | N-(3-(benzo[d]isothiazol-3-ylamino)propyl)-4-(propylamino)benzamide | A |
| 291 | N$^1$-(benzo[d]isothiazol-3-yl)-N$^3$-((4'-methoxybiphenyl-4-yl)methyl)propane-1,3-diamine | A |
| 292 | N$^1$-(benzo[d]isothiazol-3-yl)-N$^3$-((3',4'-dimethoxybiphenyl-4-yl)methyl)propane-1,3-diamine | A |
| 293 | N-(3-(benzo[d]isothiazol-3-ylamino)propyl)-N-(4-butylbenzyl)picolinamide | A |
| 294 | N$^1$-(benzo[d]isothiazol-3-yl)-N$^3$-((5'-chloro-2'-methoxybiphenyl-4-yl)methyl)propane-1,3-diamine | A |
| 295 | N$^1$-(benzo[d]isothiazol-3-yl)-N$^3$-(4-butylphenyl)propane-1,3-diamine | A |
| 296 | N-(3-(benzo[d]isothiazol-3-ylamino)propyl)-4-(4-ethylpiperazin-1-yl)benzamide | A |
| 297 | N-(3-(benzo[d]isothiazol-3-ylamino)propyl)-4-(pyridin-2-ylmethylamino)benzamide | A |
| 298 | N-(3-(benzo[d]isothiazol-3-ylamino)propyl)-4-(isopropylamino)benzamide | A |
| 299 | N$^1$-(benzo[d]isothiazol-3-yl)-N$^3$-(3-bromobenzyl)propane-1,3-diamine | A |
| 300 | N$^1$-(benzo[d]isothiazol-3-yl)-N$^3$-((4'-methoxybiphenyl-3-yl)methyl)propane-1,3-diamine | A |
| 301 | N$^1$-(benzo[d]isothiazol-3-yl)-N$^3$-((4',5'-dimethoxybiphenyl-3-yl)methyl)propane-1,3-diamine | A |
| 302 | N$^1$-(benzo[d]isothiazol-3-yl)-N$^3$-((3'-chloro-6'-methoxybiphenyl-3-yl)methyl)propane-1,3-diamine | A |
| 303 | 2-((3-(benzo[d]isothiazol-3-ylamino)propylamino)methyl)-4-bromophenol | A |
| 304 | 5-((3-(benzo[d]isothiazol-3-ylamino)propylamino)methyl)-2-methoxyphenol | A |
| 305 | 3-butoxy-N-(2-(5-chlorobenzo[d]isothiazol-3-ylamino)ethyl)-4-methoxybenzamide | A |
| 306 | N$^1$-(benzo[d]isothiazol-3-yl)-N$^3$-(1-benzylpiperidin-3-yl)propane-1,3-diamine | A |
| 307 | tert-butyl 4-(3-(benzo[d]isothiazol-3-ylamino)propylamino)piperidine-1-carboxylate | A |
| 308 | N$^1$-(benzo[d]isothiazol-3-yl)-N$^3$-(pyridin-3-ylmethyl)propane-1,3-diamine | B |
| 309 | N$^1$-(benzo[d]isothiazol-3-yl)-N$^3$-(pyridin-2-ylmethyl)propane-1,3-diamine | B |

TABLE 5-continued

| Entry | Name | IC$_{50}$ |
|---|---|---|
| 310 | 3-butoxy-4-methoxy-N-(2-(5-(propylamino)benzo[d]isothiazol-3-ylamino)ethyl)benzamide | A |
| 311 | 5-((benzo[d]isothiazol-3-ylamino)methyl)-3-(4-iodophenyl)imidazolidine-2,4-dione | B |
| 312 | N$^1$-(benzo[d]isothiazol-3-yl)-N$^3$-((4'-methoxybiphenyl-2-yl)methyl)propane-1,3-diamine | A |
| 313 | N$^1$-(benzo[d]isothiazol-3-yl)-N$^3$-((3',4'-dimethoxybiphenyl-2-yl)methyl)propane-1,3-diamine | A |
| 314 | N-(3-(benzo[d]isothiazol-3-ylamino)propyl)-N-((4'-methoxybiphenyl-4-yl)methyl)morpholine-4-carboxamide | A |
| 315 | 1-(3-(benzo[d]isothiazol-3-ylamino)propyl)-1-((4'-methoxybiphenyl-4-yl)methyl)-3,3-dimethylurea | A |
| 316 | N-(3-(benzo[d]isothiazol-3-ylamino)propyl)-N-((4'-methoxybiphenyl-4-yl)methyl)-1,2-dimethyl-1H-imidazole-4-sulfonamide | A |
| 317 | methyl 5-(N-(3-(benzo[d]isothiazol-3-ylamino)propyl)-N-((4'-methoxybiphenyl-4-yl)methyl)sulfamoyl)-1-methyl-1H-pyrrole-2-carboxylate | A |
| 318 | tert-butyl 2-(2-((3-(benzo[d]isothiazol-3-ylamino)propyl)((4'-methoxybiphenyl-4-yl)methyl)amino)-2-oxoethyl)pyrrolidine-1-carboxylate | A |
| 319 | N-(3-(benzo[d]isothiazol-3-ylamino)propyl)-2-cyano-N-((4'-methoxybiphenyl-4-yl)methyl)acetamide | A |
| 320 | N-(3-(benzo[d]isothiazol-3-ylamino)propyl)-N-((4'-methoxybiphenyl-4-yl)methyl)-2-(pyrrolidin-2-yl)acetamide | A |
| 321 | 4-butyl-N-{3-[(1-oxido-1,2-benzisothiazol-3-yl)amino]propyl}benzamide | B |
| 322 | 4-butyl-N-{3-[(1,1-dioxido-1,2-benzisothiazol-3-yl)amino]propyl}benzamide | B |
| 323 | N-[(4'-methoxybiphenyl-4-yl)methyl]-N'-(1-oxido-1,2-benzisothiazol-3-yl)propane-1,3-diamine | A |
| 324 | N-(1,1-dioxido-1,2-benzisothiazol-3-yl)-N'-[(4'-methoxybiphenyl-4-yl)methyl]propane-1,3-diamine | B |
| 325 | N-(3-(benzo[d]isothiazol-3-ylamino)propyl)-4-iodobenzenesulfonamide | A |
| 326 | N$^1$-(benzo[d]isothiazol-3-yl)-N$^3$-(2-(trifluoromethyl)benzyl)propane-1,3-diamine | A |
| 327 | N$^1$-(benzo[d]isothiazol-3-yl)-N$^3$-(2-(benzyloxy)-4,5-dimethoxybenzyl)propane-1,3-diamine | A |
| 328 | N$^1$-(benzo[d]isothiazol-3-yl)-N$^3$-(3-(benzyloxy)benzyl)propane-1,3-diamine | A |
| 329 | N$^1$-(benzo[d]isothiazol-3-yl)-N$^3$-((2-phenyl-1H-imidazol-4-yl)methyl)propane-1,3-diamine | A |
| 330 | N$^1$-(benzo[d]isothiazol-3-yl)-N$^3$-((2-phenyl-1H-indol-3-yl)methyl)propane-1,3-diamine | A |
| 331 | N-(3-(benzo[d]isothiazol-3-ylamino)propyl)-4'-methoxybiphenyl-4-sulfonamide | A |
| 332 | N-(3-(benzo[d]isothiazol-3-ylamino)propyl)-3',4'-dimethoxybiphenyl-4-sulfonamide | A |
| 333 | N-(3-(benzo[d]isothiazol-3-ylamino)propyl)-4'-(trifluoromethoxy)biphenyl-4-sulfonamide | A |
| 334 | methyl 4'-(N-(3-(benzo[d]isothiazol-3-ylamino)propyl)sulfamoyl)biphenyl-4-carboxylate | A |
| 335 | N-(3-(benzo[d]isothiazol-3-ylamino)propyl)-2'-(trifluoromethyl)biphenyl-4-sulfonamide | A |
| 336 | N$^1$-(benzo[d]isothiazol-3-yl)-N$^3$-((4'-(trifluoromethoxy)biphenyl-4-yl)methyl)propane-1,3-diamine | A |
| 337 | N$^1$-(benzo[d]isothiazol-3-yl)-N$^3$-(benzofuran-2-ylmethyl)propane-1,3-diamine | A |
| 338 | N$^1$-(benzo[d]isothiazol-3-yl)-N$^3$-(4-(pyrrolidin-1-yl)benzyl)propane-1,3-diamine | A |
| 339 | N-(3-(benzo[d]isothiazol-3-ylamino)propyl)-N-((4'-methoxybiphenyl-4-yl)methyl)-2-(methylsulfonyl)acetamide | A |
| 340 | N-{3-[(1,1-dioxido-1,2-benzisothiazol-3-yl)amino]propyl}-N-[(4'-methoxybiphenyl-4-yl)methyl]-1,2-dimethyl-1H-imidazole-4-sulfonamide | B |
| 341 | N-(3-(benzo[d]isothiazol-3-ylamino)propyl)-2-(1H-imidazol-1-yl)-N-((4'-methoxybiphenyl-4-yl)methyl)acetamide | A |
| 342 | N-(3-(benzo[d]isothiazol-3-ylamino)propyl)-N-((4'-methoxybiphenyl-4-yl)methyl)picolinamide | A |
| 343 | N$^1$-(benzo[d]isothiazol-3-yl)-N$^3$-(3-methoxybenzyl)propane-1,3-diamine | A |
| 344 | N-(3-(benzo[d]isothiazol-3-yl(methyl)amino)propyl)-3-methoxy-N-methylbenzenesulfonamide | B |
| 345 | N-(3-(benzo[d]isothiazol-3-yl(methyl)amino)propyl)-N-methyl-2-(trifluoromethyl)benzenesulfonamide | B |
| 346 | 1-(4-((3-(benzo[d]isothiazol-3-ylamino)propylamino)methyl)phenyl)pyrrolidin-2-one | B |
| 347 | N$^1$-(benzo[d]isothiazol-3-yl)-N$^3$-((4'-methoxybiphenyl-4-yl)methyl)-N$^1$,N$^3$-dimethylpropane-1,3-diamine | B |
| 348 | (R)-N-(2-(2-(benzo[d]isothiazol-3-ylamino)ethylamino)-2-oxo-1-phenylethyl)-4-chlorobenzamide | A |
| 349 | N-(2-(benzo[d]isothiazol-3-ylamino)ethyl)-2,4-difluorobenzamide | A |
| 350 | N-(2-(benzo[d]isothiazol-3-ylamino)ethyl)-2,5-difluorobenzamide | A |
| 351 | N-(2-(benzo[d]isothiazol-3-ylamino)ethyl)-2-(trifluoromethyl)benzamide | A |
| 352 | N-(2-(benzo[d]isothiazol-3-ylamino)ethyl)-5-fluoro-2-(trifluoromethyl)benzamide | B |
| 353 | N-(2-(benzo[d]isothiazol-3-ylamino)ethyl)-3-fluoro-5-(trifluoromethyl)benzamide | A |

TABLE 5-continued

| Entry | Name | IC$_{50}$ |
|---|---|---|
| 354 | N-(2-(benzo[d]isothiazol-3-ylamino)ethyl)-2-fluoro-4-(trifluoromethyl)benzamide | A |
| 355 | N-(2-(benzo[d]isothiazol-3-ylamino)ethyl)-3-fluoro-4-(trifluoromethyl)benzamide | A |
| 356 | N-(2-(benzo[d]isothiazol-3-ylamino)ethyl)-2,4-bis(trifluoromethyl)benzamide | A |
| 357 | N-(2-(benzo[d]isothiazol-3-ylamino)ethyl)-2,5-bis(trifluoromethyl)benzamide | A |
| 358 | N-(2-(benzo[d]isothiazol-3-ylamino)ethyl)-2-fluoro-6-(trifluoromethyl)benzamide | B |
| 359 | N-(2-(benzo[d]isothiazol-3-ylamino)ethyl)-3,4-difluorobenzamide | A, B |
| 360 | N-(2-(benzo[d]isothiazol-3-ylamino)ethyl)-4'-methoxybiphenyl-4-carboxamide | A |
| 361 | N-(2-(benzo[d]isothiazol-3-ylamino)ethyl)-3',4'-dimethoxybiphenyl-4-carboxamide | A |
| 362 | N-(2-(benzo[d]isothiazol-3-ylamino)ethyl)-5'-chloro-2'-methoxybiphenyl-4-carboxamide | A |
| 363 | N-(2-(benzo[d]isothiazol-3-ylamino)ethyl)-2'-isopropoxy-5'-methylbiphenyl-4-carboxamide | A |
| 364 | N-(2-(benzo[d]isothiazol-3-ylamino)ethyl)-2',3'-dimethoxybiphenyl-4-carboxamide | A |
| 365 | N-(2-(benzo[d]isothiazol-3-ylamino)ethyl)-2'-methoxy-5'-methylbiphenyl-4-carboxamide | A |
| 366 | N-(2-(benzo[d]isothiazol-3-ylamino)ethyl)-4'-methoxy-2'-methylbiphenyl-4-carboxamide | A |
| 367 | N-(2-(benzo[d]isothiazol-3-ylamino)ethyl)-5'-fluoro-2'-propoxybiphenyl-4-carboxamide | A |
| 368 | N-(3-(benzo[d]isothiazol-3-ylamino)propyl)-4'-fluoro-6'-methoxybiphenyl-3-carboxamide | A |
| 369 | N-(3-(benzo[d]isothiazol-3-ylamino)propyl)-5',6'-dimethoxybiphenyl-3-carboxamide | A |
| 370 | N-(2-(benzo[d]isothiazol-3-ylamino)ethyl)-3',4'-dimethoxybiphenyl-3-carboxamide | A |
| 371 | N-(2-(benzo[d]isothiazol-3-ylamino)ethyl)-4'-methoxybiphenyl-3-carboxamide | A |
| 372 | N-(2-(benzo[d]isothiazol-3-ylamino)ethyl)-3',4'-dimethylbiphenyl-3-carboxamide | A |
| 373 | N-(2-(benzo[d]isothiazol-3-ylamino)ethyl)-3-(naphthalen-2-yl)benzamide | A |
| 374 | N-(2-(benzo[d]isothiazol-3-ylamino)ethyl)-3-(quinolin-8-yl)benzamide | A |
| 375 | N-(2-(benzo[d]isothiazol-3-ylamino)ethyl)-3-(quinolin-3-yl)benzamide | A |
| 376 | N-(3-(benzo[d]isothiazol-3-ylamino)propyl)-6'-isopropoxybiphenyl-3-carboxamide | A |
| 377 | N-(2-(benzo[d]isothiazol-3-ylamino)ethyl)-2'-isopropoxybiphenyl-4-carboxamide | A |
| 378 | N-(3-(benzo[d]isothiazol-3-ylamino)propyl)-4'-methoxybiphenyl-3-carboxamide | A |
| 379 | 1-(3-(benzo[d]isothiazol-3-ylamino)propyl)-3-(4-butylphenyl)urea | A |
| 380 | N-(3-(benzo[d]isothiazol-3-ylamino)propyl)-3-(6-chloropyridin-3-yl)benzamide | A |
| 381 | N-(3-(benzo[d]isothiazol-3-ylamino)propyl)-3'-ethoxy-6'-methylbiphenyl-3-carboxamide | A |
| 382 | N-(3-(benzo[d]isothiazol-3-ylamino)propyl)-3',6'-dimethoxybiphenyl-3-carboxamide | A |
| 383 | N-(3-(benzo[d]isothiazol-3-ylamino)propyl)-4'-fluoro-6'-propoxybiphenyl-3-carboxaimde | A |
| 384 | N-(3-(benzo[d]isothiazol-3-ylamino)propyl)-6'-methoxybiphenyl-3-carboxamide | A |
| 385 | N-(2-(benzo[d]isothiazol-3-ylamino)ethyl)-2'-hydroxybiphenyl-4-carboxamide | A |
| 386 | N-(3-(benzo[d]isothiazol-3-ylamino)propyl)-3-iodobenzamide | A |
| 387 | 1-(3-(benzo[d]isothiazol-3-ylamino)propyl)-3-(4-iodophenyl)urea | A |
| 388 | N-(3-(benzo[d]isothiazol-3-ylamino)propyl)-3-(6-methoxypyridin-3-yl)benzamide | A |
| 389 | 1-(3-(benzo[d]isothiazol-3-ylamino)propyl)-3-(2'-isopropoxybiphenyl-4-yl)urea | A |
| 390 | tert-butyl 4-(3-(3-(benzo[d]isothiazol-3-ylamino)propylcarbamoyl)phenyl)-5,6-dihydropyridine-1(2H)-carboxylate | A |
| 391 | N-(3-(benzo[d]isothiazol-3-ylamino)propyl)-3,5-diethoxybenzamide | A |
| 392 | 1-(3-(benzo[d]isothiazol-3-ylamino)propyl)-3-(2'-isopropoxy-5'-methylbiphenyl-4-yl)urea | A |
| 393 | 1-(3-(benzo[d]isothiazol-3-ylamino)propyl)-3-(4'-fluoro-2'-methoxybiphenyl-4-yl)urea | A |
| 394 | N-(3-(benzo[d]isothiazol-3-ylamino)propyl)-3-(1,2,3,6-tetrahydropyridin-4-yl)benzamide | A |
| 395 | 1-(3-(benzo[d]isothiazol-3-ylamino)propyl)-3-(2'-methoxybiphenyl-4-yl)urea | A |
| 396 | N-(3-(benzo[d]isothiazol-3-ylamino)propyl)-3-bromo-4-hydroxybenzamide | A |
| 397 | N-(3-(benzo[d]isothiazol-3-ylamino)propyl)-3-bromo-4-(2-morpholinoethoxy)benzamide | A |
| 398 | N-(3-(4-(N-tert-butylsulfamoyl)benzo[d]isothiazol-3-ylamino)propyl)-4'-methoxybiphenyl-4-carboxamide | B |
| 399 | N-(3-(6-(N-tert-butylsulfamoyl)benzo[d]isothiazol-3-ylamino)propyl)-4'-methoxybiphenyl-4-carboxamide | B |
| 400 | N-(3-(7-(tert-butylsulfonyl)benzo[d]isothiazol-3-ylamino)propyl)-4'-methoxybiphenyl-4-carboxamide | A |
| 401 | 4'-methoxy-N-(3-(4-sulfamoylbenzo[d]isothiazol-3-ylamino)propyl)biphenyl-4-carboxamide | B |
| 402 | 4'-methoxy-N-(3-(6-sulfamoylbenzo[d]isothiazol-3-ylamino)propyl)biphenyl-4-carboxamide | A |

TABLE 5-continued

| Entry | Name | IC$_{50}$ |
|---|---|---|
| 403 | 4-butoxy-N-(3-(5-phenylbenzo[d]isothiazol-3-ylamino)propyl)benzamide | A |
| 404 | N$^1$-(5-bromobenzo[d]isothiazol-3-yl)-N$^3$-((4'-methoxybiphenyl-4-yl)methyl)propane-1,3-diamine | A |
| 405 | 4'-methoxy-N-(3-(5-phenylbenzo[d]isothiazol-3-ylamino)propyl)biphenyl-4-carboxamide | A |
| 406 | 4'-methoxy-N-(3-(5-(4-methoxyphenyl)benzo[d]isothiazol-3-ylamino)propyl)biphenyl-4-carboxamide | A |
| 407 | N-(3-(5-(2-fluoro-3-methoxyphenyl)benzo[d]isothiazol-3-ylamino)propyl)-4'-methoxybiphenyl-4-carboxamide | A |
| 408 | N-(3-(5-(3,5-difluorophenyl)benzo[d]isothiazol-3-ylamino)propyl)-4'-methoxybiphenyl-4-carboxamide | ND |
| 409 | N-(3-(5-(4-isopropoxyphenyl)benzo[d]isothiazol-3-ylamino)propyl)-4'-methoxybiphenyl-4-carboxamide | A |
| 410 | N$^1$-((4'-methoxybiphenyl-4-yl)methyl)-N$^3$-(5-(4-methoxyphenyl)benzo[d]isothiazol-3-yl)propane-1,3-diamine | A |
| 411 | N$^1$-(5-(3,5-difluorophenyl)benzo[d]isothiazol-3-yl)-N$^3$-((4'-methoxybiphenyl-4-yl)methyl)propane-1,3-diamine | A |
| 412 | N-(2-(benzo[d]isothiazol-3-ylamino)ethyl)-1-methyl-1H-indole-2-carboxamide | A |
| 413 | N-(2-(benzo[d]isothiazol-3-ylamino)ethyl)-3-phenyl-1H-pyrazole-5-carboxamide | B |
| 414 | N-(2-(benzo[d]isothiazol-3-ylamino)ethyl)-3-formylbenzamide | B |
| 415 | N-(2-(benzo[d]isothiazol-3-ylamino)ethyl)-4-formylbenzamide | B |
| 416 | N-(2-(benzo[d]isothiazol-3-ylamino)ethyl)-3-(hydroxymethyl)benzamide | B |
| 417 | N$^1$,N$^2$-di(benzo[d]isothiazol-3-yl)ethane-1,2-diamine | B |
| 418 | N$^1$-(2-(benzo[d]isothiazol-3-ylamino)ethyl)-N$^4$-propylterephthalamide | B |
| 419 | N-(3-(benzo[d]isothiazol-3-ylamino)propyl)-6-bromopicolinamide | A |
| 420 | N-(3-(benzo[d]isothiazol-3-ylamino)propyl)-6-fluoropicolinamide | B |
| 421 | 4-butyl-N-(2-(5-chlorobenzo[d]isothiazol-3-ylamino)ethyl)benzamide | A |
| 422 | N$^1$-(2-(benzo[d]isothiazol-3-ylamino)ethyl)-N$^4$-butylterephthalamide | A |
| 423 | N-(2-(5-chlorobenzo[d]isothiazol-3-ylamino)ethyl)-4-(pentyloxy)benzamide | A |
| 424 | tert-butyl 3-(2-(5-chlorobenzo[d]isothiazol-3-ylamino)ethylcarbamoyl)piperidine-1-carboxylate | A |
| 425 | (S)-tert-butyl 2-(2-(5-chlorobenzo[d]isothiazol-3-ylamino)ethylamino)-2-oxo-1-phenylethylcarbamate | A |
| 426 | N$^1$-(2-(benzo[d]isothiazol-3-ylamino)ethyl)-N$^4$-isopropylterephthalamide | A |
| 427 | N$^1$-(2-(benzo[d]isothiazol-3-ylamino)ethyl)-N$^4$-cyclopropylterephthalamide | A |
| 428 | N$^1$-(2-(benzo[d]isothiazol-3-ylamino)ethyl)-N$^3$-propylisophthalamide | A |
| 429 | N$^1$-(2-(benzo[d]isothiazol-3-ylamino)ethyl)-N$^3$-butylisophthalamide | A |
| 430 | N$^1$-(2-(benzo[d]isothiazol-3-ylamino)ethyl)-N$^3$-isopropylisophthalamide | A |
| 431 | N$^1$-(2-(benzo[d]isothiazol-3-ylamino)ethyl)-N$^3$-cyclopropylisophthalamide | A |
| 432 | N-(2-(5-chlorobenzo[d]isothiazol-3-ylamino)ethyl)-5-methoxy-1H-indole-2-carboxamide | A |
| 433 | N-(3-(benzo[d]isothiazol-3-ylamino)propyl)-6-nitrobenzo[b]thiophene-2-carboxamide | A |
| 434 | N$^1$,N$^3$-di(benzo[d]isothiazol-3-yl)propane-1,3-diamine | A |
| 435 | N-(3-(benzo[d]isothiazol-3-ylamino)propyl)-7-methoxybenzofuran-2-carboxamide | A |
| 436 | N-(3-(benzo[d]isothiazol-3-ylamino)propyl)-5-chlorobenzofuran-2-carboxamide | A |
| 437 | N-(3-(benzo[d]isothiazol-3-ylamino)propyl)-5-methoxybenzofuran-2-carboxamide | A |
| 438 | N-(3-(benzo[d]isothiazol-3-ylamino)propyl)-6-(2,4-dimethoxyphenyl)picolinamide | A |
| 439 | N-(3-(benzo[d]isothiazol-3-ylamino)propyl)-6-nitrobenzofuran-2-carboxamide | A |
| 440 | N-(3-(benzo[d]isothiazol-3-ylamino)propyl)-6-(4-(methylsulfonyl)phenyl)picolinamide | A |
| 441 | N-(2-(benzo[d]isothiazol-3-ylamino)ethyl)-4-(3-methyl-5-oxo-4,5-dihydropyrazol-1-yl)benzamide | B |
| 442 | N-(3-(benzo[d]isothiazol-3-ylamino)propyl)-6-(2-(pyridin-2-yl)ethylamino)picolinamide | A |
| 443 | N-(3-(benzo[d]isothiazol-3-ylamino)propyl)-6-bromonicotinamide | A |
| 444 | N-(3-(benzo[d]isothiazol-3-ylamino)propyl)-5-bromo-1H-indole-2-carboxamide | A |
| 445 | N-(3-(benzo[d]isothiazol-3-ylamino)propyl)-5-bromobenzo[b]thiophene-2-carboxamide | A |
| 446 | 6-amino-N-(3-(benzo[d]isothiazol-3-ylamino)propyl)benzofuran-2-carboxamide | A |
| 447 | N-(3-(benzo[d]isothiazol-3-ylamino)propyl)-6-(3-(dimethylamino)propylamino)picolinamide | A |
| 448 | N-(3-(benzo[d]isothiazol-3-ylamino)propyl)-6-(butylamino)picolinamide | B |
| 449 | N-(3-(benzo[d]isothiazol-3-ylamino)propyl)-1H-benzo[d]imidazole-5-carboxamide | B |
| 450 | N-(3-(benzo[d]isothiazol-3-ylamino)propyl)-1H-indole-5-carboxamide | A |
| 451 | N-(3-(benzo[d]isothiazol-3-ylamino)propyl)-6-hydroxynicotinamide | B |
| 452 | N-(3-(benzo[d]isothiazol-3-ylamino)propyl)-5-chloro-6-hydroxynicotinamide | B |
| 453 | N-(3-(benzo[d]isothiazol-3-ylamino)propyl)-5-pentanamidobenzofuran-2-carboxamide | A |
| 454 | N-(3-(benzo[d]isothiazol-3-ylamino)propyl)-5-butyramidobenzofuran-2-carboxamide | A |
| 455 | N-(3-(benzo[d]isothiazol-3-ylamino)propyl)-5-(3-propylureido)benzofuran-2-carboxamide | A |

TABLE 5-continued

| Entry | Name | IC$_{50}$ |
|---|---|---|
| 456 | N-(3-(benzo[d]isothiazol-3-ylamino)propyl)-5-pentanamidobenzo[b]thiophene-2-carboxamide | A |
| 457 | N-(3-(benzo[d]isothiazol-3-ylamino)propyl)-5-butyramidobenzo[b]thiophene-2-carboxamide | A |
| 458 | N-(3-(benzo[d]isothiazol-3-ylamino)propyl)-5-(3-propylureido)benzo[b]thiophene-2-carboxamide | B |
| 459 | 5-amino-N-(3-(benzo[d]isothiazol-3-ylamino)propyl)benzo[b]thiophene-2-carboxamide | A |
| 461 | N-(3-(benzo[d]isothiazol-3-ylamino)propyl)-5-(4-chlorophenyl)furan-2-carboxamide | A |
| 462 | N-(3-(benzo[d]isothiazol-3-ylamino)propyl)-5-(2,4-dichlorophenyl)furan-2-carboxamide | A |
| 463 | N-(3-(benzo[d]isothiazol-3-ylamino)propyl)-5-(4-methoxyphenyl)furan-2-carboxamide | A |
| 464 | N-(3-(benzo[d]isothiazol-3-ylamino)propyl)-3-(4-methoxyphenyl)-1H-pyrazole-5-carboxamide | A |
| 465 | N-(3-(benzo[d]isothiazol-3-ylamino)propyl)-5-(2-nitrophenyl)furan-2-carboxamide | A |
| 466 | N-(3-(benzo[d]isothiazol-3-ylamino)propyl)-5-(3-nitrophenyl)furan-2-carboxamide | A |
| 467 | N-(3-(benzo[d]isothiazol-3-ylamino)propyl)-5-(4-nitrophenyl)furan-2-carboxamide | A |
| 468 | N-(3-(benzo[d]isothiazol-3-ylamino)propyl)-5-(2-(trifluoromethyl)phenyl)furan-2-carboxamide | A |
| 469 | N-(3-(benzo[d]isothiazol-3-ylamino)propyl)-5-(3-(trifluoromethyl)phenyl)furan-2-carboxamide | A |
| 470 | 4'-methoxy-N-(3-(6-(trifluoromethyl)benzo[d]isothiazol-3-ylamino)propyl)biphenyl-4-carboxamide | A |
| 471 | $N^1$-((4'-methoxybiphenyl-4-yl)methyl)-$N^3$-(6-(trifluoromethyl)benzo[d]isothiazol-3-yl)propane-1,3-diamine | A |
| 472 | $N^1$-(5-methoxybenzo[d]isothiazol-3-yl)-$N^3$-((4'-methoxybiphenyl-4-yl)methyl)propane-1,3-diamine | A |
| 475 | $N^1$-((4'-methoxybiphenyl-4-yl)methyl)-$N^3$-(5-(trifluoromethyl)benzo[d]isothiazol-3-yl)propane-1,3-diamine | B |
| 476 | $N^1$-(benzo[d]isothiazol-3-yl)-$N^3$-((5-(2-chlorophenyl)furan-2-yl)methyl)propane-1,3-diamine | A |
| 477 | $N^1$-(benzo[d]isothiazol-3-yl)-$N^3$-((5-(4-chlorophenyl)furan-2-yl)methyl)propane-1,3-diamine | A |
| 478 | $N^1$-(2,2'-bithiophen-5-ylmethyl)-$N^3$-(benzo[d]isothiazol-3-yl)propane-1,3-diamine | A |
| 479 | $N^1$-(benzo[d]isothiazol-3-yl)-$N^3$-((5-(3-(trifluoromethyl)phenyl)furan-2-yl)methyl)propane-1,3-diamine | A |
| 480 | N-(3-(4-chlorobenzo[d]isothiazol-3-ylamino)propyl)-4'-methoxybiphenyl-4-carboxamide | B |
| 481 | $N^1$-(4-chlorobenzo[d]isothiazol-3-yl)-$N^3$-((4'-methoxybiphenyl-4-yl)methyl)propane-1,3-diamine | A |
| 482 | N-(3-(benzo[d]isothiazol-3-ylamino)propyl)-5-bromothiophene-2-carboxamide | A |
| 483 | N-(3-(benzo[d]isothiazol-3-ylamino)propyl)-5-phenylthiophene-2-carboxamide | A |
| 484 | N-(3-(benzo[d]isothiazol-3-ylamino)propyl)-5-(3-(trifluoromethyl)phenyl)thiophene-2-carboxamide | A |
| 485 | N-(3-(benzo[d]isothiazol-3-ylamino)propyl)-5-(4-(trifluoromethyl)phenyl)thiophene-2-carboxamide | A |
| 486 | N-(3-(benzo[d]isothiazol-3-ylamino)propyl)-5-(4-(methylsulfonyl)phenyl)thiophene-2-carboxamide | A |
| 487 | N-(3-(benzo[d]isothiazol-3-ylamino)propyl)-5-(3-chlorophenyl)thiophene-2-carboxamide | A |
| 488 | N-(3-(benzo[d]isothiazol-3-ylamino)propyl)-5-(3-cyanophenyl)thiophene-2-carboxamide | A |
| 489 | N-(3-(benzo[d]isothiazol-3-ylamino)propyl)-5-(4-methoxyphenyl)thiophene-2-carboxamide | A |
| 490 | $N^1$-(benzo[d]isothiazol-3-yl)-$N^3$-((4'-methoxybiphenyl-4-yl)methyl)-$N^3$-methylpropane-1,3-diamine | A |
| 491 | $N^1$-(5-chlorobenzo[d]isothiazol-3-yl)-$N^3$-((4'-methoxybiphenyl-4-yl)methyl)propane-1,3-diamine | A |
| 492 | N-(3-(benzo[d]isothiazol-3-ylamino)propyl)-5-(pyridin-3-yl)thiophene-2-carboxamide | A |
| 493 | N-(3-(benzo[d]isothiazol-3-ylamino)propyl)-5-nitrothiophene-2-carboxamide | A |
| 494 | N-(3-(benzo[d]isothiazol-3-ylamino)propyl)-4-bromothiophene-2-carboxamide | A |
| 495 | N-(3-(7-fluorobenzo[d]isothiazol-3-ylamino)propyl)-4'-methoxybiphenyl-4-carboxamide | B |
| 496 | $N^1$-(7-fluorobenzo[d]isothiazol-3-yl)-$N^3$-((4'-methoxybiphenyl-4-yl)methyl)propane-1,3-diamine | B |
| 497 | 5-amino-N-(3-(benzo[d]isothiazol-3-ylamino)propyl)thiophene-2-carboxamide | B |
| 498 | $N^1$-(5,6-dimethoxybenzo[d]isothiazol-3-yl)-$N^3$-((4'-methoxybiphenyl-4-yl)methyl)propane-1,3-diamine | A |
| 499 | N-(3-(5,6-dimethoxybenzo[d]isothiazol-3-ylamino)propyl)-4'-methoxybiphenyl-4-carboxamide | A |

TABLE 5-continued

| Entry | Name | IC$_{50}$ |
|---|---|---|
| 500 | 4'-methoxy-N-(3-(4-(trifluoromethyl)benzo[d]isothiazol-3-ylamino)propyl)biphenyl-4-carboxamide | B |
| 501 | N$^1$-((4'-methoxybiphenyl-4-yl)methyl)-N$^3$-(4-(trifluoromethyl)benzo[d]isothiazol-3-yl)propane-1,3-diamine | A |
| 502 | N$^1$-(4-methoxybenzo[d]isothiazol-3-yl)-N$^3$-((4'-methoxybiphenyl-4-yl)methyl)propane-1,3-diamine | B |
| 503 | N-(3-(benzo[d]isothiazol-3-ylamino)propyl)-2-(4-bromophenyl)acetamide | A |
| 504 | N-(3-(benzo[d]isothiazol-3-ylamino)propyl)-2-(4'-methoxybiphenyl-4-yl)acetamide | A |
| 505 | N-(3-(benzo[d]isothiazol-3-ylamino)propyl)-2-(4'-(trifluoromethyl)biphenyl-4-yl)acetamide | B |
| 506 | 3-(3-aminopropylamino)-N-tert-butylbenzo[d]isothiazole-4-sulfonamide | B |
| 507 | 3-(3-aminopropylamino)-N-tert-butylbenzo[d]isothiazole-7-sulfonamide | B |
| 508 | 3-(3-aminopropylamino)-N-tert-butylbenzo[d]isothiazole-6-sulfonamide | B |
| 509 | N-(3-(4-(N-tert-butylsulfamoyl)benzo[d]isothiazol-3-ylamino)propyl)-4-iodobenzamide | B |
| 510 | N-(3-(7-(N-tert-butylsulfamoyl)benzo[d]isothiazol-3-ylamino)propyl)-4-iodobenzamide | B |
| 511 | N-(3-(6-(N-tert-butylsulfamoyl)benzo[d]isothiazol-3-ylamino)propyl)-4-iodobenzamide | A |
| 512 | N-(3-(5-bromobenzo[d]isothiazol-3-ylamino)propyl)-4'-methoxybiphenyl-4-carboxamide | A |
| 513 | N-(3-(benzo[d]isothiazol-3-ylamino)propyl)-N-((4'-methoxybiphenyl-4-yl)methyl)acetamide | A |
| 514 | N-(3-(benzo[d]isothiazol-3-ylamino)propyl)-N-((4'-methoxybiphenyl-4-yl)methyl)-5-((3aS,4S,6aR)-2-oxo-hexahydro-1H-thieno[3,4-d]imidazol-4-yl)pentanamide | A |
| 515 | 4'-methoxy-N-(3-(5-(N-(4-methoxybenzyl)sulfamoyl)benzo[d]isothiazol-3-ylamino)propyl)biphenyl-4-carboxamide | B |
| 516 | 4'-methoxy-N-(3-(5-(N-methylsulfamoyl)benzo[d]isothiazol-3-ylamino)propyl)biphenyl-4-carboxamide | B |
| 517 | 5-bromo-N-(3-(5-(N-phenylsulfamoyl)benzo[d]isothiazol-3-ylamino)propyl)thiophene-2-carboxamide | B |
| 518 | 4-iodo-N-(3-(5-(N-phenylsulfamoyl)benzo[d]isothiazol-3-ylamino)propyl)benzamide | B |
| 519 | 5-chloro-N-(3-(5-(N-phenylsulfamoyl)benzo[d]isothiazol-3-ylamino)propyl)thiophene-2-carboxamide | B |
| 520 | 4'-methoxy-N-(3-(5-(N-phenylsulfamoyl)benzo[d]isothiazol-3-ylamino)propyl)biphenyl-4-carboxamide | B |
| 521 | N-(3-(isothiazolo[5,4-b]pyridin-3-ylamino)propyl)-2-methoxybenzamide | B |
| 522 | N-(3-(isothiazolo[5,4-b]pyridin-3-ylamino)propyl)-4-methoxybenzamide | B |
| 523 | N-(3-(isothiazolo[5,4-b]pyridin-3-ylamino)propyl)-3,5-dimethoxybenzamide | B |
| 524 | N-(3-(isothiazolo[5,4-b]pyridin-3-ylamino)propyl)-2-(trifluoromethoxy)benzamide | B |
| 525 | N-(3-(isothiazolo[5,4-b]pyridin-3-ylamino)propyl)-3-methoxybenzamide | B |
| 526 | 2-fluoro-N-(3-(isothiazolo[5,4-b]pyridin-3-ylamino)propyl)-6-(trifluoromethyl)benzamide | B |
| 527 | N-(3-(isothiazolo[5,4-b]pyridin-3-ylamino)propyl)-3-(trifluoromethoxy)benzamide | B |
| 528 | 2-chloro-N-(3-(isothiazolo[5,4-b]pyridin-3-ylamino)propyl)nicotinamide | B |
| 529 | 6-chloro-N-(3-(isothiazolo[5,4-b]pyridin-3-ylamino)propyl)nicotinamide | B |
| 530 | 4-hexyl-N-(3-(isothiazolo[5,4-b]pyridin-3-ylamino)propyl)benzamide | A |
| 531 | N-(3-(isothiazolo[5,4-b]pyridin-3-ylamino)propyl)-2,3-dihydrobenzo[b][1,4]dioxine-2-carboxamide | B |
| 532 | 3-(2-chloro-6-fluorophenyl)-N-(3-(isothiazolo[5,4-b]pyridin-3-ylamino)propyl)-5-methylisoxazole-4-carboxamide | B |
| 533 | N-(3-(isothiazolo[5,4-b]pyridin-3-ylamino)propyl)-1-(4-(trifluoromethyl)pyrimidin-2-yl)piperidine-4-carboxamide | A |
| 534 | N-(3-(isothiazolo[5,4-b]pyridin-3-ylamino)propyl)benzofuran-2-carboxamide | B |
| 535 | N-(3-(isothiazolo[5,4-b]pyridin-3-ylamino)propyl)-4-(methylsulfonyl)benzamide | B |
| 536 | N-(3-(isothiazolo[5,4-b]pyridin-3-ylamino)propyl)-2-(trifluoromethyl)benzenesulfonamide | B |
| 537 | 3-iodo-N-(3-(isothiazolo[5,4-b]pyridin-3-ylamino)propyl)benzamide | B |
| 538 | N-(3-(isothiazolo[5,4-b]pyridin-3-ylamino)propyl)-3-(naphthalen-2-yl)benzamide | A |
| 539 | N-(3-(isothiazolo[5,4-b]pyridin-3-ylamino)propyl)-3',4'-dimethylbiphenyl-3-carboxamide | A |
| 540 | 2,6-dichloro-N-(3-(isothiazolo[5,4-b]pyridin-3-ylamino)propyl)benzamide | B |
| 541 | N-(3-(isothiazolo[5,4-b]pyridin-3-ylamino)propyl)-6-methyl-4-oxo-4H-chromene-2-carboxamide | B |
| 542 | 4-hexyl-N-(3-(isothiazolo[4,5-b]pyridin-3-ylamino)propyl)benzamide | A |
| 543 | N-(3-(isothiazolo[4,5-b]pyridin-3-ylamino)propyl)-3-(trifluoromethyl)benzenesulfonamide | A |
| 544 | 3-iodo-N-(3-(isothiazolo[4,5-b]pyridin-3-ylamino)propyl)benzamide | A |
| 545 | N-(3-(4-methylbenzo[d]isothiazol-3-ylamino)propyl)-3-(trifluoromethyl)benzenesulfonamide | A |
| 546 | N$^1$-(isothiazolo[4,5-b]pyridin-3-yl)-N$^3$-((4'-methoxybiphenyl-4-yl)methyl)propane-1,3-diamine | A |

TABLE 5-continued

| Entry | Name | IC$_{50}$ |
|---|---|---|
| 547 | N-(3-(isothiazolo[4,5-b]pyridin-3-ylamino)propyl)-N-((4'-methoxybiphenyl-4-yl)methyl)-1,2-dimethyl-1H-imidazole-4-sulfonamide | A |
| 548 | methyl 5-(N-(3-(isothiazolo[4,5-b]pyridin-3-ylamino)propyl)-N-((4'-methoxybiphenyl-4-yl)methyl)sulfamoyl)-1-methyl-1H-pyrrole-2-carboxylate | A |
| 549 | 2-cyano-N-(3-(isothiazolo[4,5-b]pyridin-3-ylamino)propyl)-N-((4'-methoxybiphenyl-4-yl)methyl)acetamide | A |
| 550 | N$^1$-(isothiazolo[5,4-b]pyridin-3-yl)-N$^3$-((4'-methoxybiphenyl-4-yl)methyl)propane-1,3-diamine | A |
| 551 | N-(3-(isothiazolo[5,4-b]pyridin-3-ylamino)propyl)-N-((4'-methoxybiphenyl-4-yl)methyl)-1,2-dimethyl-1H-imidazole-4-sulfonamide | A |
| 552 | methyl 5-(N-(3-(isothiazolo[5,4-b]pyridin-3-ylamino)propyl)-N-((4'-methoxybiphenyl-4-yl)methyl)sulfamoyl)-1-methyl-1H-pyrrole-2-carboxylate | A |
| 553 | 2-cyano-N-(3-(isothiazolo[5,4-b]pyridin-3-ylamino)propyl)-N-((4'-methoxybiphenyl-4-yl)methyl)acetamide | A |

A counter screen was used to identify non-specific inhibitors of the reporter gene. In the counter screen, a cell line carrying a construct such as a CMV-driven luciferase gene was used to identify compounds that inhibit the reporter gene, and not HCV. IC$_{50}$ values were greater than 10 µM in the counter screen luciferase inhibition assay for many of the compounds. Standard cell proliferation assays were used to determine cytotoxicity of the compounds (CC$_{50}$) of the invention. The measured CC$_{50}$s for many of the compounds were greater 10 µM, which confirmed that the results reflected reduced viral production not cell death.

A TaqMan RT-PCR assay (Roche Molecular Systems, Pleasanton, Calif.) was used to analyze HCV RNA copy numbers, which confirmed that the viral genome of HCV is not being replicated. Actively dividing replicon cells were seeded at the density of 3×10$^4$ cells/well in a volume of 1 ml/well into 24-well plates. The cells were then incubated at 37° C. and 5% CO$_2$ for 24 hours. Various concentrations of compounds (in a volume of 10 ul) were added into each well 24 hours after seeding the cells. The cells were incubated with the compounds for another 24-48 hours, media was removed by aspiration and RNA samples prepared from each well. TaqMan one step RT-PCR was performed using the freshly prepared RNA samples according to the manufacturer's manual. The ratio of HCV RNA to cellular GAPDH mRNA was used as in indication of specificity of HCV inhibition and to confirm that the viral genome was not replicated.

Cytotoxicity Analysis

Compound of the invention were tested in a cytotoxicity assay with liver cells including an HCV replicon (replicon cell lines 5-2, 9-13, hepatoma cell line Huh-7, or primary human hepatocytes). In the assay, cells were seeded onto 96-well plates (approx. 7500 cells/well in a volume of 90 µl) and grown for 24 hr at 37° C. On day 2, various concentrations of test compound (in a volume of 10 µl) were added to the wells and the cells were grown for an additional 48 hr at 37° C. On day 4, an ATP-dependent R-Luciferase assay (Cell Titer Glo assay) was performed to determine the number of viable cells. The compounds of the invention are generally well-tolerated from a cell toxicity perspective.

All publications, patents and patent applications cited in this specification are herein incorporated by reference as if each individual publication, patent or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

What is claimed is:

1. A compound of Formula II,

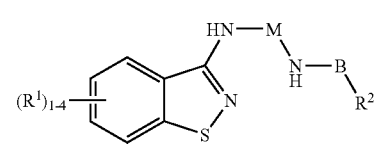

II or a pharmaceutically acceptable salt or S-oxide thereof, wherein, each R$^1$ is independently selected from —H, halogen, mono- to trihalomethyl, —NO$_2$, —N(R$^3$)R$^3$, —S(O)$_{0-2}$R$^3$, —SO$_2$N(R$^3$)R$^3$, optionally substituted C$_{1-12}$ alkoxy, optionally substituted C$_{1-6}$ alkyl, and optionally substituted aryl C$_{0-6}$ alkyl B is selected from absent, optionally substituted C$_{1-6}$ alkylene, —C═O, —C(═O)C(═O)—, —S(O)$_2$, —C(═O)N(R$^4$)—, —C(═NR$^5$)N(R$^4$)—, —C(═S)N(R$^4$)—, —C(═S)O—, and —C(═O)O—

R$^2$ is an optionally substituted aryl-aryl;

each R$^3$ is independently selected from —H, optionally substituted C$_{1-6}$ alkyl, optionally substituted —C(═O) C$_{1-6}$ alkyl, optionally substituted aryl C$_{0-6}$ alkyl, optionally substituted heteroaryl C$_{0-6}$alkyl and optionally substituted heterocyclyl C$_{0-6}$alkyl; optionally two of R$^3$, together with the nitrogen to which they are attached, combine to form an optionally substituted heterocyclyl containing one to three heteroatoms;

each R$^4$ is independently selected from —H and optionally substituted C$_{1-6}$ alkyl, —S(O)$_{0-2}$R$^3$, —C(═O)N(R$^3$)(R$^3$), optionally substituted aryl C$_{1-6}$ alkyl;

each R$^5$ is independently selected from —H, —CN, —NO$_2$, —OR$^3$, —S(O)$_{0-2}$R$^3$, —CO$_2$R$^3$, optionally substituted C$_{1-6}$ alkyl, optionally substituted C$_{2-6}$ alkenyl, and optionally substituted C$_{2-6}$ alkynyl;

M is C$_{2-4}$ alkylene, C$_{2-4}$ alkenylene, or C$_{2-4}$ alkynylene; and each R$^9$ is independently selected from —H, optionally substituted C$_{1-6}$ alkyl, optionally substituted aryl C$_{0-6}$ alkyl and optionally substituted heterocyclyl C$_{0-6}$alkyl; and optionally two of R$^9$, together with the nitrogen to which they are attached, combine to form an optionally substituted heterocyclyl containing one to three heteroatoms.

2. The compound according to claim 1, wherein $R^1$ is chloro, bromo, trifluoromethyl, methoxy, $C_{1-3}$ alkyl, —N(H)—$C_{1-3}$ alkyl, —$SO_2$·$C_{1-5}$ alkyl, —$SO_2NH_2$, —$SO_2N(H)C_{1-5}$ alkyl, or phenyl optionally substituted with one or more methoxy, isopropoxy or fluoro.

3. A compound of Formula II,

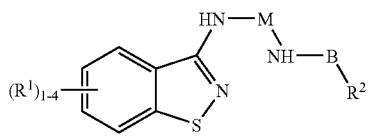

II or a pharmaceutically acceptable salt, or S-oxide thereof, wherein,

B is selected from optionally substituted $C_{1-6}$ alkyl, —C(=O)—, —S(O)$_{0-2}$—, —C(=O)N($R^4$)— or is absent each $R^1$ is independently selected from —H, halogen, mono- to trihalomethyl, —CN, —$NO_2$, —$OR^3$, —N($R^3$)$R^3$, —S(O)$_{0-2}R^3$, —N($R^3$)C(=O)N($R^3$)$R^3$, —$SO_2$N($R^3$)$R^3$, —$CO_2R^3$, —C(=O)N($R^3$)$R^3$, —C(=$NR^5$)N($R^3$)$R^3$, —C(=$NR^5$)$R^3$, —N($R^3$)$SO_2R^3$, —N($R^3$)C(O)$R^3$, —NC(=O)CH($R^3$)N($R^3$)$R^3$, —$NCO_2R^3$, —C(=O)$R^3$, optionally substituted $C_1$-$C_{12}$ alkoxy, optionally substituted $C_{1-6}$ alkyl, optionally substituted aryl $C_{0-6}$ alkyl and optionally substituted heterocyclyl $C_{0-6}$ alkyl;

$R^2$ is an optionally substituted aryl-aryl;

each $R^3$ is independently selected from —H, optionally substituted $C_{1-6}$ alkyl, optionally substituted —C(=O)$C_{1-6}$ alkyl, optionally substituted aryl $C_{0-6}$ alkyl, optionally substituted heteroaryl $C_{0-6}$alkyl and optionally substituted heterocyclyl $C_{0-6}$alkyl; optionally two of $R^3$, together with the nitrogen to which they are attached, combine to form an optionally substituted heterocyclyl containing one to three heteroatoms;

each $R^4$ is independently selected from —H and optionally substituted $C_{1-6}$ alkyl, —S(O)$_{0-2}R^3$, —C(=O)N($R^3$)($R^3$), optionally substituted aryl $C_{1-6}$ alkyl;

each $R^5$ is independently selected from —H, —CN, —$NO_2$, —$OR^3$, —S(O)$_{0-2}R^3$, —$CO_2R^3$, optionally substituted $C_{1-6}$ alkyl, optionally substituted $C_{2-6}$ alkenyl, and optionally substituted $C_{2-6}$ alkynyl;

M is $C_{2-4}$ alkylene, $C_{2-4}$ alkenylene, or $C_{2-4}$ alkynylene; and each $R^9$ is independently selected from —H, optionally substituted $C_{1-6}$ alkyl, optionally substituted aryl $C_{0-6}$ alkyl and optionally substituted heterocyclyl $C_{0-6}$alkyl; and optionally two of $R^9$, together with the nitrogen to which they are attached, combine to form an optionally substituted heterocyclyl containing one to three heteroatoms.

4. The compound according to claim 3, wherein B is $C_{1-3}$ alkyl, —S(O)$_2$— or —C(=O)N(H)—.

5. The compound according to claim 4, wherein B is methylene.

* * * * *